United States Patent
Lu et al.

(10) Patent No.: US 11,845,801 B2
(45) Date of Patent: Dec. 19, 2023

(54) IL-15 PRODRUGS AND METHODS OF USE THEREOF

(71) Applicant: ASKGENE PHARMA, INC., Camarillo, CA (US)

(72) Inventors: Yuefeng Lu, Newbury Park, CA (US); Chunxiao Yu, Santa Barbara, CA (US); Jian-Feng Lu, Oak Park, CA (US)

(73) Assignee: ASKGENE PHARMA, INC., Camarillo, CA (US)

(*) Notice: Subject to any disclaimer, the term of this patent is extended or adjusted under 35 U.S.C. 154(b) by 380 days.

(21) Appl. No.: 16/900,677

(22) Filed: Jun. 12, 2020

(65) Prior Publication Data

US 2020/0392235 A1 Dec. 17, 2020

Related U.S. Application Data

(60) Provisional application No. 62/959,973, filed on Jan. 11, 2020, provisional application No. 62/891,190, filed on Aug. 23, 2019, provisional application No. 62/888,444, filed on Aug. 17, 2019, provisional application No. 62/860,635, filed on Jun. 12, 2019, provisional application No. 63/029,473, filed on May 23, 2020.

(51) Int. Cl.
*C07K 16/00* (2006.01)
*C07K 16/28* (2006.01)
*C07K 14/81* (2006.01)

(52) U.S. Cl.
CPC ........ *C07K 16/2866* (2013.01); *C07K 14/811* (2013.01); *C07K 14/8146* (2013.01); *C07K 2317/51* (2013.01); *C07K 2317/515* (2013.01); *C07K 2317/55* (2013.01); *C07K 2317/565* (2013.01); *C12Y 304/21109* (2013.01); *C12Y 304/24024* (2013.01); *C12Y 304/24035* (2013.01)

(58) Field of Classification Search
CPC ............... C07K 16/2866; C07K 14/811; C07K 14/8146; C07K 2317/51; C07K 2317/515
See application file for complete search history.

(56) References Cited

U.S. PATENT DOCUMENTS

| | | | |
|---|---|---|---|
| 5,229,109 A | 7/1993 | Grimm et al. | |
| 6,682,736 B1 | 1/2004 | Hanson et al. | |
| 6,942,853 B2 | 9/2005 | Chernajovsky et al. | |
| 6,955,807 B1 | 10/2005 | Shanafelt et al. | |
| 6,984,720 B1 | 1/2006 | Korman et al. | |
| 7,008,624 B1 | 3/2006 | Grabstein et al. | |
| 7,153,507 B2* | 12/2006 | van de Winkel | A61P 19/02 530/388.1 |
| 7,858,081 B2 | 12/2010 | Bernard et al. | |
| 7,943,743 B2 | 5/2011 | Korman et al. | |
| 8,008,449 B2 | 8/2011 | Korman et al. | |
| 8,211,420 B2 | 7/2012 | Bondensgaard et al. | |
| 8,563,697 B2 | 10/2013 | Clarke et al. | |
| 8,642,742 B2 | 2/2014 | Hofer et al. | |
| 8,642,745 B2 | 2/2014 | Arathoon et al. | |
| 9,206,260 B2 | 12/2015 | Hofer et al. | |
| 9,428,567 B2 | 8/2016 | Garcia et al. | |
| 9,447,159 B2 | 9/2016 | Ast et al. | |
| 9,474,780 B2 | 10/2016 | Bokvist et al. | |
| 9,732,134 B2 | 8/2017 | Gavin et al. | |
| 10,301,384 B2 | 5/2019 | Vicari et al. | |
| 10,815,303 B2 | 10/2020 | Yue et al. | |
| 10,858,452 B2 | 12/2020 | Mortier et al. | |
| 11,130,806 B2 | 9/2021 | Vicari et al. | |
| 11,267,883 B2 | 3/2022 | Laine et al. | |
| 11,357,820 B2 | 6/2022 | Corvari et al. | |
| 2002/0039581 A1 | 4/2002 | Carreno et al. | |
| 2002/0086014 A1 | 7/2002 | Korman et al. | |
| 2003/0124678 A1 | 7/2003 | Epstein et al. | |
| 2004/0053829 A1* | 3/2004 | Pfizenmaier | C07K 14/7151 514/19.3 |
| 2005/0201994 A1 | 9/2005 | Korman et al. | |
| 2006/0236411 A1 | 10/2006 | Dreher et al. | |
| 2011/0250213 A1 | 10/2011 | Tso et al. | |
| 2011/0306752 A1 | 12/2011 | Wittrup et al. | |
| 2013/0022623 A1 | 1/2013 | Karsunky et al. | |
| 2013/0089516 A1 | 4/2013 | Frelinger et al. | |
| 2014/0294759 A1 | 10/2014 | Chu et al. | |
| 2014/0314709 A1 | 10/2014 | León Monzón et al. | |
| 2014/0328791 A1 | 11/2014 | Bossard et al. | |
| 2015/0266954 A1 | 9/2015 | Davies et al. | |
| 2016/0340413 A1 | 11/2016 | Duerner et al. | |
| 2017/0173149 A1 | 6/2017 | Ettinger et al. | |
| 2017/0204154 A1 | 7/2017 | Greve | |
| 2017/0240608 A1 | 8/2017 | Stagliano et al. | |
| 2018/0118828 A1 | 5/2018 | Bernett et al. | |
| 2020/0123227 A1 | 4/2020 | Fu et al. | |

(Continued)

FOREIGN PATENT DOCUMENTS

| | | | |
|---|---|---|---|
| EP | 1870459 A1 | 12/2007 | |
| EP | 2639241 A2 | 9/2013 | |
| EP | 3093295 A1 | 11/2016 | |
| EP | 2665486 B1 | 12/2019 | |
| NZ | 567242 A | 11/2009 | |
| WO | WO 99/29732 A2 | 6/1999 | |
| WO | WO 02/22833 A1 | 3/2002 | |
| WO | WO 2003/017935 A2 | 3/2003 | |

(Continued)

OTHER PUBLICATIONS

U.S. Appl. No. 16/979,404, filed Sep. 9, 2020, Chunxiao Yu.

(Continued)

*Primary Examiner* — Lei Yao

(74) *Attorney, Agent, or Firm* — Steptoe & Johnson LLP; Z. Ying Li; Mauricio Alvarez

(57) ABSTRACT

Provided herein are IL-15 cytokine prodrugs and methods of making and using thereof.

21 Claims, 22 Drawing Sheets

Specification includes a Sequence Listing.

(56) References Cited

U.S. PATENT DOCUMENTS

| | | |
|---|---|---|
| 2020/0164069 A1 | 5/2020 | Ettinger et al. |
| 2020/0207846 A1 | 7/2020 | Igawa et al. |
| 2020/0331966 A1 | 10/2020 | Stover et al. |
| 2020/0347128 A1 | 11/2020 | Tagaya et al. |
| 2021/0163562 A1 | 6/2021 | Lu et al. |
| 2021/0260163 A1 | 8/2021 | Yu et al. |
| 2022/0127352 A1 | 4/2022 | Laine et al. |
| 2022/0162280 A1 | 5/2022 | Fu et al. |
| 2022/0289822 A1 | 9/2022 | Lu et al. |
| 2022/0306714 A1 | 9/2022 | Yao et al. |
| 2022/0356221 A1 | 11/2022 | Lu et al. |
| 2023/0108562 A1 | 4/2023 | Lu et al. |

FOREIGN PATENT DOCUMENTS

| | | |
|---|---|---|
| WO | WO 2003/028630 A2 | 4/2003 |
| WO | WO 2004/021861 A2 | 3/2004 |
| WO | WO 2005/063279 A1 | 7/2005 |
| WO | WO 2005/066348 A2 | 7/2005 |
| WO | WO2005/085282 A1 | 9/2005 |
| WO | WO 2005/086798 A2 | 9/2005 |
| WO | WO 2008/003473 A2 | 1/2008 |
| WO | WO 2009/025846 A2 | 2/2009 |
| WO | WO 2009/061853 A2 | 5/2009 |
| WO | WO 2010/040105 A2 | 4/2010 |
| WO | WO 2012/061536 A2 | 5/2012 |
| WO | WO 2012/099886 A1 | 7/2012 |
| WO | WO 2012/107417 A1 | 8/2012 |
| WO | WO 2012/120125 A1 | 9/2012 |
| WO | WO 2012/146628 A1 | 11/2012 |
| WO | WO2014066527 * | 5/2014 |
| WO | WO 2014/164553 A1 | 10/2014 |
| WO | WO 2015/066279 A2 | 5/2015 |
| WO | WO 2015/110930 A1 | 7/2015 |
| WO | WO 2016/001275 A1 | 1/2016 |
| WO | WO 2016/014428 A2 | 1/2016 |
| WO | WO 2016/082677 A1 | 6/2016 |
| WO | WO 2016/086186 A2 | 6/2016 |
| WO | WO 2016/090173 A1 | 6/2016 |
| WO | 2016/115275 A1 | 7/2016 |
| WO | WO 2016/200645 A1 | 12/2016 |
| WO | WO 2017/046200 A1 | 3/2017 |
| WO | WO2017162587 * | 9/2017 |
| WO | WO 2017/201432 A2 | 11/2017 |
| WO | WO 2017/220989 A1 | 12/2017 |
| WO | WO 2018/004338 A1 | 1/2018 |
| WO | WO 2018/044105 A1 | 3/2018 |
| WO | WO 2018/119246 A1 | 6/2018 |
| WO | WO 2019/173832 A2 | 9/2019 |
| WO | WO 2019/222294 A1 | 11/2019 |
| WO | WO 2019/222295 A1 | 11/2019 |
| WO | WO 2019/246392 A1 | 12/2019 |
| WO | WO 2020/069398 A1 | 4/2020 |
| WO | WO 2020/227019 A1 | 11/2020 |
| WO | WO 2020/247843 A2 | 12/2020 |
| WO | WO 2022/159395 A1 | 7/2022 |
| WO | WO 2022/165443 A1 | 8/2022 |
| WO | WO 2022/178103 A1 | 8/2022 |
| WO | WO 2023/044290 A1 | 3/2023 |
| WO | WO 2022/155541 A1 | 4/2023 |

OTHER PUBLICATIONS

U.S. Appl. No. 17/634,890, filed Feb. 11, 2022, Chen Yao.
Bazan, "Unraveling the structure of IL-2," Science 257:410-13 (1992).
Bernard et al., "Identification of an interleukin-15alpha receptor-binding site on human interleukin-15," J Biol Chem. 279:24313-22 (2004).
Chothia et al., "Canonical structures for the hypervariable regions of immunoglobulins," J. Mol. Biol. 96(4):901-17 (1987).
Dall'Acqua et al., "Properties of human IgG1s engineered for enhanced binding to the neonatal Fc receptor (FcRn)," J Biol Chem. 281: 23514-24 (2006).
Fontenot et al., "A function for interleukin 2 in Foxp3-expressing regulatory T cells," Nature Immunol 6:1142-51 (2005).
Giri et al., "Utilization of the beta and gamma chains of the IL-2 receptor by the novel cytokine IL-15," EMBO J. 13:2822-30 (1994).
Giri et al., "IL-15, a novel T cell growth factor that shares activities and receptor components with I L-2," J Leukoc Biol. 57:763-6 (1995).
Guo et al., "Immunobiology of the IL-15/IL-15Rα complex as an antitumor and antiviral agent," Cytokine Growth Factor Rev 38:10-21 (2017).
Heaton et al. "Human interleukin 2 analogues that preferentially bind the intermediate-affinity interleukin 2 receptor lead to reduced secondary cytokine secretion: implications for the use of these interleukin 2 analogues in cancer immunotherapy," Cancer Res. 53(11):2597-602 (1993).
Hezareh et al. "Effector function activities of a panel of mutants of a broadly neutralizing antibody against human immunodeficiency virus type 1," J. Virol. 75(24):12161-8 (2001).
Johnson et al., "Soluble IL-2 receptor beta and gamma subunits: ligand binding and cooperativity," Eur Cytokine Netw. 5(1):23-34 (1994).
Kim et al., "Both integrated and differential regulation of components of the IL-2/IL-2 receptor system," Cytokine Growth Factor Rev. 17:349-66 (2006).
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology 6(3):e1277306 (2017).
Krieg et al., "Improved IL-2 immunotherapy by selective stimulation of IL-2 receptors on lymphocytes and endothelial cells," Proc Natl Acad Sci. 107:11906-11 (2010).
Lehours et al., "Subunit structure of the high and low affinity human interleukin-15 receptors," Eur Cytokine Netw. 11:207-15 (2000).
Merchant et al., "An efficient route to human bispecific IgG," Nature Biotech 16:677-81 (1998).
Minami et al., "The IL-2 receptor complex: its structure, function, and target genes," Annu Rev Immunol. 11:245-68 (1993).
Ortiz-Sanchez et al., "Antibody-cytokine fusion proteins: applications in cancer therapy," Expert Opin Biol Ther. 8(5): 609-632 (2008).
Pettit et al., "Structure-Function Studies of Interleukin 15 using Site-specific Mutagenesis, Polyethylene Glycol Conjugation, and Homology Modeling," J Biol Chem. 272: 2312-18 (1997).
Robbie et al., "A novel investigational Fc-modified humanized monoclonal antibody, motavizumab-YTE, has an extended half-life in healthy adults," Antimicrob Agents Chemother. 57(12):6147-53 (2013).
Smith, "Interleukin-2: inception, impact, and implications," Science 240:1169-76 (1988).
Spiess et al., "Alternative molecular formats and therapeutic applications for bispecific antibodies," Mol Imm. 67(2)(A):95-106 (2015).
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," J Clin Onc. 36:15 suppl (2018).
Wang et al., "Structure of the quaternary complex of interleukin-2 with its alpha, beta, and gammac receptors," Science 310:1159-63 (2005).
Wei et al., "The Sushi domain of soluble IL-15 receptor alpha is essential for binding IL-15 and inhibiting inflammatory and allogenic responses in vitro and in vivo," J Immunol. 167(1):277-82 (2001).
Ye et al., "Targeting IL-2: an unexpected effect in treating immunological diseases," ignal Transduct Target Ther. 3:2 (2018).
Zhu et al., "Novel Human Interleukin-15 Agonists," J Immnol. 183(6):3598 (2009).
Bogdan et al., "Macrophage deactivation by interleukin 10," *J Exp Med.* 174(6):1549-55 (1991).
Charych et al., "Modeling the receptor pharmacology, pharmacokinetics, and pharmacodynamics of NKTR-214, a kinetically-controlled interleukin-2 (IL2) receptor agonist for cancer immunotherapy," *PLoS One* 12(7) (2017).

(56) References Cited

OTHER PUBLICATIONS

Colombo et al., "Interleukin-12 in anti-tumor immunity and immunotherapy," *Cytokine Growth Factor Rev.* 13(2):155-68 (2002).
Conlon et al., "IL15 by Continuous Intravenous Infusion to Adult Patients with Solid Tumors in a Phase I Trial Induced Dramatic NK-Cell Subset Expansion," *Clin Cancer Res.* 25(16):4945-4954 (2019).
Database UniProt [Online] RecName: Full=High affinity IL-2 receptor subunit beta {ECO:00002561 ARBA:ARBA00014194}; retrieved from EBI accession No. UNIPROT:A0A2K6RLA0; Database accession No. A0A2K6RLA0; the whole document.
Del Vecchio et al., "Interleukin-12: biological properties and clinical application," *Clin Cancer Res.* 13(16):4677-85 (2007).
De Waal Malefyt et al., "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med.* 174(4):915-24 (1991).
Fiorentino et al., "IL-10 acts on the antigen-presenting cell to inhibit cytokine production by Th1 cells," *J Immunol.* 146(10):3444-51 (1991).
Gelebart et al., "Interleukin-21 effectively induces apoptosis in mantle cell lymphoma through a STAT1-dependent mechanism," *Leukemia* 23:1836-1846 (2009).
Gharibi et al., "Biological effects of IL-21 on different immune cells and its role in autoimmune diseases," *Immunobiology* 221(2):357-67 (2016).
Grimm et al., p. 25, Abstr 5861 (2016) [www.page-meeting.org/?abstract=5861].
Harrington et al., "Modulation of immune checkpoint molecule expression in mantle cell lymphoma," *Leuk Lymphoma* 60(10):2498-2507 (2019).
Hsu et al., "A cytokine receptor-masked IL2 prodrug selectively activates tumor-infiltrating lymphocytes for potent antitumor therapy," *Nature Communications*, vol. 12(1) (2021).
Jounaidi et al., "Tethering IL2 to Its Receptor IL2Rβ Enhances Antitumor Activity and Expansion of Natural Killer NK92 Cells," *Cancer Research*, 77 (21) 5938-5951 (2017).
Kang et al., "Rational design of interleukin-21 antagonist through selective elimination of the gammaC binding epitope," *J Biol Chem.* 285(16):12223-31 (2010).
Kirkwood, "Cancer immunotherapy: the interferon-alpha experience," *Semin Oncol.* 29(3 Suppl 7):18-26 (2002).
Korn et al., "IL-21 initiates an alternative pathway to induce proinflammatory T(H)17 cells," *Nature* 448(7152):484-87 (2007).
Kuen et al., "Antibody masked cytokines as new approach in targeted tumor therapy," (2018) (Doctoral Thesis). XP055702405.
Lasek et al., "Interleukin 12 still a promising candidate for tumor immunotherapy?" *Cancer Immunol Immunother.* 63(5):419-35 (2014).
Lopes et al., "ALKS 4230: a novel engineered IL-2 fusion protein with an improved cellular selectivity profile for cancer immunotherapy," *J Immunother Cancer* 8(1) (2020).
Macatonia et al., "Differential effect of IL-10 on dendritic cell-induced T cell proliferation and IFN-gamma production," *J Immunol.* 150(9):3755-65 (1993).
McDonald et al., "Interleukin 2-Based Fusion Proteins for the Treatment of Cancer," *Journal of Immunology Research*, vol. 2021:1-11 (2021).
Marth et al., "Interferon-gamma in combination with carboplatin and paclitaxel as a safe and effective first-line treatment option for advanced ovarian cancer: results of a phase I/II study," *Int. J. Gynecol.* (Cancer) 16:1522-1528 (2006).
Nurieva et al., "Essential autocrine regulation by IL-21 in the generation of inflammatory T cells," *Nature* 448(7152):480-83 (2007).
Parkin et al., "An overview of the immune system," *Immunology* 357(9270):1777-89 (2001).
Puskas et al., "Development of an attenuated interleukin-2 fusion protein that can be activated by tumour-expressed proteases," *Immunology* 133:206-220 (2011).
Sanjabi et al., "Regulation of the Immune Response by TGF-β: From Conception to Autoimmunity and Infection," *Cold Spring Harb Perspect Biol.* 9(6) (2017).
Schmidt et al., "Safety and Clinical Effect of Subcutaneous Human Interleukin-21 in Patients with Metastatic Melanoma or Renal Cell Carcinoma: A Phase I Trial," *Clin Cancer Res.* 16(21):5312-19 (2010).
Skrombolas et al., "Development of an Interleukin-12 Fusion Protein That Is Activated by Cleavage with Matrix Metalloproteinase 9," *J Interferon Cytokine Res.* 39(4):233-245 (2019).
Sogkas et al., "First Association of Interleukin 12 Receptor Beta 1 Deficiency with Sjögren's Syndrome," *Front Immunol.* 8:885 (2017).
Spolski et al., "The Yin and Yang of Interleukin-21 in Allergy, Autoimmunity and Cancer," *Curr Opin Immunol.* 20(3): 295-301 (2008).
Spolski et al., "Interleukin-21: basic biology and implications for cancer and autoimmunity," *Annu Rev Immunol.* 26:57-79 (2008).
Tam et al., "Functional, Biophysical, and Structural Characterization of Human IgG1 and IgG4 Fc Variants with Ablated Immune Functionality," *Antibodies* 6(12):1-34 (2017).
Vazquez-Lombardi et al., "Molecular Engineering of Therapeutic Cytokines," *Antibodies* 2(3), 426-451 (2013).
Wang et al., "Targeting IL-10 Family Cytokines for the Treatment of Human Diseases," *Cold Spring Harb Perspect Biol.* 11(2):a028548 (2019).
Watford et al., "The biology of IL-12: coordinating innate and adaptive immune responses," *Cytokine Growth Factor Rev.* 14(5):361-8 (2003).
Weerd et al. "Type I interferon receptors: biochemistry and biological functions," *The Journal of Biological Chemistry* 282 (28): 20053-7 (2007).
Worthington et al., "Regulation of TGFβ in the immune system: an emerging role for integrins and dendritic cells," *Immunobiology* 217(12):1259-65 (2012).
Young et al., "Antibody-cytokine fusion proteins for treatment of cancer: engineering cytokines for improved efficacy and safety," *Semin Oncol.* 41(5): 623-636 (2014).
Zarkavelis et al., "The emerging role of Interleukin-21 as an antineoplastic immunomodulatory treatment option," *Transl Cancer Res.* 6(Suppl 2):S328-30 (2017).
Zhang et al., "Human IL-21 and IL-4 bind to partially overlapping epitopes of common gamma-chain," *Biochem Biophys Res Commun.* 300(2):291-6 (2003).
Weidle et al., "Proteases as activators for cytotoxic prodrugs in antitumor therapy," Cancer Genomics Proteomics. (2014) 11(2):67-80.

* cited by examiner

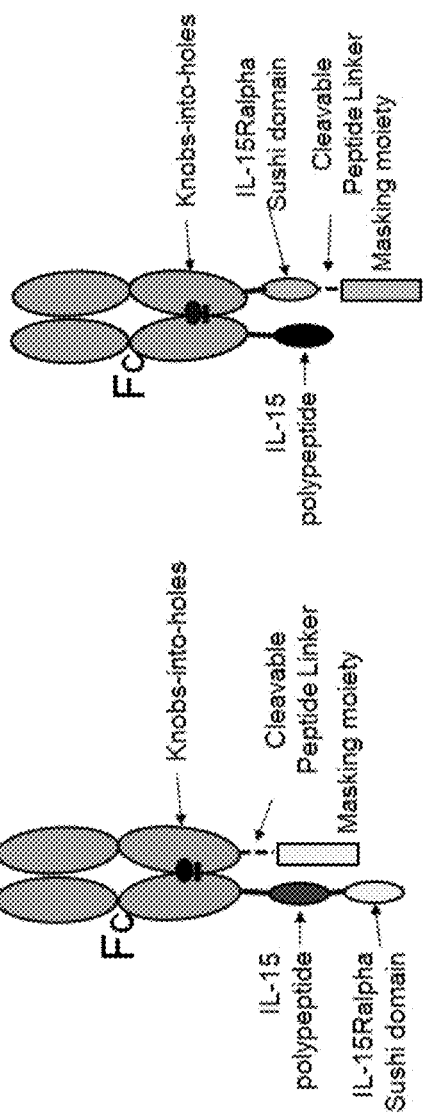
FIG. 1A
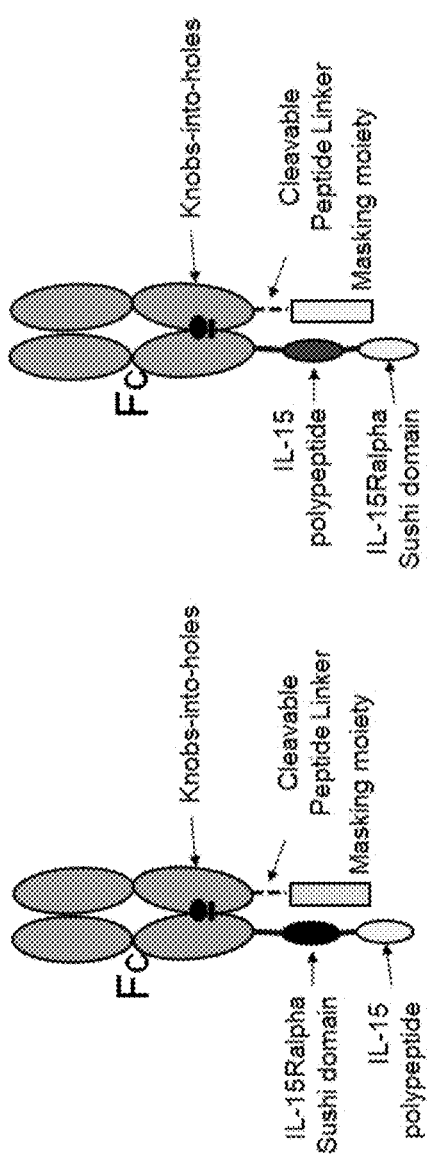
FIG. 1B
FIG. 1C
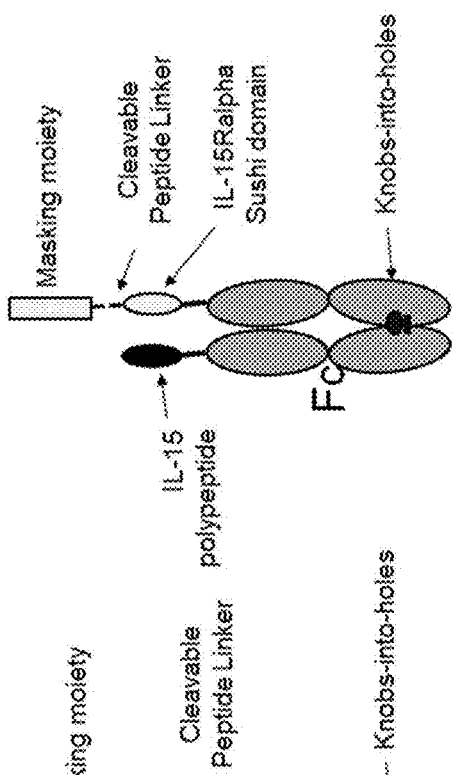
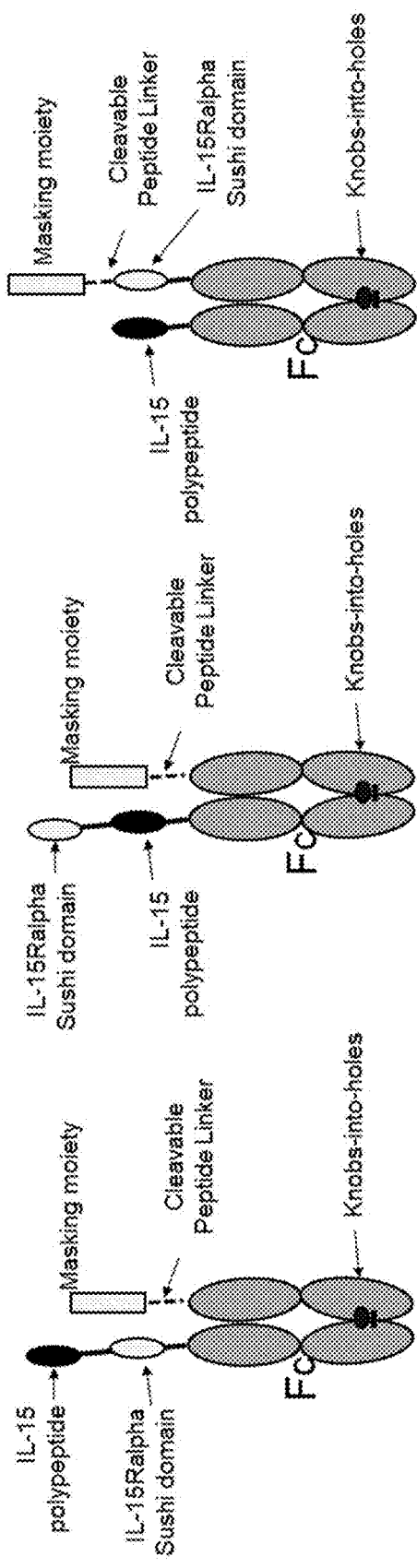
FIG. 2A
FIG. 2B
FIG. 2C

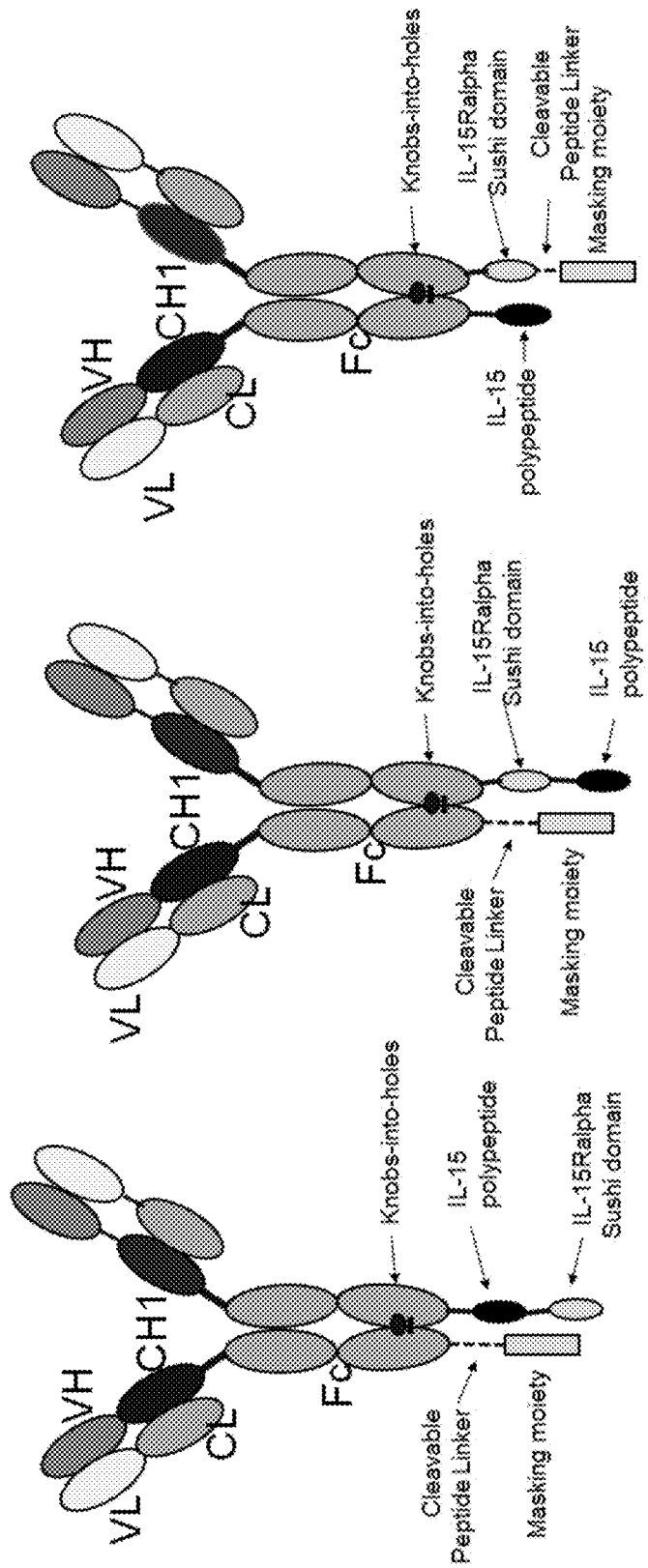

| Fusion Molecule Notebook Code | Knob Chain | | Hole Chain | |
|---|---|---|---|---|
| | Plasmid Code | Seq ID NO: | Plasmid Code | Seq ID NO: |
| JR3.68.1 | CX5.51.4 | 38 | CX5.51.1 | 37 |
| JR3.68.2 | CX5.51.5 | 40 | CX5.51.1 | 37 |
| JR3.68.3 | CX5.51.6 | 41 | CX5.51.7 | 42 |
| JR3.68.4 | CX5.51.4 | 38 | CX5.43.8 | 43 |
| JR3.68.5 | CX5.51.5 | 40 | CX5.43.8 | 43 |

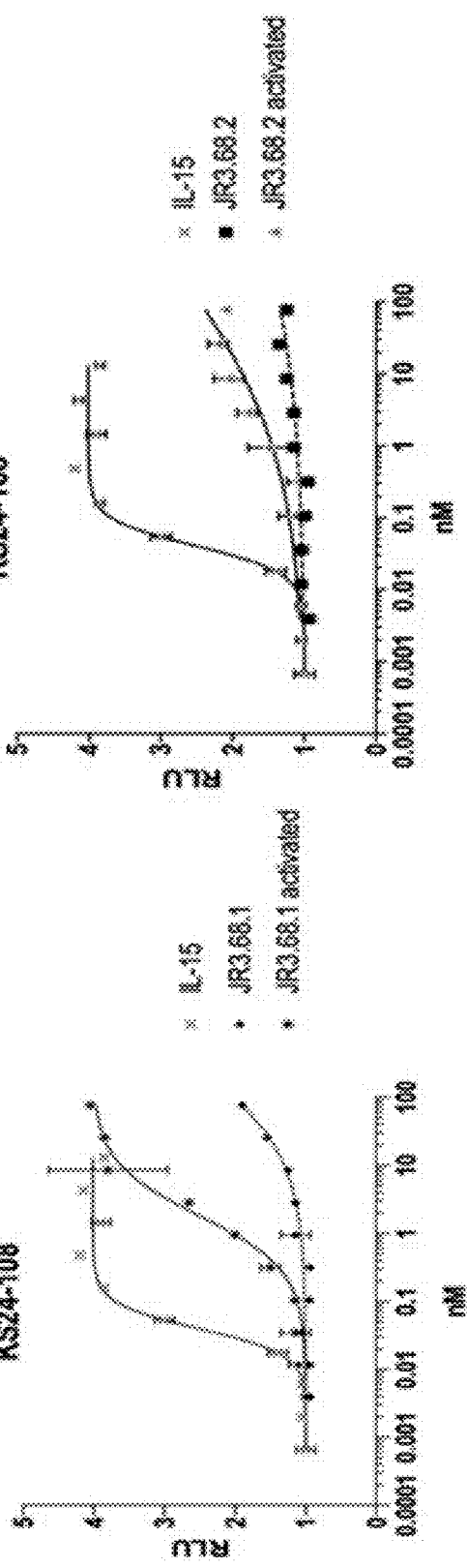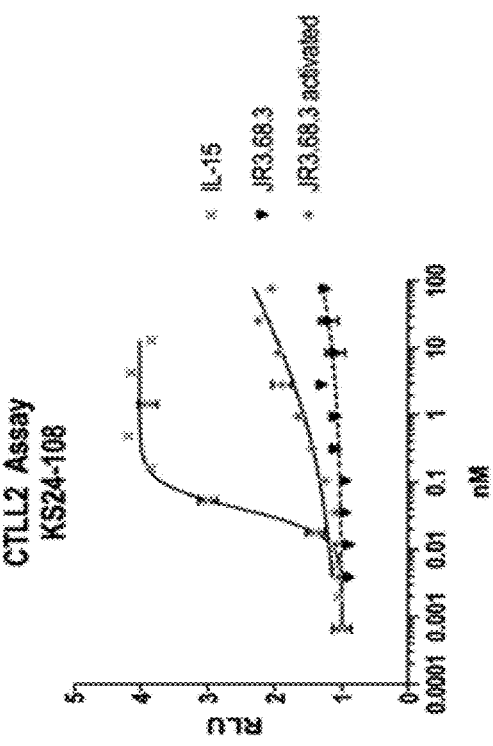
FIG. 9A
FIG. 9B
FIG. 9C

| Fusion Molecule Notebook Code | Knob Chain | | Hole Chain | | Light Chain | |
|---|---|---|---|---|---|---|
| | Plasmid Code | Seq ID NO: | Plasmid Code | Seq ID NO: | Plasmid Code | Seq ID NO: |
| JR3.74.1 | CX5.48.3 | 52 | CX3.58.4 | 57 | CX5.17.1 | 55 |
| JR3.74.2 | CX5.48.4 | 53 | CX3.58.4 | 57 | CX5.17.1 | 55 |
| JR3.73.2 | CX5.48.3 | 52 | CX3.58.3 | 54 | CX5.17.1 | 55 |
| JR3.73.4 | CX5.48.4 | 53 | CX3.58.3 | 54 | CX5.17.1 | 55 |

FIG. 10A

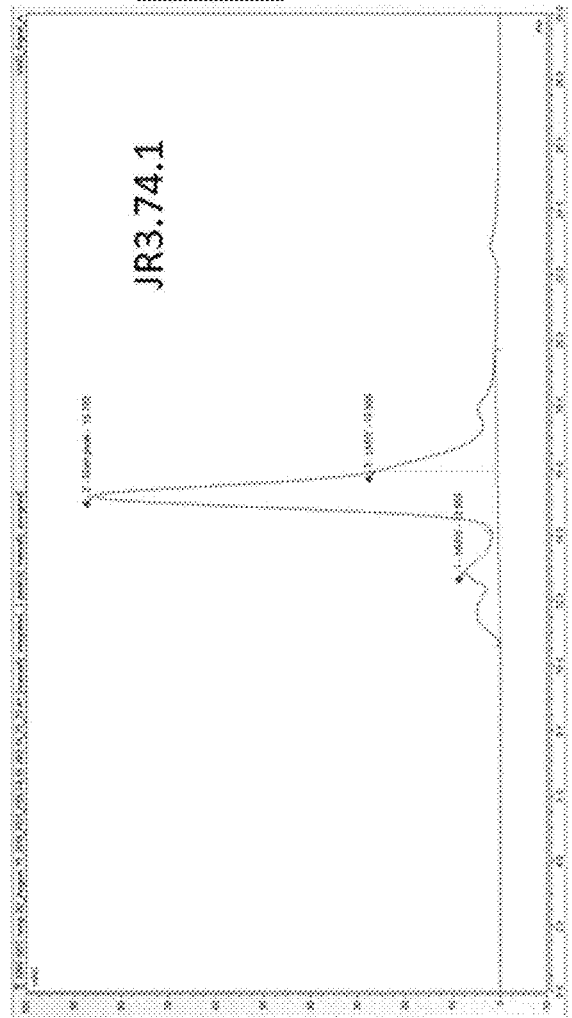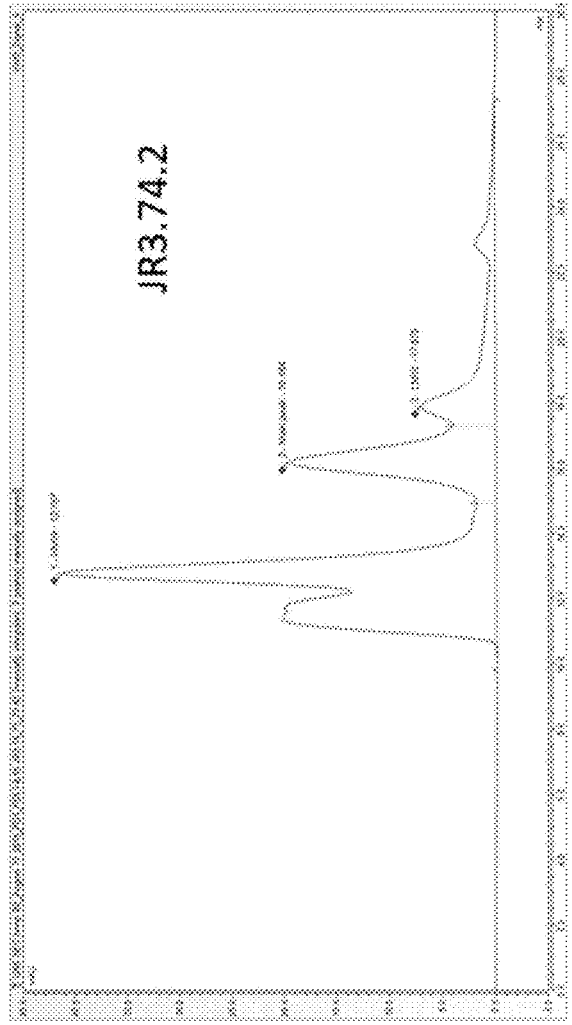
FIG. 11A

| Name | Code | Knob Chain Sequence (Fc-linker-IL15 or analog) | Hole Chain Sequence (Fc-cleavable linker– mask) |
|---|---|---|---|
| IL15wt/scfv1 | JR3.147.4 | SEQ ID NO: 77 | SEQ ID NO: 111 |
| IL15wt/scfv2 | JR3.147.5 | SEQ ID NO: 77 | SEQ ID NO: 112 |
| IL15N65D/scfv1 | JR3.148.1 | SEQ ID NO: 79 | SEQ ID NO: 111 |
| IL15N65D/scfv2 | JR3.148.2 | SEQ ID NO: 79 | SEQ ID NO: 112 |
| Fc-IL15* | PW04-11 | SEQ ID NO: 38 | SEQ ID NO: 37 |

NK92 Assay
KS29-14

| Name | Code | Knob Chain Sequence (Fc-linker – optional sushi -linker - IL15 or analog) | Hole Chain Sequence (Fc-cleavable linker– mask) |
|---|---|---|---|
| IL15wtFc-bg | JR3.159.1 | SEQ ID NO: 77 | SEQ ID NO: 113 |
| IL15wtFc-gb | JR3.159.2 | SEQ ID NO: 77 | SEQ ID NO: 114 |
| IL15wtFc-bctermg | JR3.159.3 | SEQ ID NO: 77 | SEQ ID NO: 115 |
| IL15Q108E Fc-bg | JR3.159.4 | SEQ ID NO: 116 | SEQ ID NO: 113 |
| IL15Q108E Fc-gb | JR3.159.5 | SEQ ID NO: 116 | SEQ ID NO: 114 |
| IL15Q108E Fc-bctermg | JR3.160.1 | SEQ ID NO: 116 | SEQ ID NO: 115 |
| Fc-IL15wt/beta (Fc-IL15*) | PW04-11 | SEQ ID NO: 38 | SEQ ID NO: 37 |
| IL15Q108E Fc-scFv2 | JR3.156.3 | SEQ ID NO: 116 | SEQ ID NO: 112 |
| IL15Q108E Fc-b Non-cleavable | JR3.156.4 | SEQ ID NO: 116 | SEQ ID NO: 117 |
| JR2.145.1 IL15vN65D /scFv no sushi | JR2.145.1 | SEQ ID NO: 121 | SEQ ID NO: 119 |
| JR2.145.1 IL15vN65D /scFv longer linker | JR2.145.2 | SEQ ID NO: 122 | SEQ ID NO: 119 |

FIG. 14A

SEQUENCE LISTING

<160> NUMBER OF SEQ ID NOS: 140

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
```

130

<210> SEQ ID NO 2
<211> LENGTH: 113
<212> TYPE: PRT
<213> ORGANISM: Homo sapiens

<400> SEQUENCE: 2

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr

<210> SEQ ID NO 3
<211> LENGTH: 214
<212> TYPE: PRT
<213> ORGANISM: Homo sapiens

<400> SEQUENCE: 3

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 4
<211> LENGTH: 214
<212> TYPE: PRT
<213> ORGANISM: Homo sapiens

<400> SEQUENCE: 4

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Glu Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 5
<211> LENGTH: 214
<212> TYPE: PRT
<213> ORGANISM: Homo sapiens

<400> SEQUENCE: 5

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

```
Asp Phe Lys Pro Phe Glu Asn Leu Arg Leu Met Ala Pro Ile Ser Leu
             100                 105                 110

Gln Val Val His Val Glu Thr His Arg Cys Asn Ile Ser Trp Glu Ile
         115                 120                 125

Ser Gln Ala Ser His Tyr Phe Gln Arg Arg Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 6
<211> LENGTH: 240
<212> TYPE: PRT
<213> ORGANISM: Homo sapiens

<400> SEQUENCE: 6

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240
```

```
<210> SEQ ID NO 7
<211> LENGTH: 75
<212> TYPE: PRT
<213> ORGANISM: Homo sapiens

<400> SEQUENCE: 7

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala
65                  70                  75

<210> SEQ ID NO 8
<211> LENGTH: 267
<212> TYPE: PRT
<213> ORGANISM: Homo sapiens

<400> SEQUENCE: 8

Met Ala Pro Arg Arg Ala Arg Gly Cys Arg Thr Leu Gly Leu Pro Ala
1               5                   10                  15

Leu Leu Leu Leu Leu Leu Leu Arg Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
            195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
```

```
                   260                 265

<210> SEQ ID NO 9
<211> LENGTH: 65
<212> TYPE: PRT
<213> ORGANISM: Homo sapiens

<400> SEQUENCE: 9

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 10
<211> LENGTH: 76
<212> TYPE: PRT
<213> ORGANISM: Homo sapiens

<400> SEQUENCE: 10

Thr Asn Asp Ala Glu Asp Cys Cys Leu Ser Val Thr Gln Lys Pro Ile
1               5                   10                  15

Pro Gly Tyr Ile Val Arg Asn Phe His Tyr Leu Leu Ile Lys Asp Gly
            20                  25                  30

Cys Arg Val Pro Ala Val Val Phe Thr Thr Leu Arg Gly Arg Gln Leu
        35                  40                  45

Cys Ala Pro Pro Asp Gln Pro Trp Val Glu Arg Ile Ile Gln Arg Leu
    50                  55                  60

Gln Arg Thr Ser Ala Lys Met Lys Arg Arg Ser Ser
65                  70                  75

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser
1               5                   10

<210> SEQ ID NO 13
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ala or Asn

<400> SEQUENCE: 14

Gly Gly Gly Gly Ser Gly Gly Gly Gly Ser Xaa Gly Gly Gly Gly Ser
1               5                   10                  15

Gly Gly Gly Gly Ser
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ser, Ala or Asn
<220> FEATURE:
<221> NAME/KEY: MOD_RES
<222> LOCATION: (16)..(16)
<223> OTHER INFORMATION: Ala or Asn

<400> SEQUENCE: 15

Gly Gly Gly Gly Ser Gly Gly Gly Gly Ser Xaa Gly Gly Gly Gly Xaa
1               5                   10                  15

Gly Gly Gly Gly Ser
            20

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Gly Gly Ser Gly Gly Gly Gly Ser Gly Gly Gly Gly Ser Ala
1               5                   10                  15

Ala Gly Gly Gly Gly Ser Gly Gly Gly Gly Ser Gly Gly Gly Gly Ser
            20                  25                  30

<210> SEQ ID NO 17
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 17

Gly Pro Leu Gly Val Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Leu Gly Met Trp Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Leu Gly Leu Trp Ala Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Gln Gly Ile Ala Gly Gln Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Leu Gly Leu Ala Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Ala Leu Gly Pro Arg
1               5
```

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Pro Leu Gly Met Leu Ser Gln Ser
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Arg Arg Gly Gly Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Gly Arg Gly Pro Ser Trp Val
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Arg Gly Pro Ser Arg Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Ala Arg Gly Pro Ser Phe Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Thr Ala Arg Gly Pro Ser Trp
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Trp His Thr Gly Arg Asn
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Thr Gly Arg Ser Gly Ala Leu
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Leu Thr Gly Arg Ser Gly Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Thr Gly Arg Ser Gly Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Gln Ala Arg Val Val Asn Gly
1               5

<210> SEQ ID NO 34
<211> LENGTH: 18
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 34

Val His Met Pro Leu Gly Phe Leu Gly Pro Arg Gln Ala Arg Val Val
1               5                   10                  15

Asn Gly

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Ser Leu Ser Gly Arg Ser Asp Asn His Gly Gly Gly Gly Ser
1               5                   10                  15

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Gly Gly Gly Ser Gly Gly Gly Ser Gly Gly Gly Gly Ser Ile
1               5                   10                  15

Ser Ser Gly Leu Leu Ser Ser Gly Gly Ser Gly Gly Ser Leu Ser Gly
                20                  25                  30

Arg Ser Asp Asn His Gly Gly Gly Gly Ser
            35                  40

<210> SEQ ID NO 37
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val

```
            115                 120                 125
Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Ala Gly Gly Gly Ser Gly Gly Gly Ser Gly Pro Leu
225                 230                 235                 240

Gly Val Arg Gly Gly Gly Ser Gly Gly Gly Ser Ala Val Asn
                245                 250                 255

Gly Thr Ser Gln Phe Thr Cys Phe Tyr Asn Ser Arg Ala Asn Ile Ser
                260                 265                 270

Cys Val Trp Ser Gln Asp Gly Ala Leu Gln Asp Thr Ser Cys Gln Val
                275                 280                 285

His Ala Trp Pro Asp Arg Arg Arg Trp Asn Gln Thr Cys Glu Leu Leu
            290                 295                 300

Pro Val Ser Gln Ala Ser Trp Ala Cys Asn Leu Ile Leu Gly Ala Pro
305                 310                 315                 320

Asp Ser Gln Lys Leu Thr Thr Val Asp Ile Val Thr Leu Arg Val Leu
                325                 330                 335

Cys Arg Glu Gly Val Arg Trp Arg Val Met Ala Ile Gln Asp Phe Lys
                340                 345                 350

Pro Phe Glu Asn Leu Arg Leu Met Ala Pro Ile Ser Leu Gln Val Val
            355                 360                 365

His Val Glu Thr His Arg Cys Asn Ile Ser Trp Glu Ile Ser Gln Ala
            370                 375                 380

Ser His Tyr Phe Glu Arg His Leu Glu Phe Glu Ala Arg Thr Leu Ser
385                 390                 395                 400

Pro Gly His Thr Trp Glu Glu Ala Pro Leu Leu Thr Leu Lys Gln Lys
                405                 410                 415

Gln Glu Trp Ile Cys Leu Glu Thr Leu Thr Pro Asp Thr Gln Tyr Glu
                420                 425                 430

Phe Gln Val Arg Val Lys Pro Leu Gln Gly Glu Phe Thr Thr Trp Ser
            435                 440                 445

Pro Trp Ser Gln Pro Leu Ala Phe Arg Thr Lys Pro Ala Ala Leu Gly
450                 455                 460

Lys Asp Thr
465

<210> SEQ ID NO 38
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (399)..(399)
```

```
<223> OTHER INFORMATION: Asn or Asp
<220> FEATURE:
<221> NAME/KEY: MOD_RES
<222> LOCATION: (442)..(442)
<223> OTHER INFORMATION: Gln or Glu

<400> SEQUENCE: 38
```

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Ala Gly Gly Gly Ser Gly Gly Ser Gly Gly Gly Gly Gly Gly
225                 230                 235                 240

Ser Ile Thr Cys Pro Pro Pro Met Ser Val Glu His Ala Asp Ile Trp
                245                 250                 255

Val Lys Ser Tyr Ser Leu Tyr Ser Arg Glu Arg Tyr Ile Cys Asn Ser
            260                 265                 270

Gly Phe Lys Arg Lys Ala Gly Thr Ser Ser Leu Thr Glu Cys Val Leu
        275                 280                 285

Asn Lys Ala Thr Asn Val Ala His Trp Thr Thr Pro Ser Leu Lys Cys
290                 295                 300

Ile Arg Asp Pro Ala Leu Val His Gln Arg Pro Ala Pro Pro Ser Gly
305                 310                 315                 320

Gly Gly Gly Ser Gly Gly Gly Ser Gly Gly Gly Gly Ser Asn Trp
                325                 330                 335

Val Asn Val Ile Ser Asp Leu Lys Lys Ile Glu Asp Leu Ile Gln Ser
            340                 345                 350

Met His Ile Asp Ala Thr Leu Tyr Thr Glu Ser Asp Val His Pro Ser
        355                 360                 365

Cys Lys Val Thr Ala Met Lys Cys Phe Leu Leu Glu Leu Gln Val Ile
370                 375                 380

```
Ser Leu Glu Ser Gly Asp Ala Ser Ile His Asp Thr Val Glu Xaa Leu
385                 390                 395                 400

Ile Ile Leu Ala Asn Asn Ser Leu Ser Ser Asn Gly Asn Val Thr Glu
                405                 410                 415

Ser Gly Cys Lys Glu Cys Glu Glu Leu Glu Glu Lys Asn Ile Lys Glu
            420                 425                 430

Phe Leu Gln Ser Phe Val His Ile Val Xaa Met Phe Ile Asn Thr Ser
            435                 440                 445
```

<210> SEQ ID NO 39
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (416)..(416)
<223> OTHER INFORMATION: Asn or Asp
<220> FEATURE:
<221> NAME/KEY: MOD_RES
<222> LOCATION: (459)..(459)
<223> OTHER INFORMATION: Gln or Glu

<400> SEQUENCE: 39

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Gly Gly Gly Gly Ser Gly Gly Gly Ser Gly Gly Gly Gly
225                 230                 235                 240

Ser Ile Thr Cys Pro Pro Pro Met Ser Val Glu His Ala Asp Ile Trp
                245                 250                 255
```

Val Lys Ser Tyr Ser Leu Tyr Ser Arg Glu Arg Tyr Ile Cys Asn Ser
                260                 265                 270

Gly Phe Lys Arg Lys Ala Gly Thr Ser Ser Leu Thr Glu Cys Val Leu
                275                 280                 285

Asn Lys Ala Thr Asn Val Ala His Trp Thr Thr Pro Ser Leu Lys Cys
                290                 295                 300

Ile Arg Asp Pro Ala Leu Val His Gln Arg Pro Ala Pro Pro Ser Gly
305                 310                 315                 320

Gly Gly Gly Ser Gly Gly Gly Ser Gly Gly Gly Ser Ala Ala
                325                 330                 335

Gly Gly Gly Gly Ser Gly Gly Gly Ser Gly Gly Gly Ser Asn
                340                 345                 350

Trp Val Asn Val Ile Ser Asp Leu Lys Lys Ile Glu Asp Leu Ile Gln
                355                 360                 365

Ser Met His Ile Asp Ala Thr Leu Tyr Thr Glu Ser Asp Val His Pro
                370                 375                 380

Ser Cys Lys Val Thr Ala Met Lys Cys Phe Leu Leu Glu Leu Gln Val
385                 390                 395                 400

Ile Ser Leu Glu Ser Gly Asp Ala Ser Ile His Asp Thr Val Glu Xaa
                405                 410                 415

Leu Ile Ile Leu Ala Asn Asn Ser Leu Ser Ser Asn Gly Asn Val Thr
                420                 425                 430

Glu Ser Gly Cys Lys Glu Cys Glu Glu Leu Glu Glu Lys Asn Ile Lys
                435                 440                 445

Glu Phe Leu Gln Ser Phe Val His Ile Val Xaa Met Phe Ile Asn Thr
450                 455                 460

Ser
465

<210> SEQ ID NO 40
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Asp Glu Leu Thr Lys Asn Gln Val Ser

```
                  130                 135                 140
Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Ala Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                    245                 250                 255

Ile Gln Ser Met His Ile Asp Ala Thr Leu Tyr Thr Glu Ser Asp Val
                260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Ser Ile His Asp Thr Val
        290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                    325                 330                 335

Ile Lys Glu Phe Leu Gln Ser Phe Val His Ile Val Gln Met Phe Ile
                340                 345                 350

Asn Thr Ser Gly Gly Ser Gly Gly Gly Gly Ser Gly Gly Gly Gly Ser
            355                 360                 365

Gly Gly Gly Gly Ser Ile Thr Cys Pro Pro Met Ser Val Glu His
        370                 375                 380

Ala Asp Ile Trp Val Lys Ser Tyr Ser Leu Tyr Ser Arg Glu Arg Tyr
385                 390                 395                 400

Ile Cys Asn Ser Gly Phe Lys Arg Lys Ala Gly Thr Ser Ser Leu Thr
                    405                 410                 415

Glu Cys Val Leu Asn Lys Ala Thr Asn Val Ala His Trp Thr Thr Pro
                420                 425                 430

Ser Leu Lys Cys Ile Arg Asp Pro Ala Leu Val His Gln Arg Pro Ala
            435                 440                 445

Pro Pro Ser
450

<210> SEQ ID NO 41
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Ala Gly Gly Gly Ser Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Ser Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 42
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
                 20                  25                  30
```

-continued

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Ala Gly Gly Ser Gly Gly Gly Ser Gly Gly Gly Gly Ser
225                 230                 235                 240

Gly Gly Gly Gly Ser Ile Thr Cys Pro Pro Pro Met Ser Val Glu His
                245                 250                 255

Ala Asp Ile Trp Val Lys Ser Tyr Ser Leu Tyr Ser Arg Glu Arg Tyr
            260                 265                 270

Ile Cys Asn Ser Gly Phe Lys Arg Lys Ala Gly Thr Ser Ser Leu Thr
    275                 280                 285

Glu Cys Val Leu Asn Lys Ala Thr Asn Val Ala His Trp Thr Thr Pro
    290                 295                 300

Ser Leu Lys Cys Ile Arg Asp Pro Ala Leu Val His Gln Arg Pro Ala
305                 310                 315                 320

Pro Pro Ser Gly Gly Gly Gly Ser Gly Gly Gly Gly Ser Gly Pro Leu
                325                 330                 335

Gly Val Arg Gly Gly Gly Ser Gly Gly Gly Gly Ser Ala Val Asn
            340                 345                 350

Gly Thr Ser Gln Phe Thr Cys Phe Tyr Asn Ser Arg Ala Asn Ile Ser
            355                 360                 365

Cys Val Trp Ser Gln Asp Gly Ala Leu Gln Asp Thr Ser Cys Gln Val
    370                 375                 380

His Ala Trp Pro Asp Arg Arg Arg Trp Asn Gln Thr Cys Glu Leu Leu
385                 390                 395                 400

Pro Val Ser Gln Ala Ser Trp Ala Cys Asn Leu Ile Leu Gly Ala Pro
                405                 410                 415

Asp Ser Gln Lys Leu Thr Thr Val Asp Ile Val Thr Leu Arg Val Leu
            420                 425                 430

Cys Arg Glu Gly Val Arg Trp Arg Val Met Ala Ile Gln Asp Phe Lys
            435                 440                 445
```

```
Pro Phe Glu Asn Leu Arg Leu Met Ala Pro Ile Ser Leu Gln Val Val
    450                 455                 460

His Val Glu Thr His Arg Cys Asn Ile Ser Trp Glu Ile Ser Gln Ala
465                 470                 475                 480

Ser His Tyr Phe Glu Arg His Leu Glu Phe Glu Ala Arg Thr Leu Ser
                485                 490                 495

Pro Gly His Thr Trp Glu Glu Ala Pro Leu Leu Thr Leu Lys Gln Lys
            500                 505                 510

Gln Glu Trp Ile Cys Leu Glu Thr Leu Thr Pro Asp Thr Gln Tyr Glu
            515                 520                 525

Phe Gln Val Arg Val Lys Pro Leu Gln Gly Glu Phe Thr Thr Trp Ser
530                 535                 540

Pro Trp Ser Gln Pro Leu Ala Phe Arg Thr Lys Pro Ala Ala Leu Gly
545                 550                 555                 560

Lys Asp Thr

<210> SEQ ID NO 43
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

```
<210> SEQ ID NO 44
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Gly Gly Gly Ser Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Lys Leu
        275                 280                 285

Gln Val Ile Ser Leu Glu Ser Gly Asp Ala Ser Ile His Asp Thr Val
    290                 295                 300

Glu Asp Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355
```

```
<210> SEQ ID NO 45
<211> LENGTH: 692
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (643)..(643)
<223> OTHER INFORMATION: Asn or Asp
<220> FEATURE:
<221> NAME/KEY: MOD_RES
<222> LOCATION: (686)..(686)
<223> OTHER INFORMATION: Gln or Glu

<400> SEQUENCE: 45

Glu Val Gln Leu Gln Gln Ser Gly Ala Glu Val Lys Lys Pro Gly Ala
1               5                   10                  15

Thr Val Lys Ile Ser Cys Thr Ala Ser Gly Phe Asn Ile Lys Asp Asp
            20                  25                  30

Tyr Leu His Trp Val Arg Gln Ala Pro Gly Lys Gly Leu Glu Trp Ile
        35                  40                  45

Gly Arg Ile Asp Pro Ala Asn Ala Asn Thr Lys Tyr Ala Pro Lys Phe
    50                  55                  60

Gln Asp Arg Val Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ala Ala Arg Phe Gly Tyr Phe Tyr Gly Ser Ser Phe Tyr Ala Val Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

Leu Asn Gly Lys Glu Tyr Lys Cys Lys Val Ser Asn Lys Ala Leu Pro
              325                 330                 335

Ala Pro Ile Glu Lys Thr Ile Ser Lys Ala Lys Gly Gln Pro Arg Glu
              340                 345                 350

Pro Gln Val Tyr Thr Leu Pro Pro Cys Arg Asp Glu Leu Thr Lys Asn
              355                 360                 365

Gln Val Ser Leu Trp Cys Leu Val Lys Gly Phe Tyr Pro Ser Asp Ile
          370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
              405                 410                 415

Leu Thr Val Asp Lys Ser Arg Trp Gln Gln Gly Asn Val Phe Ser Cys
              420                 425                 430

Ser Val Met His Glu Ala Leu His Asn His Tyr Thr Gln Lys Ser Leu
              435                 440                 445

Ser Leu Ser Pro Gly Ala Gly Gly Gly Ser Gly Gly Ser Gly
              450                 455                 460

Gly Gly Gly Ser Ile Thr Cys Pro Pro Met Ser Val Glu His Ala
465                 470                 475                 480

Asp Ile Trp Val Lys Ser Tyr Ser Leu Tyr Ser Arg Glu Arg Tyr Ile
              485                 490                 495

Cys Asn Ser Gly Phe Lys Arg Lys Ala Gly Thr Ser Ser Leu Thr Glu
              500                 505                 510

Cys Val Leu Asn Lys Ala Thr Asn Val Ala His Trp Thr Thr Pro Ser
              515                 520                 525

Leu Lys Cys Ile Arg Asp Pro Ala Leu Val His Gln Arg Pro Ala Pro
              530                 535                 540

Pro Ser Gly Gly Gly Ser Gly Gly Gly Ser Gly Gly Gly
545                 550                 555                 560

Ser Ala Ala Gly Gly Gly Ser Gly Gly Gly Ser Gly Gly
              565                 570                 575

Gly Ser Asn Trp Val Asn Val Ile Ser Asp Leu Lys Lys Ile Glu Asp
              580                 585                 590

Leu Ile Gln Ser Met His Ile Asp Ala Thr Leu Tyr Thr Glu Ser Asp
              595                 600                 605

Val His Pro Ser Cys Lys Val Thr Ala Met Lys Cys Phe Leu Leu Glu
              610                 615                 620

Leu Gln Val Ile Ser Leu Glu Ser Gly Asp Ala Ser Ile His Asp Thr
625                 630                 635                 640

Val Glu Xaa Leu Ile Ile Leu Ala Asn Asn Ser Leu Ser Ser Asn Gly
              645                 650                 655

Asn Val Thr Glu Ser Gly Cys Lys Glu Cys Glu Glu Leu Glu Glu Lys
              660                 665                 670

Asn Ile Lys Glu Phe Leu Gln Ser Phe Val His Ile Val Xaa Met Phe
              675                 680                 685

Ile Asn Thr Ser
    690

<210> SEQ ID NO 46
<211> LENGTH: 690
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 46

```
Glu Val Gln Leu Gln Gln Ser Gly Ala Glu Val Lys Lys Pro Gly Ala
1               5                   10                  15

Thr Val Lys Ile Ser Cys Thr Ala Ser Gly Phe Asn Ile Lys Asp Asp
            20                  25                  30

Tyr Leu His Trp Val Arg Gln Ala Pro Gly Lys Gly Leu Glu Trp Ile
        35                  40                  45

Gly Arg Ile Asp Pro Ala Asn Ala Asn Thr Lys Tyr Ala Pro Lys Phe
    50                  55                  60

Gln Asp Arg Val Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ala Ala Arg Phe Gly Tyr Phe Tyr Gly Ser Ser Phe Tyr Ala Val Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Cys Arg Asp Glu Leu Thr Lys Asn
        355                 360                 365

Gln Val Ser Leu Trp Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

Thr Pro Pro Val Leu Asp Ser Asp Gly Ser Phe Phe Leu Tyr Ser Lys
             405                 410                 415

Leu Thr Val Asp Lys Ser Arg Trp Gln Gln Gly Asn Val Phe Ser Cys
             420                 425                 430

Ser Val Met His Glu Ala Leu His Asn His Tyr Thr Gln Lys Ser Leu
             435                 440                 445

Ser Leu Ser Pro Gly Ala Gly Gly Gly Ser Gly Gly Gly Ser Gly
         450                 455                 460

Gly Gly Gly Ser Asn Trp Val Asn Val Ile Ser Asp Leu Lys Lys Ile
465                 470                 475                 480

Glu Asp Leu Ile Gln Ser Met His Ile Asp Ala Thr Leu Tyr Thr Glu
             485                 490                 495

Ser Asp Val His Pro Ser Cys Lys Val Thr Ala Met Lys Cys Phe Leu
             500                 505                 510

Leu Glu Leu Gln Val Ile Ser Leu Glu Ser Gly Asp Ala Ser Ile His
             515                 520                 525

Asp Thr Val Glu Asn Leu Ile Ile Leu Ala Asn Asn Ser Leu Ser Ser
             530                 535                 540

Asn Gly Asn Val Thr Glu Ser Gly Cys Lys Glu Cys Glu Glu Leu Glu
545                 550                 555                 560

Glu Lys Asn Ile Lys Glu Phe Leu Gln Ser Phe Val His Ile Val Gln
             565                 570                 575

Met Phe Ile Asn Thr Ser Gly Gly Gly Gly Ser Gly Gly
             580                 585                 590

Gly Gly Ser Ala Ala Gly Gly Gly Ser Gly Gly Gly Ser Gly
             595                 600                 605

Gly Gly Ser Ile Thr Cys Pro Pro Met Ser Val Glu His Ala
         610                 615                 620

Asp Ile Trp Val Lys Ser Tyr Ser Leu Tyr Ser Arg Glu Arg Tyr Ile
625                 630                 635                 640

Cys Asn Ser Gly Phe Lys Arg Lys Ala Gly Thr Ser Ser Leu Thr Glu
             645                 650                 655

Cys Val Leu Asn Lys Ala Thr Asn Val Ala His Trp Thr Thr Pro Ser
             660                 665                 670

Leu Lys Cys Ile Arg Asp Pro Ala Leu Val His Gln Arg Pro Ala Pro
             675                 680                 685

Pro Ser
    690

<210> SEQ ID NO 47
<211> LENGTH: 694
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Gln Gln Ser Gly Ala Glu Val Lys Lys Pro Gly Ala
1               5                   10                  15

Thr Val Lys Ile Ser Cys Thr Ala Ser Gly Phe Asn Ile Lys Asp Asp
             20                  25                  30

Tyr Leu His Trp Val Arg Gln Ala Pro Gly Lys Gly Leu Glu Trp Ile
         35                  40                  45

Gly Arg Ile Asp Pro Ala Asn Ala Asn Thr Lys Tyr Ala Pro Lys Phe

```
         50                  55                  60
Gln Asp Arg Val Thr Ile Thr Ala Asp Thr Ser Thr Asn Thr Ala Tyr
 65                  70                  75                  80

Leu Glu Leu Ser Ser Leu Arg Ser Glu Asp Thr Ala Val Tyr Tyr Cys
                 85                  90                  95

Ala Ala Arg Phe Gly Tyr Phe Tyr Gly Ser Ser Phe Tyr Ala Val Ala
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ala Gly Gly Gly Ser Gly Gly Gly Gly Ser
450                 455                 460

Gly Pro Leu Gly Val Arg Gly Gly Gly Ser Gly Gly Gly Gly Ser
465                 470                 475                 480
```

```
Ala Val Asn Gly Thr Ser Gln Phe Thr Cys Phe Tyr Asn Ser Arg Ala
                485                 490                 495

Asn Ile Ser Cys Val Trp Ser Gln Asp Gly Ala Leu Gln Asp Thr Ser
            500                 505                 510

Cys Gln Val His Ala Trp Pro Asp Arg Arg Trp Asn Gln Thr Cys
        515                 520                 525

Glu Leu Leu Pro Val Ser Gln Ala Ser Trp Ala Cys Asn Leu Ile Leu
        530                 535                 540

Gly Ala Pro Asp Ser Gln Lys Leu Thr Thr Val Asp Ile Val Thr Leu
545                 550                 555                 560

Arg Val Leu Cys Arg Glu Gly Val Arg Trp Arg Val Met Ala Ile Gln
                565                 570                 575

Asp Phe Lys Pro Phe Glu Asn Leu Arg Leu Met Ala Pro Ile Ser Leu
                580                 585                 590

Gln Val Val His Val Glu Thr His Arg Cys Asn Ile Ser Trp Glu Ile
                595                 600                 605

Ser Gln Ala Ser His Tyr Phe Glu Arg His Leu Glu Phe Glu Ala Arg
            610                 615                 620

Thr Leu Ser Pro Gly His Thr Trp Glu Ala Pro Leu Leu Thr Leu
625                 630                 635                 640

Lys Gln Lys Gln Glu Trp Ile Cys Leu Glu Thr Leu Thr Pro Asp Thr
                645                 650                 655

Gln Tyr Glu Phe Gln Val Arg Val Lys Pro Leu Gln Gly Glu Phe Thr
            660                 665                 670

Thr Trp Ser Pro Trp Ser Gln Pro Leu Ala Phe Arg Thr Lys Pro Ala
                675                 680                 685

Ala Leu Gly Lys Asp Thr
        690

<210> SEQ ID NO 48
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Gln Gln Ser Gly Ala Glu Val Lys Lys Pro Gly Ala
1               5                   10                  15

Thr Val Lys Ile Ser Cys Thr Ala Ser Gly Phe Asn Ile Lys Asp Asp
            20                  25                  30

Tyr Leu His Trp Val Arg Gln Ala Pro Gly Lys Gly Leu Glu Trp Ile
        35                  40                  45

Gly Arg Ile Asp Pro Ala Asn Ala Asn Thr Lys Tyr Ala Pro Lys Phe
    50                  55                  60

Gln Asp Arg Val Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ala Ala Arg Phe Gly Tyr Phe Tyr Gly Ser Ser Phe Tyr Ala Val Ala
                100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
```

```
            130                 135                 140
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ala Gly Gly Gly Ser Gly Gly Gly Gly Ser
    450                 455                 460

Gly Pro Leu Gly Val Arg Gly Gly Gly Gly Ser Gly Gly Gly Gly Ser
465                 470                 475                 480

Glu Val Gln Leu Val Gln Ser Gly Ala Glu Val Lys Lys Pro Gly Glu
                485                 490                 495

Ser Leu Lys Ile Ser Cys Lys Val Ser Gly Tyr Phe Phe Thr Thr Tyr
            500                 505                 510

Trp Ile Gly Trp Val Arg Gln Met Pro Gly Lys Gly Leu Glu Tyr Met
        515                 520                 525

Gly Ile Ile Tyr Pro Gly Asp Ser Asp Thr Arg Tyr Ser Pro Ser Phe
    530                 535                 540

Gln Gly Gln Val Thr Ile Ser Ala Asp Lys Ser Ile Ser Thr Ala Tyr
545                 550                 555                 560
```

```
Leu Gln Trp Ser Ser Leu Lys Ala Ser Asp Thr Ala Met Tyr Tyr Cys
            565                 570                 575

Ala Arg Gly Gly Asn Trp Asn Cys Phe Asp Tyr Trp Gly Gln Gly Thr
        580                 585                 590

Leu Val Thr Val Ser Ser Gly Gly Gly Ser Gly Gly Gly Gly Ser
    595                 600                 605

Gly Gly Gly Gly Ser Glu Ile Val Leu Thr Gln Ser Pro Gly Thr Leu
    610                 615                 620

Ser Leu Ser Pro Gly Arg Glu Ala Thr Leu Ser Cys Arg Ala Ser Gln
625                 630                 635                 640

Ser Val Ser Ser Ser Tyr Leu Ala Trp Tyr Gln Gln Lys Pro Gly Gln
                645                 650                 655

Ala Pro Arg Leu Leu Ile Tyr Gly Ala Ser Arg Arg Ala Thr Gly Ile
            660                 665                 670

Pro Asp Arg Phe Ser Gly Ser Gly Ser Gly Thr Asp Phe Thr Leu Thr
        675                 680                 685

Ile Ser Arg Leu Glu Pro Glu Asp Phe Ala Val Tyr Tyr Cys Gln Arg
    690                 695                 700

Tyr Gly Ser Ser His Thr Phe Gly Gln Gly Thr Lys Leu Glu Ile Ser
705                 710                 715                 720

Arg

<210> SEQ ID NO 49
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Gln Gln Ser Gly Ala Glu Val Lys Lys Pro Gly Ala
1               5                   10                  15

Thr Val Lys Ile Ser Cys Thr Ala Ser Gly Phe Asn Ile Lys Asp Asp
            20                  25                  30

Tyr Leu His Trp Val Arg Gln Ala Pro Gly Lys Gly Leu Glu Trp Ile
        35                  40                  45

Gly Arg Ile Asp Pro Ala Asn Ala Asn Thr Lys Tyr Ala Pro Lys Phe
    50                  55                  60

Gln Asp Arg Val Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ala Ala Arg Phe Gly Tyr Phe Tyr Gly Ser Ser Phe Tyr Ala Val Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ala Gly Gly Gly Ser Gly Gly Gly Gly Ser
    450                 455                 460

Gly Pro Leu Gly Val Arg Gly Gly Gly Ser Gly Gly Gly Gly Ser
465                 470                 475                 480

Glu Ile Val Leu Thr Gln Ser Pro Gly Thr Leu Ser Leu Ser Pro Gly
                485                 490                 495

Arg Glu Ala Thr Leu Ser Cys Arg Ala Ser Gln Ser Val Ser Ser Ser
            500                 505                 510

Tyr Leu Ala Trp Tyr Gln Gln Lys Pro Gly Gln Ala Pro Arg Leu Leu
        515                 520                 525

Ile Tyr Gly Ala Ser Arg Arg Ala Thr Gly Ile Pro Asp Arg Phe Ser
    530                 535                 540

Gly Ser Gly Ser Gly Thr Asp Phe Thr Leu Thr Ile Ser Arg Leu Glu
545                 550                 555                 560

Pro Glu Asp Phe Ala Val Tyr Tyr Cys Gln Arg Tyr Gly Ser Ser His
                565                 570                 575

Thr Phe Gly Gln Gly Thr Lys Leu Glu Ile Ser Arg Gly Gly Gly
            580                 585                 590

Ser Gly Gly Gly Gly Ser Gly Gly Gly Ser Glu Val Gln Leu Val
    595                 600                 605
```

```
Gln Ser Gly Ala Glu Val Lys Lys Pro Gly Glu Ser Leu Lys Ile Ser
    610                 615                 620
Cys Lys Val Ser Gly Tyr Phe Phe Thr Thr Tyr Trp Ile Gly Trp Val
625                 630                 635                 640
Arg Gln Met Pro Gly Lys Gly Leu Glu Tyr Met Gly Ile Ile Tyr Pro
                645                 650                 655
Gly Asp Ser Asp Thr Arg Tyr Ser Pro Ser Phe Gln Gly Gln Val Thr
                660                 665                 670
Ile Ser Ala Asp Lys Ser Ile Ser Thr Ala Tyr Leu Gln Trp Ser Ser
            675                 680                 685
Leu Lys Ala Ser Asp Thr Ala Met Tyr Tyr Cys Ala Arg Gly Gly Asn
690                 695                 700
Trp Asn Cys Phe Asp Tyr Trp Gly Gln Gly Thr Leu Val Thr Val Ser
705                 710                 715                 720
Ser
```

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Ile Ala Thr Tyr Phe Cys Gln Gln Gly Lys Thr Leu Pro Pro
                85                  90                  95
Thr Phe Gly Gly Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 51
<211> LENGTH: 362

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Lys Thr Leu Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Ala Pro Ala Ser Ser Ser Thr Lys Lys Thr Gln
225                 230                 235                 240

Leu Gln Leu Glu His Leu Leu Leu Asp Leu Gln Met Ile Leu Asn Gly
                245                 250                 255

Ile Asn Asn Tyr Lys Asn Pro Lys Leu Thr Ser Met Leu Thr Ala Lys
            260                 265                 270

Phe Ala Met Pro Lys Lys Ala Thr Glu Leu Lys His Leu Gln Cys Leu
        275                 280                 285

Glu Glu Ala Leu Lys Pro Leu Glu Glu Val Leu Asn Leu Ala Gln Ser
290                 295                 300

Lys Asn Phe His Leu Arg Pro Arg Asp Leu Ile Ser Glu Ile Asn Val
305                 310                 315                 320

Ile Val Leu Glu Leu Lys Gly Ser Glu Thr Thr Phe Met Cys Glu Tyr
                325                 330                 335

Ala Asp Glu Thr Ala Thr Ile Val Glu Phe Leu Asn Arg Trp Ile Thr
            340                 345                 350

Phe Ser Gln Ser Ile Ile Ser Thr Leu Thr
        355                 360

<210> SEQ ID NO 52

```
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Cys Gln Glu Glu Met Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
```

```
                    370             375             380
Lys Thr Thr Pro Pro Val Leu Asp Ser Gly Ser Phe Phe Leu Tyr
385                 390             395                 400

Ser Arg Leu Thr Val Asp Lys Ser Arg Trp Gln Glu Gly Asn Val Phe
                405             410                 415

Ser Cys Ser Val Met His Glu Ala Leu His Asn His Tyr Thr Gln Lys
                420             425                 430

Ser Leu Ser Leu Ser Leu Gly Ala Gly Gly Gly Ser Gly Gly Gly
            435             440                 445

Gly Ser Gly Gly Gly Ser Ile Thr Cys Pro Pro Met Ser Val
    450             455             460

Glu His Ala Asp Ile Trp Val Lys Ser Tyr Ser Leu Tyr Ser Arg Glu
465                 470             475                 480

Arg Tyr Ile Cys Asn Ser Gly Phe Lys Arg Lys Ala Gly Thr Ser Ser
                485             490                 495

Leu Thr Glu Cys Val Leu Asn Lys Ala Thr Asn Val Ala His Trp Thr
                500             505                 510

Thr Pro Ser Leu Lys Cys Ile Arg Asp Pro Ala Leu Val His Gln Arg
            515             520                 525

Pro Ala Pro Pro Ser Gly Gly Ser Gly Gly Gly Ser Gly Gly Gly
        530             535                 540

Gly Ser Gly Gly Gly Ser Asn Trp Val Asn Val Ile Ser Asp Leu
545             550             555                 560

Lys Lys Ile Glu Asp Leu Ile Gln Ser Met His Ile Asp Ala Thr Leu
                565             570                 575

Tyr Thr Glu Ser Asp Val His Pro Ser Cys Lys Val Thr Ala Met Lys
            580             585                 590

Cys Phe Leu Leu Glu Leu Gln Val Ile Ser Leu Glu Ser Gly Asp Ala
            595             600                 605

Ser Ile His Asp Thr Val Glu Asn Leu Ile Ile Leu Ala Asn Asn Ser
        610             615             620

Leu Ser Ser Asn Gly Asn Val Thr Glu Ser Gly Cys Lys Glu Cys Glu
625             630             635                 640

Glu Leu Glu Glu Lys Asn Ile Lys Glu Phe Leu Gln Ser Phe Val His
                645             650                 655

Ile Val Gln Met Phe Ile Asn Thr Ser
            660             665

<210> SEQ ID NO 53
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
             85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Cys Gln Glu Glu Met Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Gly Ser Gly Gly Gly Gly Ser Asn Trp Val Asn Val Ile Ser Asp Leu
    450                 455                 460

Lys Lys Ile Glu Asp Leu Ile Gln Ser Met His Ile Asp Ala Thr Leu
465                 470                 475                 480

Tyr Thr Glu Ser Asp Val His Pro Ser Cys Lys Val Thr Ala Met Lys
```

```
                        485                 490                 495
Cys Phe Leu Leu Glu Leu Gln Val Ile Ser Leu Glu Ser Gly Asp Ala
                500                 505                 510

Ser Ile His Asp Thr Val Glu Asn Leu Ile Ile Leu Ala Asn Asn Ser
            515                 520                 525

Leu Ser Ser Asn Gly Asn Val Thr Glu Ser Gly Cys Lys Glu Cys Glu
        530                 535                 540

Glu Leu Glu Glu Lys Asn Ile Lys Glu Phe Leu Gln Ser Phe Val His
545                 550                 555                 560

Ile Val Gln Met Phe Ile Asn Thr Ser Gly Ser Gly Gly Gly Gly Gly
                565                 570                 575

Ser Gly Gly Gly Gly Ser Gly Gly Gly Ser Ile Thr Cys Pro Pro
            580                 585                 590

Pro Met Ser Val Glu His Ala Asp Ile Trp Val Lys Ser Tyr Ser Leu
        595                 600                 605

Tyr Ser Arg Glu Arg Tyr Ile Cys Asn Ser Gly Phe Lys Arg Lys Ala
    610                 615                 620

Gly Thr Ser Ser Leu Thr Glu Cys Val Leu Asn Lys Ala Thr Asn Val
625                 630                 635                 640

Ala His Trp Thr Thr Pro Ser Leu Lys Cys Ile Arg Asp Pro Ala Leu
                645                 650                 655

Val His Gln Arg Pro Ala Pro Pro Ser
            660                 665

<210> SEQ ID NO 54
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175
```

```
Ser Leu Ser Ser Val Val Thr Val Pro Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
            340                 345                 350

Lys Asn Gln Val Ser Leu Ser Cys Ala Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Gly Ser Gly Pro Leu Gly Val Arg Gly Gly Gly Ser Gly Gly Gly
    450                 455                 460

Gly Ser Ala Val Asn Gly Thr Ser Gln Phe Thr Cys Phe Tyr Asn Ser
465                 470                 475                 480

Arg Ala Asn Ile Ser Cys Val Trp Ser Gln Asp Gly Ala Leu Gln Asp
                485                 490                 495

Thr Ser Cys Gln Val His Ala Trp Pro Asp Arg Arg Trp Asn Gln
            500                 505                 510

Thr Cys Glu Leu Leu Pro Val Ser Gln Ala Ser Trp Ala Cys Asn Leu
        515                 520                 525

Ile Leu Gly Ala Pro Asp Ser Gln Lys Leu Thr Thr Val Asp Ile Val
    530                 535                 540

Thr Leu Arg Val Leu Cys Arg Glu Gly Val Arg Trp Arg Val Met Ala
545                 550                 555                 560

Ile Gln Asp Phe Lys Pro Phe Glu Asn Leu Arg Leu Met Ala Pro Ile
                565                 570                 575

Ser Leu Gln Val Val His Val Glu Thr His Arg Cys Asn Ile Ser Trp
            580                 585                 590

Glu Ile Ser Gln Ala Ser His Tyr Phe Glu Arg His Leu Glu Phe Glu
```

```
            595                 600                 605
Ala Arg Thr Leu Ser Pro Gly His Thr Trp Glu Glu Ala Pro Leu Leu
    610                 615                 620

Thr Leu Lys Gln Lys Gln Glu Trp Ile Cys Leu Glu Thr Leu Thr Pro
625                 630                 635                 640

Asp Thr Gln Tyr Glu Phe Gln Val Arg Val Lys Pro Leu Gln Gly Glu
                645                 650                 655

Phe Thr Trp Ser Pro Trp Ser Gln Pro Leu Ala Phe Arg Thr Lys
            660                 665                 670

Pro Ala Ala Leu Gly Lys Asp Thr
            675                 680

<210> SEQ ID NO 55
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 56
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Ala Pro Ala Ser Ser Ser Thr Lys Lys Thr Gln
225                 230                 235                 240

Leu Gln Leu Glu His Leu Leu Leu Asp Leu Gln Met Ile Leu Asn Gly
                245                 250                 255

Ile Asn Asn Tyr Lys Asn Pro Lys Leu Thr Ser Met Leu Thr Ala Lys
            260                 265                 270

Phe Ala Met Pro Lys Lys Ala Thr Glu Leu Lys His Leu Gln Cys Leu
        275                 280                 285

Glu Glu Ala Leu Lys Pro Leu Glu Glu Val Leu Asn Leu Ala Gln Ser
290                 295                 300

Lys Asn Phe His Leu Arg Pro Arg Asp Leu Ile Ser Glu Ile Asn Val
305                 310                 315                 320

Ile Val Leu Glu Leu Lys Gly Ser Glu Thr Thr Phe Met Cys Glu Tyr
                325                 330                 335

Ala Asp Glu Thr Ala Thr Ile Val Glu Phe Leu Asn Arg Trp Ile Thr
            340                 345                 350

Phe Ser Gln Ser Ile Ile Ser Thr Leu Thr
        355                 360

<210> SEQ ID NO 57
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
            340                 345                 350

Lys Asn Gln Val Ser Leu Ser Cys Ala Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
```

405                 410                 415
Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 58
<211> LENGTH: 661
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

```
Leu Pro Ser Ser Ile Glu Lys Thr Ile Ser Lys Ala Lys Gly Gln Pro
            325                 330                 335

Arg Glu Pro Gln Val Tyr Thr Leu Pro Pro Cys Gln Glu Glu Met Thr
        340                 345                 350

Lys Asn Gln Val Ser Leu Trp Cys Leu Val Lys Gly Phe Tyr Pro Ser
    355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Ser Gly Gly Gly Gly Ser Ile Thr Cys Pro Pro Met Ser Val Glu
    450                 455                 460

His Ala Asp Ile Trp Val Lys Ser Tyr Ser Leu Tyr Ser Arg Glu Arg
465                 470                 475                 480

Tyr Ile Cys Asn Ser Gly Phe Lys Arg Lys Ala Gly Thr Ser Ser Leu
                485                 490                 495

Thr Glu Cys Val Leu Asn Lys Ala Thr Asn Val Ala His Trp Thr Thr
            500                 505                 510

Pro Ser Leu Lys Cys Ile Arg Asp Pro Ala Leu Val His Gln Arg Pro
        515                 520                 525

Ala Pro Pro Ser Gly Gly Gly Ser Gly Gly Gly Ser Gly Gly
    530                 535                 540

Gly Gly Ser Asn Trp Val Asn Val Ile Ser Asp Leu Lys Lys Ile Glu
545                 550                 555                 560

Asp Leu Ile Gln Ser Met His Ile Asp Ala Thr Leu Tyr Thr Glu Ser
                565                 570                 575

Asp Val His Pro Ser Cys Lys Val Thr Ala Met Lys Cys Phe Leu Leu
            580                 585                 590

Glu Leu Gln Val Ile Ser Leu Glu Ser Gly Asp Ala Ser Ile His Asp
        595                 600                 605

Thr Val Glu Asp Leu Ile Ile Leu Ala Asn Asn Ser Leu Ser Ser Asn
    610                 615                 620

Gly Asn Val Thr Glu Ser Gly Cys Lys Glu Cys Glu Glu Leu Glu Glu
625                 630                 635                 640

Lys Asn Ile Lys Glu Phe Leu Gln Ser Phe Val His Ile Val Gln Met
                645                 650                 655

Phe Ile Asn Thr Ser
            660

<210> SEQ ID NO 59
<211> LENGTH: 661
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Ser Gly Gly Gly Val Val Gln Pro Gly Arg
1               5                   10                  15
```

```
Ser Leu Arg Leu Asp Cys Lys Ala Ser Gly Ile Thr Phe Ser Asn Ser
         20                  25                  30

Gly Met His Trp Val Arg Gln Ala Pro Gly Lys Gly Leu Glu Trp Val
         35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
             100                 105                 110

Ser Ala Ser Thr Lys Gly Pro Ser Val Phe Pro Leu Ala Pro Cys Ser
             115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                 165                 170                 175

Ser Leu Ser Ser Val Val Thr Val Pro Ser Ser Ser Leu Gly Thr Lys
             180                 185                 190

Thr Tyr Thr Cys Asn Val Asp His Lys Pro Ser Asn Thr Lys Val Asp
         195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                 245                 250                 255

Val Asp Val Ser Gln Glu Asp Pro Glu Val Gln Phe Asn Trp Tyr Val
             260                 265                 270

Asp Gly Val Glu Val His Asn Ala Lys Thr Lys Pro Arg Glu Glu Gln
         275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                 325                 330                 335

Arg Glu Pro Gln Val Tyr Thr Leu Pro Pro Cys Gln Glu Glu Met Thr
             340                 345                 350

Lys Asn Gln Val Ser Leu Trp Cys Leu Val Lys Gly Phe Tyr Pro Ser
         355                 360                 365

Asp Ile Ala Val Glu Trp Glu Ser Asn Gly Gln Pro Glu Asn Asn Tyr
     370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                 405                 410                 415

Ser Cys Ser Val Met His Glu Ala Leu His Asn His Tyr Thr Gln Lys
             420                 425                 430
```

-continued

```
Ser Leu Ser Leu Ser Leu Gly Ala Gly Gly Gly Ser Gly Gly
            435                 440                 445

Ser Gly Gly Gly Gly Ser Ile Thr Cys Pro Pro Met Ser Val Glu
450                 455                 460

His Ala Asp Ile Trp Val Lys Ser Tyr Ser Leu Tyr Ser Arg Glu Arg
465                 470                 475                 480

Tyr Ile Cys Asn Ser Gly Phe Lys Arg Lys Ala Gly Thr Ser Ser Leu
                485                 490                 495

Thr Glu Cys Val Leu Asn Lys Ala Thr Asn Val Ala His Trp Thr Thr
                500                 505                 510

Pro Ser Leu Lys Cys Ile Arg Asp Pro Ala Leu Val His Gln Arg Pro
                515                 520                 525

Ala Pro Pro Ser Gly Gly Gly Ser Gly Gly Gly Ser Gly Gly
            530                 535                 540

Gly Gly Ser Asn Trp Val Asn Val Ile Ser Asp Leu Lys Lys Ile Glu
545                 550                 555                 560

Asp Leu Ile Gln Ser Met His Ile Asp Ala Thr Leu Tyr Thr Glu Ser
                565                 570                 575

Asp Val His Pro Ser Cys Lys Val Thr Ala Met Lys Cys Phe Leu Leu
                580                 585                 590

Glu Leu Gln Val Ile Ser Leu Glu Ser Gly Asp Ala Ser Ile His Asp
                595                 600                 605

Thr Val Glu Asn Leu Ile Ile Leu Ala Asn Asn Ser Leu Ser Ser Asn
                610                 615                 620

Gly Asn Val Thr Glu Ser Gly Cys Lys Glu Cys Glu Glu Leu Glu Glu
625                 630                 635                 640

Lys Asn Ile Lys Glu Phe Leu Gln Ser Phe Val His Ile Val Glu Met
                645                 650                 655

Phe Ile Asn Thr Ser
                660

<210> SEQ ID NO 60
<211> LENGTH: 702
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125
```

-continued

```
Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
            340                 345                 350

Lys Asn Gln Val Ser Leu Ser Cys Ala Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Pro Leu
        435                 440                 445

Gly Val Arg Gly Gly Gly Ser Gly Gly Gly Ser Glu Val Gln
450                 455                 460

Leu Val Gln Ser Gly Ala Glu Val Lys Lys Pro Gly Glu Ser Leu Lys
465                 470                 475                 480

Ile Ser Cys Lys Val Ser Gly Tyr Phe Phe Thr Thr Tyr Trp Ile Gly
                485                 490                 495

Trp Val Arg Gln Met Pro Gly Lys Gly Leu Glu Tyr Met Gly Ile Ile
            500                 505                 510

Tyr Pro Gly Asp Ser Asp Thr Arg Tyr Ser Pro Ser Phe Gln Gly Gln
        515                 520                 525

Val Thr Ile Ser Ala Asp Lys Ser Ile Ser Thr Ala Tyr Leu Gln Trp
530                 535                 540
```

```
Ser Ser Leu Lys Ala Ser Asp Thr Ala Met Tyr Tyr Cys Ala Arg Gly
545                 550                 555                 560

Gly Asn Trp Asn Cys Phe Asp Tyr Trp Gly Gln Gly Thr Leu Val Thr
                565                 570                 575

Val Ser Ser Gly Gly Gly Gly Ser Gly Gly Gly Gly Ser Gly Gly Gly
            580                 585                 590

Gly Ser Glu Ile Val Leu Thr Gln Ser Pro Gly Thr Leu Ser Leu Ser
        595                 600                 605

Pro Gly Arg Glu Ala Thr Leu Ser Cys Arg Ala Ser Gln Ser Val Ser
    610                 615                 620

Ser Ser Tyr Leu Ala Trp Tyr Gln Gln Lys Pro Gly Gln Ala Pro Arg
625                 630                 635                 640

Leu Leu Ile Tyr Gly Ala Ser Arg Arg Ala Thr Gly Ile Pro Asp Arg
                645                 650                 655

Phe Ser Gly Ser Gly Ser Gly Thr Asp Phe Thr Leu Thr Ile Ser Arg
                660                 665                 670

Leu Glu Pro Glu Asp Phe Ala Val Tyr Tyr Cys Gln Arg Tyr Gly Ser
            675                 680                 685

Ser His Thr Phe Gly Gln Gly Thr Lys Leu Glu Ile Ser Arg
        690                 695                 700

<210> SEQ ID NO 61
<211> LENGTH: 702
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205
```

-continued

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
                340                 345                 350

Lys Asn Gln Val Ser Leu Ser Cys Ala Val Lys Gly Phe Tyr Pro Ser
                355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Pro Leu
                435                 440                 445

Gly Val Arg Gly Gly Gly Ser Gly Gly Gly Ser Glu Ile Val
    450                 455                 460

Leu Thr Gln Ser Pro Gly Thr Leu Ser Leu Ser Pro Gly Arg Glu Ala
465                 470                 475                 480

Thr Leu Ser Cys Arg Ala Ser Gln Ser Val Ser Ser Ser Tyr Leu Ala
                485                 490                 495

Trp Tyr Gln Gln Lys Pro Gly Gln Ala Pro Arg Leu Leu Ile Tyr Gly
                500                 505                 510

Ala Ser Arg Arg Ala Thr Gly Ile Pro Asp Arg Phe Ser Gly Ser Gly
                515                 520                 525

Ser Gly Thr Asp Phe Thr Leu Thr Ile Ser Arg Leu Glu Pro Glu Asp
        530                 535                 540

Phe Ala Val Tyr Tyr Cys Gln Arg Tyr Gly Ser Ser His Thr Phe Gly
545                 550                 555                 560

Gln Gly Thr Lys Leu Glu Ile Ser Arg Gly Gly Gly Gly Ser Gly Gly
                565                 570                 575

Gly Gly Ser Gly Gly Gly Gly Ser Glu Val Gln Leu Val Gln Ser Gly
            580                 585                 590

Ala Glu Val Lys Lys Pro Gly Glu Ser Leu Lys Ile Ser Cys Lys Val
                595                 600                 605

Ser Gly Tyr Phe Phe Thr Thr Tyr Trp Ile Gly Trp Val Arg Gln Met
    610                 615                 620

-continued

```
Pro Gly Lys Gly Leu Glu Tyr Met Gly Ile Ile Tyr Pro Gly Asp Ser
625                 630                 635                 640

Asp Thr Arg Tyr Ser Pro Ser Phe Gln Gly Gln Val Thr Ile Ser Ala
            645                 650                 655

Asp Lys Ser Ile Ser Thr Ala Tyr Leu Gln Trp Ser Ser Leu Lys Ala
        660                 665                 670

Ser Asp Thr Ala Met Tyr Tyr Cys Ala Arg Gly Gly Asn Trp Asn Cys
    675                 680                 685

Phe Asp Tyr Trp Gly Gln Gly Thr Leu Val Thr Val Ser Ser
690                 695                 700

<210> SEQ ID NO 62
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285
```

```
Phe Asn Ser Thr Tyr Arg Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Cys Gln Glu Met Thr
                340                 345                 350

Lys Asn Gln Val Ser Leu Trp Cys Leu Val Lys Gly Phe Tyr Pro Ser
                355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Gly Gly
                435                 440                 445

Ser Gly Gly Gly Gly Ser Asn Trp Val Asn Val Ile Ser Asp Leu Lys
450                 455                 460

Lys Ile Glu Asp Leu Ile Gln Ser Met His Ile Asp Ala Thr Leu Tyr
465                 470                 475                 480

Thr Glu Ser Asp Val His Pro Ser Cys Lys Val Thr Ala Met Lys Cys
                485                 490                 495

Phe Leu Leu Lys Leu Gln Val Ile Ser Leu Glu Ser Gly Asp Ala Ser
                500                 505                 510

Ile His Asp Thr Val Glu Glu Leu Ile Ile Leu Ala Asn Asn Ser Leu
                515                 520                 525

Ser Ser Asn Gly Asn Val Thr Glu Ser Gly Cys Lys Glu Cys Glu Glu
                530                 535                 540

Leu Glu Glu Lys Asn Ile Lys Glu Phe Leu Gln Ser Phe Val His Ile
545                 550                 555                 560

Val Gln Met Phe Ile Asn Thr Ser
                565

<210> SEQ ID NO 63
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
                35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
```

```
                65                  70                  75                  80
Leu Gln Met Asn Ser Leu Arg Ala Glu Asp Thr Ala Val Tyr Tyr Cys
                    85                  90                  95

Ala Thr Asn Asp Asp Tyr Trp Gly Gln Gly Thr Leu Val Thr Val Ser
                    100                 105                 110

Ser Ala Ser Thr Lys Gly Pro Ser Val Phe Pro Leu Ala Pro Cys Ser
                    115                 120                 125

Arg Ser Thr Ser Glu Ser Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                    165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Cys Gln Glu Glu Met Thr
            340                 345                 350

Lys Asn Gln Val Ser Leu Trp Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Ser Gly Gly Gly Gly Ser Asn Trp Val Asn Val Ile Ser Asp Leu Lys
    450                 455                 460

Lys Ile Glu Asp Leu Ile Gln Ser Met His Ile Asp Ala Thr Leu Tyr
465                 470                 475                 480

Thr Glu Ser Asp Val His Pro Ser Cys Lys Val Thr Ala Met Lys Cys
                485                 490                 495
```

Phe Leu Leu Lys Leu Gln Val Ile Ser Leu Glu Ser Gly Asp Ala Ser
              500                 505                 510

Ile His Asp Thr Val Glu Asp Leu Ile Ile Leu Ala Asn Asn Ser Leu
          515                 520                 525

Ser Ser Asn Gly Asn Val Thr Glu Ser Gly Cys Lys Glu Cys Glu Glu
    530                 535                 540

Leu Glu Glu Lys Asn Ile Lys Glu Phe Leu Gln Ser Phe Val His Ile
545                 550                 555                 560

Val Gln Met Phe Ile Asn Thr Ser
                565

<210> SEQ ID NO 64
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln

```
                    275                 280                 285
Phe Asn Ser Thr Tyr Arg Val Ser Val Leu Thr Val Leu His Gln
            290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
                325                 330                 335
Arg Glu Pro Gln Val Tyr Thr Leu Pro Pro Ser Gln Glu Glu Met Thr
            340                 345                 350
Lys Asn Gln Val Ser Leu Thr Cys Leu Val Lys Gly Phe Tyr Pro Ser
            355                 360                 365
Asp Ile Ala Val Glu Trp Glu Ser Asn Gly Gln Pro Glu Asn Asn Tyr
        370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
                420                 425                 430
Ser Leu Ser Leu Ser Leu Gly Ala Gly Gly Gly Ser Gly Gly Gly
            435                 440                 445
Gly Ser Gly Gly Gly Ser Asn Trp Val Asn Val Ile Ser Asp Leu
        450                 455                 460
Lys Lys Ile Glu Asp Leu Ile Gln Ser Met His Ile Asp Ala Thr Leu
465                 470                 475                 480
Tyr Thr Glu Ser Asp Val His Pro Ser Cys Lys Val Thr Ala Met Lys
                485                 490                 495
Cys Phe Leu Leu Lys Leu Gln Val Ile Ser Leu Glu Ser Gly Asp Ala
                500                 505                 510
Ser Ile His Asp Thr Val Glu Asn Leu Ile Ile Leu Ala Asn Asn Ser
            515                 520                 525
Leu Ser Ser Asn Gly Asn Val Thr Glu Ser Gly Cys Lys Glu Cys Glu
        530                 535                 540
Glu Leu Glu Glu Lys Asn Ile Lys Glu Phe Leu Gln Ser Phe Val His
545                 550                 555                 560
Ile Val Gln Met Phe Ile Asn Thr Ser
                565

<210> SEQ ID NO 65
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Val Val Gln Pro Gly Arg
1               5                   10                  15
Ser Leu Arg Leu Asp Cys Lys Ala Ser Gly Ile Thr Phe Ser Asn Ser
            20                  25                  30
Gly Met His Trp Val Arg Gln Ala Pro Gly Lys Gly Leu Glu Trp Val
        35                  40                  45
Ala Val Ile Trp Tyr Asp Gly Ser Lys Arg Tyr Tyr Ala Asp Ser Val
    50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
             85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Gly Ser Gly Gly Gly Ser Asn Trp Val Asn Val Ile Ser Asp Leu
            450                 455                 460

Lys Lys Ile Glu Asp Leu Ile Gln Ser Met His Ile Asp Ala Thr Leu
465                 470                 475                 480

Tyr Thr Glu Ser Asp Val His Pro Ser Cys Lys Val Thr Ala Met Lys
```

```
                        485                 490                 495

Cys Phe Leu Leu Lys Leu Gln Val Ile Ser Leu Glu Ser Gly Asp Ala
            500                 505                 510

Ser Ile His Asp Thr Val Glu Asp Leu Ile Ile Leu Ala Asn Asn Ser
            515                 520                 525

Leu Ser Ser Asn Gly Asn Val Thr Glu Ser Gly Cys Lys Glu Cys Glu
            530                 535                 540

Glu Leu Glu Glu Lys Asn Ile Lys Glu Phe Leu Gln Ser Phe Val His
545                 550                 555                 560

Ile Val Gln Met Phe Ile Asn Thr Ser
                565

<210> SEQ ID NO 66
<211> LENGTH: 706
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270
```

```
Asp Gly Val Glu Val His Asn Ala Lys Thr Lys Pro Arg Glu Glu Gln
            275                 280                 285

Phe Asn Ser Thr Tyr Arg Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
            435                 440                 445

Gly Ser Gly Pro Leu Gly Val Arg Gly Gly Gly Ser Gly Gly Gly
            450                 455                 460

Gly Ser Glu Ile Val Leu Thr Gln Ser Pro Gly Thr Leu Ser Leu Ser
465                 470                 475                 480

Pro Gly Glu Arg Ala Thr Leu Ser Cys Arg Ala Ser Gln Ser Val Ser
                485                 490                 495

Ser Ser Tyr Leu Ala Trp Tyr Gln Gln Lys Pro Gly Gln Ala Pro Arg
            500                 505                 510

Leu Leu Ile Tyr Gly Ala Ser Arg Arg Ala Thr Gly Ile Pro Asp Arg
            515                 520                 525

Phe Ser Gly Ser Gly Ser Gly Thr Asp Phe Thr Leu Thr Ile Ser Arg
530                 535                 540

Leu Glu Pro Glu Asp Phe Ala Val Tyr Tyr Cys Gln Arg Tyr Gly Ser
545                 550                 555                 560

Ser His Thr Phe Gly Gln Gly Thr Lys Leu Glu Ile Ser Gly Gly Gly
            565                 570                 575

Gly Ser Gly Gly Gly Gly Ser Gly Gly Gly Gly Ser Glu Val Gln Leu
            580                 585                 590

Val Gln Ser Gly Ala Glu Val Lys Lys Pro Gly Glu Ser Leu Lys Ile
            595                 600                 605

Ser Cys Lys Val Ser Gly Tyr Phe Thr Thr Tyr Trp Ile Gly Trp
    610                 615                 620

Val Arg Gln Met Pro Gly Lys Gly Leu Glu Tyr Met Gly Ile Ile Tyr
625                 630                 635                 640

Pro Gly Asp Ser Asp Thr Arg Tyr Ser Pro Ser Phe Gln Gly Gln Val
                645                 650                 655

Thr Ile Ser Ala Asp Lys Ser Ile Ser Thr Ala Tyr Leu Gln Trp Ser
            660                 665                 670

Ser Leu Lys Ala Ser Asp Thr Ala Met Tyr Tyr Cys Ala Arg Gly Gly
            675                 680                 685

Asn Trp Asn Cys Phe Asp Tyr Trp Gly Gln Gly Thr Leu Val Thr Val
```

690                 695                 700

Ser Ser
705

<210> SEQ ID NO 67
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Glu Ser Gly Gly Gly Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Gly Ser Gly Gly Gly Ser Ile Thr Cys Pro Pro Pro Met Ser Val
    450                 455                 460

Glu His Ala Asp Ile Trp Val Lys Ser Tyr Ser Leu Tyr Ser Arg Glu
465                 470                 475                 480

Arg Tyr Ile Cys Asn Ser Gly Phe Lys Arg Lys Ala Gly Thr Ser Ser
                485                 490                 495

Leu Thr Glu Cys Val Leu Asn Lys Ala Thr Asn Val Ala His Trp Thr
            500                 505                 510

Thr Pro Ser Leu Lys Cys Ile Arg Gly Gly Ser Gly Gly Gly Gly Ser
        515                 520                 525

Gly Gly Gly Ser Gly Gly Gly Ser Asn Trp Val Asn Val Ile Ser
    530                 535                 540

Asp Leu Lys Lys Ile Glu Asp Leu Ile Gln Ser Met His Ile Asp Ala
545                 550                 555                 560

Thr Leu Tyr Thr Glu Ser Asp Val His Pro Ser Cys Lys Val Thr Ala
                565                 570                 575

Met Lys Cys Phe Leu Leu Glu Leu Gln Val Ile Ser Leu Glu Ser Gly
            580                 585                 590

Asp Ala Ser Ile His Asp Thr Val Glu Asp Leu Ile Ile Leu Ala Asn
        595                 600                 605

Asn Ser Leu Ser Ser Asn Gly Asn Val Thr Glu Ser Gly Cys Lys Glu
    610                 615                 620

Cys Glu Glu Leu Glu Glu Lys Asn Ile Lys Glu Phe Leu Gln Ser Phe
625                 630                 635                 640

Val His Ile Val Gln Met Phe Ile Asn Thr Ser
                645                 650

<210> SEQ ID NO 68
<211> LENGTH: 668
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 68

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
        435                 440                 445

Gly Ser Gly Gly Gly Gly Ser Ile Thr Cys Pro Pro Pro Met Ser Val
    450                 455                 460

```
Glu His Ala Asp Ile Trp Val Lys Ser Tyr Ser Leu Tyr Ser Arg Glu
465                 470                 475                 480

Arg Tyr Ile Cys Asn Ser Gly Phe Lys Arg Lys Ala Gly Thr Ser Ser
                485                 490                 495

Leu Thr Glu Cys Val Leu Asn Lys Ala Thr Asn Val Ala His Trp Thr
            500                 505                 510

Thr Pro Ser Leu Lys Cys Ile Arg Gly Gly Ser Gly Gly Gly Gly Ser
        515                 520                 525

Gly Gly Gly Ser Gly Gly Gly Ser Ala Ala Gly Gly Gly Gly Ser
    530                 535                 540

Gly Gly Gly Gly Ser Gly Gly Gly Ser Asn Trp Val Asn Val Ile
545                 550                 555                 560

Ser Asp Leu Lys Lys Ile Glu Asp Leu Ile Gln Ser Met His Ile Asp
                565                 570                 575

Ala Thr Leu Tyr Thr Glu Ser Asp Val His Pro Ser Cys Lys Val Thr
            580                 585                 590

Ala Met Lys Cys Phe Leu Leu Glu Leu Gln Val Ile Ser Leu Glu Ser
        595                 600                 605

Gly Asp Ala Ser Ile His Asp Thr Val Glu Asp Leu Ile Ile Leu Ala
610                 615                 620

Asn Asn Ser Leu Ser Ser Asn Gly Asn Val Thr Glu Ser Gly Cys Lys
625                 630                 635                 640

Glu Cys Glu Glu Leu Glu Glu Lys Asn Ile Lys Glu Phe Leu Gln Ser
                645                 650                 655

Phe Val His Ile Val Gln Met Phe Ile Asn Thr Ser
                660                 665

<210> SEQ ID NO 69
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Cys Gln Glu Glu Met Thr
            340                 345                 350

Lys Asn Gln Val Ser Leu Trp Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
            435                 440                 445

Ser Gly Gly Gly Ser Ile Thr Cys Pro Pro Met Ser Val Glu
    450                 455                 460

His Ala Asp Ile Trp Val Lys Ser Tyr Ser Leu Tyr Ser Arg Glu Arg
465                 470                 475                 480

Tyr Ile Cys Asn Ser Gly Phe Lys Arg Lys Ala Gly Thr Ser Ser Leu
            485                 490                 495

Thr Glu Cys Val Leu Asn Lys Ala Thr Asn Val Ala His Trp Thr Thr
            500                 505                 510

Pro Ser Leu Lys Cys Ile Arg Asp Pro Ala Leu Val His Gln Arg Pro
            515                 520                 525

Ala Pro Pro Ser Gly Gly Gly Ser Gly Gly Gly Ser Gly Gly
            530                 535                 540

Gly Gly Ser Ala Ala Gly Gly Gly Ser Gly Gly Gly Ser Gly
545                 550                 555                 560

Gly Gly Gly Ser Asn Trp Val Asn Val Ile Ser Asp Leu Lys Lys Ile
            565                 570                 575
```

```
Glu Asp Leu Ile Gln Ser Met His Ile Asp Ala Thr Leu Tyr Thr Glu
            580                 585                 590

Ser Asp Val His Pro Ser Cys Lys Val Thr Ala Met Lys Cys Phe Leu
        595                 600                 605

Leu Glu Leu Gln Val Ile Ser Leu Glu Ser Gly Asp Ala Ser Ile His
    610                 615                 620

Asp Thr Val Glu Asp Leu Ile Ile Leu Ala Asn Asn Ser Leu Ser Ser
625                 630                 635                 640

Asn Gly Asn Val Thr Glu Ser Gly Cys Lys Cys Glu Glu Leu Glu
                645                 650                 655

Glu Lys Asn Ile Lys Glu Phe Leu Gln Ser Phe Val His Ile Val Gln
            660                 665                 670

Met Phe Ile Asn Thr Ser
        675

<210> SEQ ID NO 70
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Gly Gly Gly Ser Val His Met Pro Leu Gly Phe Leu
225                 230                 235                 240

Gly Pro Arg Gln Ala Arg Val Val Asn Gly Gly Gly Gly Ser Gly
                245                 250                 255
```

Gly Gly Gly Ser Glu Val Gln Leu Val Gln Ser Gly Ala Glu Val Lys
            260                 265                 270

Lys Pro Gly Glu Ser Leu Lys Ile Ser Cys Lys Val Ser Gly Tyr Phe
            275                 280                 285

Phe Thr Thr Tyr Trp Ile Gly Trp Val Arg Gln Met Pro Gly Lys Gly
        290                 295                 300

Leu Glu Tyr Met Gly Ile Ile Tyr Pro Gly Asp Ser Asp Thr Arg Tyr
305                 310                 315                 320

Ser Pro Ser Phe Gln Gly Gln Val Thr Ile Ser Ala Asp Lys Ser Ile
                325                 330                 335

Ser Thr Ala Tyr Leu Gln Trp Ser Ser Leu Lys Ala Ser Asp Thr Ala
            340                 345                 350

Met Tyr Tyr Cys Ala Arg Gly Gly Asn Trp Asn Cys Phe Asp Tyr Trp
        355                 360                 365

Gly Gln Gly Thr Leu Val Thr Val Ser Gly Gly Gly Gly Ser Gly
        370                 375                 380

Gly Gly Gly Ser Gly Gly Gly Ser Glu Ile Val Leu Thr Gln Ser
385                 390                 395                 400

Pro Gly Thr Leu Ser Leu Ser Pro Gly Arg Glu Ala Thr Leu Ser Cys
                405                 410                 415

Arg Ala Ser Gln Ser Val Ser Ser Ser Tyr Leu Ala Trp Tyr Gln Gln
            420                 425                 430

Lys Pro Gly Gln Ala Pro Arg Leu Leu Ile Tyr Gly Ala Ser Arg Arg
        435                 440                 445

Ala Thr Gly Ile Pro Asp Arg Phe Ser Gly Ser Gly Ser Gly Thr Asp
        450                 455                 460

Phe Thr Leu Thr Ile Ser Arg Leu Glu Pro Glu Asp Phe Ala Val Tyr
465                 470                 475                 480

Tyr Cys Gln Arg Tyr Gly Ser Ser His Thr Phe Gly Gln Gly Thr Lys
                485                 490                 495

Leu Glu Ile Ser Arg
            500

<210> SEQ ID NO 71
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile

```
                100             105                 110
Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130             135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Ala Gly Gly Gly Ser Val His Met Pro Leu Gly Phe Leu
225                 230                 235                 240

Gly Pro Arg Gln Ala Arg Val Val Asn Gly Gly Gly Gly Ser Gly
                245                 250                 255

Gly Gly Gly Ser Glu Ile Val Leu Thr Gln Ser Pro Gly Thr Leu Ser
                260                 265                 270

Leu Ser Pro Gly Arg Glu Ala Thr Leu Ser Cys Arg Ala Ser Gln Ser
            275                 280                 285

Val Ser Ser Ser Tyr Leu Ala Trp Tyr Gln Gln Lys Pro Gly Gln Ala
            290                 295                 300

Pro Arg Leu Leu Ile Tyr Gly Ala Ser Arg Arg Ala Thr Gly Ile Pro
305                 310                 315                 320

Asp Arg Phe Ser Gly Ser Gly Ser Gly Thr Asp Phe Thr Leu Thr Ile
                325                 330                 335

Ser Arg Leu Glu Pro Glu Asp Phe Ala Val Tyr Tyr Cys Gln Arg Tyr
            340                 345                 350

Gly Ser Ser His Thr Phe Gly Gln Gly Thr Lys Leu Glu Ile Ser Arg
            355                 360                 365

Gly Gly Gly Gly Ser Gly Gly Gly Ser Gly Gly Gly Gly Ser Glu
370                 375                 380

Val Gln Leu Val Gln Ser Gly Ala Glu Val Lys Lys Pro Gly Glu Ser
385                 390                 395                 400

Leu Lys Ile Ser Cys Lys Val Ser Gly Tyr Phe Phe Thr Thr Tyr Trp
                405                 410                 415

Ile Gly Trp Val Arg Gln Met Pro Gly Lys Gly Leu Glu Tyr Met Gly
                420                 425                 430

Ile Ile Tyr Pro Gly Asp Ser Asp Thr Arg Tyr Ser Pro Ser Phe Gln
            435                 440                 445

Gly Gln Val Thr Ile Ser Ala Asp Lys Ser Ile Ser Thr Ala Tyr Leu
            450                 455                 460

Gln Trp Ser Ser Leu Lys Ala Ser Asp Thr Ala Met Tyr Tyr Cys Ala
465                 470                 475                 480

Arg Gly Gly Asn Trp Asn Cys Phe Asp Tyr Trp Gly Gln Gly Thr Leu
                485                 490                 495

Val Thr Val Ser Ser
            500

<210> SEQ ID NO 72
```

<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ala Gly Gly Gly Ser Val His Met Pro Leu Gly Phe Leu
225                 230                 235                 240

Gly Pro Arg Gln Ala Arg Val Val Asn Gly Gly Gly Gly Ser Gly
                245                 250                 255

Gly Gly Gly Ser Glu Val Gln Leu Val Gln Ser Gly Ala Glu Val Lys
            260                 265                 270

Lys Pro Gly Glu Ser Leu Lys Ile Ser Cys Lys Val Ser Gly Tyr Phe
        275                 280                 285

Phe Thr Thr Tyr Trp Ile Gly Trp Val Arg Gln Met Pro Gly Lys Gly
    290                 295                 300

Leu Glu Tyr Met Gly Ile Ile Tyr Pro Gly Asp Ser Asp Thr Arg Tyr
305                 310                 315                 320

Ser Pro Ser Phe Gln Gly Gln Val Thr Ile Ser Ala Asp Lys Ser Ile
                325                 330                 335

Ser Thr Ala Tyr Leu Gln Trp Ser Ser Leu Lys Ala Ser Asp Thr Ala
            340                 345                 350

Met Tyr Tyr Cys Ala Arg Gly Gly Asn Trp Asn Cys Phe Asp Tyr Trp
        355                 360                 365

Gly Gln Gly Thr Leu Val Thr Val Ser Ser Gly Gly Gly Gly Ser Gly

```
                    370                 375                 380
Gly Gly Gly Ser Gly Gly Gly Ser Glu Ile Val Leu Thr Gln Ser
385                 390                 395                 400

Pro Gly Thr Leu Ser Leu Ser Pro Gly Arg Glu Ala Thr Leu Ser Cys
                405                 410                 415

Arg Ala Ser Gln Ser Val Ser Ser Tyr Leu Ala Trp Tyr Gln Gln
            420                 425                 430

Lys Pro Gly Gln Ala Pro Arg Leu Leu Ile Tyr Gly Ala Ser Arg Arg
            435                 440                 445

Ala Thr Gly Ile Pro Asp Arg Phe Ser Gly Ser Gly Ser Gly Thr Asp
450                 455                 460

Phe Thr Leu Thr Ile Ser Arg Leu Glu Pro Glu Asp Phe Ala Val Tyr
465                 470                 475                 480

Tyr Cys Gln Arg Tyr Gly Ser Ser His Thr Phe Gly Gly Gly Thr Lys
            485                 490                 495

Leu Glu Ile Ser Arg
            500

<210> SEQ ID NO 73
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Ala Gly Gly Gly Ser Val His Met Pro Leu Gly Phe Leu
225                 230                 235                 240

Gly Pro Arg Gln Ala Arg Val Val Asn Gly Gly Gly Gly Ser Gly
            245                 250                 255

Gly Gly Gly Ser Glu Ile Val Leu Thr Gln Ser Pro Gly Thr Leu Ser
            260                 265                 270

Leu Ser Pro Gly Arg Glu Ala Thr Leu Ser Cys Arg Ala Ser Gln Ser
        275                 280                 285

Val Ser Ser Ser Tyr Leu Ala Trp Tyr Gln Gln Lys Pro Gly Gln Ala
    290                 295                 300

Pro Arg Leu Leu Ile Tyr Gly Ala Ser Arg Arg Ala Thr Gly Ile Pro
305                 310                 315                 320

Asp Arg Phe Ser Gly Ser Gly Ser Gly Thr Asp Phe Thr Leu Thr Ile
            325                 330                 335

Ser Arg Leu Glu Pro Glu Asp Phe Ala Val Tyr Tyr Cys Gln Arg Tyr
            340                 345                 350

Gly Ser Ser His Thr Phe Gly Gln Gly Thr Lys Leu Glu Ile Ser Arg
        355                 360                 365

Gly Gly Gly Gly Ser Gly Gly Gly Ser Gly Gly Gly Gly Ser Glu
    370                 375                 380

Val Gln Leu Val Gln Ser Gly Ala Glu Val Lys Lys Pro Gly Glu Ser
385                 390                 395                 400

Leu Lys Ile Ser Cys Lys Val Ser Gly Tyr Phe Phe Thr Thr Tyr Trp
            405                 410                 415

Ile Gly Trp Val Arg Gln Met Pro Gly Lys Gly Leu Glu Tyr Met Gly
            420                 425                 430

Ile Ile Tyr Pro Gly Asp Ser Asp Thr Arg Tyr Ser Pro Ser Phe Gln
            435                 440                 445

Gly Gln Val Thr Ile Ser Ala Asp Lys Ser Ile Ser Thr Ala Tyr Leu
        450                 455                 460

Gln Trp Ser Ser Leu Lys Ala Ser Asp Thr Ala Met Tyr Tyr Cys Ala
465                 470                 475                 480

Arg Gly Gly Asn Trp Asn Cys Phe Asp Tyr Trp Gly Gln Gly Thr Leu
            485                 490                 495

Val Thr Val Ser Ser
            500

<210> SEQ ID NO 74
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro Gly Lys Gly Gly Gly Ser Gly Gly Gly Ser Gly Gly Gly Gly
225                 230                 235                 240

Gly Ser Ile Thr Cys Pro Pro Met Ser Val Glu His Ala Asp Ile
            245                 250                 255

Trp Val Lys Ser Tyr Ser Leu Tyr Ser Arg Glu Arg Tyr Ile Cys Asn
                260                 265                 270

Ser Gly Phe Lys Arg Lys Ala Gly Thr Ser Ser Leu Thr Glu Cys Val
            275                 280                 285

Leu Asn Lys Ala Thr Asn Val Ala His Trp Thr Thr Pro Ser Leu Lys
        290                 295                 300

Cys Ile Arg Gly Gly Ser Gly Gly Gly Ser Gly Gly Gly Ser Gly
305                 310                 315                 320

Gly Gly Gly Ser Asn Trp Val Asn Val Ile Ser Asp Leu Lys Lys Ile
            325                 330                 335

Glu Asp Leu Ile Gln Ser Met His Ile Asp Ala Thr Leu Tyr Thr Glu
            340                 345                 350

Ser Asp Val His Pro Ser Cys Lys Val Thr Ala Met Lys Cys Phe Leu
        355                 360                 365

Leu Glu Leu Gln Val Ile Ser Leu Glu Ser Gly Asp Ala Ser Ile His
    370                 375                 380

Asp Thr Val Glu Asn Leu Ile Ile Leu Ala Asn Asn Ser Leu Ser Ser
385                 390                 395                 400

Asn Gly Asn Val Thr Glu Ser Gly Cys Lys Glu Cys Glu Glu Leu Glu
                405                 410                 415

Glu Lys Asn Ile Lys Glu Phe Leu Gln Ser Phe Val His Ile Val Gln
            420                 425                 430

Met Phe Ile Asn Thr Ser
        435

<210> SEQ ID NO 75
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 75

Asp Lys Thr His Thr Cys Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly Gly
225                 230                 235                 240

Gly Ser Ile Thr Cys Pro Pro Met Ser Val Glu His Ala Asp Ile
                245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
        275                 280                 285

Leu Asn Lys Ala Thr Asn Val Ala His Trp Thr Thr Pro Ser Leu Lys
    290                 295                 300

Cys Ile Arg Gly Gly Ser Gly Gly Gly Ser Gly Gly Gly Ser Gly
305                 310                 315                 320

Gly Gly Ser Asn Trp Val Asn Val Ile Ser Asp Leu Lys Lys Ile
                325                 330                 335

Glu Asp Leu Ile Gln Ser Met His Ile Asp Ala Thr Leu Tyr Thr Glu
            340                 345                 350

Ser Asp Val His Pro Ser Cys Lys Val Thr Ala Met Lys Cys Phe Leu
        355                 360                 365

Leu Lys Leu Gln Val Ile Ser Leu Glu Ser Gly Asp Ala Ser Ile His
    370                 375                 380

Asp Thr Val Glu Asp Leu Ile Ile Leu Ala Asn Asn Ser Leu Ser Ser
385                 390                 395                 400

Asn Gly Asn Val Thr Glu Ser Gly Cys Lys Glu Cys Glu Glu Leu Glu
                405                 410                 415
```

```
Glu Lys Asn Ile Lys Glu Phe Leu Gln Ser Phe Val His Ile Val Gln
            420                 425                 430

Met Phe Ile Asn Thr Ser
            435

<210> SEQ ID NO 76
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn Arg Phe Thr Gln Lys Ser Leu Ser Leu Ser
            210                 215                 220

Pro Gly Lys Gly Gly Gly Gly Ser Gly Gly Gly Gly Ser Gly Gly Gly
225                 230                 235                 240

Gly Ser Ile Thr Cys Pro Pro Pro Met Ser Val Glu His Ala Asp Ile
            245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
            275                 280                 285

Leu Asn Lys Ala Thr Asn Val Ala His Trp Thr Thr Pro Ser Leu Lys
            290                 295                 300

Cys Ile Arg Gly Gly Ser Gly Gly Gly Gly Ser Gly Gly Gly Gly Ser
305                 310                 315                 320

Gly Gly Gly Ser Asn Trp Val Asn Val Ile Ser Asp Leu Lys Lys Ile
```

```
                    325                 330                 335
Glu Asp Leu Ile Gln Ser Met His Ile Asp Ala Thr Leu Tyr Thr Glu
                340                 345                 350

Ser Asp Val His Pro Ser Cys Lys Val Thr Ala Met Lys Cys Phe Leu
                355                 360                 365

Leu Glu Leu Gln Val Ile Ser Leu Glu Ser Gly Asp Ala Ser Ile His
                370                 375                 380

Asp Thr Val Glu Asp Leu Ile Ile Leu Ala Asn Asn Ser Leu Ser Ser
385                 390                 395                 400

Asn Gly Asn Val Thr Glu Ser Gly Cys Lys Glu Cys Glu Glu Leu Glu
                405                 410                 415

Glu Lys Asn Ile Lys Glu Phe Leu Gln Ser Phe Val His Ile Val Gln
                420                 425                 430

Met Phe Ile Asn Thr Ser
                435

<210> SEQ ID NO 77
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Tyr
                20                  25                  30

Ile Thr Arg Glu Pro Glu Val Thr Cys Val Val Val Asp Val Ser His
                35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Glu Glu Met Thr Lys Asn Gln Val Ser
                130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn Arg Phe Thr Gln Lys Ser Leu Ser Leu Ser
                210                 215                 220

Pro Gly Lys Gly Gly Gly Gly Ser Gly Gly Gly Gly Ser Gly Gly Gly
225                 230                 235                 240
```

```
Gly Ser Ile Thr Cys Pro Pro Met Ser Val Glu His Ala Asp Ile
                245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
            275                 280                 285

Leu Asn Lys Ala Thr Asn Val Ala His Trp Thr Thr Pro Ser Leu Lys
            290                 295                 300

Cys Ile Arg Gly Gly Ser Gly Gly Gly Ser Gly Gly Gly Ser Gly
305                 310                 315                 320

Gly Gly Gly Ser Asn Trp Val Asn Val Ile Ser Asp Leu Lys Lys Ile
                325                 330                 335

Glu Asp Leu Ile Gln Ser Met His Ile Asp Ala Thr Leu Tyr Thr Glu
                340                 345                 350

Ser Asp Val His Pro Ser Cys Lys Val Thr Ala Met Lys Cys Phe Leu
                355                 360                 365

Leu Glu Leu Gln Val Ile Ser Leu Glu Ser Gly Asp Ala Ser Ile His
                370                 375                 380

Asp Thr Val Glu Asn Leu Ile Ile Leu Ala Asn Asn Ser Leu Ser Ser
385                 390                 395                 400

Asn Gly Asn Val Thr Glu Ser Gly Cys Lys Glu Cys Glu Glu Leu Glu
                405                 410                 415

Glu Lys Asn Ile Lys Glu Phe Leu Gln Ser Phe Val His Ile Val Gln
                420                 425                 430

Met Phe Ile Asn Thr Ser
            435

<210> SEQ ID NO 78
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
            35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
            115                 120                 125

Ile Glu Lys Thr Ile Ser Lys Ala Lys Gly Gln Pro Arg Glu Pro Gln
            130                 135                 140

Val Tyr Thr Leu Pro Pro Cys Arg Glu Glu Met Thr Lys Asn Gln Val
145                 150                 155                 160
```

```
Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn Arg Phe Thr Gln Lys Ser Leu Ser Leu
225                 230                 235                 240

Ser Pro Gly Lys Gly Gly Gly Ser Gly Gly Gly Ser Gly Gly Gly Gly
                245                 250                 255

Gly Gly Ser Ile Thr Cys Pro Pro Met Ser Val Glu His Ala Asp
            260                 265                 270

Ile Trp Val Lys Ser Tyr Ser Leu Tyr Ser Arg Glu Arg Tyr Ile Cys
                275                 280                 285

Asn Ser Gly Phe Lys Arg Lys Ala Gly Thr Ser Ser Leu Thr Glu Cys
            290                 295                 300

Val Leu Asn Lys Ala Thr Asn Val Ala His Trp Thr Thr Pro Ser Leu
305                 310                 315                 320

Lys Cys Ile Arg Gly Gly Ser Gly Gly Gly Ser Gly Gly Gly Ser
                325                 330                 335

Gly Gly Gly Gly Ser Asn Trp Val Asn Val Ile Ser Asp Leu Lys Lys
            340                 345                 350

Ile Glu Asp Leu Ile Gln Ser Met His Ile Asp Ala Thr Leu Tyr Thr
                355                 360                 365

Glu Ser Asn Val His Pro Ser Cys Lys Val Thr Ala Met Lys Cys Phe
370                 375                 380

Leu Leu Glu Leu Gln Val Ile Ser Leu Glu Ser Gly Asp Ala Ser Ile
385                 390                 395                 400

His Asp Thr Val Gln Asp Leu Ile Ile Leu Ala Asn Asn Ser Leu Ser
                405                 410                 415

Ser Asn Gly Asn Val Thr Glu Ser Gly Cys Lys Glu Cys Glu Glu Leu
            420                 425                 430

Glu Glu Lys Asn Ile Lys Glu Phe Leu Gln Ser Phe Val His Ile Val
            435                 440                 445

Gln Met Phe Ile Asn Thr Ser
        450                 455

<210> SEQ ID NO 79
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
```

```
                50                  55                  60
His Glu Asp Pro Glu Val Lys Phe Asn Trp Tyr Val Asp Gly Val Glu
 65                  70                  75                  80

Val His Asn Ala Lys Thr Lys Pro Arg Glu Glu Gln Tyr Asn Ser Thr
                 85                  90                  95

Tyr Arg Val Val Ser Val Leu Thr Val Leu His Gln Asp Trp Leu Asn
                100                 105                 110

Gly Lys Glu Tyr Lys Cys Lys Val Ser Asn Lys Ala Leu Pro Ala Pro
                115                 120                 125

Ile Glu Lys Thr Ile Ser Lys Ala Lys Gly Gln Pro Arg Glu Pro Gln
130                 135                 140

Val Tyr Thr Leu Pro Pro Cys Arg Glu Glu Met Thr Lys Asn Gln Val
145                 150                 155                 160

Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
                180                 185                 190

Pro Val Leu Asp Ser Asp Gly Ser Phe Phe Leu Tyr Ser Lys Leu Thr
                195                 200                 205

Val Asp Lys Ser Arg Trp Gln Gln Gly Asn Val Phe Ser Cys Ser Val
210                 215                 220

Met His Glu Ala Leu His Asn Arg Phe Thr Gln Lys Ser Leu Ser Leu
225                 230                 235                 240

Ser Pro Gly Lys Gly Gly Gly Ser Gly Gly Gly Ser Gly Gly
                245                 250                 255

Gly Gly Ser Ile Thr Cys Pro Pro Met Ser Val Glu His Ala Asp
                260                 265                 270

Ile Trp Val Lys Ser Tyr Ser Leu Tyr Ser Arg Glu Arg Tyr Ile Cys
                275                 280                 285

Asn Ser Gly Phe Lys Arg Lys Ala Gly Thr Ser Ser Leu Thr Glu Cys
                290                 295                 300

Val Leu Asn Lys Ala Thr Asn Val Ala His Trp Thr Thr Pro Ser Leu
305                 310                 315                 320

Lys Cys Ile Arg Gly Gly Ser Gly Gly Gly Ser Gly Gly Gly Ser
                325                 330                 335

Gly Gly Gly Gly Ser Asn Trp Val Asn Val Ile Ser Asp Leu Lys Lys
                340                 345                 350

Ile Glu Asp Leu Ile Gln Ser Met His Ile Asp Ala Thr Leu Tyr Thr
                355                 360                 365

Glu Ser Asp Val His Pro Ser Cys Lys Val Thr Ala Met Lys Cys Phe
                370                 375                 380

Leu Leu Glu Leu Gln Val Ile Ser Leu Glu Ser Gly Asp Ala Ser Ile
385                 390                 395                 400

His Asp Thr Val Glu Asp Leu Ile Ile Leu Ala Asn Asn Ser Leu Ser
                405                 410                 415

Ser Asn Gly Asn Val Thr Glu Ser Gly Cys Lys Glu Cys Glu Glu Leu
                420                 425                 430

Glu Glu Lys Asn Ile Lys Glu Phe Leu Gln Ser Phe Val His Ile Val
                435                 440                 445

Gln Met Phe Ile Asn Thr Ser
450                 455

<210> SEQ ID NO 80
```

<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Ala Gly Gly Gly Ser Val His Met Pro Leu Gly
225                 230                 235                 240

Phe Leu Gly Pro Arg Gln Ala Arg Val Val Asn Gly Gly Gly Gly
                245                 250                 255

Ser Gly Gly Gly Gly Ser Glu Val Gln Leu Val Gln Ser Gly Ala Glu
            260                 265                 270

Val Lys Lys Pro Gly Glu Ser Leu Lys Ile Ser Cys Lys Val Ser Gly
        275                 280                 285

Tyr Phe Phe Thr Thr Tyr Trp Ile Gly Trp Val Arg Gln Met Pro Gly
    290                 295                 300

Lys Gly Leu Glu Tyr Met Gly Ile Ile Tyr Pro Gly Asp Ser Asp Thr
305                 310                 315                 320

Arg Tyr Ser Pro Ser Phe Gln Gly Gln Val Thr Ile Ser Ala Asp Lys
                325                 330                 335

Ser Ile Ser Thr Ala Tyr Leu Gln Trp Ser Ser Leu Lys Ala Ser Asp
            340                 345                 350

Thr Ala Met Tyr Tyr Cys Ala Arg Gly Gly Asn Trp Asn Cys Phe Asp
        355                 360                 365

Tyr Trp Gly Gln Gly Thr Leu Val Thr Val Ser Ser Gly Gly Gly Gly
```

370                 375                 380
Ser Gly Gly Gly Ser Gly Gly Gly Ser Glu Ile Val Leu Thr
385                 390                 395                 400

Gln Ser Pro Gly Thr Leu Ser Leu Ser Pro Gly Arg Glu Ala Thr Leu
                405                 410                 415

Ser Cys Arg Ala Ser Gln Ser Val Ser Ser Tyr Leu Ala Trp Tyr
                420                 425                 430

Gln Gln Lys Pro Gly Gln Ala Pro Arg Leu Leu Ile Tyr Gly Ala Ser
                435                 440                 445

Arg Arg Ala Thr Gly Ile Pro Asp Arg Phe Ser Gly Ser Gly Ser Gly
450                 455                 460

Thr Asp Phe Thr Leu Thr Ile Ser Arg Leu Glu Pro Glu Asp Phe Ala
465                 470                 475                 480

Val Tyr Tyr Cys Gln Arg Tyr Gly Ser Ser His Thr Phe Gly Gln Gly
                485                 490                 495

Thr Lys Leu Glu Ile Ser Arg
                500

<210> SEQ ID NO 81
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
    115                 120                 125

Gln Val Cys Thr Leu Pro Pro Ser Gln Glu Glu Met Thr Lys Asn Gln
130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
    195                 200                 205

Val Met His Glu Ala Leu His Asn His Tyr Thr Gln Lys Ser Leu Ser
    210                 215                 220

```
Leu Ser Leu Gly Ala Gly Gly Gly Ser Val His Met Pro Leu Gly
225                 230                 235                 240

Phe Leu Gly Pro Arg Gln Ala Arg Val Val Asn Gly Gly Gly Gly
                245                 250                 255

Ser Gly Gly Gly Ser Glu Ile Val Leu Thr Gln Ser Pro Gly Thr
            260                 265                 270

Leu Ser Leu Ser Pro Gly Arg Glu Ala Thr Leu Ser Cys Arg Ala Ser
        275                 280                 285

Gln Ser Val Ser Ser Tyr Leu Ala Trp Tyr Gln Gln Lys Pro Gly
    290                 295                 300

Gln Ala Pro Arg Leu Leu Ile Tyr Gly Ala Ser Arg Arg Ala Thr Gly
305                 310                 315                 320

Ile Pro Asp Arg Phe Ser Gly Ser Gly Ser Gly Thr Asp Phe Thr Leu
                325                 330                 335

Thr Ile Ser Arg Leu Glu Pro Glu Asp Phe Ala Val Tyr Tyr Cys Gln
            340                 345                 350

Arg Tyr Gly Ser Ser His Thr Phe Gly Gln Gly Thr Lys Leu Glu Ile
        355                 360                 365

Ser Arg Gly Gly Gly Gly Ser Gly Gly Gly Ser Gly Gly Gly Gly
370                 375                 380

Ser Glu Val Gln Leu Val Gln Ser Gly Ala Glu Val Lys Lys Pro Gly
385                 390                 395                 400

Glu Ser Leu Lys Ile Ser Cys Lys Val Ser Gly Tyr Phe Phe Thr Thr
                405                 410                 415

Tyr Trp Ile Gly Trp Val Arg Gln Met Pro Gly Lys Gly Leu Glu Tyr
            420                 425                 430

Met Gly Ile Ile Tyr Pro Gly Asp Ser Asp Thr Arg Tyr Ser Pro Ser
        435                 440                 445

Phe Gln Gly Gln Val Thr Ile Ser Ala Asp Lys Ser Ile Ser Thr Ala
    450                 455                 460

Tyr Leu Gln Trp Ser Ser Leu Lys Ala Ser Asp Thr Ala Met Tyr Tyr
465                 470                 475                 480

Cys Ala Arg Gly Gly Asn Trp Asn Cys Phe Asp Tyr Trp Gly Gln Gly
                485                 490                 495

Thr Leu Val Thr Val Ser Ser
            500

<210> SEQ ID NO 82
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
           100                 105                 110

Ser Ile Glu Lys Thr Ile Ser Lys Ala Lys Gly Gln Pro Arg Glu Pro
       115                 120                 125

Gln Val Tyr Thr Leu Pro Pro Cys Gln Glu Glu Met Thr Lys Asn Gln
   130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
               165                 170                 175

Pro Pro Val Leu Asp Ser Asp Gly Ser Phe Phe Leu Tyr Ser Arg Leu
           180                 185                 190

Thr Val Asp Lys Ser Arg Trp Gln Glu Gly Asn Val Phe Ser Cys Ser
       195                 200                 205

Val Met His Glu Ala Leu His Asn His Tyr Thr Gln Lys Ser Leu Ser
210                 215                 220

Leu Ser Leu Gly Ala Gly Gly Gly Ser Gly Gly Gly Gly Ser Gly
225                 230                 235                 240

Gly Gly Gly Ser Ile Thr Cys Pro Pro Met Ser Val Glu His Ala
               245                 250                 255

Asp Ile Trp Val Lys Ser Tyr Ser Leu Tyr Ser Arg Glu Arg Tyr Ile
               260                 265                 270

Cys Asn Ser Gly Phe Lys Arg Lys Ala Gly Thr Ser Ser Leu Thr Glu
       275                 280                 285

Cys Val Leu Asn Lys Ala Thr Asn Val Ala His Trp Thr Thr Pro Ser
       290                 295                 300

Leu Lys Cys Ile Arg Gly Gly Ser Gly Gly Gly Ser Gly Gly Gly
305                 310                 315                 320

Ser Gly Gly Gly Gly Ser Asn Trp Val Asn Val Ile Ser Asp Leu Lys
               325                 330                 335

Lys Ile Glu Asp Leu Ile Gln Ser Met His Ile Asp Ala Thr Leu Tyr
           340                 345                 350

Thr Glu Ser Asp Val His Pro Ser Cys Lys Val Thr Ala Met Lys Cys
       355                 360                 365

Phe Leu Leu Glu Leu Gln Val Ile Ser Leu Glu Ser Gly Asp Ala Ser
       370                 375                 380

Ile His Asp Thr Val Glu Asp Leu Ile Ile Leu Ala Asn Asn Ser Leu
385                 390                 395                 400

Ser Ser Asn Gly Asn Val Thr Glu Ser Gly Cys Lys Glu Cys Glu Glu
               405                 410                 415

Leu Glu Glu Lys Asn Ile Lys Glu Phe Leu Gln Ser Phe Val His Ile
           420                 425                 430

Val Gln Met Phe Ile Asn Thr Ser
           435                 440

<210> SEQ ID NO 83
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 83

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Ala Gly Gly Gly Ser Gly Gly Gly Ser Gly
225                 230                 235                 240

Gly Gly Gly Ser Ile Thr Cys Pro Pro Met Ser Val Glu His Ala
                245                 250                 255

Asp Ile Trp Val Lys Ser Tyr Ser Leu Tyr Ser Arg Glu Arg Tyr Ile
                260                 265                 270

Cys Asn Ser Gly Phe Lys Arg Lys Ala Gly Thr Ser Ser Leu Thr Glu
            275                 280                 285

Cys Val Leu Asn Lys Ala Thr Asn Val Ala His Trp Thr Thr Pro Ser
    290                 295                 300

Leu Lys Cys Ile Arg Gly Gly Ser Gly Gly Gly Ser Gly Gly Gly
305                 310                 315                 320

Ser Gly Gly Gly Ser Ala Ala Gly Ser Gly Gly Gly Ser
                325                 330                 335

Gly Gly Gly Ser Gly Gly Gly Ser Asn Trp Val Asn Val Ile Ser
            340                 345                 350

Asp Leu Lys Lys Ile Glu Asp Leu Ile Gln Ser Met His Ile Asp Ala
                355                 360                 365

Thr Leu Tyr Thr Glu Ser Asp Val His Pro Ser Cys Lys Val Thr Ala
    370                 375                 380

Met Lys Cys Phe Leu Leu Glu Leu Gln Val Ile Ser Leu Glu Ser Gly
385                 390                 395                 400

Asp Ala Ser Ile His Asp Thr Val Glu Asp Leu Ile Ile Leu Ala Asn
                405                 410                 415
```

```
Asn Ser Leu Ser Ser Asn Gly Asn Val Thr Glu Ser Gly Cys Lys Glu
            420                 425                 430

Cys Glu Glu Leu Glu Glu Lys Asn Ile Lys Glu Phe Leu Gln Ser Phe
        435                 440                 445

Val His Ile Val Gln Met Phe Ile Asn Thr Ser
    450                 455

<210> SEQ ID NO 84
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Ala Gly Gly Gly Ser Gly Gly Gly Ser Gly
225                 230                 235                 240

Gly Gly Gly Ser Ile Thr Cys Pro Pro Met Ser Val Glu His Ala
            245                 250                 255

Asp Ile Trp Val Lys Ser Tyr Ser Leu Tyr Ser Arg Glu Arg Tyr Ile
            260                 265                 270

Cys Asn Ser Gly Phe Lys Arg Lys Ala Gly Thr Ser Ser Leu Thr Glu
        275                 280                 285

Cys Val Leu Asn Lys Ala Thr Asn Val Ala His Trp Thr Thr Pro Ser
    290                 295                 300

Leu Lys Cys Ile Arg Gly Gly Ser Gly Gly Gly Ser Gly Gly Gly
```

```
                305                 310                 315                 320
Ser Gly Gly Gly Gly Ser Asn Trp Val Asn Val Ile Ser Asp Leu Lys
                    325                 330                 335

Lys Ile Glu Asp Leu Ile Gln Ser Met His Ile Asp Ala Thr Leu Tyr
                340                 345                 350

Thr Glu Ser Asp Val His Pro Ser Cys Lys Val Thr Ala Met Lys Cys
                355                 360                 365

Phe Leu Leu Glu Leu Gln Val Ile Ser Leu Glu Ser Gly Asp Ala Ser
            370                 375                 380

Ile His Asp Thr Val Glu Asn Leu Ile Ile Leu Ala Asn Asn Ser Leu
385                 390                 395                 400

Ser Ser Asn Gly Asn Val Thr Glu Ser Gly Cys Lys Glu Cys Glu Glu
                405                 410                 415

Leu Glu Glu Lys Asn Ile Lys Glu Phe Leu Gln Ser Phe Val His Ile
            420                 425                 430

Val Glu Met Phe Ile Asn Thr Ser
            435                 440

<210> SEQ ID NO 85
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

-continued

Leu Ser Leu Gly Ala Gly Gly Ser Gly Gly Gly Ser Gly Gly Gly
225                 230                 235                 240

Ser Gly Gly Gly Ser Asn Trp Val Asn Val Ile Ser Asp Leu Lys
            245                 250                 255

Lys Ile Glu Asp Leu Ile Gln Ser Met His Ile Asp Ala Thr Leu Tyr
        260                 265                 270

Thr Glu Ser Asp Val His Pro Ser Cys Lys Val Thr Ala Met Lys Cys
        275                 280                 285

Phe Leu Leu Lys Leu Gln Val Ile Ser Leu Glu Ser Gly Asp Ala Ser
        290                 295                 300

Ile His Asp Thr Val Glu Asn Leu Ile Ile Leu Ala Asn Asn Ser Leu
305                 310                 315                 320

Ser Ser Asn Gly Asn Val Thr Glu Ser Gly Cys Lys Glu Cys Glu Glu
            325                 330                 335

Leu Glu Glu Lys Asn Ile Lys Glu Phe Leu Gln Ser Phe Val His Ile
            340                 345                 350

Val Gln Met Phe Ile Asn Thr Ser
            355                 360

<210> SEQ ID NO 86
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

-continued

Leu Ser Leu Gly Ala Gly Gly Ser Gly Gly Gly Ser Gly Gly
225                 230                 235                 240

Ser Gly Gly Gly Ser Asn Trp Val Asn Val Ile Ser Asp Leu Lys
            245                 250                 255

Lys Ile Glu Asp Leu Ile Gln Ser Met His Ile Asp Ala Thr Leu Tyr
            260                 265                 270

Thr Glu Ser Asp Val His Pro Ser Cys Lys Val Thr Ala Met Lys Cys
            275                 280                 285

Phe Leu Leu Lys Leu Gln Val Ile Ser Leu Glu Ser Gly Asp Ala Ser
            290                 295                 300

Ile His Asp Thr Val Glu Asp Leu Ile Ile Leu Ala Asn Asn Ser Leu
305                 310                 315                 320

Ser Ser Asn Gly Asn Val Thr Glu Ser Gly Cys Lys Glu Cys Glu Glu
                325                 330                 335

Leu Glu Glu Lys Asn Ile Lys Glu Phe Leu Gln Ser Phe Val His Ile
                340                 345                 350

Val Gln Met Phe Ile Asn Thr Ser
                355                 360

<210> SEQ ID NO 87
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser

```
                210                 215                 220
Leu Ser Leu Gly Ala Gly Gly Gly Ser Val His Met Pro Leu Gly
225                 230                 235                 240

Phe Leu Gly Pro Arg Gln Ala Arg Val Val Asn Gly Gly Gly Gly
                245                 250                 255

Ser Gly Gly Gly Gly Ser Gly Gly Gly Ser Ala Val Asn Gly Thr
                260                 265                 270

Ser Gln Phe Thr Cys Phe Tyr Asn Ser Arg Ala Asn Ile Ser Cys Val
        275                 280                 285

Trp Ser Gln Asp Gly Ala Leu Gln Asp Thr Ser Cys Gln Val His Ala
    290                 295                 300

Trp Pro Asp Arg Arg Arg Trp Asn Gln Thr Cys Glu Leu Leu Pro Val
305                 310                 315                 320

Ser Gln Ala Ser Trp Ala Cys Asn Leu Ile Leu Gly Ala Pro Asp Ser
                325                 330                 335

Gln Lys Leu Thr Thr Val Asp Ile Val Thr Leu Arg Val Leu Cys Arg
                340                 345                 350

Glu Gly Val Arg Trp Arg Val Met Ala Ile Gln Asp Phe Lys Pro Phe
        355                 360                 365

Glu Asn Leu Arg Leu Met Ala Pro Ile Ser Leu Gln Val Val His Val
    370                 375                 380

Glu Thr His Arg Cys Asn Ile Ser Trp Glu Ile Ser Gln Ala Ser His
385                 390                 395                 400

Tyr Phe Glu Arg His Leu Glu Phe Glu Ala Arg Thr Leu Ser Pro Gly
                405                 410                 415

His Thr Trp Glu Glu Ala Pro Leu Leu Thr Leu Lys Gln Lys Gln Glu
                420                 425                 430

Trp Ile Cys Leu Glu Thr Leu Thr Pro Asp Thr Gln Tyr Glu Phe Gln
        435                 440                 445

Val Arg Val Lys Pro Leu Gln Gly Glu Phe Thr Thr Trp Ser Pro Trp
    450                 455                 460

Ser Gln Pro Leu Ala Phe Arg Thr Lys Pro Ala Ala Leu Gly Lys Asp
465                 470                 475                 480

Thr

<210> SEQ ID NO 88
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
```

```
                 85                   90                  95
Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 89
<211> LENGTH: 449
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 89

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 91
<211> LENGTH: 385
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 91

```
Gly His Ile Tyr Tyr Ser Gly Asn Thr Asn Tyr Asn Pro Ser Leu Lys
1               5                   10                  15
Ser Arg Leu Thr Ile Ser Ile Asp Thr Ser Lys Thr Gln Phe Ser Leu
                20                  25                  30
Lys Leu Ser Ser Val Thr Ala Ala Asp Thr Ala Ile Tyr Tyr Cys Val
            35                  40                  45
Arg Asp Arg Val Thr Gly Ala Phe Asp Ile Trp Gly Gln Gly Thr Met
    50                  55                  60
Val Thr Val Ser Ser Ala Ser Thr Lys Gly Pro Ser Val Phe Pro Leu
65                  70                  75                  80
Ala Pro Cys Ser Arg Ser Thr Ser Glu Ser Thr Ala Ala Leu Gly Cys
                85                  90                  95
Leu Val Lys Asp Tyr Phe Pro Glu Pro Val Thr Val Ser Trp Asn Ser
            100                 105                 110
Gly Ala Leu Thr Ser Gly Val His Thr Phe Pro Ala Val Leu Gln Ser
        115                 120                 125
Ser Gly Leu Tyr Ser Leu Ser Ser Val Val Thr Val Pro Ser Ser Asn
    130                 135                 140
Phe Gly Thr Gln Thr Tyr Thr Cys Asn Val Asp His Lys Pro Ser Asn
145                 150                 155                 160
Thr Lys Val Asp Glu Arg Lys Cys Cys Val Glu Cys Pro Ala Gly Pro
                165                 170                 175
Ser Val Phe Leu Phe Pro Pro Lys Pro Lys Asp Thr Leu Met Ile Ser
            180                 185                 190
Arg Thr Pro Glu Val Thr Cys Val Val Val Asp Val Ser His Glu Asp
        195                 200                 205
Pro Glu Val Gln Phe Asn Trp Tyr Val Asp Gly Val Glu Val His Asn
    210                 215                 220
Ala Lys Thr Lys Pro Arg Glu Glu Gln Phe Asn Ser Thr Phe Arg Val
225                 230                 235                 240
Val Ser Val Leu Thr Val Val His Gln Asp Trp Leu Asn Gly Lys Glu
                245                 250                 255
Tyr Lys Cys Lys Val Ser Asn Lys Gly Leu Pro Ala Pro Ile Glu Lys
            260                 265                 270
```

```
Thr Ile Ser Lys Thr Lys Gly Gln Pro Arg Glu Pro Gln Val Tyr Thr
            275                 280                 285

Leu Pro Pro Ser Arg Glu Glu Met Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
                325                 330                 335

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
        370                 375                 380

Lys
385

<210> SEQ ID NO 92
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Val Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Arg Arg Val Glu Ala Glu Asp Val Gly Val Tyr Tyr Cys Met Gln Asn
                85                  90                  95

Leu Glu Tyr Pro Phe Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 93
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Gln Gln Ser Gly Pro Glu Leu Val Lys Ser Gly Ala
1               5                   10                  15

Ser Val Lys Met Ser Cys Lys Ala Ser Gly Asn Thr Leu Lys Asp Asp
                20                  25                  30

His Val His Trp Val Lys Gln Arg Pro Gly Gln Gly Leu Glu Trp Ile
            35                  40                  45

Gly Trp Ile Tyr Pro Gly Gly Arg Thr Arg Tyr Asn Glu Lys Phe
    50                  55                  60

Lys Gly Lys Thr Thr Leu Thr Ala Asp Lys Pro Ser Ser Thr Val Asn
65                  70                  75                  80

Met Leu Leu Ser Ser Leu Thr Ser Glu Asp Ser Ala Ile Tyr Phe Cys
                85                  90                  95

Thr Asn Leu Val Phe Asp Val Trp Gly Ala Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 94
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 95
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

His Tyr Thr Gln Lys Ser Leu Ser Leu Ser Pro Gly Lys
        435                 440                 445

<210> SEQ ID NO 96
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Lys Gln Ser Pro Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Trp Thr Val Ser Ser
        115                 120

<210> SEQ ID NO 97
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 98
<211> LENGTH: 107
<212> TYPE: PRT

<213> ORGANISM: Artificial Sequence
<220> FEATURE:
<223> OTHER INFORMATION: Description of Artificial Sequence: Synthetic
       polypeptide

<400> SEQUENCE: 98

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Ser Tyr Thr Ser Ser Arg Tyr Ala Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 99

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Thr Ser Ser Arg Tyr Ala Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 100

Thr Tyr Trp Ile Gly
1               5

<210> SEQ ID NO 101
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 101

Ile Ile Tyr Pro Gly Asp Ser Asp Thr Arg Tyr Ser Pro Ser Phe Gln
1               5                   10                  15

Gly

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Asn Trp Asn Cys Phe Asp Tyr
1               5

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Gln Ser Val Ser Ser Ser Tyr Leu Ala
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ala Ser Arg Arg Ala Thr
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Arg Tyr Gly Ser Ser His Thr
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Asn Trp Asn Ser Phe Asp Tyr
```

<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser
        115

<210> SEQ ID NO 108
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Ile Val Leu Thr Gln Ser Pro Gly Thr Leu Ser Leu Ser Pro Gly
1               5                   10                  15

Arg Glu Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser Arg Thr Val Ala Ala
            100                 105                 110

Pro Ser Val Phe Ile Phe Pro
        115

<210> SEQ ID NO 109
<211> LENGTH: 241
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 109

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Leu Thr Gln Ser Pro Gly Thr Leu
130                 135                 140

Ser Leu Ser Pro Gly Arg Glu Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Arg Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Arg
    210                 215                 220

Tyr Gly Ser Ser His Thr Phe Gly Gln Gly Thr Lys Leu Glu Ile Ser
225                 230                 235                 240

Arg

<210> SEQ ID NO 110
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Ile Val Leu Thr Gln Ser Pro Gly Thr Leu Ser Leu Ser Pro Gly
1               5                   10                  15

Arg Glu Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

```
Thr Phe Gly Gln Gly Thr Lys Leu Glu Ile Ser Arg Gly Gly Gly
                100                 105                 110

Ser Gly Gly Gly Gly Ser Gly Gly Gly Ser Glu Val Gln Leu Val
            115                 120                 125

Gln Ser Gly Ala Glu Val Lys Lys Pro Gly Glu Ser Leu Lys Ile Ser
130                 135                 140

Cys Lys Val Ser Gly Tyr Phe Phe Thr Thr Tyr Trp Ile Gly Trp Val
145                 150                 155                 160

Arg Gln Met Pro Gly Lys Gly Leu Glu Tyr Met Gly Ile Ile Tyr Pro
                165                 170                 175

Gly Asp Ser Asp Thr Arg Tyr Ser Pro Ser Phe Gln Gly Gln Val Thr
            180                 185                 190

Ile Ser Ala Asp Lys Ser Ile Ser Thr Ala Tyr Leu Gln Trp Ser Ser
        195                 200                 205

Leu Lys Ala Ser Asp Thr Ala Met Tyr Tyr Cys Ala Arg Gly Gly Asn
    210                 215                 220

Trp Asn Cys Phe Asp Tyr Trp Gly Gln Gly Thr Leu Val Thr Val Ser
225                 230                 235                 240

Ser

<210> SEQ ID NO 111
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Cys Thr Leu Pro Pro Ser Arg Glu Glu Met Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Val Ser Lys Leu Thr
        195                 200                 205
```

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Pro
        245                 250                 255

Leu Gly Val Arg Gly Gly Gly Ser Gly Gly Gly Ser Glu Val
        260                 265                 270

Gln Leu Val Gln Ser Gly Ala Glu Val Lys Lys Pro Gly Glu Ser Leu
        275                 280                 285

Lys Ile Ser Cys Lys Val Ser Gly Tyr Phe Phe Thr Thr Tyr Trp Ile
290                 295                 300

Gly Trp Val Arg Gln Met Pro Gly Lys Gly Leu Glu Tyr Met Gly Ile
305                 310                 315                 320

Ile Tyr Pro Gly Asp Ser Asp Thr Arg Tyr Ser Pro Ser Phe Gln Gly
                325                 330                 335

Gln Val Thr Ile Ser Ala Asp Lys Ser Ile Ser Thr Ala Tyr Leu Gln
                340                 345                 350

Trp Ser Ser Leu Lys Ala Ser Asp Thr Ala Met Tyr Tyr Cys Ala Arg
        355                 360                 365

Gly Gly Asn Trp Asn Cys Phe Asp Tyr Trp Gly Gln Gly Thr Leu Val
        370                 375                 380

Thr Val Ser Ser Gly Gly Gly Ser Gly Gly Gly Ser Gly Gly
385                 390                 395                 400

Gly Gly Ser Gly Ile Val Leu Thr Gln Ser Pro Gly Thr Leu Ser Leu
                405                 410                 415

Ser Pro Gly Glu Arg Ala Thr Leu Ser Cys Arg Ala Ser Gln Ser Val
        420                 425                 430

Ser Ser Ser Tyr Leu Ala Trp Tyr Gln Gln Lys Pro Gly Gln Ala Pro
        435                 440                 445

Arg Leu Leu Ile Tyr Gly Ala Ser Arg Arg Ala Thr Gly Ile Pro Asp
        450                 455                 460

Arg Phe Ser Gly Ser Gly Ser Gly Thr Asp Phe Thr Leu Thr Ile Ser
465                 470                 475                 480

Arg Leu Glu Pro Glu Asp Phe Ala Val Tyr Tyr Cys Gln Arg Tyr Gly
                485                 490                 495

Ser Ser His Thr Phe Gly Gln Gly Thr Lys Leu Glu Ile Ser
        500                 505                 510

<210> SEQ ID NO 112
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
                20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser

-continued

```
                50                  55                  60
His Glu Asp Pro Glu Val Lys Phe Asn Trp Tyr Val Asp Gly Val Glu
 65                  70                  75                  80

Val His Asn Ala Lys Thr Lys Pro Arg Glu Glu Gln Tyr Asn Ser Thr
                 85                  90                  95

Tyr Arg Val Val Ser Val Leu Thr Val Leu His Gln Asp Trp Leu Asn
                100                 105                 110

Gly Lys Glu Tyr Lys Cys Lys Val Ser Asn Lys Ala Leu Pro Ala Pro
                115                 120                 125

Ile Glu Lys Thr Ile Ser Lys Ala Lys Gly Gln Pro Arg Glu Pro Gln
130                 135                 140

Val Cys Thr Leu Pro Pro Ser Arg Glu Glu Met Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
                180                 185                 190

Pro Val Leu Asp Ser Asp Gly Ser Phe Phe Leu Val Ser Lys Leu Thr
                195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Pro
                245                 250                 255

Leu Gly Val Arg Gly Gly Gly Ser Gly Gly Gly Ser Gly Ile
                260                 265                 270

Val Leu Thr Gln Ser Pro Gly Thr Leu Ser Leu Ser Pro Gly Glu Arg
                275                 280                 285

Ala Thr Leu Ser Cys Arg Ala Ser Gln Ser Val Ser Ser Ser Tyr Leu
                290                 295                 300

Ala Trp Tyr Gln Gln Lys Pro Gly Gln Ala Pro Arg Leu Leu Ile Tyr
305                 310                 315                 320

Gly Ala Ser Arg Arg Ala Thr Gly Ile Pro Asp Arg Phe Ser Gly Ser
                325                 330                 335

Gly Ser Gly Thr Asp Phe Thr Leu Thr Ile Ser Arg Leu Glu Pro Glu
                340                 345                 350

Asp Phe Ala Val Tyr Tyr Cys Gln Arg Tyr Gly Ser Ser His Thr Phe
                355                 360                 365

Gly Gln Gly Thr Lys Leu Glu Ile Ser Gly Gly Gly Ser Gly Gly
                370                 375                 380

Gly Gly Ser Gly Gly Gly Ser Glu Val Gln Leu Val Gln Ser Gly
385                 390                 395                 400

Ala Glu Val Lys Lys Pro Gly Glu Ser Leu Lys Ile Ser Cys Lys Val
                405                 410                 415

Ser Gly Tyr Phe Phe Thr Thr Tyr Trp Ile Gly Trp Val Arg Gln Met
                420                 425                 430

Pro Gly Lys Gly Leu Glu Tyr Met Gly Ile Ile Tyr Pro Gly Asp Ser
                435                 440                 445

Asp Thr Arg Tyr Ser Pro Ser Phe Gln Gly Gln Val Thr Ile Ser Ala
                450                 455                 460

Asp Lys Ser Ile Ser Thr Ala Tyr Leu Gln Trp Ser Ser Leu Lys Ala
465                 470                 475                 480
```

```
Ser Asp Thr Ala Met Tyr Tyr Cys Ala Arg Gly Gly Asn Trp Asn Cys
            485                 490                 495

Phe Asp Tyr Trp Gly Gln Gly Thr Leu Val Thr Val Ser Ser
            500                 505                 510

<210> SEQ ID NO 113
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
130                 135                 140

Val Cys Thr Leu Pro Pro Ser Arg Asp Glu Leu Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Val Ser Lys Leu Thr
        195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Pro Leu Gly Val Arg Gly
                245                 250                 255

Gly Gly Gly Ser Gly Gly Gly Ser Ala Val Asn Gly Thr Ser Gln
            260                 265                 270

Phe Thr Cys Phe Tyr Asn Ser Arg Ala Asn Ile Ser Cys Val Trp Ser
        275                 280                 285

Gln Asp Gly Ala Leu Gln Asp Thr Ser Cys Gln Val His Ala Trp Pro
        290                 295                 300

Asp Arg Arg Arg Trp Asn Gln Thr Cys Glu Leu Leu Pro Val Ser Gln
305                 310                 315                 320

Ala Ser Trp Ala Cys Asn Leu Ile Leu Gly Ala Pro Asp Ser Gln Lys
```

```
                  325                 330                 335
Leu Thr Thr Val Asp Ile Val Thr Leu Arg Val Leu Cys Arg Glu Gly
            340                 345                 350
Val Arg Trp Arg Val Met Ala Ile Gln Asp Phe Lys Pro Phe Glu Asn
            355                 360                 365
Leu Arg Leu Met Ala Pro Ile Ser Leu Gln Val Val His Val Glu Thr
370                 375                 380
His Arg Cys Asn Ile Ser Trp Glu Ile Ser Gln Ala Ser His Tyr Phe
385                 390                 395                 400
Glu Arg His Leu Glu Phe Glu Ala Arg Thr Leu Ser Pro Gly His Thr
                405                 410                 415
Trp Glu Glu Ala Pro Leu Leu Thr Leu Lys Gln Lys Gln Glu Trp Ile
            420                 425                 430
Cys Leu Glu Thr Leu Thr Pro Asp Thr Gln Tyr Glu Phe Gln Val Arg
            435                 440                 445
Val Lys Pro Leu Gln Gly Glu Phe Thr Thr Trp Ser Pro Trp Ser Gln
450                 455                 460
Pro Leu Ala Phe Arg Thr Lys Pro Ala Ala Leu Gly Lys Asp Thr Gly
465                 470                 475                 480
Gly Gly Gly Ser Gly Gly Gly Ser Gly Gly Gly Ser Gly Gly Gly Gly
                485                 490                 495
Gly Gly Ser Gly Gly Gly Gly Ser Gly Gly Gly Ser Gly Gly Gly Gly
            500                 505                 510
Gly Ser Gly Gly Gly Gly Ser Pro Leu Pro Glu Val Gln Cys Phe Val
        515                 520                 525
Phe Asn Val Glu Tyr Met Asn Cys Thr Trp Asn Ser Ser Ser Glu Pro
530                 535                 540
Gln Pro Thr Asn Leu Thr Leu His Tyr Trp Tyr Lys Asn Ser Asp Asn
545                 550                 555                 560
Asp Lys Val Gln Lys Cys Ser His Tyr Leu Phe Ser Glu Glu Ile Thr
                565                 570                 575
Ser Gly Cys Gln Leu Gln Lys Lys Glu Ile His Leu Tyr Gln Thr Phe
            580                 585                 590
Val Val Gln Leu Gln Asp Pro Arg Glu Pro Arg Arg Gln Ala Thr Gln
        595                 600                 605
Met Leu Lys Leu Gln Asn Leu Val Ile Pro Trp Ala Pro Glu Asn Leu
        610                 615                 620
Thr Leu His Lys Leu Ser Glu Ser Gln Leu Glu Leu Asn Trp Asn Asn
625                 630                 635                 640
Arg Phe Leu Asn His Cys Leu Glu His Leu Val Gln Tyr Arg Thr Asp
                645                 650                 655
Trp Asp His Ser Trp Thr Glu Gln Ser Val Asp Tyr Arg His Lys Phe
            660                 665                 670
Ser Leu Pro Ser Val Asp Gly Gln Lys Arg Tyr Thr Phe Arg Val Arg
            675                 680                 685
Ser Arg Phe Asn Pro Leu Cys Gly Ser Ala Gln His Trp Ser Glu Trp
        690                 695                 700
Ser His Pro Ile His Trp
705                 710

<210> SEQ ID NO 114
<211> LENGTH: 710
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 114

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
            85                  90                  95

Tyr Arg Val Val Ser Val Leu Thr Val Leu His Gln Asp Trp Leu Asn
        100                 105                 110

Gly Lys Glu Tyr Lys Cys Lys Val Ser Asn Lys Ala Leu Pro Ala Pro
    115                 120                 125

Ile Glu Lys Thr Ile Ser Lys Ala Lys Gly Gln Pro Arg Glu Pro Gln
130                 135                 140

Val Cys Thr Leu Pro Pro Ser Arg Asp Glu Leu Thr Lys Asn Gln Val
145                 150                 155                 160

Ser Leu Ser Cys Ala Val Lys Gly Phe Tyr Pro Ser Asp Ile Ala Val
            165                 170                 175

Glu Trp Glu Ser Asn Gly Gln Pro Glu Asn Asn Tyr Lys Thr Thr Pro
        180                 185                 190

Pro Val Leu Asp Ser Asp Gly Ser Phe Phe Leu Val Ser Lys Leu Thr
    195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Pro Leu Gly Val Arg Gly
            245                 250                 255

Gly Gly Gly Ser Gly Gly Gly Ser Pro Leu Pro Glu Val Gln Cys
        260                 265                 270

Phe Val Phe Asn Val Glu Tyr Met Asn Cys Thr Trp Asn Ser Ser Ser
    275                 280                 285

Glu Pro Gln Pro Thr Asn Leu Thr Leu His Tyr Trp Tyr Lys Asn Ser
290                 295                 300

Asp Asn Asp Lys Val Gln Lys Cys Ser His Tyr Leu Phe Ser Glu Glu
305                 310                 315                 320

Ile Thr Ser Gly Cys Gln Leu Gln Lys Lys Glu Ile His Leu Tyr Gln
            325                 330                 335

Thr Phe Val Val Gln Leu Gln Asp Pro Arg Glu Pro Arg Arg Gln Ala
        340                 345                 350

Thr Gln Met Leu Lys Leu Gln Asn Leu Val Ile Pro Trp Ala Pro Glu
    355                 360                 365

Asn Leu Thr Leu His Lys Leu Ser Glu Ser Gln Leu Glu Leu Asn Trp
370                 375                 380

Asn Asn Arg Phe Leu Asn His Cys Leu Glu His Leu Val Gln Tyr Arg

```
             385                 390                 395                 400
Thr Asp Trp Asp His Ser Trp Thr Glu Gln Ser Val Asp Tyr Arg His
                405                 410                 415
Lys Phe Ser Leu Pro Ser Val Asp Gly Gln Lys Arg Tyr Thr Phe Arg
                420                 425                 430
Val Arg Ser Arg Phe Asn Pro Leu Cys Gly Ser Ala Gln His Trp Ser
                435                 440                 445
Glu Trp Ser His Pro Ile His Trp Gly Gly Gly Ser Gly Gly Gly
                450                 455                 460
Gly Ser Gly Gly Gly Ser Gly Gly Gly Ser Gly Gly Gly Gly
465                 470                 475                 480
Ser Gly Gly Gly Ser Gly Gly Gly Ser Gly Gly Gly Ser
                485                 490                 495
Ala Val Asn Gly Thr Ser Gln Phe Thr Cys Phe Tyr Asn Ser Arg Ala
                500                 505                 510
Asn Ile Ser Cys Val Trp Ser Gln Asp Gly Ala Leu Gln Asp Thr Ser
                515                 520                 525
Cys Gln Val His Ala Trp Pro Asp Arg Arg Arg Trp Asn Gln Thr Cys
                530                 535                 540
Glu Leu Leu Pro Val Ser Gln Ala Ser Trp Ala Cys Asn Leu Ile Leu
545                 550                 555                 560
Gly Ala Pro Asp Ser Gln Lys Leu Thr Thr Val Asp Ile Val Thr Leu
                565                 570                 575
Arg Val Leu Cys Arg Glu Gly Val Arg Trp Arg Val Met Ala Ile Gln
                580                 585                 590
Asp Phe Lys Pro Phe Glu Asn Leu Arg Leu Met Ala Pro Ile Ser Leu
                595                 600                 605
Gln Val Val His Val Glu Thr His Arg Cys Asn Ile Ser Trp Glu Ile
                610                 615                 620
Ser Gln Ala Ser His Tyr Phe Glu Arg His Leu Glu Phe Glu Ala Arg
625                 630                 635                 640
Thr Leu Ser Pro Gly His Thr Trp Glu Glu Ala Pro Leu Leu Thr Leu
                645                 650                 655
Lys Gln Lys Gln Glu Trp Ile Cys Leu Glu Thr Leu Thr Pro Asp Thr
                660                 665                 670
Gln Tyr Glu Phe Gln Val Arg Val Lys Pro Leu Gln Gly Glu Phe Thr
                675                 680                 685
Thr Trp Ser Pro Trp Ser Gln Pro Leu Ala Phe Arg Thr Lys Pro Ala
                690                 695                 700
Ala Leu Gly Lys Asp Thr
705                 710

<210> SEQ ID NO 115
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Gly Val Lys Val Leu Phe Ala Leu Ile Cys Ile Ala Val Ala Glu
1               5                   10                  15
Ala Asp Lys Thr His Thr Cys Pro Pro Cys Pro Ala Pro Glu Ala Ala
                20                  25                  30
```

Gly Gly Pro Ser Val Phe Leu Phe Pro Pro Lys Pro Lys Asp Thr Leu
            35                  40                  45
Met Ile Ser Arg Thr Pro Glu Val Thr Cys Val Val Val Asp Val Ser
 50                  55                  60
His Glu Asp Pro Glu Val Lys Phe Asn Trp Tyr Val Asp Gly Val Glu
 65                  70                  75                  80
Val His Asn Ala Lys Thr Lys Pro Arg Glu Glu Gln Tyr Asn Ser Thr
                 85                  90                  95
Tyr Arg Val Val Ser Val Leu Thr Val Leu His Gln Asp Trp Leu Asn
                100                 105                 110
Gly Lys Glu Tyr Lys Cys Lys Val Ser Asn Lys Ala Leu Pro Ala Pro
            115                 120                 125
Ile Glu Lys Thr Ile Ser Lys Ala Lys Gly Gln Pro Arg Glu Pro Gln
130                 135                 140
Val Cys Thr Leu Pro Pro Ser Arg Asp Glu Leu Thr Lys Asn Gln Val
145                 150                 155                 160
Ser Leu Ser Cys Ala Val Lys Gly Phe Tyr Pro Ser Asp Ile Ala Val
                165                 170                 175
Glu Trp Glu Ser Asn Gly Gln Pro Glu Asn Asn Tyr Lys Thr Thr Pro
            180                 185                 190
Pro Val Leu Asp Ser Asp Gly Ser Phe Phe Leu Val Ser Lys Leu Thr
            195                 200                 205
Val Asp Lys Ser Arg Trp Gln Gln Gly Asn Val Phe Ser Cys Ser Val
        210                 215                 220
Met His Glu Ala Leu His Asn His Tyr Thr Gln Lys Ser Leu Ser Leu
225                 230                 235                 240
Ser Pro Gly Ala Gly Gly Gly Ser Gly Pro Leu Gly Val Arg Gly
                245                 250                 255
Gly Gly Gly Ser Gly Gly Gly Ser Ala Val Asn Gly Thr Ser Gln
            260                 265                 270
Phe Thr Cys Phe Tyr Asn Ser Arg Ala Asn Ile Ser Cys Val Trp Ser
            275                 280                 285
Gln Asp Gly Ala Leu Gln Asp Thr Ser Cys Gln Val His Ala Trp Pro
        290                 295                 300
Asp Arg Arg Arg Trp Asn Gln Thr Cys Glu Leu Leu Pro Val Ser Gln
305                 310                 315                 320
Ala Ser Trp Ala Cys Asn Leu Ile Leu Gly Ala Pro Asp Ser Gln Lys
                325                 330                 335
Leu Thr Thr Val Asp Ile Val Thr Leu Arg Val Leu Cys Arg Glu Gly
            340                 345                 350
Val Arg Trp Arg Val Met Ala Ile Gln Asp Phe Lys Pro Phe Glu Asn
        355                 360                 365
Leu Arg Leu Met Ala Pro Ile Ser Leu Gln Val Val His Val Glu Thr
370                 375                 380
His Arg Cys Asn Ile Ser Trp Glu Ile Ser Gln Ala Ser His Tyr Phe
385                 390                 395                 400
Glu Arg His Leu Glu Phe Glu Ala Arg Thr Leu Ser Pro Gly His Thr
                405                 410                 415
Trp Glu Glu Ala Pro Leu Leu Thr Leu Lys Gln Lys Gln Glu Trp Ile
            420                 425                 430
Cys Leu Glu Thr Leu Thr Pro Asp Thr Gln Tyr Glu Phe Gln Val Arg
        435                 440                 445
Val Lys Pro Leu Gln Gly Glu Phe Thr Thr Trp Ser Pro Trp Ser Gln

```
                    450                 455                 460
Pro Leu Ala Phe Arg Thr Lys Pro Ala Ala Leu Gly Lys Asp Thr Gly
465                 470                 475                 480

Gly Gly Gly Ser Gly Gly Gly Ser Gly Gly Gly Ser Gly Gly
                485                 490                 495

Gly Gly Ser Gly Gly Gly Ser Gly Gly Gly Ser Gly Gly
            500                 505                 510

Gly Ser Gly Gly Gly Ser Ala Pro Glu Asn Leu Thr Leu His Lys
        515                 520                 525

Leu Ser Glu Ser Gln Leu Glu Leu Asn Trp Asn Asn Arg Phe Leu Asn
        530                 535                 540

His Cys Leu Glu His Leu Val Gln Tyr Arg Thr Asp Trp Asp His Ser
545                 550                 555                 560

Trp Thr Glu Gln Ser Val Asp Tyr Arg His Lys Phe Ser Leu Pro Ser
                565                 570                 575

Val Asp Gly Gln Lys Arg Tyr Thr Phe Arg Val Arg Ser Arg Phe Asn
            580                 585                 590

Pro Leu Cys Gly Ser Ala Gln His Trp Ser Glu Trp Ser His Pro Ile
        595                 600                 605

His Trp
    610

<210> SEQ ID NO 116
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Cys Arg Glu Glu Met Thr Lys Asn Gln Val
145                 150                 155                 160

Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190
```

```
Pro Val Leu Asp Ser Asp Gly Ser Phe Phe Leu Tyr Ser Lys Leu Thr
            195                 200                 205

Val Asp Lys Ser Arg Trp Gln Gln Gly Asn Val Phe Ser Cys Ser Val
210                 215                 220

Met His Glu Ala Leu His Asn Arg Phe Thr Gln Lys Ser Leu Ser Leu
225                 230                 235                 240

Ser Pro Gly Lys Gly Gly Gly Ser Gly Gly Gly Ser Gly Gly
                245                 250                 255

Gly Gly Ser Ile Thr Cys Pro Pro Met Ser Val Glu His Ala Asp
            260                 265                 270

Ile Trp Val Lys Ser Tyr Ser Leu Tyr Ser Arg Glu Arg Tyr Ile Cys
            275                 280                 285

Asn Ser Gly Phe Lys Arg Lys Ala Gly Thr Ser Ser Leu Thr Glu Cys
290                 295                 300

Val Leu Asn Lys Ala Thr Asn Val Ala His Trp Thr Thr Pro Ser Leu
305                 310                 315                 320

Lys Cys Ile Arg Gly Gly Ser Gly Gly Gly Ser Gly Gly Gly Ser
            325                 330                 335

Gly Gly Gly Gly Ser Asn Trp Val Asn Val Ile Ser Asp Leu Lys Lys
            340                 345                 350

Ile Glu Asp Leu Ile Gln Ser Met His Ile Asp Ala Thr Leu Tyr Thr
            355                 360                 365

Glu Ser Asp Val His Pro Ser Cys Lys Val Thr Ala Met Lys Cys Phe
    370                 375                 380

Leu Leu Glu Leu Gln Val Ile Ser Leu Glu Ser Gly Asp Ala Ser Ile
385                 390                 395                 400

His Asp Thr Val Glu Asn Leu Ile Ile Leu Ala Asn Asn Ser Leu Ser
            405                 410                 415

Ser Asn Gly Asn Val Thr Glu Ser Gly Cys Lys Glu Cys Glu Glu Leu
            420                 425                 430

Glu Glu Lys Asn Ile Lys Glu Phe Leu Gln Ser Phe Val His Ile Val
            435                 440                 445

Glu Met Phe Ile Asn Thr Ser
    450                 455

<210> SEQ ID NO 117
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
                20                  25                  30

Gly Gly Pro Ser Val Phe Leu Phe Pro Pro Lys Pro Lys Asp Thr Leu
            35                  40                  45

Met Ile Ser Arg Thr Pro Glu Val Thr Cys Val Val Val Asp Val Ser
50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95
```

```
Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
130                 135                 140

Val Cys Thr Leu Pro Pro Ser Arg Asp Glu Leu Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Val Ser Lys Leu Thr
        195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Gly
                245                 250                 255

Gly Gly Ser Gly Gly Gly Gly Ser Ala Val Asn Gly Thr Ser Gln Phe
            260                 265                 270

Thr Cys Phe Tyr Asn Ser Arg Ala Asn Ile Ser Cys Val Trp Ser Gln
        275                 280                 285

Asp Gly Ala Leu Gln Asp Thr Ser Cys Gln Val His Ala Trp Pro Asp
290                 295                 300

Arg Arg Arg Trp Asn Gln Thr Cys Glu Leu Leu Pro Val Ser Gln Ala
305                 310                 315                 320

Ser Trp Ala Cys Asn Leu Ile Leu Gly Ala Pro Glu Ser Gln Lys Leu
                325                 330                 335

Thr Thr Val Asp Ile Val Thr Leu Arg Val Leu Cys Arg Glu Gly Val
            340                 345                 350

Arg Trp Arg Val Met Ala Ile Gln Asp Phe Lys Pro Phe Glu Asn Leu
        355                 360                 365

Arg Leu Met Ala Pro Ile Ser Leu Gln Val Val His Val Glu Thr His
370                 375                 380

Arg Cys Asn Ile Ser Trp Glu Ile Ser Gln Ala Ser His Tyr Phe Glu
385                 390                 395                 400

Arg His Leu Glu Phe Glu Ala Arg Thr Leu Ser Pro Gly His Thr Trp
                405                 410                 415

Glu Glu Ala Pro Leu Leu Thr Leu Lys Gln Lys Gln Glu Trp Ile Cys
            420                 425                 430

Leu Glu Thr Leu Thr Pro Asp Thr Gln Tyr Glu Phe Gln Val Arg Val
        435                 440                 445

Lys Pro Leu Gln Gly Glu Phe Thr Thr Trp Ser Pro Trp Ser Gln Pro
450                 455                 460

Leu Ala Phe Arg Thr Lys Pro Ala Ala Leu Gly Lys Asp Thr
465                 470                 475

<210> SEQ ID NO 118
<211> LENGTH: 455
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 118

```
Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Cys Arg Glu Glu Met Thr Lys Asn Gln Val
145                 150                 155                 160

Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Gly Gly Gly
                245                 250                 255

Gly Gly Ser Ile Thr Cys Pro Pro Pro Met Ser Val Glu His Ala Asp
            260                 265                 270

Ile Trp Val Lys Ser Tyr Ser Leu Tyr Ser Arg Glu Arg Tyr Ile Cys
        275                 280                 285

Asn Ser Gly Phe Lys Arg Lys Ala Gly Thr Ser Ser Leu Thr Glu Cys
    290                 295                 300

Val Leu Asn Lys Ala Thr Asn Val Ala His Trp Thr Thr Pro Ser Leu
305                 310                 315                 320

Lys Cys Ile Arg Gly Gly Ser Gly Gly Gly Ser Gly Gly Gly Gly Ser
                325                 330                 335

Gly Gly Gly Gly Ser Asn Trp Val Asn Val Ile Ser Asp Leu Lys Lys
            340                 345                 350

Ile Glu Asp Leu Ile Gln Ser Met His Ile Asp Ala Thr Leu Tyr Thr
        355                 360                 365

Glu Ser Asp Val His Pro Ser Cys Lys Val Thr Ala Met Lys Cys Phe
    370                 375                 380

Leu Leu Glu Leu Gln Val Ile Ser Leu Glu Ser Gly Asp Ala Ser Ile
385                 390                 395                 400
```

His Asp Thr Val Glu Asp Leu Ile Ile Leu Ala Asn Ser Leu Ser
            405                 410                 415

Ser Asn Gly Asn Val Thr Glu Ser Gly Cys Lys Glu Cys Glu Leu
        420                 425                 430

Glu Glu Lys Asn Ile Lys Glu Phe Leu Gln Ser Phe Val His Ile Val
            435                 440                 445

Gln Met Phe Ile Asn Thr Ser
    450                 455

<210> SEQ ID NO 119
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Cys Thr Leu Pro Pro Ser Arg Glu Glu Met Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Val Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Ala Gly Gly Gly Ser Val His Met Pro Leu Gly Phe
                245                 250                 255

Leu Gly Pro Arg Gln Ala Arg Val Val Asn Gly Gly Gly Gly Ser
        260                 265                 270

Gly Gly Gly Gly Ser Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln

```
            290                 295                 300
Ser Val Ser Ser Tyr Leu Ala Trp Tyr Gln Gln Lys Pro Gly Gln
305                 310                 315                 320

Ala Pro Arg Leu Leu Ile Tyr Gly Ala Ser Arg Ala Thr Gly Ile
                325                 330                 335

Pro Asp Arg Phe Ser Gly Ser Gly Ser Gly Thr Asp Phe Thr Leu Thr
                340                 345                 350

Ile Ser Arg Leu Glu Pro Glu Asp Phe Ala Val Tyr Tyr Cys Gln Arg
            355                 360                 365

Tyr Gly Ser Ser His Thr Phe Gly Gln Gly Thr Lys Leu Glu Ile Ser
            370                 375                 380

Gly Gly Gly Gly Ser Gly Gly Gly Ser Gly Gly Gly Ser Glu
385                 390                 395                 400

Val Gln Leu Val Gln Ser Gly Ala Glu Val Lys Lys Pro Gly Glu Ser
                405                 410                 415

Leu Lys Ile Ser Cys Lys Val Ser Gly Tyr Phe Phe Thr Thr Tyr Trp
                420                 425                 430

Ile Gly Trp Val Arg Gln Met Pro Gly Lys Gly Leu Glu Tyr Met Gly
            435                 440                 445

Ile Ile Tyr Pro Gly Asp Ser Asp Thr Arg Tyr Ser Pro Ser Phe Gln
            450                 455                 460

Gly Gln Val Thr Ile Ser Ala Asp Lys Ser Ile Ser Thr Ala Tyr Leu
465                 470                 475                 480

Gln Trp Ser Ser Leu Lys Ala Ser Asp Thr Ala Met Tyr Tyr Cys Ala
                485                 490                 495

Arg Gly Gly Asn Trp Asn Cys Phe Asp Tyr Trp Gly Gln Gly Thr Leu
                500                 505                 510

Val Thr Val Ser Ser
            515

<210> SEQ ID NO 120
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
                20                  25                  30

Gly Gly Pro Ser Val Phe Leu Phe Pro Pro Lys Pro Lys Asp Thr Leu
            35                  40                  45

Tyr Ile Thr Arg Glu Pro Glu Val Thr Cys Val Val Val Asp Val Ser
        50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125
```

```
Ile Glu Lys Thr Ile Ser Lys Ala Lys Gly Gln Pro Arg Glu Pro Gln
    130                 135                 140

Val Cys Thr Leu Pro Pro Ser Arg Glu Met Thr Lys Asn Gln Val
145                 150                 155                 160

Ser Leu Ser Cys Ala Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
                180                 185                 190

Pro Val Leu Asp Ser Asp Gly Ser Phe Phe Leu Val Ser Lys Leu Thr
                195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Pro
                245                 250                 255

Leu Gly Val Arg Gly Gly Gly Ser Gly Gly Gly Ser Glu Ile
                260                 265                 270

Val Leu Thr Gln Ser Pro Gly Thr Leu Ser Leu Ser Pro Gly Glu Arg
    275                 280                 285

Ala Thr Leu Ser Cys Arg Ala Ser Gln Ser Val Ser Ser Ser Tyr Leu
    290                 295                 300

Ala Trp Tyr Gln Gln Lys Pro Gly Gln Ala Pro Arg Leu Leu Ile Tyr
305                 310                 315                 320

Gly Ala Ser Arg Arg Ala Thr Gly Ile Pro Asp Arg Phe Ser Gly Ser
                325                 330                 335

Gly Ser Gly Thr Asp Phe Thr Leu Thr Ile Ser Arg Leu Glu Pro Glu
                340                 345                 350

Asp Phe Ala Val Tyr Tyr Cys Gln Arg Tyr Gly Ser Ser His Thr Phe
                355                 360                 365

Gly Gln Gly Thr Lys Leu Glu Ile Ser Gly Gly Gly Ser Gly Gly
    370                 375                 380

Gly Gly Ser Arg Gln Ala Arg Val Val Asn Gly Gly Gly Gly Ser
385                 390                 395                 400

Glu Val Gln Leu Val Gln Ser Gly Ala Glu Val Lys Lys Pro Gly Glu
                405                 410                 415

Ser Leu Lys Ile Ser Cys Lys Val Ser Gly Tyr Phe Phe Thr Thr Tyr
                420                 425                 430

Trp Ile Gly Trp Val Arg Gln Met Pro Gly Lys Gly Leu Glu Tyr Met
                435                 440                 445

Gly Ile Ile Tyr Pro Gly Asp Ser Asp Thr Arg Tyr Ser Pro Ser Phe
450                 455                 460

Gln Gly Gln Val Thr Ile Ser Ala Asp Lys Ser Ile Ser Thr Ala Tyr
465                 470                 475                 480

Leu Gln Trp Ser Ser Leu Lys Ala Ser Asp Thr Ala Met Tyr Tyr Cys
                485                 490                 495

Ala Arg Gly Gly Asn Trp Asn Cys Phe Asp Tyr Trp Gly Gln Gly Thr
                500                 505                 510

Leu Val Thr Val Ser Ser
                515

<210> SEQ ID NO 121
<211> LENGTH: 373
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 121

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Cys Arg Glu Glu Met Thr Lys Asn Gln Val
145                 150                 155                 160

Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Gly Ser Gly Gly Gly
                245                 250                 255

Gly Gly Ser Asn Trp Val Asn Val Ile Ser Asp Leu Lys Lys Ile Glu
            260                 265                 270

Asp Leu Ile Gln Ser Met His Ile Asp Ala Thr Leu Tyr Thr Glu Ser
        275                 280                 285

Asp Val His Pro Ser Cys Lys Val Thr Ala Met Lys Cys Phe Leu Leu
    290                 295                 300

Glu Leu Gln Val Ile Ser Leu Glu Ser Gly Asp Ala Ser Ile His Asp
305                 310                 315                 320

Thr Val Glu Asp Leu Ile Ile Leu Ala Asn Asn Ser Leu Ser Ser Asn
                325                 330                 335

Gly Asn Val Thr Glu Ser Gly Cys Lys Glu Cys Glu Glu Leu Glu Glu
            340                 345                 350

Lys Asn Ile Lys Glu Phe Leu Gln Ser Phe Val His Ile Val Gln Met
        355                 360                 365

Phe Ile Asn Thr Ser
    370

<210> SEQ ID NO 122
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Cys Arg Glu Glu Met Thr Lys Asn Gln Val
145                 150                 155                 160

Ser Leu Trp Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Ala Gly Gly Gly Ser Gly Gly Gly Ser Gly Gly
                245                 250                 255

Gly Gly Ser Ile Thr Cys Pro Pro Pro Met Ser Val Glu His Ala Asp
            260                 265                 270

Ile Trp Val Lys Ser Tyr Ser Leu Tyr Ser Arg Glu Arg Tyr Ile Cys
        275                 280                 285

Asn Ser Gly Phe Lys Arg Lys Ala Gly Thr Ser Ser Leu Thr Glu Cys
    290                 295                 300

Val Leu Asn Lys Ala Thr Asn Val Ala His Trp Thr Thr Pro Ser Leu
305                 310                 315                 320

Lys Cys Ile Arg Gly Gly Gly Gly Ser Gly Gly Gly Ser Gly Gly Gly
                325                 330                 335

Gly Ser Ala Ala Gly Gly Gly Ser Gly Gly Gly Ser Gly Gly
            340                 345                 350

Gly Gly Ser Asn Trp Val Asn Val Ile Ser Asp Leu Lys Lys Ile Glu
        355                 360                 365

Asp Leu Ile Gln Ser Met His Ile Asp Ala Thr Leu Tyr Thr Glu Ser
            370                 375                 380

Asp Val His Pro Ser Cys Lys Val Thr Ala Met Lys Cys Phe Leu Leu
385                 390                 395                 400

Glu Leu Gln Val Ile Ser Leu Glu Ser Gly Asp Ala Ser Ile His Asp
                405                 410                 415

Thr Val Glu Asp Leu Ile Ile Leu Ala Asn Asn Ser Leu Ser Ser Asn
            420                 425                 430

Gly Asn Val Thr Glu Ser Gly Cys Lys Glu Cys Glu Glu Leu Glu Glu
        435                 440                 445

Lys Asn Ile Lys Glu Phe Leu Gln Ser Phe Val His Ile Val Gln Met
    450                 455                 460

Phe Ile Asn Thr Ser
465

<210> SEQ ID NO 123
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Val Leu Thr Gln Ser Pro Gly Thr Leu Ser Leu Ser Pro Gly
1               5                   10                  15

Arg Glu Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu
            100                 105

<210> SEQ ID NO 124
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Arg Glu Ala Thr Leu Ser Cys Arg Ala Ser Gln
145                 150                 155                 160

Ser Val Ser Ser Tyr Leu Ala Trp Tyr Gln Gln Lys Pro Gly Gln
                165                 170                 175

Ala Pro Arg Leu Leu Ile Tyr Gly Ala Ser Arg Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Arg
    210                 215                 220

Tyr Gly Ser Ser His Thr Phe Gly Gln Gly Thr Lys Leu Glu
225                 230                 235
```

```
<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Ala Ser Gln Asp Val Ser Ile Ala Val Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ala Ser Tyr Arg Tyr Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln His Tyr Ile Thr Pro Leu Thr
1               5

<210> SEQ ID NO 128
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 128

Asn Tyr Gly Met Asn
1               5

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Ile Asn Thr Tyr Thr Gly Glu Pro Thr Tyr Thr Asp Asp Phe Lys
1               5                   10                  15
Gly

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Phe Gly Ser Ser Tyr Trp Tyr Phe Asp Val
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ala Ser Ser Ser Val Ser Tyr Met His
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Thr Ser Lys Leu Ala Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Gln Trp Ser Gly Tyr Pro Leu Thr
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Tyr Thr Met Asn
1               5

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Ile Thr Pro Tyr Asn Gly Ala Ser Ser Tyr Asn Gln Lys Phe Arg
1               5                   10                  15

Gly

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Tyr Asp Gly Arg Gly Phe Asp Tyr
1               5                   10

<210> SEQ ID NO 137
<211> LENGTH: 1566
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
ctgggcagcg ctcgcccggg gagtccagcg gtgtcctgtg gagctgccgc catggccccg      60
cggcgggcgc gcggctgccg gaccctcggt ctccggcgc tgctactgct gctgctgctc     120
cggccgccgg cgacgcgggg catcacgtgc cctcccccca tgtccgtgga acacgcagac     180
atctgggtca agagctacag cttgtactcc agggagcggt acatttgtaa ctctggtttc     240
aagcgtaaag ccggcacgtc cagcctgacg gagtgcgtgt tgaacaaggc cacgaatgtc     300
gcccactgga caacccccag tctcaaatgc attagagacc ctgccctggt tcaccaaagg     360
ccagcgccac cctccacagt aacgacggca ggggtgaccc cacagccaga gagcctctcc     420
ccttctggaa aagagcccgc agcttcatct cccagctcaa acaacacagc ggccacaaca     480
gcagctattg tcccgggctc ccagctgatg ccttcaaaat caccttccac aggaaccaca     540
gagataagca gtcatgagtc ctcccacggc acccctctc agacaacagc caagaactgg     600
gaactcacag catccgcctc ccaccagccg ccaggtgtgt atccagggg ccacagcgac     660 accactgtgg ctatctccac gtccactgtc ctgctgtgtg ggctgagcgc tgtgtctctc     720

```
ctggcatgct acctcaagtc aaggcaaact cccccgctgg ccagcgttga aatggaagcc      780
atggaggctc tgccggtgac ttgggggacc agcagcagag atgaagactt ggaaaactgc      840
tctcaccacc tatgaaactc ggggaaacca gcccagctaa gtccggagtg aaggagcctc      900
tctgctttag ctaaagacga ctgagaagag gtgcaaggaa gcgggctcca ggagcaagct      960
caccaggcct ctcagaagtc ccagcaggat ctcacggact gccgggtcgg cgcctcctgc     1020
gcgagggagc aggttctccg cattcccatg ggcaccacct gctgcctgt cgtgccttgg      1080 acccagggcc cagcttccca ggagagacca aaggcttctg agcaggattt ttatttcatt     1140
acagtgtgag ctgcctggaa tacatgtggt aatgaaataa aaaccctgcc ccgaatcttc     1200
cgtccctcat cctaactttc agttcacaga gaaaagtgac atacccaaag ctctctgtca     1260
attacaaggc ttctcctggc gtgggagacg tctacaggga agacaccagc gtttgggctt     1320
ctaaccaccc tgtctccagc tgctctgcac acatggacag ggacctggga aaggtgggag     1380
agatgctgag cccagcgaat cctctccatt gaaggattca ggaagaagaa aactcaactc     1440
agtgccattt tacgaatata tgcgtttata tttatacttc cttgtctatt atatctatac     1500
attatatatt atttgtattt tgacattgta ccttgtataa acaaaataaa acatctattt     1560
tcaata                                                               1566
```

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ser Ala Gly Ser Ala Ala Gly Ser Gly Glu Phe
1               5                   10

<210> SEQ ID NO 139
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(15)
<223> OTHER INFORMATION: This region may encompass 1-3 "Gly Gly Gly Gly
      Ser" repeating units
<220> FEATURE:
<221> NAME/KEY: MISC_FEATURE
<222> LOCATION: (28)..(42)
<223> OTHER INFORMATION: This region may encompass 1-3 "Gly Gly Gly Gly
      Ser" repeating units

<400> SEQUENCE: 139

Gly Gly Gly Gly Ser Gly Gly Gly Gly Ser Gly Gly Gly Gly Ser Gly
1               5                   10                  15

Ser Ala Gly Ser Ala Ala Gly Ser Gly Glu Phe Gly Gly Gly Gly Ser
            20                  25                  30

Gly Gly Gly Gly Ser Gly Gly Gly Gly Ser
        35                  40

<210> SEQ ID NO 140
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(15)
<223> OTHER INFORMATION: This region may encompass 2-3 "Gly Gly Gly Gly
      Ser" repeating units
<220> FEATURE:
<221> NAME/KEY: MISC_FEATURE
<222> LOCATION: (18)..(32)
<223> OTHER INFORMATION: This region may encompass 2-3 "Gly Gly Gly Gly
      Ser" repeating units

<400> SEQUENCE: 140

Gly Gly Gly Gly Ser Gly Gly Gly Gly Ser Gly Gly Gly Gly Ser Ala
1               5                   10                  15

Ala Gly Gly Gly Gly Ser Gly Gly Gly Gly Ser Gly Gly Gly Gly Ser
            20                  25                  30
```

IL-15 PRODRUGS AND METHODS OF USE THEREOF

CROSS-REFERENCE TO RELATED APPLICATIONS

This application claims priority from U.S. Provisional Applications 62/860,635, filed Jun. 12, 2019; 62/888,444, filed Aug. 17, 2019; 62/891,190, filed Aug. 23, 2019; 62/959,973, filed Jan. 11, 2020; and 63/029,473, filed May 23, 2020. The disclosures of the aforementioned priority applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 8, 2020, is named 025471_US004_SL.txt and is 359,580 bytes in size.

BACKGROUND OF THE INVENTION

Interleukin-15 (IL-15) is a cytokine with structural similarities to IL-2. IL-15 is secreted by mononuclear phagocytes and other immune cells following viral infection. IL-15 induces proliferation of natural killer (NK) and other cells of the immune system and is involved in the killing of virally infected cells and cancer cells. Like IL-2, IL-15 binds to the IL-2 receptor (IL-2R) β/γ complex, the intermediate affinity receptor, with a $K_D$ of about 1 nM (Giri et al., *EMBO J.* (1994) 13:2822-30). IL-15 binds to IL-15 receptor (IL-15R) a with a much higher affinity ($K_D$=~0.05 nM). IL-15Rα can associate with the IL-2Rβ/γ complex to form an IL-15-specific, functional high-affinity receptor (αβγ) (Minami et al., *Annu Rev Immunol.* (1993) 11:245-67; Giri et al., *J Leukoc Biol.* (1995) 5745:763-6; and Lehours et al., *Eur Cytokine Netw.* (2000) 11:207-15).

The extracellular region of IL-15Rα contains a Sushi domain, which is a common motif in protein-protein interaction. It has been shown that the IL-15Rα N-terminal fragment with the first 65 amino acids is partially active, while the fragment with the first 85 amino acids is fully functional (Wei et al., *J. Immunol.* (2001) 167(1):277-82).

Mutations of IL-15 have been made to study IL-15's interaction with its receptors. D8 and Q108, for example, have been shown to be involved in IL-15's binding to the IL-2Rβ and γ subunits, respectively (Pettit et al., *J Biol Chem.* (1997) 272: 2312-18). Additional mutations of IL-15 have been disclosed (U.S. Pat. No. 7,858,081), including those at residues L45, Q48, S51, L52, E64, N65, I68 and L69 of IL-15, which are involved in IL-15 binding to IL-15Rα or IL-2Rβ. IL-15 muteins with mutation E64K, N65K, N65D, L66D, L66E, I67D, I67E or I68D have been shown to have reduced biological activities in cell-based assays (Zhu et al., *J Immnol.* (2009) 183(6):3598; and WO2005/085282A1). Mutations targeting IL-15 interaction with IL-15Rα have also been reported. For example, E46, V49, L45, S51, and L52 have been shown to be involved in IL-15Rα binding (Bernard et al., *J Biol Chem.* (2004) 279:24313-22). E46 appears to be particularly crucial because replacement of its acidic side chain with a basic one (E46K) results in a complete loss of IL-15 binding to IL-15Rα and bioactivity.

Unfortunately, the adverse effects of the current IL-15 drug candidates are significant, limiting the dosing amounts of such drugs. In addition, the activation of T, NK, and other immune cells by these drug candidates are not site specific. Further, there appears to be "PK sinkers" for IL-15 muteins even though their affinities for the IL-15/2 receptors have been significantly reduced. There are also numerous difficulties in the production of IL-15-based protein therapeutics. All of the above underscore the need to develop improved IL-15-based therapeutics.

SUMMARY OF THE INVENTION

The present disclosure provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the masking moiety is fused to the carrier moiety, the Sushi domain is fused to the carrier moiety, and the IL-15 cytokine moiety is fused to the Sushi domain. In some embodiments, the masking moiety is fused to the carrier moiety through a first peptide linker, the Sushi domain is fused to the carrier moiety through a second peptide linker, and the IL-15 cytokine moiety is fused to the Sushi domain through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the peptide linkers are noncleavable. In particular embodiments, the third peptide linker is at least 15, 20, 25, or 30 amino acids in length (e.g., 15-50 or 15-100 amino acids in length), optionally wherein the third peptide linker comprises SEQ ID NO: 139 or 140.

The present disclosure also provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the IL-15 cytokine moiety is fused to the carrier moiety, the Sushi domain is fused to the carrier moiety, and the masking moiety is fused to the Sushi domain. In some embodiments, the IL-15 cytokine moiety is fused to the carrier moiety through a first peptide linker, the Sushi domain is fused to the carrier moiety through a second peptide linker, and the masking moiety is fused to the Sushi domain through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the three peptide linkers are noncleavable.

The present disclosure further provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the masking moiety is fused to the carrier moiety, the IL-15 moiety is fused to the carrier moiety, and the Sushi domain is fused to the IL-15 moiety. In some embodiments, the masking moiety is fused to the carrier moiety through a first peptide linker, the IL-15 moiety is fused to the carrier moiety through a second peptide linker, and the Sushi domain is fused to the IL-15 moiety through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the peptide linkers are noncleavable. In particular embodiments, the third peptide linker is at least 15, 20, 25, or 30 amino acids in length (e.g., 15-50 or 15-100 amino acids in length), optionally wherein the third peptide linker comprises SEQ ID NO: 139 or 140.

The present disclosure also provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the IL-15 cytokine moiety is fused to the carrier moiety, the masking moiety is fused to the carrier moiety, and the Sushi domain is fused to the masking moiety. In some embodiments, the IL-15 cytokine moiety is fused to the carrier moiety through a first peptide linker, the masking moiety is fused to the carrier moiety through a second peptide linker, and the Sushi domain is fused to the masking moiety through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the three peptide linkers are noncleavable.

The present disclosure also provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the IL-15 cytokine moiety is fused to the carrier moiety, the masking moiety is fused to the IL-15 moiety, and the Sushi domain is fused to the carrier moiety. In some embodiments, the IL-15 cytokine moiety is fused to the carrier moiety through a first peptide linker, the masking moiety is fused to the IL-15 moiety through a second peptide linker, and the Sushi domain is fused to the carrier through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the three peptide linkers are noncleavable.

The present disclosure also provides a prodrug comprising an IL-15 cytokine moiety (A), a masking moiety (M), a carrier moiety (C), and a Sushi domain (S), wherein the masking moiety binds to the IL-15 cytokine moiety and inhibits a biological activity of the IL-15 cytokine moiety, the masking moiety is fused to the carrier moiety, the IL-15 moiety is fused to the masking moiety, and the Sushi domain is fused to the carrier moiety. In some embodiments, the masking moiety is fused to the carrier moiety through a first peptide linker, the IL-15 moiety is fused to the masking moiety through a second peptide linker, and the Sushi domain is fused to the carrier through a third peptide linker, and wherein at least one of the three peptide linkers (e.g., one, two, or three) is cleavable. In some embodiments, at least one of the three peptide linkers (e.g., one, two, or three) is noncleavable. In some embodiments, all of the three peptide linkers are noncleavable.

In some embodiments, the masking moiety comprises an extracellular domain (ECD) of a receptor of the IL-15 cytokine moiety. For example, the masking moiety comprises an ECD of human IL-2Rβ or a functional analog thereof, and/or an ECD of human IL-2Rγ or a functional analog thereof. In particular embodiments, the ECD of human IL-2Rγ or a functional analog thereof comprises SEQ ID NO: 6, or an amino acid sequence at least 90% identical thereto. In other particular embodiments, the ECD of human IL-2Rβ or a functional analog thereof comprises SEQ ID NO: 3, 4, or 5, or an amino acid sequence at least 90% identical thereto. In other embodiments, the masking moiety comprises an antibody fragment that binds to the IL-15 cytokine moiety.

The present disclosure further provides a prodrug comprising an IL-15 cytokine moiety (A), a masking moiety (M), a carrier moiety (C), and optionally a Sushi domain (S), wherein the masking moiety comprises an antibody fragment that binds to the IL-15 cytokine moiety and inhibits a biological activity of the IL-15 cytokine moiety, and the masking moiety is fused to the carrier moiety, to the IL-15 cytokine moiety, or to the Sushi domain optionally through a peptide linker.

In some embodiments, the antibody fragment in the prodrug is an ScFv or Fab comprising heavy chain CDR1-3 and light chain CDR1-3 of an anti-IL-15 antibody selected from 146B7, 146H5, 404E4, and 404A8. For example, the antibody fragment comprises heavy chain CDR (HCDR) 1 comprising SEQ ID NO: 100, HCDR2 comprising SEQ ID NO: 101, HCDR3 comprising SEQ ID NO: 102 or 106, light chain CDR (LCDR) 1 comprising SEQ ID NO: 103, LCDR2 comprising SEQ ID NO: 104, and LCDR3 comprising SEQ ID NO: 105. In particular embodiments, the antibody fragment comprises (i) a heavy chain variable domain comprising SEQ ID NO: 107 or an amino acid sequence at least 95% identical thereto, and a light chain variable domain comprising SEQ ID NO: 108 or 123 or an amino acid sequence at least 95% identical thereto; (ii) SEQ ID NO: 109; (iii) SEQ ID NO: 110; or (iv) SEQ ID NO: 124. In certain embodiments, the Cys residue of the heavy chain CDR3 (SEQ ID NO: 102) is mutated to Ser, Thr, Met, Ala, Gly, Asn or Gln.

In some embodiments, the masking moiety does not interfere with or has minimum impact on the binding of the IL-15 cytokine moiety to IL-15Rα.

In some embodiments, the IL-15 cytokine moiety is a human IL-15 polypeptide comprising SEQ ID NO: 2 or a mutein thereof. In particular embodiments, the human IL-15 polypeptide comprises one or more mutations selected from N1A, N1D, N4A, N4D, I6T, S7A, D8A, D8T, D8E, D8N, K10A, K10D, K11A, K11D, E46, V49, L45, S51, L52, D61A, D61N, T62L, T62A, E64A, E64L, E64K, E64Q, N65A, N65L, N65D, L66D, L66E, I67D, I67E, I68S, 168E, L69S, L69E, N72A, N72D, V63E, V63D, L66E, L66D, I67E, I67D, Q108E, N112A, N1D/D61N, N1D/E64Q, N4D/D61N, N4D/E64Q, D8N/D61N, D8N/E64Q, D61N/E64Q, E64Q/Q108E, N1D/N4D/D8N, D61N/E64Q/N65D, N1D/D61N/E64Q, N1D/Q108E, N1D/D61N/E64Q/Q108E, N4D/D61N/E64Q/Q108E, and D30N/E64Q/N65D relative to SEQ ID NO: 2.

In some embodiments, the carrier moiety is a PEG molecule, an albumin, an albumin fragment, an antibody Fc domain, or an antibody or an antigen-binding fragment thereof. In further embodiments, the carrier moiety is an antibody Fc domain or an antibody comprising mutations L234A and L235A ("LALA") (EU numbering). In some embodiments, the carrier moiety is an antibody Fc domain or an antibody comprising knobs-into-holes mutations, and wherein the IL-15 cytokine moiety and the masking moiety are fused to different polypeptide chains of the antibody Fc domain or to the different heavy chains of the antibody. In certain embodiments, the knobs-into-holes mutations comprise a T366Y "knob" mutation on a polypeptide chain of the Fc domain or a heavy chain of the antibody, and a Y407T "hole" mutation in the other polypeptide of the Fc domain or the other heavy chain of the antibody, or the knobs-into-holes mutations comprise Y349C and/or T366W mutations in the CH3 domain of the "knob chain" and E356C, T366S, L368A, and/or Y407V mutations in the CH3 domain of the "hole chain" (EU numbering). In certain embodiments, the carrier moiety is an IgG$_4$ Fc domain, and wherein said first polypeptide comprises an amino acid sequence at least 99% identical as one shown in SEQ ID NOs: 80, 81 or 87, and said second polypeptide chain comprises an amino acid sequence at least 99% identical as one selected from SEQ ID NOs: 82-86.

In some embodiments, the carrier moiety is an anti-PD-1 antibody comprising a light chain having an amino acid sequence at least 99% identical to SEQ ID NO: 55 or 56; a first heavy chain having an amino acid sequence at least 99% identical to SEQ ID NO: 54, 60, or 61; and a second heavy chain having an amino acid sequence at least 99% identical to SEQ ID NO: 52, 53, 58, 59, 62, 63, or 69. In further embodiments, the carrier moiety is an anti-PD-1 antibody comprising a light chain having an amino acid sequence at least 99% identical to SEQ ID NO: 55; a first heavy chain having an amino acid sequence at least 99% identical to SEQ ID NO: 66; and a second heavy chain having an amino acid sequence at least 99% identical to SEQ ID NO: 64, 65, 67, or 68.

In some embodiments, the carrier moiety is an anti-PD-L1 antibody comprising a light chain having an amino acid sequence at least 99% identical to SEQ ID NO: 50 or 51; a first heavy chain having an amino acid at least 99% identical to SEQ ID NO: 47, 48 or 49; and a second heavy chain having an amino acid sequence at least 99% identical to SEQ ID NO: 45 or 46.

In some embodiments, the carrier moiety is an antibody or an antigen-binding fragment thereof that specifically binds to one or more antigens selected from PD-1, PD-L1, CTLA-4, LAG-3, TIM-3, and TIGIT.

In some embodiments, the carrier moiety is an antibody Fc domain or an antibody, and the prodrug comprises the following polypeptide pairs (from N-terminus to C-terminus): C1-A and C2-S-M, A-C1 and M-S-C2, C1-S-A and C2-M, C1-A-S and C2-M, S-A-C1 and M-C2, or A-S-C1 and M-C2; and wherein C1 and C2 are the first and second polypeptide chains, respectively, of the Fc domain, or are the first and second heavy chains, respectively, of the antibody; and "—" is a direct peptidyl bond or a peptide linker.

In some embodiments, the Sushi domain comprises SEQ ID NO: 7 or 9, or an amino acid sequence at least 90% identical thereto.

In some embodiments, at least one of the first, second, and third peptide linkers is a noncleavable peptide linker, optionally selected from SEQ ID NOs: 11-16.

In some embodiments, at least one of the first, second, and third peptide linkers is a cleavable peptide linker comprising a substrate sequence of urokinase-type plasminogen activator (uPA), matriptase, matrix metallopeptidase (MMP) 2, or MMP9. For example, the cleavable peptide linker comprises substrate sequences of (i) both uPA and MMP2, (ii) both uPA and MMP9, (iii) uPA, MMP2 and MMP9, or (iv) MMP2 and matriptase. In particular embodiments, the cleavable peptide linker comprises an amino acid sequence selected from SEQ ID NOs: 17-36. The cleavable peptide linker is cleavable by one or more proteases located at a tumor site or its surrounding environment, and the cleavage leads to activation of the prodrug at the tumor site or surrounding environment.

In other aspects, the present disclosure provides a pharmaceutical composition comprising the present prodrug and a pharmaceutically acceptable excipient; a polynucleotide or polynucleotides encoding the present prodrug; an expression vector or vectors comprising the polynucleotide or polynucleotides; and a host cell comprising the vector(s). In some embodiments, the gene(s) encoding uPA, matriptase, MMP-2, and/or MMP-9 are knocked out in the host cell.

Also provided is a method of making the present prodrug, comprising culturing the host cell under conditions that allow expression of the prodrug, wherein the host cell is a mammalian cell, and isolating the prodrug.

In another aspect, the present disclosure provides a method of treating a cancer or an infectious disease or stimulating the immune system in a patient in need thereof, comprising administering to the patient a therapeutically effective amount of the pharmaceutical composition comprising the present prodrug. The patient may have, for example, HIV infection, or a cancer selected from the group consisting of breast cancer, lung cancer, pancreatic cancer, esophageal cancer, medullary thyroid cancer, ovarian cancer, uterine cancer, prostate cancer, testicular cancer, colorectal cancer, and stomach cancer. Also provided are IL-15 prodrugs for use in such treatment, and the use of IL-15 prodrugs for the manufacture of a medicament for such treatment.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTIONS OF THE DRAWINGS

FIGS. 1A-C are schematic illustrations of IL-15 prodrugs with an Fc domain as the carrier moiety. FIG. 1A shows an IL-15Rα Sushi domain polypeptide fused to the C-terminus of one Fc polypeptide, optionally through a noncleavable peptide linker. An IL-15 polypeptide is fused to the C-terminus of the Sushi domain, optionally through a noncleavable linker. A masking moiety is fused to the C-terminus of the other Fc polypeptide through a cleavable linker. FIG. 1B shows an IL-15 polypeptide fused to the C-terminus of one Fc polypeptide, optionally through a noncleavable peptide linker. An IL-15Rα Sushi domain is fused to the C-terminus of the IL-15 polypeptide, optionally through a noncleavable linker. A masking moiety is fused to the C-terminus of the other Fc polypeptide through a cleavable linker. FIG. 1C shows an IL-15 polypeptide fused to the C-terminus of one Fc polypeptide, optionally through a noncleavable peptide linker. An IL-15Rα Sushi domain is fused to the C-terminus of the other Fc polypeptide, optionally through a noncleavable linker. A masking moiety is fused to the C-terminus of the Sushi domain through a cleavable linker. In all three configurations, the Fc domain contains a knobs-into-holes mutation.

FIGS. 2A-C are schematic illustrations IL-15 prodrugs with an Fc domain as the carrier moiety. FIG. 2A shows an IL-15Rα Sushi domain is fused to the N-terminus of one Fc polypeptide, optionally through a noncleavable linker. An IL-15 polypeptide is fused to the N-terminus of the Sushi domain, optionally through a noncleavable peptide linker. A masking moiety is fused to the N-terminus of the other Fc polypeptide through a cleavable linker. FIG. 2B shows an IL-15 polypeptide fused to the N-terminus of one Fc polypeptide, optionally through a noncleavable linker. An IL-15Rα Sushi domain polypeptide is fused to the N-terminus of the IL-15 polypeptide, optionally through a noncleavable peptide linker. A masking moiety is fused to the N-terminus of the other Fc polypeptide through a cleavable linker. FIG. 2C shows an IL-15 polypeptide fused to the N-terminus of one Fc polypeptide, optionally through a noncleavable peptide linker. An IL-15Rα Sushi domain is fused to the N-terminus of the other Fc polypeptide, optionally through a noncleavable linker. A masking moiety is fused to the N-terminus of the Sushi domain through a cleavable linker. In all three configurations, the Fc domain contains a knobs-into-holes mutation.

FIGS. 3A-C are schematic illustrations of IL-15 prodrugs with an antibody (having two antigen-binding sites) as the carrier moiety. FIG. 3A shows an IL-15 polypeptide fused to the C-terminus of one of the heavy chains of the antibody, optionally through a noncleavable peptide linker. An IL-15Rα Sushi domain is fused to the C-terminus of the IL-15 polypeptide, optionally through a noncleavable linker. A masking moiety is fused to the C-terminus of the other heavy chain of the antibody through a cleavable linker. FIG. 3B shows an IL-15Rα Sushi domain polypeptide fused to the C-terminus of one of the heavy chains of the antibody, optionally through a noncleavable peptide linker. An IL-15 polypeptide is fused to the C-terminus of the Sushi domain, optionally through a noncleavable linker. A masking moiety is fused to the C-terminus of the other heavy chain of the antibody through a cleavable linker. FIG. 3C shows an IL-15 polypeptide fused to the C-terminus of one of the heavy chains of the antibody, optionally through a noncleavable peptide linker. An IL-15Rα Sushi domain is fused to the C-terminus of the other heavy chain of the antibody, optionally through a noncleavable linker. A masking moiety is fused to the C-terminus of the Sushi domain through a cleavable linker. In all three FIGs, the antibody contains a knobs-into-holes mutation.

FIGS. 4A and 4B are schematic illustrations of IL-15 prodrugs with an antibody as the carrier moiety. The antibody has a single antigen-binding site. FIG. 4A shows an IL-15 polypeptide fused to the C-terminus of one of the heavy chains of the antibody, optionally through a noncleavable peptide linker. An IL-15Rα Sushi domain is fused to the C-terminus of the IL-15 polypeptide, optionally through a noncleavable linker. A masking moiety is fused to the C-terminus of the other heavy chain of the antibody through a cleavable linker. FIG. 4B shows an IL-15Rα Sushi domain polypeptide fused to the C-terminus of one of the heavy chains of the antibody, optionally through a noncleavable peptide linker. An IL-15 polypeptide is fused to the C-terminus of the Sushi domain, optionally through a noncleavable linker. A masking moiety is fused to the C-terminus of the other heavy chain of the antibody through a cleavable linker. In both configurations, the antibody contains a knobs-into-holes mutation and the masking moiety is on the same polypeptide chain as the heavy chain variable region of the antibody.

FIGS. 5A and 5B are schematic illustrations of IL-15 prodrugs with an antibody as the carrier moiety. The antibody has a single antigen-binding moiety. FIG. 5A shows an IL-15 polypeptide fused to the C-terminus of one of the heavy chains of the antibody, optionally through a noncleavable peptide linker. An IL-15Rα Sushi domain is fused to the C-terminus of the IL-15 polypeptide, optionally through a noncleavable linker. A masking moiety is fused to the C-terminus of the other heavy chain of the antibody through a cleavable linker. FIG. 5B shows an IL-15Rα Sushi domain polypeptide fused to the C-terminus of one of the heavy chains of the antibody, optionally through a noncleavable peptide linker. An IL-15 polypeptide is fused to the C-terminus of the Sushi domain, optionally through a noncleavable linker. A masking moiety is fused to the C-terminus of the other heavy chain of the antibody through a cleavable linker. In both configurations, the antibody contains a knobs-into-holes mutation, and the IL-15 polypeptide and Sushi domain are on the same polypeptide chain as the heavy chain variable region of the antibody.

FIG. 6A shows the sequence information for the Fc-IL-15 prodrugs (JR3.68.1, JR3.68.2 and JR3.68.3) and the control molecules (Fc-IL-15 fusion polypeptides, JR3.68.4 and JR3.68.5).

FIG. 6B illustrates the structures of the molecules of FIG. 6A. All of the molecules have an Fc domain as the carrier moiety. In JR3.68.1, the Sushi domain is fused to the C-terminus of one Fc polypeptide, through a noncleavable linker. The IL-15 polypeptide is fused to the C-terminus of the Sushi domain via a noncleavable linker. A masking moiety is fused to the C-terminus of the other Fc polypeptide via a cleavable linker. In JR3.68.2, an IL-15 polypeptide is fused to the C-terminus of one Fc domain polypeptide via a noncleavable linker. The Sushi domain is fused to the C-terminus of the IL-15 polypeptide through a noncleavable linker. A masking moiety is fused to the C-terminus of the other Fc polypeptide via a cleavable linker. In JR3.68.3, an IL-15 polypeptide is fused to the C-terminus of one Fc polypeptide via a noncleavable linker. The Sushi domain is fused to the C-terminus of the other Fc polypeptide via a noncleavable linker. A masking moiety is fused to the C-terminus of the Sushi domain via a cleavable linker. JR3.68.4 and JR3.68.5 are the activated forms (where the masking moiety was not designed in the constructs) of JR3.68.1 and JR3.68.2, respectively.

FIGS. 7A and 7B are photographs of SDS-PAGE gels analyzing the activatable fusion polypeptides prior to and after activation, as shown in FIG. 6B.

FIGS. 8A-C are graphs show the SEC-HPLC analysis of the Fc-IL-15/Sushi fusion protein samples JR3.68.1, JR3.68.2 and JR3.68.3, respectively, purified by Protein A columns.

FIGS. 9A-C illustrate the cell-based activities of the activatable Fc-IL-15 fusion polypeptides JR3.68.1, JR3.68.2, and JR3.68.3, respectively, before and after activation. In all three figures, IL-15 was used as a positive control.

FIG. 10A is a table shows the sequence information for the antibody-IL-15 fusion polypeptides JR3.74.1 and JR3.74.2 (without mask) and activatable antibody-IL-15 fusion polypeptides JR3.73.2 and JR3.73.4.

FIGS. 11A and 11B are graphs shows the SEC-HPLC analysis of JR3.74.1, JR3.74.2, JR3.73.2, and JR3.73.4 samples purified by Protein A columns.

Figures 12A, 12B:
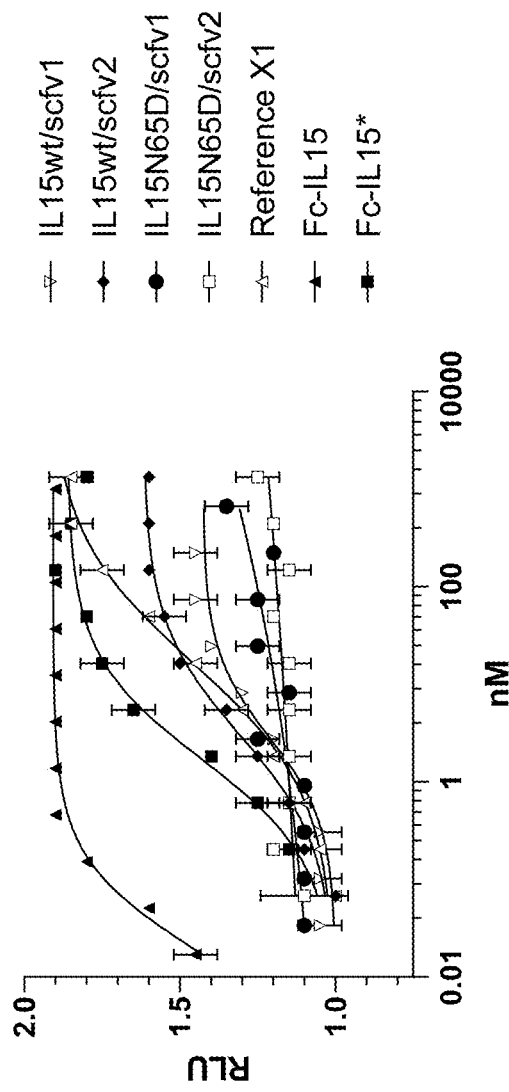

FIGS. 12A and 12B show the NK92 proliferation assay results of the IL-15 prodrugs masked by an scFv (scFv1 or scFv2) derived from the anti-IL-15 antibody 146B7. FIG. 12A shows the sequence information of the activatable IL-15 fusion proteins. FIG. 12B shows the results of the NK92 proliferation assay. Reference X1: XmAb®24306, which is an IL-15/IL-15-receptor alpha complex fused to a XmAb Fc domain (IL-15/IL-15Rα-Fc). Fc-IL-15*: activatable IL-15 fusion protein with an IL-2Rβ extracellular domain (ECD) as the masking moiety. Fc-IL-15: an Fc-IL-15 fusion protein without the masking moiety. RLU: relative luminescence units.

Figure 13A:
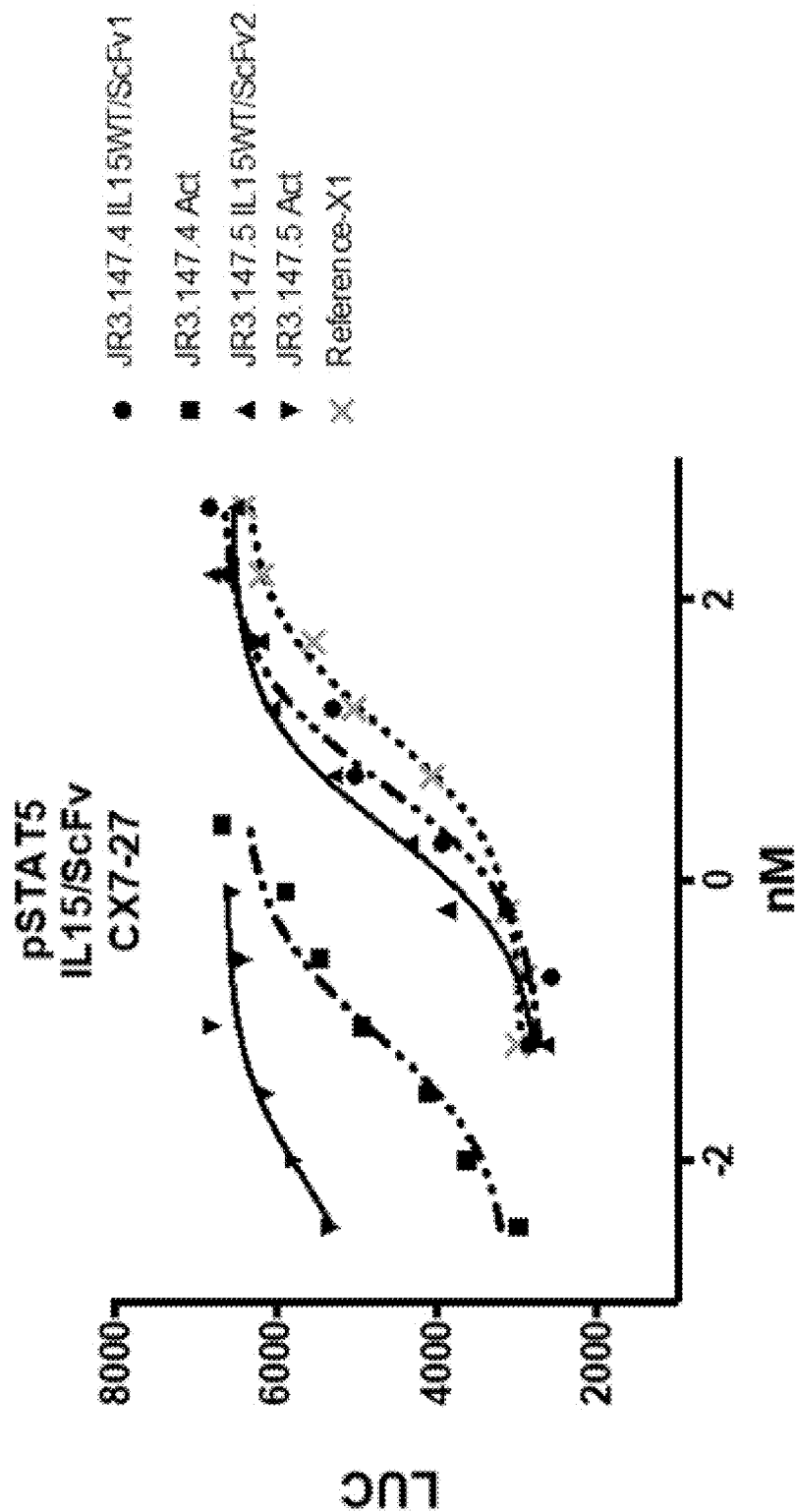
Figure 13B:
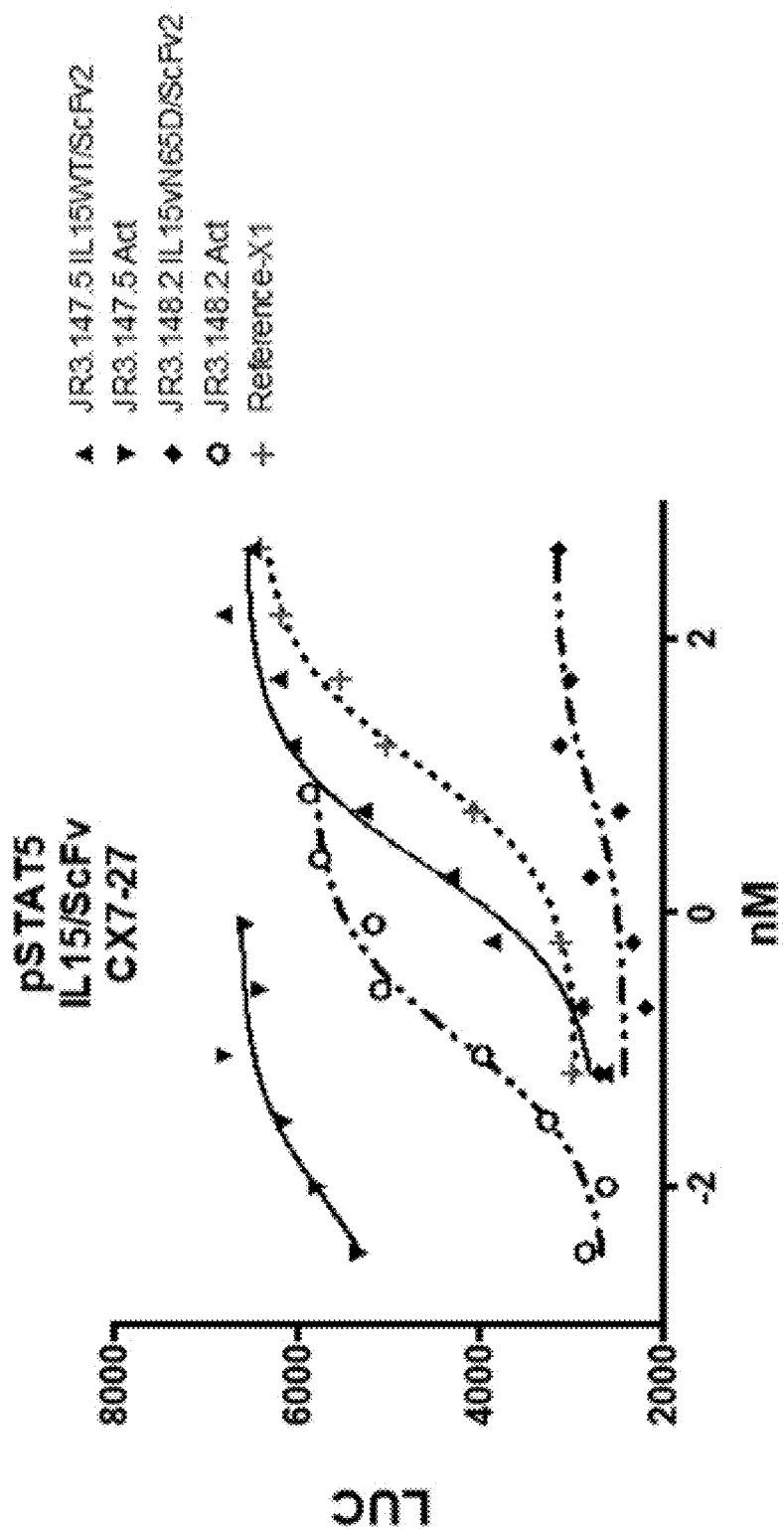

FIGS. 13A and 13B show the NK92 cell-based activities of the activatable IL-15 fusion proteins prior to and after activation. FIG. 13A shows the NK92 cell-based activities of IL-15 fusion proteins comprising wild type IL-15. FIG. 13B shows the NK92 cell-based activities of IL-15 fusion polypeptides comprising an IL-15 mutein with an N65D mutation. Reference X1: XmAb®24306, which is an IL-15/IL-15-receptor alpha complex fused to a XmAb Fc domain (IL-15/IL-15Rα-Fc). LUC: signal in luminescence units. Act: activated.

FIG. 14A is a table showing the sequence information for activatable IL-15 fusion proteins.

Figure 14B:
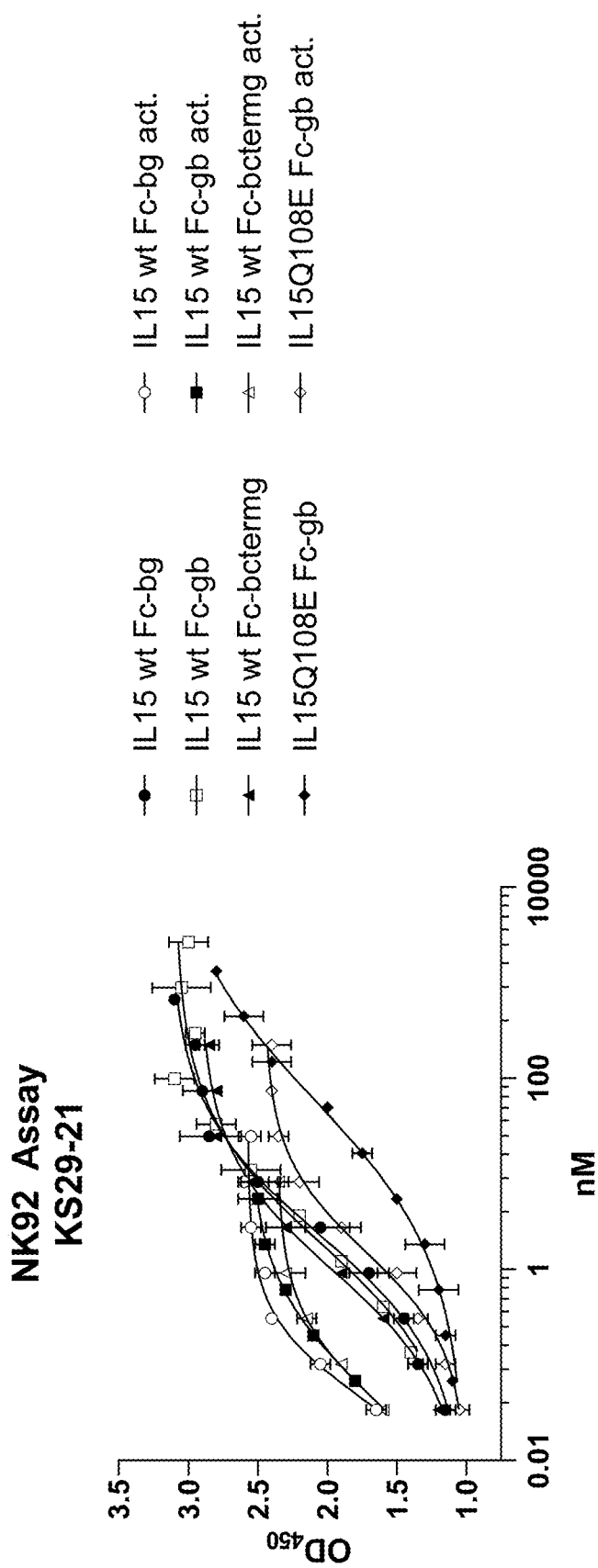
Figure 14C:
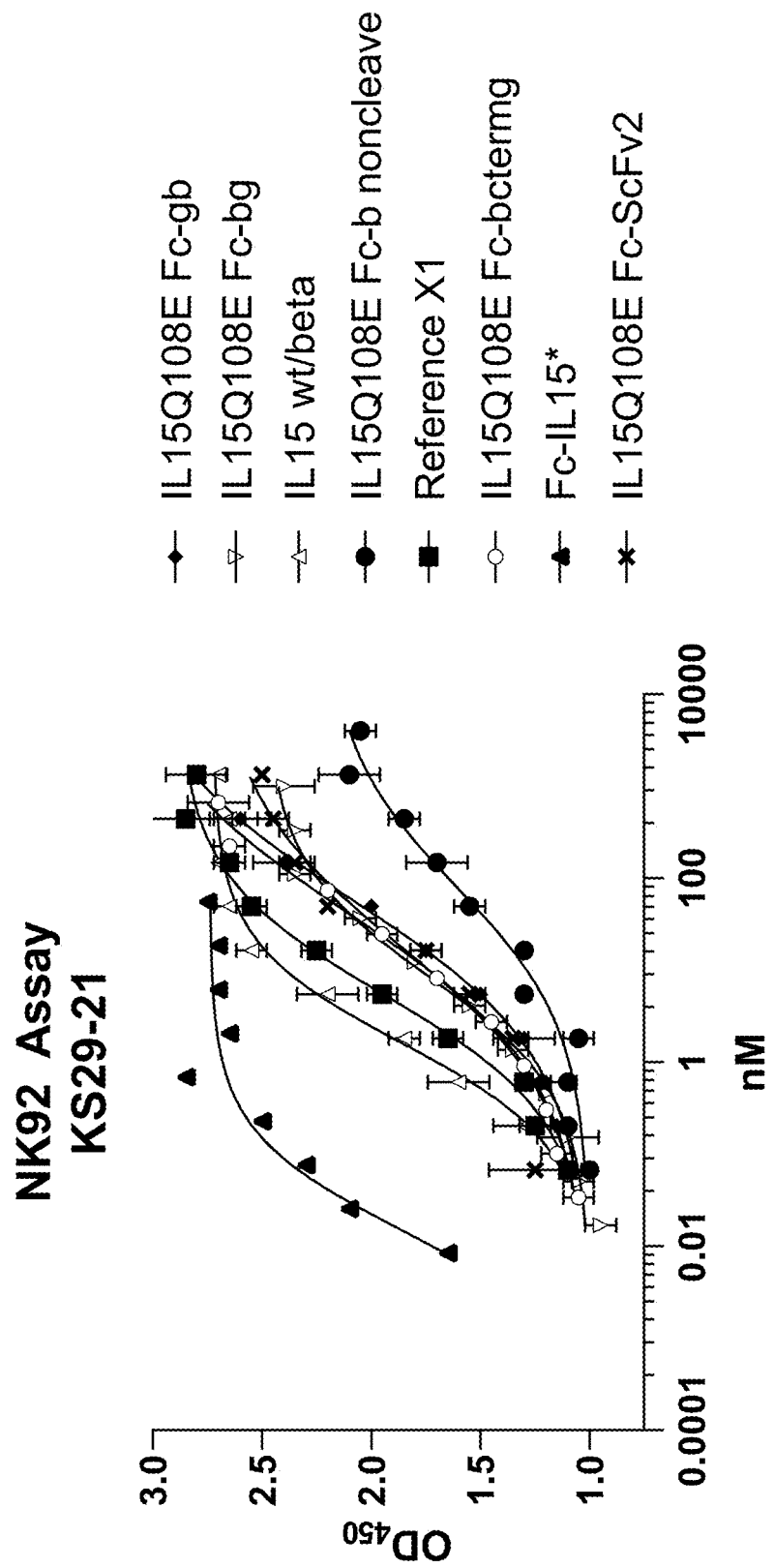
Figure 14D:
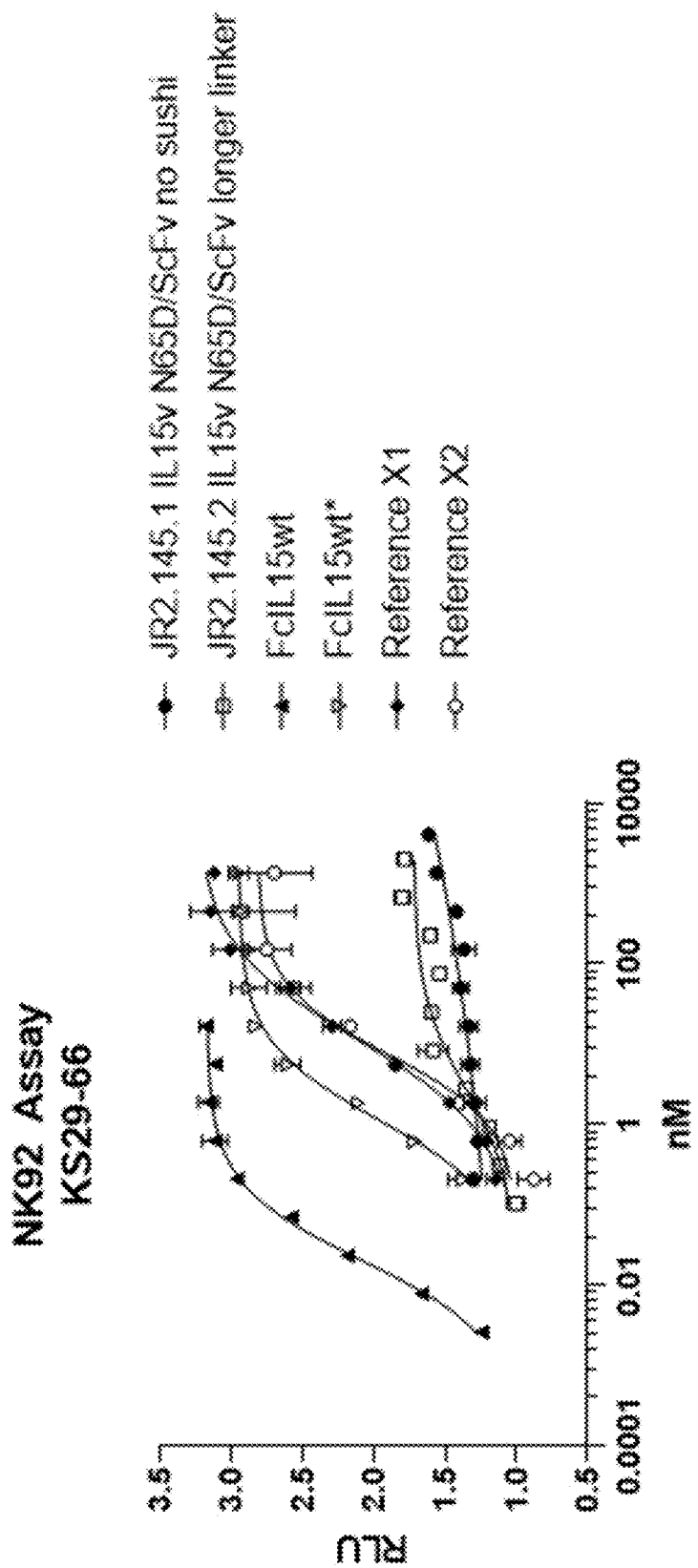

FIGS. 14B-D show the NK92 proliferation assay results of the activatable IL-15 fusion proteins before and after activation. FIG. 14B shows the results of wild type IL-15 masked by an IL-2Rβ ECD and an IL-2Rγ ECD. FIG. 14C shows the results of IL-15 mutein Q108E masked with an IL-2Rβ ECD and an IL-2Rγ ECD. FIG. 14D shows the results of the activatable Fc-IL-15 fusion protein without a Sushi domain (JR2.145.1) and one with a longer linker between the Sushi domain and the IL-15 polypeptide moiety (JR2.145.2). Reference X1: XmAb 24306, which is an IL-15/IL-15-receptor alpha complex fused to a XmAb Fc domain (IL-15/IL-15Rα-Fc). Reference X2: is a PD-1 antibody-IL-15 mutein fusion protein without a Sushi domain.

DETAILED DESCRIPTION OF THE INVENTION

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X." Additionally, use of "about" preceding any series of numbers includes "about" each of the recited numbers in that series. For example, description referring to "about X, Y, or Z" is intended to describe "about X, about Y, or about Z."

The term "antigen-binding moiety" refers to a polypeptide or a set of interacting polypeptides that specifically bind to an antigen, and includes, but is not limited to, an antibody (e.g., a monoclonal antibody, polyclonal antibody, a multi-specific antibody, a dual specific or bispecific antibody, an anti-idiotypic antibody, or a bifunctional hybrid antibody) or an antigen-binding fragment thereof (e.g., a Fab, a Fab', a F(ab')2, a Fv, a disulfide linked Fv, a scFv, a single domain antibody (dAb), or a diabody), a single chain antibody, and an Fc-containing polypeptide such as an immunoadhesin. In some embodiments, the antibody may be of any heavy chain isotype (e.g., IgG, IgA, IgM, IgE, or IgD) or subtype (e.g., $IgG_1$, $IgG_2$, $IgG_3$, or $IgG_4$). In some embodiments, the antibody may be of any light chain isotype (e.g., kappa or lambda). The antibody may be human, non-human (e.g., from mouse, rat, rabbit, goat, or another non-human animal), chimeric (e.g., with a non-human variable region and a human constant region), or humanized (e.g., with non-human CDRs and human framework and constant regions). In some embodiments, the antibody is a derivatized antibody.

The term "cytokine agonist polypeptide" refers to a wildtype cytokine, or an analog thereof. An analog of a wildtype cytokine has the same biological specificity (e.g., binding to the same receptor(s) and activating the same target cells) as the wildtype cytokine, although the activity level of the analog may be different from that of the wildtype cytokine. The analog may be, for example, a mutein (i.e., mutated polypeptide) of the wildtype cytokine, and may comprise at least one, at least two, at least three, at least four, at least five, at least six, at least seven, at least eight, at least nine, or at least ten mutations relative to the wildtype cytokine.

The term "cytokine antagonist" or "cytokine mask" refers to a moiety (e.g., a polypeptide) that binds to a cytokine and thereby inhibiting the cytokine from binding to its receptor on the surface of a target cell and/or exerting its biological functions while being bound by the antagonist or mask. Examples of a cytokine antagonist or mask include, without limitations, a polypeptide derived from an extracellular domain of the cytokine's natural receptor that makes contact with the cytokine.

The term "effective amount" or "therapeutically effective amount" refers to an amount of a compound or composition sufficient to treat a specified disorder, condition, or disease, such as ameliorate, palliate, lessen, and/or delay one or more of its symptoms. In reference to a disease such as cancer, an effective amount may be an amount sufficient to delay cancer development or progression (e.g., decrease tumor growth rate, and/or delay or prevent tumor angiogenesis, metastasis, or infiltration of cancer cells into peripheral organs), reduce the number of epithelioid cells, cause cancer regression (e.g., shrink or eradicate a tumor), and/or prevent or delay cancer occurrence or recurrence. An effective amount can be administered in one or more administrations.

The term "functional analog" refers to a molecule that has the same biological specificity (e.g., binding to the same ligand) and/or activity (e.g., activating or inhibiting a target cell) as a reference molecule.

The term "fused" or "fusion" in reference to two polypeptide sequences refers to the joining of the two polypeptide sequences through a backbone peptide bond. Two polypeptides may be fused directly or through a peptide linker that is one or more amino acids long. A fusion polypeptide may be made by recombinant technology from a coding sequence containing the respective coding sequences for the two fusion partners, with or without a coding sequence for a peptide linker in between. In some embodiments, fusion encompasses chemical conjugation.

The term "pharmaceutically acceptable excipient" when used to refer to an ingredient in a composition means that the excipient is suitable for administration to a treatment subject, including a human subject, without undue deleterious side effects to the subject and without affecting the biological activity of the active pharmaceutical ingredient (API).

The term "subject" refers to a mammal and includes, but is not limited to, a human, a pet (e.g., a canine or a feline), a farm animal (e.g., cattle or horse), a rodent, or a primate.

As used herein, "treatment" or "treating" is an approach for obtaining beneficial or desired clinical results. Beneficial or desired clinical results include, but are not limited to, one or more of the following: alleviating one or more symptoms resulting from a disease, diminishing the extent of a disease, ameliorating a disease state, stabilizing a disease (e.g., preventing or delaying the worsening or progression of the disease), preventing or delaying the spread (e.g., metastasis) of a disease, preventing or delaying the recurrence of a disease, providing partial or total remission of a disease, decreasing the dose of one or more other medications required to treat a disease, increasing the patient's quality of life, and/or prolonging survival. The methods of the present disclosure contemplate any one or more of these aspects of treatment.

It is to be understood that one, some or all of the properties of the various embodiments described herein may be combined to form other embodiments of the present invention. The section headings used herein are for organizational purposes only and are not to be construed as limiting the subject matter described thereunder.

I. IL-15 Prodrugs

The present disclosure IL-15 prodrugs that are metabolized in vivo to become active IL-15 therapeutics. The IL-15 prodrugs have fewer side effects, better in vivo PK profiles (e.g., longer half-life) and better target specificity, and are more efficacious as compared to prior IL-15 therapeutics. The IL-15 prodrugs of the present disclosure have configurations that lead to lower levels of aggregation and improved manufacturing efficiency, thereby overcoming common challenges in the manufacturing of fusion molecules and bispecific molecules.

The present prodrugs comprise an IL-15 polypeptide (A) (i.e., a cytokine agonist polypeptide or IL-15 cytokine moiety), an optional IL-15Rα Sushi domain (S), a masking moiety (M) (i.e., a cytokine antagonist) and a carrier moiety (C). The components are operationally linked to each other through peptide linkers, one of which may be cleavable such that upon activation by proteases at a target site, the masking moiety and the IL-15 cytokine moiety detach from each other. In some embodiments, the masking moiety (IL-15 antagonist), which may be, for example, an extracellular domain of a receptor for IL-15 or a binding fragment of an antibody which binds to the cytokine, is linked to the cytokine moiety, to the Sushi domain, or to the carrier moiety through a cleavable linker (e.g., a cleavable peptide linker). In other embodiments, the masking moiety is linked to the other moiety through a noncleavable linker.

The mask inhibits the IL-15 cytokine moiety's biological functions while the mask is binding to it. In some embodiments, a masking moiety of the present prodrugs specifically binds to an epitope located on the IL-2Rβ- and/or γ-chain interacting domain of the IL-15 polypeptide. A masking moiety's inhibitory effect may be removed upon protease digestion of the cleavable linker in the prodrug, allowing the masking moiety and the cytokine moiety to separate. In some embodiments, a masking moiety of the present prodrugs does not block or interfere with the binding of the IL-15 polypeptide (A) to IL-15Rα. The prodrugs may be activated at a target site (e.g., at a tumor site or the surrounding environment, or an infection site) in the patient by cleavage of the linker and the consequent release of the cytokine mask or the IL-15 cytokine moiety from the remainder of the prodrug, exposing the previously masked IL-15 cytokine moiety and allowing the IL-15 cytokine moiety to bind to its receptor on a target cell and exert its biological functions on the target cell. In some embodiments, the carriers for the prodrugs are antigen-binding moieties, such as antibodies, that bind an antigen at the target site.

In some embodiments of the IL-15 prodrugs of the present disclosure, the Sushi domain is fused to the carrier, the masking moiety, and/or the IL-15 cytokine moiety through a peptide linker (noncleavable or cleavable). In some embodiments, the IL-15 cytokine moiety is fused to the carrier moiety, the masking moiety, and/or the Sushi domain through a peptide linker (noncleavable or cleavable). In some embodiments, the masking moiety is fused to the carrier moiety, the cytokine moiety, and/or the Sushi domain through a peptide linker (noncleavable or cleavable).

In some embodiments, the present prodrugs are metabolized to become active IL-15 cytokines, which are pro-inflammatory, at a target site in the body targeted by the carrier. In further embodiments, the carrier in the prodrug is an antibody targeting a tumor antigen such that the prodrug is delivered to a tumor site in a patient and is metabolized locally (e.g., inside or in the vicinity of the tumor microenvironment) through cleavage of the linker linking the cytokine mask to the carrier or the cytokine moiety, making the pro-inflammatory cytokine moiety available to interact with its receptor on a target cell and stimulating the target immune cells locally.

A. IL-15 Moieties of the Prodrugs

In the present IL-15 prodrugs, the IL-15 cytokine moiety may be a wildtype IL-15 polypeptide such as a wildtype human IL-15 polypeptide (SEQ ID NO: 2), or an IL-15 mutein, such as an IL-15 mutein derived from a human wildtype IL-15, with reduced affinity for IL-2Rβ (CD122) compared to wild type IL-15. The IL-15 mutein may have significantly reduced affinity for CD122 or the dimeric IL-2R, as compared to the wild type IL-15.

In some embodiments, the IL-15 moiety, when masked, has its biological activity reduced by at least 5 times, at least 10 times, at least 20 times, at least 50 times, or at least 100 times; or has its $EC_{50}$ value increased by at least 5 times, at least 10 times, at least 20 times, at least 50 times or at least 100 times.

In some embodiments, the IL-15 moiety is an IL-15 mutein comprising at least 1, 2, 3, 4, or 5 mutations at positions selected from N1, N4, 16, S7, D8, K10, K11, E46, D61, T62, E64, N65, 168, L69, N72, V63, L66, 167, A70, N71, Q108, N112 of human IL-15. Exemplary IL-15 muteins are those with one or more mutations selected from N1A, N1D, N4A, N4D, I6T, S7A, D8A, DAT, D8E, D8N, K10A, K10D, K11A, K11D, D61A, D61N, T62L, T62A, E64A, E64L, E64K, E64Q, N65A, N65L, N65D, L66D, L66E, I67D, 167E, 1685, 168E, L69S, L69E, N72A, N72D, V63E, V63D, L66E, L66D, 167E, I67D, Q108E, and N112A. In some embodiments, the IL-15 moiety comprises a mutation or positions selected from E46, V49, L45, S51, and L52. Unless otherwise indicated, all residue numbers in IL-15 and IL-15 muteins described herein are in accordance with the numbering in SEQ ID NO: 2. In other embodiments, the IL-15 moiety comprises an amino acid sequence that is at least 90%, 91%, 92%, 93%, 94%, 95%, 96%, 97%, 98%, or 99% identical to SEQ ID NO: 2.

In particular embodiments, the IL-15 mutein contains mutations selected from N1D/D61N, N1D/E64Q, N4D/D61N, N4D/E64Q, D8N/D61N, D8N/E64Q, D30N/E64Q/N65D, D61N/E64Q, E64Q/Q108E, N1D/N4D/D8N, D61N/E64Q/N65D, N1D/D61N/E64Q, N1D/D61N/E64Q/Q108E, and N4D/D61N/E64Q/Q108E.

B. IL-15 Receptor Alpha Sushi Domain

In some embodiments, the present IL-15 prodrug comprises an IL-15Rα Sushi domain. The Sushi domain may be fused to the carrier directly or to the IL-15 cytokine moiety, optionally through a linker (e.g., a noncleavable or cleavable peptide linker). The masking moiety may be fused to the Sushi domain or to the carrier through a cleavable or noncleavable peptide linker. In a particular embodiment, the Sushi domain is fused to the carrier and the cytokine moiety is fused to the Sushi domain through a peptide linker. In the present IL-15 prodrugs, the Sushi domain may be a wildtype Sushi domain, or a Sushi domain comprising an amino acid sequence of SEQ ID NO: 7 or 9. In other embodiments, the Sushi domain comprises an amino acid sequence that is at least 90%, 91%, 92%, 93%, 94%, 95%, 96%, 97%, 98%, or 99% identical to SEQ ID NO: 7 or SEQ ID NO: 9.

In some embodiments, the human IL-15 receptor alpha (IL-15Rα) protein has the amino acid sequence set forth in SEQ ID NO: 8. In some cases, the coding sequence of human IL-15Rα is set forth in SEQ ID NO: 137. An exemplary IL-15Rα protein of the prodrug outlined herein can comprise or consist of the Sushi domain of SEQ ID NO: 8 (e.g., amino acids 31-95 or 31-105 of SEQ ID NO: 8), or in other words, the amino acid sequence of SEQ ID NO: 9 or SEQ ID NO: 7. In some embodiments, the IL-15Rα protein has the amino acid sequence of SEQ ID NO: 7 and an amino acid insertion selected from the group consisting of D96, P97, A98, D96/P97, D96/C97, D96/P97/A98, D96/P97/C98, and D96/C97/A98, wherein the amino acid position is relative to full-length human IL-15Rα protein or SEQ ID NO: 8. For instance, amino acid(s) such as D, P, A, DP, DC, DPA, DPC, or DCA can be added to the C-terminus of the IL-15Rα protein (e.g., SEQ ID NO: 9). In some embodiments, the IL-15Rα protein has the amino acid sequence of SEQ ID NO: 9 and one or more amino acid substitutions selected from the group consisting of K34C, A37C, G38C, S40C, and L42C, wherein the amino acid position is relative to SEQ ID NO:9. In certain embodiments, the IL-15 analog and the Sushi domain have a set of amino acid substitutions or additions selected from the group consisting of E87C: D96/P97/C98; E87C:D96/C97/A98; V49C: S40C; L52C: S40C; E89C: K34C; Q48C: G38C; E53C: L42C; C42S: A37C; and L45C: A37C, respectively (the mutations in IL-15 are shown before the colon; and the mutations in the Sushi domain are shown after the colon).

C. Masking Moieties of the Prodrugs

The cytokine antagonist, i.e., the masking moiety, in the present prodrug may comprise a peptide or an antibody or antibody fragment that binds to the cytokine moiety in the prodrug, masking the cytokine moiety and inhibiting its biological functions. In some embodiments, the masking moiety comprises an antigen-binding moiety or a binding fragment of an antibody, which binds to a human IL-15 polypeptide and inhibits a biological activity of the IL-15 polypeptide.

By way of example, IL-15 antagonists may comprise peptides and antibodies that bind IL-15 and interfere with the binding of the IL-15 moiety to its receptors, leading to the reduced biological activities of the IL-15 moiety while masked. In some embodiments, the IL-15 antagonist comprises an IL-2Rβ or IL-2Rγ extracellular domain or its functional analog such as one derived from human IL-2Rβ or IL-2Rγ (e.g., one of SEQ ID NOs: 3-6). In some embodiments, the IL-15 antagonist comprises a peptide identified from the screening of a peptide library. In some embodiments, the IL-15 antagonist comprises an antibody or fragment thereof that blocks the binding of IL-15 or IL-15 muteins to an IL-15 receptor. In other embodiments, the antagonist inhibits biological activity of an IL-15 polypeptide. In some embodiments, the antagonist comprises a scFv, a Fab, or other type of antibody fragment known in the art. In preferred embodiments, the antibody fragment is a scFv specific for IL-15. In other preferred embodiments, the antagonist specifically binds to an epitope located on the β- and/or γ-chain interacting domain of the IL-15 agonist polypeptide. In particular embodiments, the masking moiety does not block or interfere with the binding of the IL-15 polypeptide to IL-15Rα. By way of example, the IL-15-binding antibody may be selected from 146B7, 146H5, 404E4, and 404A8. In some embodiments, a scFv or Fab IL-15 antagonist comprises the CDR1, CDR2 and CDR3 domains of an anti-IL-15 antibody selected from 146B7, 146H5, 404E4, and 404A8; and the CDR1, CDR2 and CDR3 domains from the light chain of an anti-IL-15 antibody selected from 146B7, 146H5, 404E4, and 404A8, all of which are described in described in WO2003/017935A2.

In some embodiments, an IL-15 antagonist comprises heavy chain CDR1, CDR2 and CDR3 domains with amino acid sequences of SEQ ID NO: 100, 101, and 102, respectively; and light chain CDR1, CDR2 and CDR3 domains with amino acid sequences of SEQ ID NO: 103, 104, and 105, respectively. In some embodiments, the heavy chain CDR3 domain of SEQ ID NO: 102 comprises a substitution mutation of its Cys residue. The Cys residue within the CDR3 domain of SEQ ID NO: 102 may be mutated to Ser, Thr, Ala, Asn, or Gln. In another embodiment, the CDR3 domain comprises the amino acid sequence of SEQ ID NO: 106. In some embodiments, the antagonist or masking moiety is a scFv or a Fab comprising a heavy chain variable domain with an amino acid sequence of SEQ ID NO: 107 or at least 95% identical to SEQ ID NO: 107, and a light chain variable domain with an amino acid sequence of SEQ ID NO: 108 or 123 or at least 95% identical to SEQ ID NO: 108 or 123. In some specific moiety, the masking moiety comprises an amino acid sequence SEQ ID NO: 110 or 124.

D. Carrier Moieties of the Prodrugs

The carrier moieties of the present prodrugs may be an antigen-binding moiety, or a moiety that is not an antigen-binding moiety. The carrier moiety may improve the PK profiles such as serum half-life of the cytokine agonist polypeptide, and may also target the cytokine agonist polypeptide to a target site in the body, such as a tumor site.

In some embodiments, the carrier moiety (C) is an Fc domain comprising a first and a second polypeptide chain (i.e., two different heavy chains), wherein said polypeptide chains comprise molecular formulas (from N-terminus to C-terminus) selected from one of the following pairs:
  a) F1-PL1-A-PL2-S, F2-CL-M (FIG. 1A);
  b) F1-PL1-S-PL2-A, F2-CL-M (FIG. 1B); and
  c) F1-PL1-S-PL2-A, F2-CL-M (FIG. 1C);
wherein F1 and F2 are subunits of the carrier moiety (e.g., Fc domain), which form a heterodimer; PL1 and PL2 are peptide linkers; CL is a cleavable peptide linker; S is the Sushi domain; and A is an IL-15 polypeptide.

In some embodiments, the carrier moiety (C) is an Fc domain comprising a first and a second polypeptide chain (i.e., two different heavy chains), wherein said polypeptide chains comprise molecular formulas (from N-terminus to C-terminus) selected from one of the following pairs:
  a) A-PL1-S-F1, M-CL-F2 (FIG. 2A);
  b) S-PL1-A-F1, M-CL-F2 (FIG. 2B); and
  c) A-PL1-F1, M-CL-S-F2 (FIG. 2C);
wherein F1 and F2 are subunits of the carrier moiety (e.g., Fc domain), which form a heterodimer; PL1 and PL2 are peptide linkers; CL is a cleavable peptide linker; S is the Sushi domain; and A is an IL-15 polypeptide.

In some embodiment, the carrier moiety (C) is an antibody comprising two light chains of an antibody, a first antibody heavy chain, and a second antibody heavy chain, wherein
  a) the first heavy chain comprises the molecular formula (from N-terminal to C-terminal) C1-CL-M; and
  b) the second heavy chain comprises the molecular formula (from N-terminal to C-terminal) C2-PL1-S-PL2-A,
  wherein the C1 and C2 are the antibody heavy chains; said PL1 and PL2 are peptide linkers; CL is a cleavable peptide linker; S is the Sushi domain; and A is an IL-15 polypeptide. In other embodiments, the order of the above first and second heavy chains are reversed (FIGS. 3A and 3B).

In some embodiment, the carrier moiety (C) is an antibody comprising two light chains of an antibody, a first antibody heavy chain, and a second antibody heavy chain, wherein
 a) the first heavy chain comprises the molecular formula (from N-terminal to C-terminal) C1-A; and
 b) the second heavy chain polypeptide chain comprises the molecular formula (from N-terminal to C-terminal) C2-PL1-S-CL-M,
 wherein the C1 and C2 are the antibody heavy chains; said PL1 and PL2 are peptide linkers; CL is a cleavable peptide linker; S is the Sushi domain; and A is an IL-15 polypeptide (FIG. 3C).

Figure 4B:
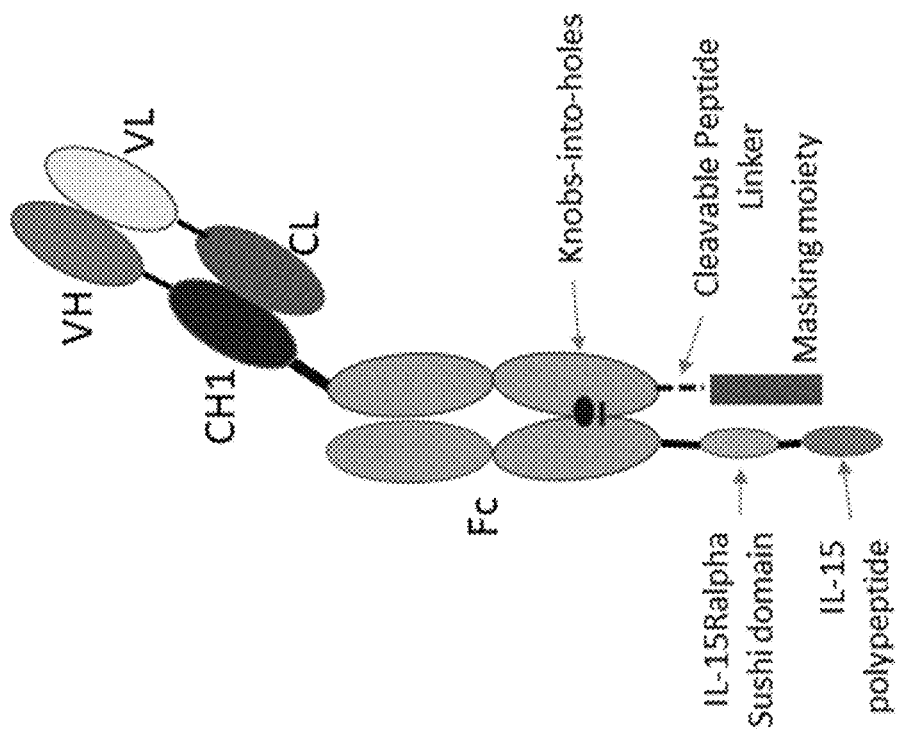
Figure 4A:
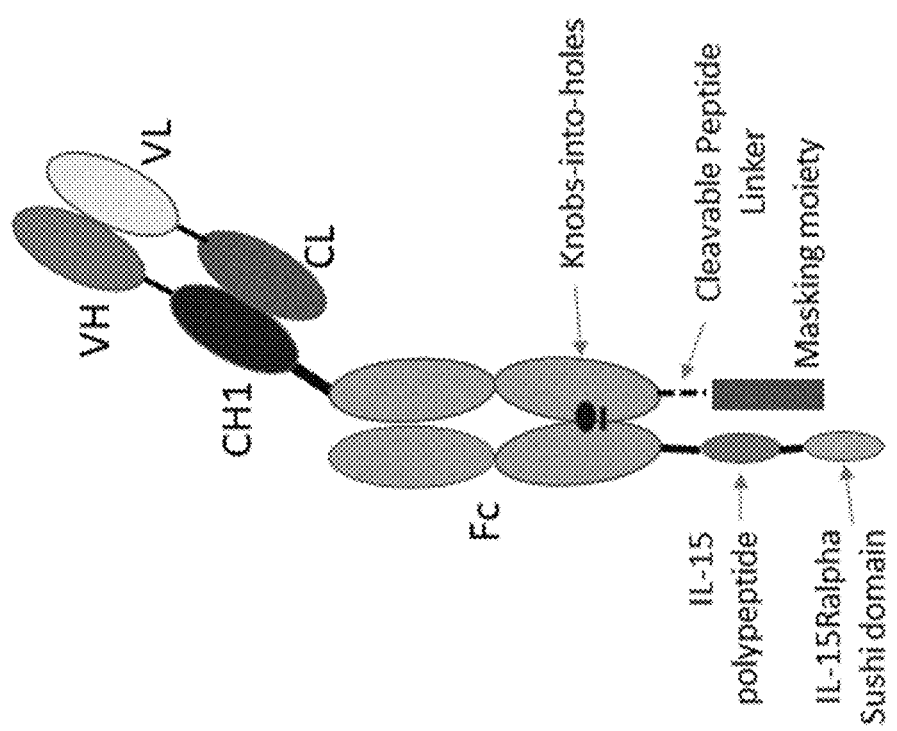
Figures 5A, 5B:
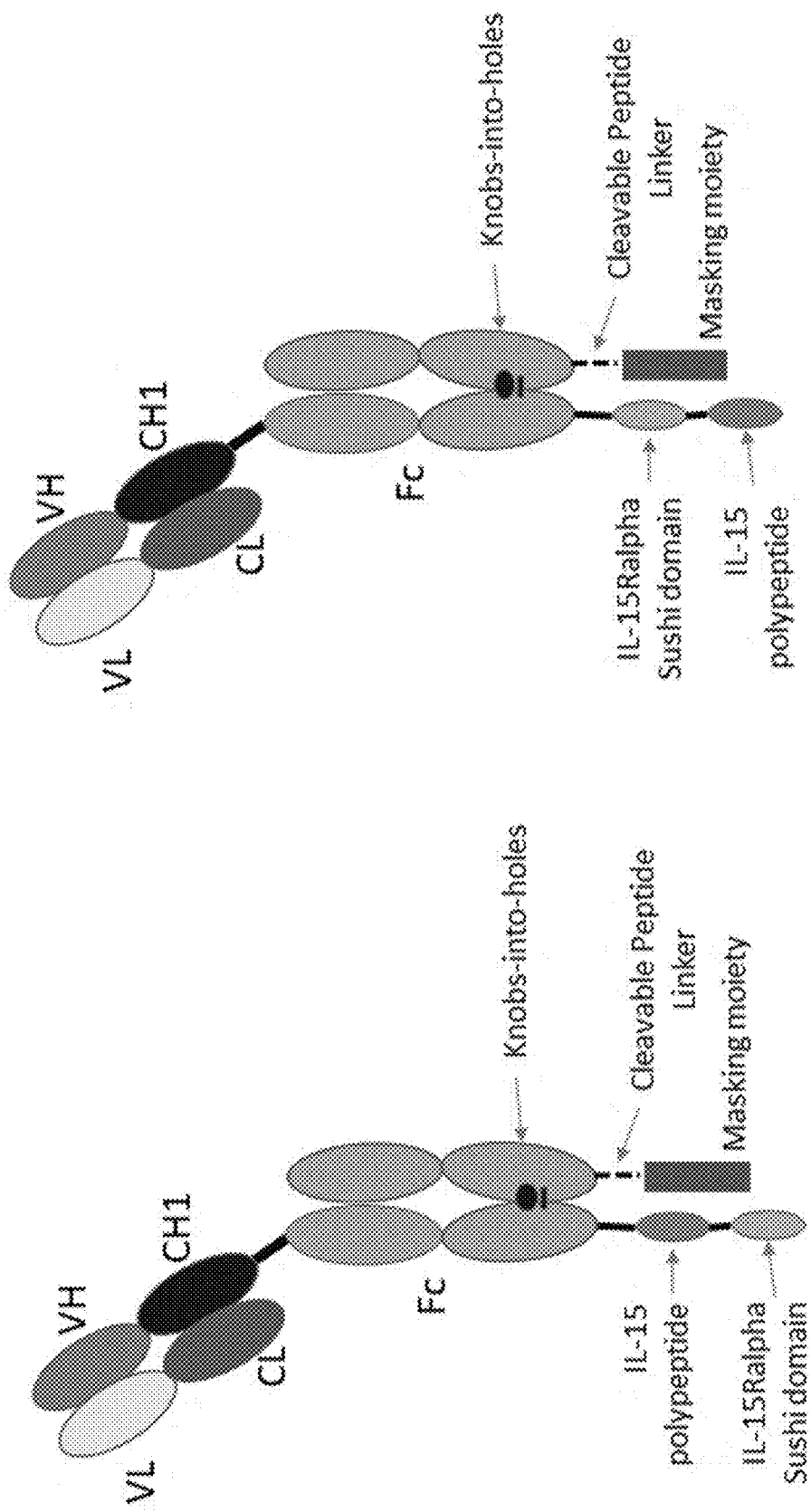

In some embodiments, the prodrugs of the present disclosure comprise three polypeptide chains—one antibody light chain and two heavy chains,—wherein the first polypeptide chain is an antibody light chain variable region, the first heavy chain comprises an antibody's heavy chain variable and constant regions, and the second heavy chain comprises a CH2 and a CH3 domain, wherein the first and second heavy chains comprise molecular formulas (from N-terminal to C-terminal) selected from one of the following pairs:
 a) F-PL1-A-PL2-S, HC-CL-M (FIG. 4A);
 b) F-PL1-S-PL2-A, HC-CL-M (FIG. 4B);
 c) HC-PL1-A-PL2-S, F-CL-M (FIG. 5A); and
 d) HC-PL1-S-PL2-A, F-CL-M (FIG. 5B).
 wherein F is a subunit of a Fc domain (comprising the CH2 and CH3 domains); HC is the heavy chain of an antibody which forms an antigen binding moiety with said light chain; PL1 and PL2 are peptide linkers; CL is a cleavable peptide linker; S is the Sushi domain; and A is an IL-15 polypeptide.

1. Antigen-Binding Carrier Moieties

The carrier moiety may be an antibody or an antigen-binding fragment thereof, or an immunoadhesin. In some embodiments, the antigen-binding moiety is a full-length antibody with two heavy chains and two light chains, a Fab fragment, a Fab' fragment, a F(ab')2 fragment, a Fv fragment, a disulfide linked Fv fragment, a single domain antibody, a nanobody, or a single-chain variable fragment (scFv). In some embodiments, the antigen-binding moiety is a bispecific antigen-binding moiety and can bind to two different antigens or two different epitopes on the same antigen. The antigen-binding moiety may provide additional and potentially synergetic therapeutic efficacy to the cytokine agonist polypeptide.

The cytokine (IL-15) polypeptide and its mask may be fused to the N-terminus or C-terminus of the light chains and/or heavy chains of the antigen-binding moiety. By way of example, the cytokine (e.g., IL-15 polypeptide and its mask may be fused to the antibody heavy chain or an antigen-binding fragment thereof or to the antibody light chain or an antigen-binding fragment thereof. In some embodiments, the cytokine (IL-15) polypeptide is fused to the C-terminus of one or both of the heavy chains of an antibody, and the cytokine's mask is fused to the other terminus of the heavy chain, or to the C-terminus of the cytokine agonist polypeptide, through a cleavable or non-cleavable peptide linker. In some embodiments, the cytokine (IL-15) polypeptide is fused to the C-terminus of one of the heavy chains of an antibody, and the cytokine's mask is fused to the C-terminus of the other heavy chain of the antibody through a cleavable peptide linker, wherein the two heavy chains optionally contain mutations that allow the specific pairing of the two different heavy chains.

Strategies of forming heterodimers for Fc-fusion polypeptides or bispecific antibodies are well known (see, e.g., Spies et al., Mol Imm. (2015) 67(2)(A):95-106). For example, the two heavy chain polypeptides in the prodrug may form stable heterodimers through "knobs-into-holes" mutations. "Knobs-into-holes" mutations are made to promote the formation of the heterodimers of the antibody heavy chains and are commonly used to make bispecific antibodies (see, e.g., U.S. Pat. No. 8,642,745). For example, the Fc domain of the antibody may comprise a T366W mutation in the CH3 domain of the "knob chain" and T366S, L368A, and/or Y407V mutations in the CH3 domain of the "hole chain." An additional interchain disulfide bridge between the CH3 domains can also be used, e.g., by introducing a Y349C mutation into the CH3 domain of the "knobs chain" and an E356C or S354C mutation into the CH3 domain of the "hole chain" (see, e.g., Merchant et al., Nature Biotech (1998)16:677-81). In other embodiments, the antibody moiety may comprise Y349C and/or T366W mutations in one of the two CH3 domains, and E356C, T366S, L368A, and/or Y407V mutations in the other CH3 domain. In certain embodiments, the antibody moiety may comprise Y349C and/or T366W mutations in one of the two CH3 domains, and S354C (or E356C), T366S, L368A, and/or Y407V mutations in the other CH3 domain, with the additional Y349C mutation in one CH3 domain and the additional E356C or S354C mutation in the other CH3 domain, forming an interchain disulfide bridge (numbering always according to EU index of Kabat; Kabat et al., "Sequences of Proteins of Immunological Interest," 5th ed., Public Health Service, National Institutes of Health, Bethesda, Md. (1991)). Other knobs-into-holes technologies, such as those described in EP1870459A1, can be used alternatively or additionally. Thus, another example of knobs-into-holes mutations for an antibody moiety is having R409D/K370E mutations in the CH3 domain of the "knob chain" and D399K/E357K mutations in the CH3 domain of the "hole chain" (EU numbering).

In some embodiments, the antibody moiety in the prodrug comprises L234A and L235A ("LALA") mutations in its Fc domain. The LALA mutations eliminate complement binding and fixation as well as Fcγ dependent ADCC (see, e.g., Hezareh et al. J. Virol. (2001) 75(24):12161-8). In further embodiments, the LALA mutations are present in the antibody moiety in addition to the knobs-into-holes mutations.

In some embodiments, the antibody moiety comprises the M252Y/S254T/T256E ("YTE") mutations in the Fc domain. The YTE mutations allow the simultaneous modulation of serum half-life, tissue distribution and activity of $IgG_1$ (see Dall'Acqua et al., J Blot Chem. (2006) 281: 23514-24; and Robbie et al., Antimicrob Agents Chemother. (2013) 57(12): 6147-53). In further embodiments, the YTE mutations are present in the antibody moiety in addition to the knobs-into-holes mutations. In particular embodiments, the antibody moiety has YTE, LALA and knobs-into-holes mutations or any combination thereof.

The antigen-binding moiety may bind to an antigen on the surface of a cell, such as an immune cell, for example, T cells, NK cells, and macrophages, or bind to a cytokine. For example, the antigen-binding moiety may bind to PD-1, LAG-3, TIM-3, TIGIT, CTLA-4, or TGF-beta and may be an antibody. The antibody may have the ability to activate the immune cell and enhance its anti-cancer activity.

The antigen-binding moiety may bind to an antigen on the surface of a tumor cell. For example, the antigen-binding moiety may bind to FAP alpha, 5T4, Trop-2, PD-L1, HER-2, EGFR, Claudin 18.2, DLL-3, GCP3, or carcinoembryonic antigen (CEA), and may be an antibody. The antibody may or may not have ADCC activity. The antibody may also be further conjugated to a cytotoxic drug.

In some embodiments, the antigen-binding moiety binds to guanyl cyclase C (GCC), carbohydrate antigen 19-9 (CA19-9), glycoprotein A33 (gpA33), mucin 1 (MUC1), insulin-like growth factor 1 receptor (IGF1-R), human epidermal growth factor receptor 2 (HER2), human epidermal growth factor receptor 3 (HER3), delta-like protein 3 (DLL3), delta-like protein 4 (DLL4), epidermal growth factor receptor (EGFR), glypican-3 (GPC3), c-MET, vascular endothelial growth factor receptor 1 (VEGFR1), vascular endothelial growth factor receptor 2 (VEGFR2), Nectin-4, Liv-1, glycoprotein NMB (GPNMB), prostate-specific membrane antigen (PSMA), Trop-2, carbonic anhydrase IX (CA9), endothelin B receptor (ETBR), six transmembrane epithelial antigen of the prostate 1 (STEAP1), folate receptor alpha (FR-α), SLIT and NTRK-like protein 6 (SLITRK6), carbonic anhydrase VI (CA6), ectonucleotide pyrophosphatase/phosphodiesterase family member 3 (ENPP3), mesothelin, trophoblast glycoprotein (TPBG), CD19, CD20, CD22, CD33, CD40, CD56, CD66e, CD70, CD74, CD79b, CD98, CD123, CD138, CD352, CD47, signal-regulatory protein alpha (SIRPα), Claudin 18.2, Claudin 6, BCMA, or EPCAM. In some embodiments, the antigen-binding moiety binds to an epidermal growth factor (EGF)-like domain of DLL3. In some embodiments, the antigen-binding moiety binds to a Delta/Serrate/Lag2 (DSL)-like domain of DLL3. In some embodiments, the antigen-binding moiety binds to an epitope located after the 374th amino acid of GPC3. In some embodiments, the antigen-binding moiety binds to a heparin sulfate glycan of GPC3. In some embodiments, the antigen-binding moiety binds to Claudin 18.2 and does not bind to Claudin 18.1. In some embodiments, the antigen-binding moiety binds to Claudin 18.1 with at least 10 times weaker binding affinity than to Claudin 18.2.

In some embodiments, the antigen-binding moiety (carrier moiety) includes an antibody or fragment thereof known in the art that binds to PD-1 and disrupts the interaction between the PD-1 and its ligand (PD-L1) to stimulate an anti-tumor immune response. In some embodiments, the antibody or antigen-binding portion thereof binds specifically to PD-1. For example, antibodies that target PD-1 and which can find use in the present invention include, but are not limited to, nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat # BP0146. Other suitable anti-PD-1 antibodies include those disclosed in U.S. Pat. No. 8,008,449. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in combination treatment methods disclosed herein. As an example, antibodies that target PD-L1 include BMS-936559 (Bristol-Myers Squibb) and MPDL3280A (Genetech; currently in human trials). Other suitable antibodies that target PD-L1 are disclosed in U.S. Pat. No. 7,943,743. It will be understood by one of ordinary skill that any antibody which binds to PD-1 or PD-L1, disrupts the PD-1/PD-L1 interaction, and stimulates an anti-tumor immune response, is suitable for use in the combination treatment methods disclosed herein.

In some embodiments, wherein the carrier is an antibody against human PD-L1, which is selected from ASKB1296, avelumab, atezolizumab and durvalumab.

In some embodiments, the carrier is an antibody, which binds to an antigen expressed on a cancer cell. In some embodiments, the carrier antibody has ADCC activity. In some embodiments, the carrier antibody binds to an antigen selected from HER2, HER3, EGFR, CMET, Trop-2, GPC3, Claudin 18.2, Claudin 6, 5T4, BCMA, CD38, CD20, CD30, CD47, and VEGFR2.

In some embodiments, the carrier is a bispecific antibody which binds to two antigens selected from PD-1, PD-L1, CTLA-4, LAG-4, TIM-3, CD47, and TIGIT.

In some embodiments, the carrier antibody binds to human PD-1, wherein the PD-1 antibody comprises the same heavy chain CDR1, CDR2 and CDR3 domains, and light chain CDR1, CDR2, and CDR3 domains as derived from the heavy chain and light chain of nivolumab, pembrolizumab, toripalimab, sintilimab, or tislelizumab.

In some embodiments, the carrier antibody binds to human PD-1, wherein the light chain comprises an amino acid sequence at least 99% identical as one selected from SEQ ID NO: 55 and 56; wherein the first heavy chain polypeptide chain comprises an amino acid sequence at least 99% identical as that of SEQ ID NO: 54, 60, or 61; and wherein the second heavy chain polypeptide chain comprises an amino acid sequence at least 99% identical as one selected from SEQ ID NO: 52, 53, 58, 59, 62, 63 and 69.

In some embodiments, the antibody binds to human PD-1, wherein the light chain comprises an amino acid sequence at least 99% identical as SEQ ID NO: 55; wherein the first heavy chain polypeptide chain comprises an amino acid sequence at least 99% identical as that of SEQ ID NO: 66; and wherein the second heavy chain polypeptide chain comprises an amino acid sequence at least 99% identical as one selected from SEQ ID NO: 64, 65, 67 and 68.

In some embodiments, the carrier antibody binds to PD-1, wherein the light chain comprises an amino acid sequence at least 99% identical as one selected from SEQ ID NOs: 55 and 56; wherein the first heavy chain comprises an amino acid sequence at least 99% identical as one selected from SEQ ID NO: 80, 81, or 87; and wherein the second heavy chain comprises an amino acid sequence at least 99% identical as one selected from SEQ ID NOs: 52, 53, 58, 59, 62, 63 and 69.

In some embodiments, the carrier antibody binds to PD-1, wherein the light chain comprises an amino acid sequence at least 99% identical as one selected from SEQ ID NOs: 55 and 56; wherein the first heavy chain comprises an amino acid sequence at least 99% identical as that of SEQ ID NO: 54, 60, or 61; and wherein second heavy chain comprises an amino acid sequence at least 99% identical as one selected from SEQ ID NOs: 82, 83, 84, 85 and 86.

In some embodiments, the carrier antibody binds to PD-L1, wherein the light chain comprises an amino acid sequence at least 99% identical as that of SEQ ID NO: 50 or 51; wherein the first heavy chain polypeptide chain comprises an amino acid at least 99% identical as that of SEQ ID NO: 47, 48 or 49; and wherein the second heavy chain polypeptide chain comprises an amino acid sequence at least 99% identical as that of SEQ ID NO: 45 or 46.

In some embodiments, the carrier antibody is a bispecific antibody, which binds to two antigens selected from HER2, HER3, EGFR, CMET, Trop-2, GPC3, Claudin 18.2, Claudin 6, 5T4, BCMA, CD38, CD20, CD30, and VEGFR2. In some embodiments, the carrier is a bispecific antibody, which binds to cMet and EGFR; wherein the EGFR binding domain comprises light chain CDR1, CDR2 and CDR3 derived from SEQ ID NO: 88 or 90, and heavy chain CDR1, CDR2, and CDR3 derived from SEQ ID NO: 89 or 91.

In some embodiments, the carrier moiety is an IgG1 Fc domain; and wherein the first polypeptide comprises an amino acid sequence at least 99% identical as one selected from SEQ ID NO: 37, 70-72 and 73, and the second polypeptide chain comprises an amino acid sequence at least 99% identical as one selected from SEQ ID NOs: 38, 39, 75-78, and 79.

In some embodiments, the carrier moiety is an IgG4 Fc domain; and wherein the first polypeptide comprises an amino acid sequence at least 99% identical as one shown in SEQ ID NO: 80, 81 or 87, and the second polypeptide chain comprises an amino acid sequence at least 99% identical as one selected from SEQ ID NOs: 82-85 and 86.

In some embodiments, the antigen-binding moiety includes an antibody or fragment thereof known in the art that binds CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), which is currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994. It will be understood by one of ordinary skill that any antibody which binds to CTLA-4, disrupts its interaction with CD80 and CD86, and stimulates an anti-tumor immune response, is suitable for use in the combination treatment methods disclosed herein.

In some embodiments, the combination therapy includes an antibody known in the art that binds LAG-3 and disrupts its interaction with MEW class II molecules. An exemplary antibody that targets LAG-3 is IMP321 (Immutep), currently undergoing human trials. Other suitable antibodies that target LAG-3 are disclosed in U.S. Patent Application 2011/0150892. It will be understood by one of ordinary skill that any antibody which binds to LAG-3, disrupts its interaction with MHC class II molecules, and stimulates an anti-tumor immune response, is suitable for use in the combination treatment methods disclosed herein.

In some embodiments, the antigen-binding moiety comprises an antibody or fragment thereof known in the art that binds TIM-3 and disrupts its interaction with galectin 9. Suitable antibodies that target TIM-3 are disclosed in U.S. Patent Application 2013/0022623. It will be understood by one of ordinary skill that any antibody which binds to TIM-3, disrupts its interaction with galectin 9, and stimulates an anti-tumor immune response, is suitable for use in the combination treatment methods disclosed herein.

In some embodiments, the antigen-binding moiety comprises an antibody or fragment thereof known in the art that binds 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the combination treatment methods disclosed herein.

In some embodiments, the antigen-binding moiety comprises an antibody or fragment thereof known in the art that binds GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the combination treatment methods disclosed herein.

In some embodiments, the antigen-binding moiety comprises an antibody or fragment thereof known in the art that binds OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the combination treatment methods disclosed herein.

In some embodiments, the antigen-binding moiety comprises an antibody or fragment thereof known in the art that binds CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the combination treatment methods disclosed herein.

In some embodiments, the antigen-binding moiety comprises an antibody or fragment thereof known in the art that binds ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the combination treatment methods disclosed herein.

In some embodiments, the antigen-binding moiety comprises an antibody or fragment thereof known in the art that binds CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the combination treatment methods disclosed herein.

Additional exemplary antigen-binding moieties (carrier moieties) include trastuzumab, rituximab, brentuximab, cetuximab, panitumumab, GC33 (or a humanized version thereof), and anti-EGFR antibody mAb806 (or a humanized version thereof). In some embodiments, the antigen-binding moiety has at least 90%, 91%, 92%, 93%, 94%, 95%, 96%, 97%, 98%, or 99% identity to trastuzumab, rituximab, brentuximab, cetuximab, or panitumumab, GC33 (or a humanized version thereof), or anti-EGFR antibody mAb806 (or a humanized version thereof). In some embodiments, the antigen-binding moiety has an antibody heavy chain with at least 90%, 91%, 92%, 93%, 94%, 95%, 96%, 97%, 98%, or 99% identity to the antibody heavy chain of trastuzumab, rituximab, brentuximab, cetuximab, panitumumab, GC33 (or a humanized version thereof), anti-EGFR antibody mAb806 (or a humanized version thereof), or a fragment thereof. In some embodiments, the antigen-binding moiety has an antibody light chain with at least 90%, 91%, 92%, 93%, 94%, 95%, 96%, 97%, 98%, or 99% identity to the antibody light chain of trastuzumab, rituximab, brentuximab, cetuximab, panitumumab, GC33 (or a humanized version thereof), anti-EGFR antibody mAb806

(or a humanized version thereof), or a fragment thereof. The antigen-binding moiety is fused to an IL-15 polypeptide. In some embodiments, the antigen-binding moiety comprises the six complementarity-determining regions (CDRs) of trastuzumab, rituximab, brentuximab, cetuximab, panitumumab, GC33, or anti-EGFR antibody mAb806.

A number of CDR delineations are known in the art and are encompassed herein. A person of skill in the art can readily determine a CDR for a given delineation based on the sequence of the heavy or light chain variable region. The "Kabat" CDRs are based on sequence variability and are the most commonly used (Kabat et al., *Sequences of Proteins of Immunological Interest*, 5th Ed. Public Health Service, National Institutes of Health, Bethesda, Md. (1991)). "Chothia" CDRs refer to the location of the structural loops (Chothia & Lesk, *Canonical structures for the hypervariable regions of immunoglobulins*, J. Mol. Biol., vol. 196, pp. 901-917 (1987)). The "AbM" CDRs represent a compromise between the Kabat CDRs and Chothia structural loops are used by Oxford Molecular's AbM antibody modeling software. The "Contact" CDRs are based on an analysis of the available complex crystal structures. The residues from each of these CDRs are noted below in Table 1, in reference to common antibody numbering schemes. Unless otherwise specified herein, amino acid numbers in antibodies refer to the Kabat numbering scheme as described in Kabat et al., supra, including when CDR delineations are made in reference to Kabat, Chothia, AbM, or Contact schemes. Using this numbering system, the actual linear amino acid sequence may contain fewer or additional amino acids corresponding to a shortening of, or insertion into, a framework region (FR) or CDR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

TABLE 1

CDR Delineations According to Various Schemes

| CDR | Kabat | AbM | Chothia | Contact |
|---|---|---|---|---|
| VL-CDR1 | L24-L34 | L24-L34 | L26-L32 | L30-L36 |
| VL-CDR2 | L50-L56 | L50-L56 | L50-L52 | L46-L55 |
| VL-CDR3 | L89-L97 | L89-L97 | L91-L96 | L89-L96 |
| VH-CDR1 (Kabat nos.) | H31-H35B | H26-H35B | H26-H32 | H30-H35B |
| VH-CDR1 (Chothia nos.) | H31-H35 | H26-H35 | H26-H32 | H30-H35 |
| VH-CDR2 | H50-H65 | H50-H58 | H53-H55 | H47-H58 |
| VH-CDR3 | H95-H102 | H95-H102 | H95-H101 | H93-H101 |

In some embodiments, the CDRs are "extended CDRs," and encompass a region that begins or terminates according to a different scheme. For example, an extended CDR can be as follows: L24-L36, L26-L34, or L26-L36 (VL-CDR1); L46-L52, L46-L56, or L50-L55 (VL-CDR2); L91-L97 (VL-CDR3); H47-H55, H47-H65, H50-H55, H53-H58, or H53-H65 (VH-CDR2); and/or H93-H102 (VH-CDR3).

In some embodiments, the antigen-binding moiety binds to EGFR, and comprises a light chain having an amino acid sequence with at least 90%, 91%, 92%, 93%, 94%, 95%, 96%, 97%, 98%, or 99% identity to SEQ ID NO: 88, or a fragment thereof, and a heavy chain having an amino acid sequence with at least 90%, 91%, 92%, 93%, 94%, 95%, 96%, 97%, 98%, or 99% identity to SEQ ID NO: 89, or a fragment thereof. In some embodiments, the antigen-binding domain comprises CDR1, CDR2, and CDR3 from SEQ ID NO: 88, and CDR1, CDR2, and CDR3 from SEQ ID NO: 89.

In some embodiments, the antigen-binding moiety binds to EGFR, and comprises a light chain having an amino acid sequence with at least 90%, 91%, 92%, 93%, 94%, 95%, 96%, 97%, 98%, or 99% identity to SEQ ID NO: 90, or a fragment thereof, and a heavy chain having an amino acid sequence with at least 90%, 91%, 92%, 93%, 94%, 95%, 96%, 97%, 98%, or 99% identity to SEQ ID NO: 91, or a fragment thereof. In some embodiments, the antigen-binding domain comprises CDR1, CDR2, and CDR3 from SEQ ID NO: 90, and CDR1, CDR2, and CDR3 from SEQ ID NO: 91.

In some embodiments, the antigen-binding moiety binds to c-MET, and comprises a light chain having an amino acid sequence with at least 90%, 91%, 92%, 93%, 94%, 95%, 96%, 97%, 98%, or 99% identity to SEQ ID NO: 92, or a fragment thereof, and a heavy chain having an amino acid sequence with at least 90%, 91%, 92%, 93%, 94%, 95%, 96%, 97%, 98%, or 99% identity to SEQ ID NO: 93, or a fragment thereof. In some embodiments, the antigen-binding domain comprises CDR1, CDR2, and CDR3 from SEQ ID NO: 92, and CDR1, CDR2, and CDR3 from SEQ ID NO: 93.

In some embodiments, the antigen-binding moiety binds to GPC3, and comprises a light chain having an amino acid sequence with at least 90%, 91%, 92%, 93%, 94%, 95%, 96%, 97%, 98%, or 99% identity to SEQ ID NO: 94, or a fragment thereof, and a heavy chain having an amino acid sequence with at least 90%, 91%, 92%, 93%, 94%, 95%, 96%, 97%, 98%, or 99% identity to SEQ ID NO: 95, or a fragment thereof. In some embodiments, the antigen-binding domain comprises CDR1, CDR2, and CDR3 from SEQ ID NO: 94, and CDR1, CDR2, and CDR3 from SEQ ID NO: 95.

In some embodiments, the antigen-binding moiety binds to 5T4, and comprises a light chain variable domain having an amino acid sequence with at least 90%, 91%, 92%, 93%, 94%, 95%, 96%, 97%, 98%, or 99% identity to SEQ ID NO: 98 or 99, and a heavy chain variable domain having an amino acid sequence with at least 90%, 91%, 92%, 93%, 94%, 95%, 96%, 97%, 98%, or 99% identity to SEQ ID NO: 96 or 97, or a fragment thereof. In some embodiments, the antigen-binding domain comprises CDR1, CDR2, and CDR3 from SEQ ID NO: 98 or 99, and CDR1, CDR2, and CDR3 from SEQ ID NO: 96 or 97.

In some embodiments, the antigen-binding moiety binds to Trop-2, and comprises a light chain variable region comprising a CDR1 comprising an amino acid sequence of KASQDVSIAVA (SEQ ID NO:125), a CDR2 comprising an amino acid sequence of SASYRYT (SEQ ID NO:126), and a CDR3 comprising an amino acid sequence of QQHYITPLT (SEQ ID NO:127); and a heavy chain variable region comprising a CDR1 comprising an amino acid sequence of NYGMN (SEQ ID NO:128), a CDR2 comprising an amino acid sequence of WINTYTGEPTYTDDFKG (SEQ ID NO: 129), and a CDR3 comprising an amino acid sequence of GGFGSSYWYFDV (SEQ ID NO: 130).

In some embodiments, the antigen-binding moiety binds to mesothelin, and comprises light chain variable region comprising a CDR1 comprising an amino acid sequence of SASSSVSYMH (SEQ ID NO: 131), a CDR2 comprising an amino acid sequence of DTSKLAS (SEQ ID NO: 132), and a CDR3 comprising an amino acid sequence of QQWSGY-PLT (SEQ ID NO: 133); and a heavy chain variable region comprising a CDR1 comprising an amino acid sequence of GYTMN (SEQ ID NO: 134), a CDR2 comprising an amino acid sequence of LITPYNGASSYNQKFRG (SEQ ID NO: 135), and a CDR3 comprising an amino acid sequence of GGYDGRGFDY (SEQ ID NO: 136).

In some embodiments, the antigen-binding moiety comprises one, two, or three antigen-binding domains. For example, the antigen-binding moiety may be bispecific and binds to two different antigens selected from the group consisting of HER2, HER3, EGFR, 5T4, FAP alpha, Trop-2, GPC3, VEGFR2, Claudin 18.2, and PD-L1. In some embodiments, the bispecific antigen-binding moiety may bind two different epitopes of the same antigen. For example, the bispecific antibody may bind to two different epitopes of HER2.

2. Other Carrier Moieties

Other non-antigen-binding carrier moieties may be used for the present prodrugs. For example, an antibody Fc domain (e.g., a human $IgG_1$, $IgG_2$, $IgG_3$, or $IgG_4$ Fc), a polymer (e.g., PEG), an albumin (e.g., a human albumin) or a fragment thereof, or a nanoparticle can be used.

By way of example, the IL-15 polypeptide and the Sushi domain and the IL-15 antagonist may be fused to an antibody Fc domain, forming an Fc fusion protein. In some embodiments, the Sushi domain is optionally fused to the C-terminus or N-terminus of one of the heavy chains of the Fc domain, the IL-15 polypeptide is fused to the C-terminus or N-terminus of the Sushi domain through a noncleavable linker, and the masking moiety is fused to the C-terminus or N-terminus of the other heavy domain of the Fc domain through a cleavable peptide or noncleavable linker. In some embodiments, each of the heavy chains of the Fc domain contain mutations that allow their pairing. In some embodiments, mutations may be knobs-into-holes, YTE and/or LALA mutations.

The carrier moiety of the prodrug may comprise an albumin (e.g., human serum albumin) or a fragment thereof. In some embodiments, the albumin or albumin fragment is about 85% or more, about 90% or more, about 91% or more, about 92% or more, about 93% or more, about 94% or more, about 95% or more, about 96% or more, about 97% or more, about 98% or more, about 99% or more, about 99.5% or more, or about 99.8% or more identical to human serum albumin or a fragment thereof.

In some embodiments, the carrier moiety comprises an albumin fragment (e.g., a human serum albumin fragment) that is about 10 or more, 20 or more, 30 or more 40 or more, 50 or more, 60 or more, 70 or more, 80 or more, 90 or more, 100 or more, 120 or more, 140 or more, 160 or more, 180 or more, 200 or more, 250 or more, 300 or more, 350 or more, 400 or more, 450 or more, 500 or more, or 550 or more amino acids in length. In some embodiments, the albumin fragment is between about 10 amino acids and about 584 amino acids in length (such as between about 10 and about 20, about 20 and about 40, about 40 and about 80, about 80 and about 160, about 160 and about 250, about 250 and about 350, about 350 and about 450, or about 450 and about 550 amino acids in length). In some embodiments, the albumin fragment includes the Sudlow I domain or a fragment thereof, or the Sudlow II domain or the fragment thereof.

D. Linker Components of the Prodrugs

The IL-15 polypeptide and the Sushi domain may be fused to the carrier moiety with or without a peptide linker. The peptide linker may be noncleavable. In some embodiments, the peptide linker is selected from SEQ ID NOs: 11-16. In particular embodiments, the peptide linker comprises the amino acid sequence GGGGSGGGGSGGGGS (SEQ ID NO: 13). In some embodiments, the IL-15 polypeptide (A) is fused to the Sushi domain (S) through a peptide linker. The peptide linker may be at least 25, 30, or 35 amino acids long. In some embodiments, the peptide linker may be 25-45 amino acids. In other embodiments, peptide linker has 25, 26, 27, 28, 29, 30, 31, 32, 33, 34, 35, 36, 37, 38, 39, 40, 41, 42, 43, 44 or 45 amino acids. In some embodiments, the linker comprises an amino acid sequence GSAGSAAGSGEF (SEQ ID NO: 138). In some embodiments, the linker comprises an amino acid sequence $(GGGGS)_{n1}GSAGSAAGSGEF(GGGGS)_{n2}$ (SEQ ID NO: 139), wherein n1=1, 2, or 3, and n2=1, 2, or 3. In some embodiments, the linker comprises an amino acid sequence $(GGGGS)_{n1}AA(GGGGS)_{n2}$ (SEQ ID NO: 140); wherein n1=2 or 3, and n2=2 or 3.

The masking moiety may be fused to the carrier through a cleavable linker. The cleavable linker may contain one or more (e.g., two or three) cleavable moieties (CM). Each CM may be a substrate for an enzyme or protease selected from legumain, plasmin, TMPRSS-3/4, MMP-2, MMP-9, MT1-MMP, cathepsin, caspase, human neutrophil elastase, beta-secretase, uPA, and PSA. Examples of cleavable linkers include, without limitation, those comprising an amino acid sequence selected from SEQ ID NOs: 17-35, and 36.

In some embodiments, the IL-15 prodrugs of the present disclosure comprise the IL-15 receptor alpha Sushi domain (S), fused to the IL-15 polypeptide through a peptide linker. In certain embodiments, the peptide linker comprises at least 20 amino acids, 25 amino acids, at least 30 amino acids, at least 35 amino acids, or at least 40 amino acids; or 27 amino acids, 32 amino acids, 37 amino acids, 42 amino acids, or 47 amino acids.

II. Example of IL-15 Prodrugs

In some embodiments, an activatable IL-15 prodrug has a molecular structure illustrated in any one of FIGS. 1A-1C and FIGS. 2A-2C. In a particular embodiment, the IL-15 prodrug has a molecular structure illustrated in any one of FIG. 1B or FIG. 2B. In some embodiments, the IL-15 prodrug comprises a structure illustrated in any one of FIGS. 3A-3C. In a particular embodiment, the IL-15 prodrug comprises a structure illustrated in FIG. 3B. In some embodiments, the carrier moiety is an antibody that comprises one antigen-binding moiety, as illustrated in FIG. 4A, 4B, 5A, or 5B. In a preferred embodiment, the IL-15 prodrug comprises a structure selected from FIG. 4B and FIG. 5B.

The IL-15 prodrug may not contain the Sushi domain or any of its functional analogs. In some embodiments, the IL-15 prodrug comprises an IL-15 polypeptide comprising one or more mutations at a position or positions selected from E46, V49, L45, S51, and L52 (numbering according to SEQ ID NO: 2). In some embodiments, the IL-15 polypeptide comprises the mutation E46K (numbering according to SEQ ID NO: 2). In other embodiments, the IL-15 polypeptide comprises the mutations E46K/N65D (numbering according to SEQ ID NO: 2). In yet other embodiments, IL-15 polypeptide comprises the mutations E46K/Q108E (numbering according to SEQ ID NO: 2).

In some embodiments, an IL-15 prodrug of the present disclosure comprises an $IgG_1$ Fc domain as the carrier moiety. For example, the IL-15 prodrug may be selected from Table 2. In other embodiments, an IL-15 prodrug of the present invention comprises an IgG4 Fc domain. For example, the IL-15 prodrug may be selected from Table 3. In some embodiments, an IL-15 prodrug of the present invention comprises an antibody that binds to human PD-L1 as the carrier moiety. For example, the IL-15 prodrug may be selected from Table 4. In some embodiments, an IL-15 prodrug of the present invention comprises an antibody that binds to human PD-1 as the carrier moiety. For example, the IL-15 prodrug may be selected from Table 5.

TABLE 2

Examples of activatable IgG$_1$ Fc-IL-15 fusion polypeptides

| Name | Fc fused with IL-15 or its analog | Fc fused with the masking moiety |
|---|---|---|
| IgG1 Fc-IL-15 Fusion A | SEQ ID NO: 38 | SEQ ID NO: 37 |
| IgG1 Fc-IL-15 Fusion B | SEQ ID NO: 39 | SEQ ID NO: 37 |
| IgG1 Fc-IL-15 Fusion C | SEQ ID NO: 39 | SEQ ID NO: 70, 71, 72, 73, or 74 |
| IgG1 Fc-IL-15 Fusion D | SEQ ID NO: 75 | |
| IgG1 Fc-IL-15 Fusion E | SEQ ID NO: 76 | |
| IgG1 Fc-IL-15 Fusion F | SEQ ID NO: 77 | |
| IgG1 Fc-IL-15 Fusion G | SEQ ID NO: 78 | |
| IgG1 Fc-IL-15 Fusion H | SEQ ID NO: 79 | |

TABLE 3

Examples of activatable IgG$_4$ Fc-IL-15 fusion polypeptides

| Name | Fc fused with IL-15 or its analog | Fc fused with the masking moiety |
|---|---|---|
| IgG4 Fc-IL-15 Fusion A | SEQ ID NO: 82 | SEQ ID NO: 80 or 87 |
| IgG4 Fc-IL-15 Fusion B | SEQ ID NO: 83 | SEQ ID NO: 80 or 87 |
| IgG4 Fc-IL-15 Fusion C | SEQ ID NO: 84 | SEQ ID NO: 80 or 87 |
| IgG4 Fc-IL-15 Fusion D | SEQ ID NO: 85 | SEQ ID NO: 80 or 87 |
| IgG4 Fc-IL-15 Fusion E | SEQ ID NO: 86 | SEQ ID NO: 80 or 87 |
| IgG4 Fc-IL-15 Fusion F | SEQ ID NO: 82 | SEQ ID NO: 81 |
| IgG4 Fc-IL-15 Fusion G | SEQ ID NO: 83 | SEQ ID NO: 81 |
| IgG4 Fc-IL-15 Fusion H | SEQ ID NO: 84 | SEQ ID NO: 81 |
| IgG4 Fc-IL-15 Fusion I | SEQ ID NO: 85 | SEQ ID NO: 81 |
| IgG4 Fc-IL-15 Fusion J | SEQ ID NO: 86 | SEQ ID NO: 81 |

TABLE 4

Examples of activatable PD-L1 antibody/IL-15 fusion polypeptides

| Name | HC Polypeptide Chain fused with IL-15 or its analog | HC Polypeptide Chain fused with the masking moiety | Light Chain |
|---|---|---|---|
| PDL1 antibody-IL-15 Fusion A | SEQ ID NO: 45 | SEQ ID NO: 47 | SEQ ID NO: 50 or 51 |
| PDL1 antibody-IL-15 Fusion B | SEQ ID NO: 46 | SEQ ID NO: 47 | SEQ ID NO: 50 or 51 |
| PDL1 antibody-IL-15 Fusion C | SEQ ID NO: 45 | SEQ ID NO: 48 | SEQ ID NO: 50 or 51 |
| PDL1 antibody-IL-15 Fusion D | SEQ ID NO: 45 | SEQ ID NO: 49 | SEQ ID NO: 50 or 51 |

TABLE 5

Examples of activatable PD-1 antibody-IL-15 fusion polypeptides

| Name | HC fused with IL-15 or its analog | HC fused with the masking moiety | Light Chain | Comments |
|---|---|---|---|---|
| PD1 antibody-IL-15 Fusion A | SEQ ID NO: 52 | SEQ ID NO: 54 | SEQ ID NO: 55 or 56 | Masked with IL-2Rβ ECD |
| PD1 antibody-IL-15 Fusion B | SEQ ID NO: 53 | SEQ ID NO: 54 | SEQ ID NO: 55 or 56 | |
| PD1 antibody-IL-15 Fusion C | SEQ ID NO: 52 | SEQ ID NO: 60 or 61 | SEQ ID NO: 55 or 56 | Masked with scFv1 or scFv2 |
| PD1 antibody-IL-15 Fusion D | SEQ ID NO: 58 | SEQ ID NO: 60 or 61 | SEQ ID NO: 55 or 56 | |
| PD1 antibody-IL-15 Fusion E | SEQ ID NO: 59 | SEQ ID NO: 60 or 61 | SEQ ID NO: 55 or 56 | |
| PD1 antibody-IL-15 Fusion F | SEQ ID NO: 62 | SEQ ID NO: 61 | SEQ ID NO: 55 | IL-15 with E46K, no Sushi |
| PD1 antibody-IL-15 Fusion G | SEQ ID NO: 63 | SEQ ID NO: 61 | SEQ ID NO: 55 | IL-15 with E46K/ N65D, no Sushi |
| PD1 antibody-IL-15 Fusion H | SEQ ID NO: 69 | SEQ ID NO: 61 | SEQ ID NO: 55 | Long linker between Sushi and IL-15 mutein |
| PD1 antibody-IL-15 Fusion I | SEQ ID NO: 64 | SEQ ID NO: 66 | SEQ ID NO: 55 | Fc domains are identical; no Fc mutations to promote heterodimerization |
| PD1 antibody-IL-15 Fusion J | SEQ ID NO: 65 | SEQ ID NO: 66 | SEQ ID NO: 55 | |
| PD1 antibody-IL-15 Fusion K | SEQ ID NO: 67 | SEQ ID NO: 66 | SEQ ID NO: 55 | |
| PD1 antibody-IL-15 Fusion L | SEQ ID NO: 68 | SEQ ID NO: 66 | SEQ ID NO: 55 | |

Specific, nonlimiting examples of IL-15 polypeptides, Sushi domains, cytokine antagonists/masks, carriers, peptide linkers, and prodrugs are shown in the Sequences section below. Further, the prodrugs of the present disclosure may be made by well-known recombinant technology. For examples, one more expression vectors comprising the coding sequences for the polypeptide chains of the prodrugs may be transfected into mammalian host cells (e.g., CHO cells), and cells are cultured under conditions that allow the expression of the coding sequences and the assembly of the expressed polypeptides into the prodrug complex. In order for the prodrug to remain inactive, the host cells that express no or little uPA, MMP-2 and/or MMP-9 may be used. In some embodiments, the host cells may contain null mutations (knockout) of the genes for these proteases.

III. Pharmaceutical Compositions

Pharmaceutical compositions comprising the prodrugs and muteins (i.e., the active pharmaceutical ingredient or API) of the present disclosure may be prepared by mixing the API having the desired degree of purity with one or more optional pharmaceutically acceptable excipients (see, e.g., *Remington's Pharmaceutical Sciences*, 16th Edition, Osol, A. Ed. (1980)) in the form of lyophilized formulations or aqueous solutions. Pharmaceutically acceptable excipients (or carriers) are generally nontoxic to recipients at the dosages and concentrations employed, and include, but are not limited to: buffers containing, for example, phosphate, citrate, succinate, histidine, acetate, or another inorganic or organic acid or salt thereof; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including sucrose, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof, such as citrate, phosphate, succinate, tartrate, fumarate, gluconate, oxalate, lactate, and acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

The choice of pharmaceutical carrier, excipient or diluent may be selected with regard to the intended route of administration and standard pharmaceutical practice. Pharmaceutical compositions may additionally comprise any suitable binder(s), lubricant(s), suspending agent(s), coating agent(s) or solubilizing agent(s).

There may be different composition/formulation requirements dependent on the different delivery systems. By way of example, pharmaceutical compositions useful in the present invention may be formulated to be administered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route.

In some embodiments, the pharmaceutical composition of the present disclosure is a lyophilized protein formulation. In other embodiments, the pharmaceutical composition may be an aqueous liquid formulation.

IV. Methods of Treatment

The IL-15 prodrug can be used to treat a disease, depending on the antigen bound by the antigen-binding domain. In some embodiments, the IL-15 prodrug is used to treat cancer. In some embodiments, the IL-15 prodrug is used to treat an infection, for example when the drug molecule is an antibacterial agent or an antiviral agent.

In some embodiments, a method of treating a disease (such as cancer, a viral infection, or a bacterial infection) in a subject comprises administering to the subject an effective amount of an IL-15 prodrug. In other embodiments, the method of treatment further comprises administering an additional therapeutic agent in combination with (before, after, or concurrently with) the IL-15 prodrug. The additional agent may be an antibody or fragment thereof, small-molecule drug, or other type of therapeutic drug, some of which are disclosed herein.

In some embodiments, the cancer is a solid cancer. In some embodiments, the cancer is a blood cancer or a solid tumor. Exemplary cancers that may be treated include, but are not limited to, leukemia, lymphoma, kidney cancer, bladder cancer, urinary tract cancer, cervical cancer, brain cancer, head and neck cancer, skin cancer, uterine cancer, testicular cancer, esophageal cancer, liver cancer, colorectal cancer, stomach cancer, squamous cell carcinoma, prostate cancer, pancreatic cancer, lung cancer such as non-small cell lung cancer, cholangiocarcinoma, breast cancer, and ovarian cancer.

In some embodiments, the IL-15 prodrug is used to treat a bacterial infection such as sepsis. In some embodiments, the bacteria causing the bacterial infection are drug-resistant bacteria. In some embodiments, the antigen-binding moiety binds to a bacterial antigen.

In some embodiments, the IL-15 prodrug is used to treat a viral infection. In some embodiments, the virus causing the viral infection is hepatitis C (HCV), hepatitis B (HBV), human immunodeficiency virus (HIV), a human papilloma virus (HPV). In some embodiments, the antigen-binding moiety binds to a viral antigen.

Generally, dosages, and routes of administration of the present pharmaceutical compositions are determined according to the size and conditions of the subject, according to standard pharmaceutical practice. In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, intracranially, or intraspinally. In some embodiments, the composition is administered to a subject intravenously.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2, 3, 4, 5, 6, or 7 or more) doses are given in a week. In some embodiments, the pharmaceutical composition is administered weekly, once every 2 weeks, once every 3 weeks, once every 4 weeks, weekly for two weeks out of 3 weeks, or weekly for 3 weeks out of 4 weeks. In some embodiments, multiple doses are given over the course of days, weeks, months, or years. In some embodiments, a course of treatment is about 1 or more doses (such as about 2, 3, 4, 5, 7, 10, 15, or 20 or more doses).

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. It is understood that aspects and variations of the invention described herein include "consisting" and/or "consisting essentially of" aspects and variations. All publications and other references mentioned herein are incorporated by reference in their entirety. Although a number of documents are cited herein, this citation does not constitute an admission that any of these documents forms part of the common general knowledge in the art.

EXAMPLES

Transient Transfection of HEK293 Cells

Expression plasmids were co-transfected into $3\times10^6$ cell/ml freestyle HEK293 cells at 2.5-3 µg/ml using polyethylenimine (PEI). For Fc-based IL-15 prodrugs, the Fc-IL-15 mutein fusion polypeptide and the Fc-masking moiety fusion polypeptide were in a 1:2 ratio. For antibody-based IL-15 prodrugs, the knob heavy chain (containing IL-15 polypeptide), hole heavy chain (containing the masking moiety), and the light chain DNA were in a 2:1:2 molar ratio. The cell cultures were harvested 6 days after transfection by centrifuging at 9,000 rpm for 45 min followed by 0.22 µM filtration.

Protein Purification

The Fc- and antibody-based IL-15 fusion polypeptides were, in general, purified by Protein A affinity chromatography followed by ion exchange chromatography, hydrophobic interaction chromatography, and/or size exclusion chromatography. In some cases, the purifications of the proteins of the antibody-based IL-15 prodrugs were carried out by using four steps of chromatography, including: 1) Protein A affinity chromatography; 2) Capto™ Adhere operated in a flow-through mode; 3) Capto™ MMC ImpRes, and 4) Q Sepharose® HP operated in a flow-through mode. Capto™ Adhere was equilibrated by the buffer containing 50 mM acetic acid, 30 mM NaCl (pH 5.5). Capto™ MMC ImpRes was equilibrated using the buffer A (50 mM acetic acid, 30 mM NaCl, pH 5.5) and eluted using a 30 CV linear gradient with buffer B (50 mM acetic acid, 0.5 M Arginine, pH 5.5). Q Sepharose® HP was equilibrated with 40 mM Bis Tris, pH 6.5.

SEC-HPLC Analysis

SEC-HPLC was carried out using an Agilent 1100 Series HPLC system with a TSKgel® G3000SWXL column (7.8 mmIDX 30 cm, 5 µm particle size) from Tosoh Bioscience. A sample of up to 100 µl was loaded. The column was run with a buffer containing 200 mM $K_3PO_4$, 250 mM KCl, pH 6.5. The flow rate was 0.5 ml/min. The column was run at room temperature. The protein elution was monitored both at 220 nm and 280 nm.

SDS-PAGE Analysis

10 µl of the culture supernatants or 20 µg of purified protein samples were mixed with Bolt™ LDS Sample Buffer (Novex) with or without reduce reagents. The samples were heated at 70° C. for 3 min and then loaded to a NuPAGE™ 4-12% BisTris Gel (Invitrogen). The gel was run in NuPAGE™ MOPS SDS Running buffer (Invitrogen) at 200 Volts for 40 min and then stained with Coomassie.

Proteolytic Treatment

One μg of the protease, human MMP-2 (R&D systems), human MMP-9 (R&D systems), mouse MMP-2 (R&D systems), or mouse MMP-9 (R&D systems) was added to 50 of the precursor protein, and incubated at 37° C. overnight.

CTLL2 Assay

CTLL2 cells were grown in the RPMI 1640 medium supplemented with L-glutamine, 10% fetal bovine serum, 10% non-essential amino acids, 10% sodium pyruvate, and 55 μM beta-mercaptoethanol. CTLL2 cells were non-adherent and maintained at $5 \times 10^4$-$1 \times 10^6$ cells/ml in medium with 100 ng/ml of IL-15. Generally, cells were split twice per week. For bioassays, it was best to use cells no less than 48 hours after passage.

Samples were diluted at 2× concentration in 50 μl/well in a 96 well plate. The IL-15 standards were titrated from 20 ng/ml (2× concentration) to 3× serial dilutions for 12 wells. Samples were titer tested as appropriate. CTLL2 cells were washed 5 times to remove IL-15, dispensed 5000 cells/well in 50 μl and cultured overnight or for at least 18 hours with the samples. Subsequently, 100 μl/well Cell Titer Glo reagents (Promega) were added and luminescence was measured.

NK92 Proliferation Assay

NK92 cell proliferation assays were also carried out, according to the protocols below.

The NK92 cell line is a factor dependent cell line that requires IL-2 for growth and survival. Prior to assay, the cells are washed to remove IL-2 and cultured overnight without growth factor. Cells are harvested and washed again to remove residual growth factor. Cells (20,000/well) are then added to 96 well plates containing serial dilution of test articles and controls. Plates are incubated overnight, and Cell Titer Glo (Promega) is added and luminescence measured. This provides a measure of ATP levels as an indicator of cell viability.

The assays were carried out using several IL-15 prodrugs masked with IL-2Rβ extra-cellular domain (ECD), IL-2Rβ ECD and IL-2Rγ ECD, and scFv molecules derived from the IL-15 antibody 146B7.

pSTAT5 Analysis

NK92/pSTAT5 stable cell line were starved in RPMI 1640 medium supplemented with 0.1% FBS overnight. $5 \times 10^5$ of cells were seeded in each well of a 96-well plate prior to incubation at 37° C. and 5% $CO_2$ overnight. IL-15 fusion polypeptides were added to the cells and incubated for 5-6 hours in the incubator. Subsequently, 100 μl of Pierce™ Firefly Luc One-Step Glow Assay solution was added and the bioluminescent were read using a luminometer.

Enzyme-linked Immunosorbent Assay (ELISA)

10 μg/ml of IL-15 fusion proteins in PBS were seeded to the 96-well plate at 100 μl/well and coated at 4 degree for overnight. The wells were washed by PBS three times and blocked with 100 μl 2% milk/PBS for 1 hr. The wells were then washed three times by PBS and 100 μl protein samples with 3-fold serial dilution were added for 1 hr incubation at room temperature (RT). After three times of PBS washing, 100 μl of HRP conjugated anti-IgG antibody was added and incubated at RT for 1 hr. Subsequently, the wells were washed again 3 times using PBS, followed by the addition of detection reagents and measurement of optical density (OD) at 450 nM.

Example 1: Expression and Testing of IL-15 Prodrugs

Figures 6A, 6B:
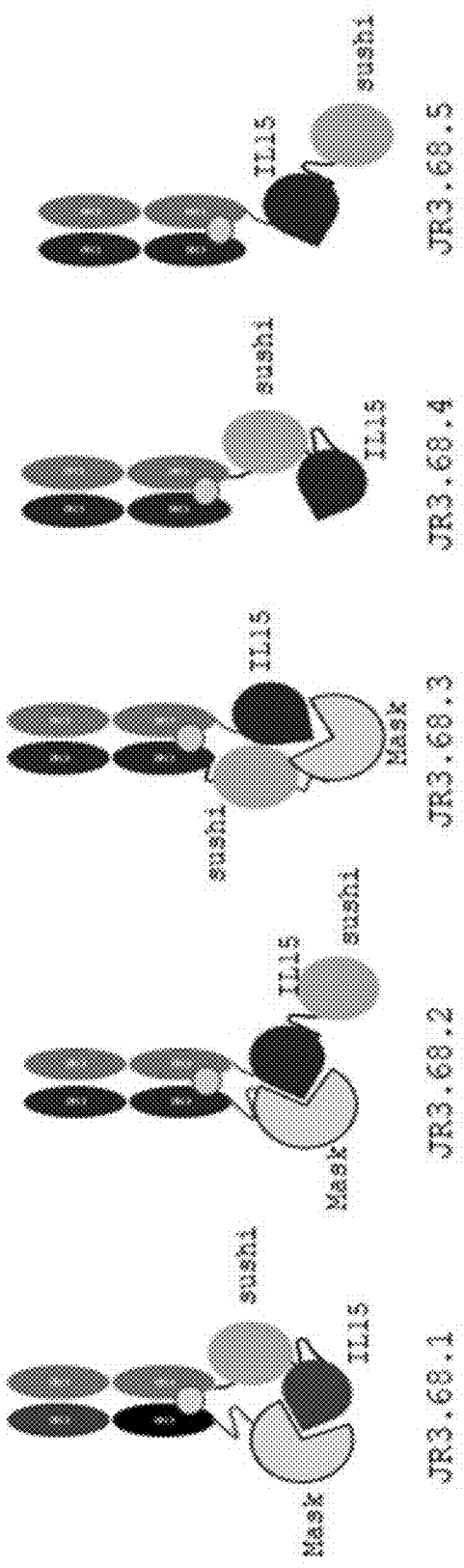
Figure 10B:
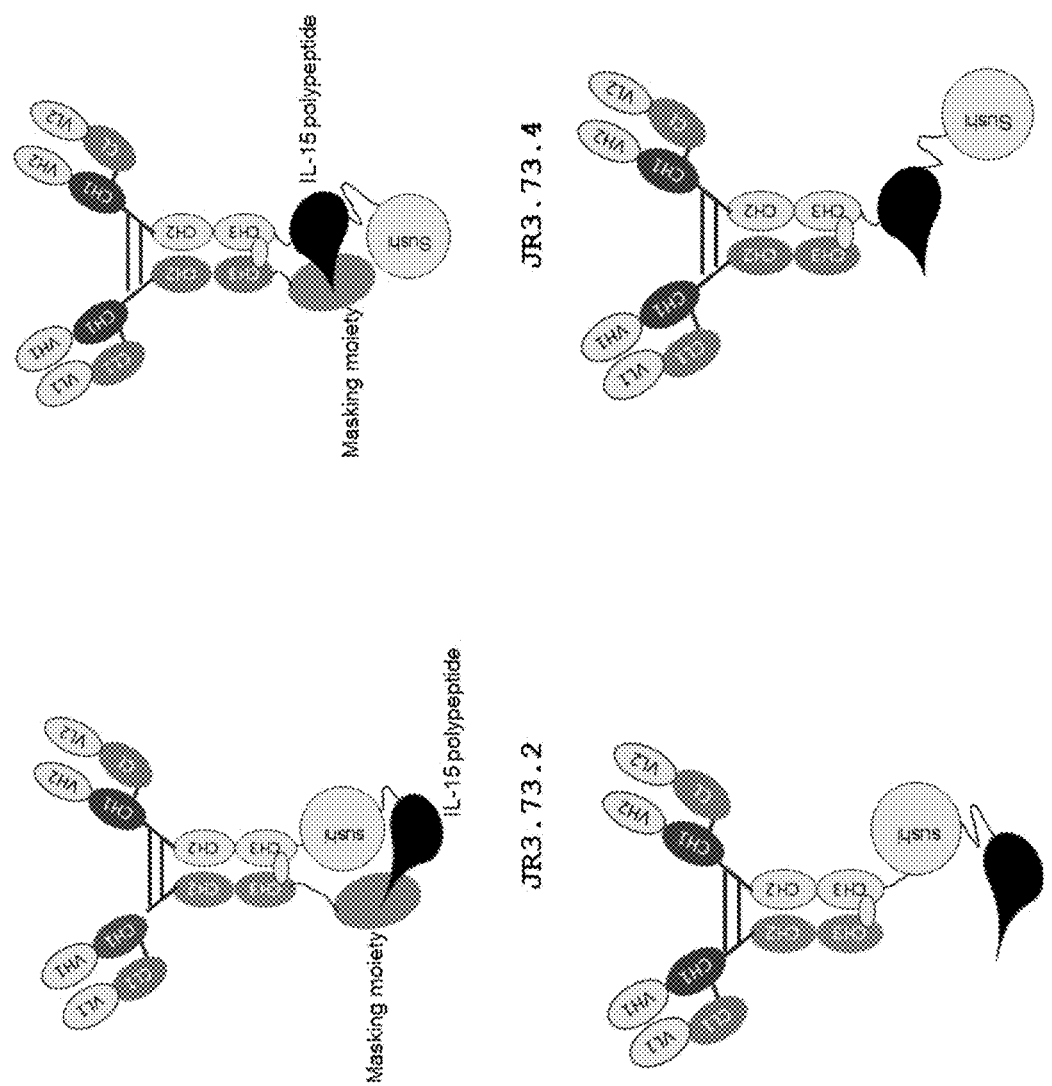
FIG. 10B illustrates the structures of the molecules of FIG. 10A.

A number of the prodrugs were constructed and recombinantly expressed in HEK293 cells (see FIG. 6A and FIG. 10A). In the IL-15 prodrugs, IL-15 polypeptides were expressed as part of a fusion polypeptide and tested for their biological activities. Some of the sequences of the IL-15 fusion polypeptides expressed are listed in FIG. 6A, FIG. 10A, and FIG. 12A.

Figure 7B:
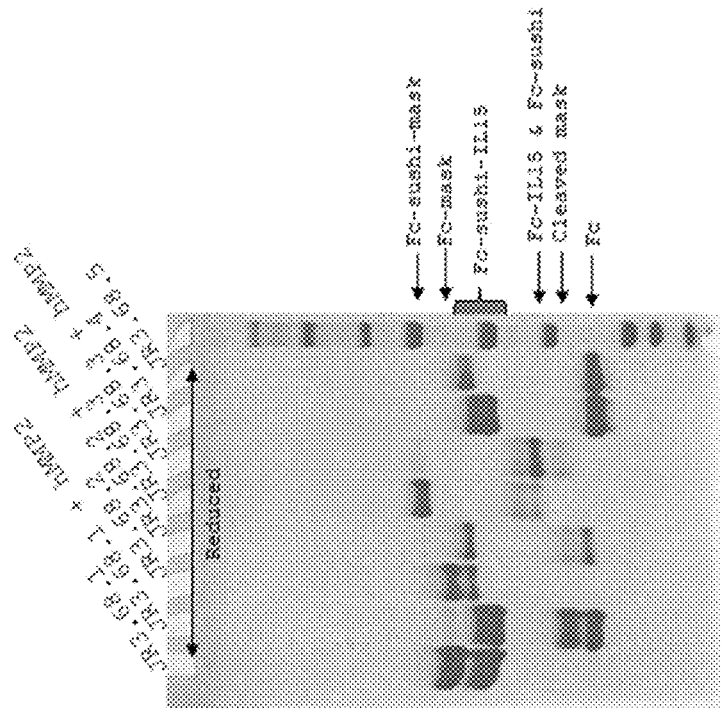
Figure 7A:
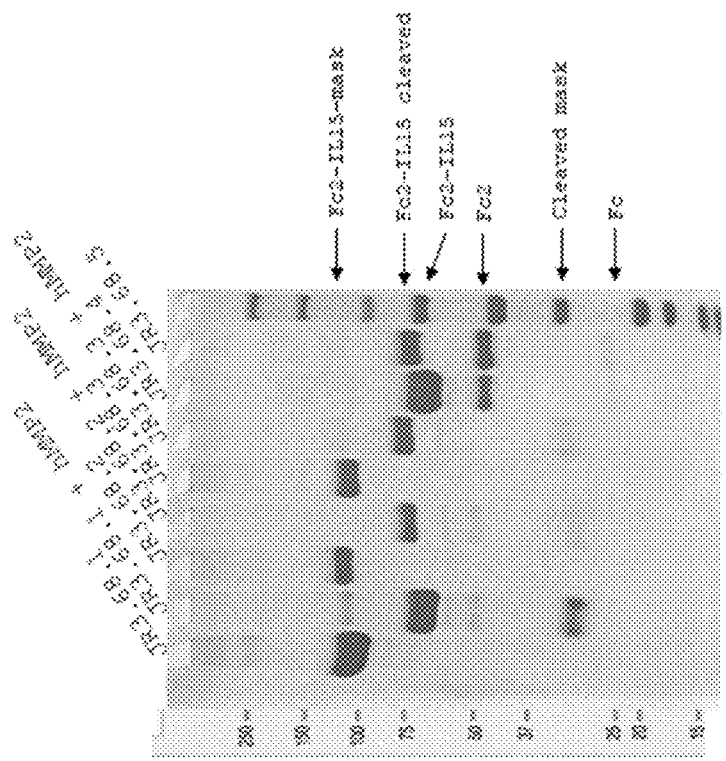

The expressed IL-15 fusion polypeptides were tested by SDS-PAGE prior to and after activation (FIG. 7A; non-reduced; and FIG. 7B; reduced). The data shows that the masking moieties of JR3.68.1, JR3.68.2, and JR3.68.3 samples were successfully cleaved by the protease treatment.

Example 2: Purification of Activatable IL-15 Prodrug Components

Activatable IL-15 prodrugs JR3.68.1, JR3.68.2 and JR3.68.3 were purified via Protein A column and analyzed using SEC-HPLC. JR3.68.1 (FIG. 1A) has a Sushi domain fused via a peptide linker to the C-terminus of one of the heavy chains of the Fc domain, the IL-15 polypeptide is fused to the C-terminus of the Sushi domain through a peptide linker, and the masking moiety (IL2Rβ ECD) is fused to the C-terminus of the other heavy chain of the Fc domain. JR3.68.2 is illustrated on FIG. 1B, and JR3.68.3 is illustrated on FIG. 1C.

Figure 8A:
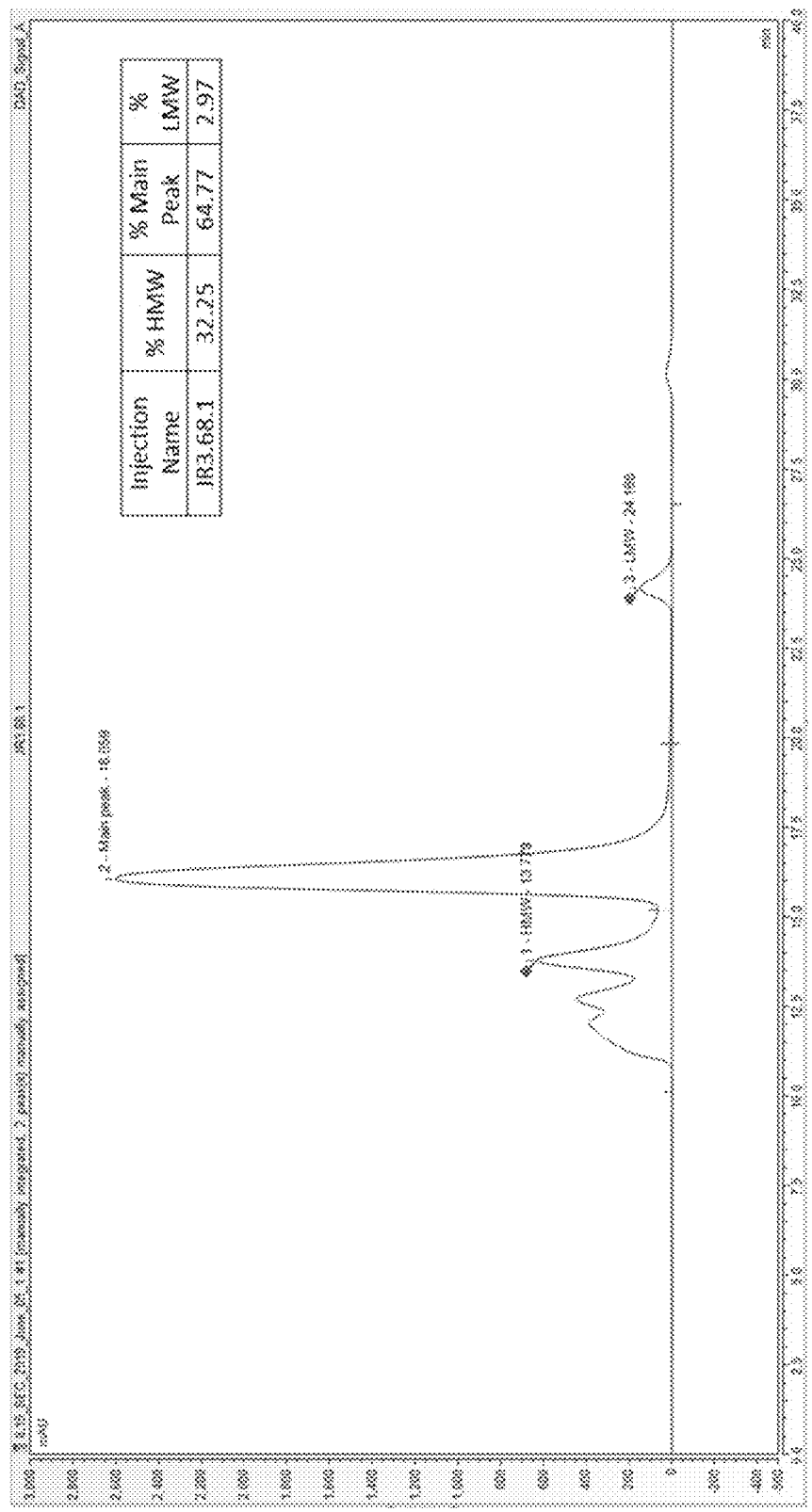
Figure 8B:
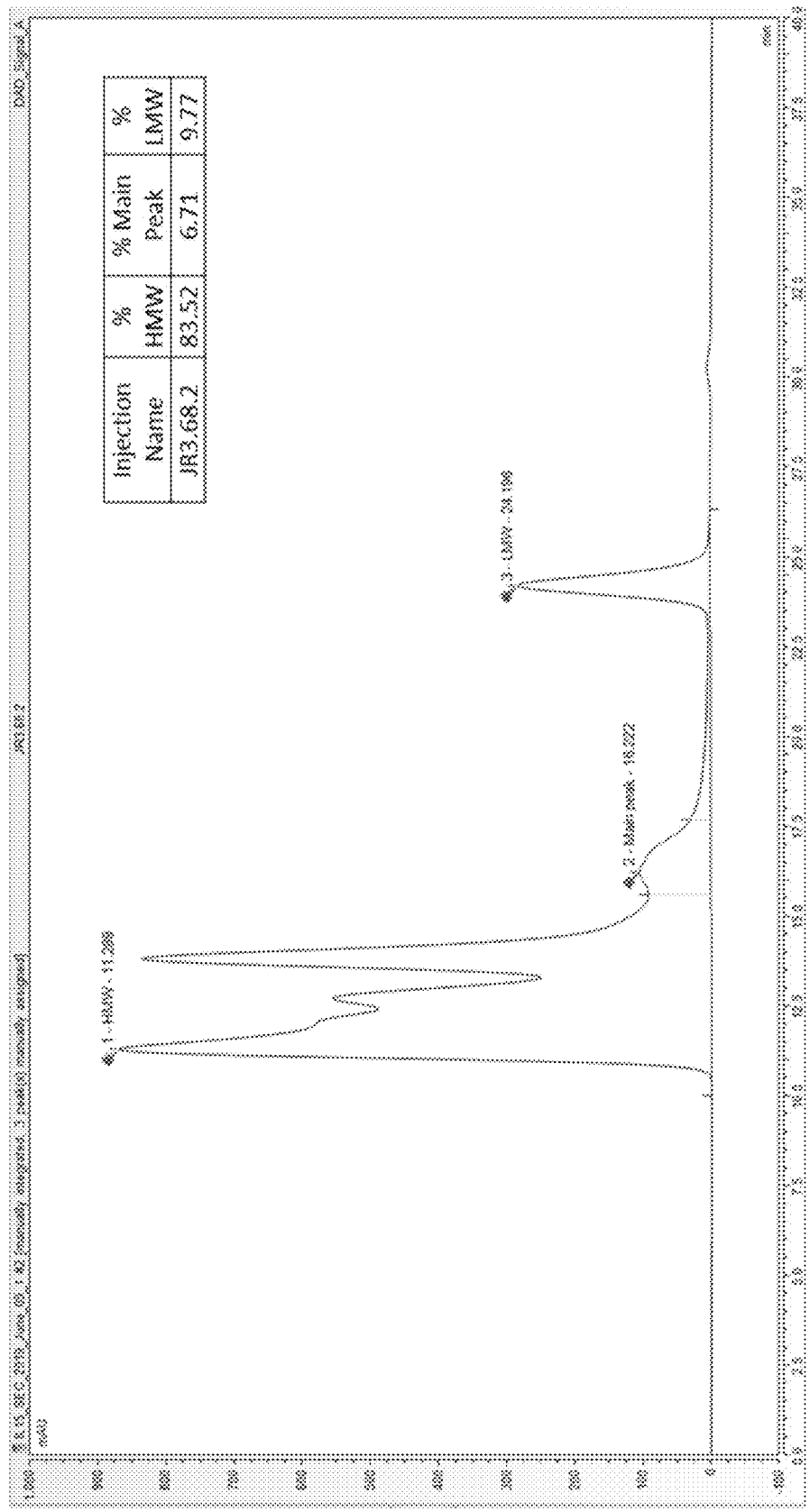
Figure 8C:
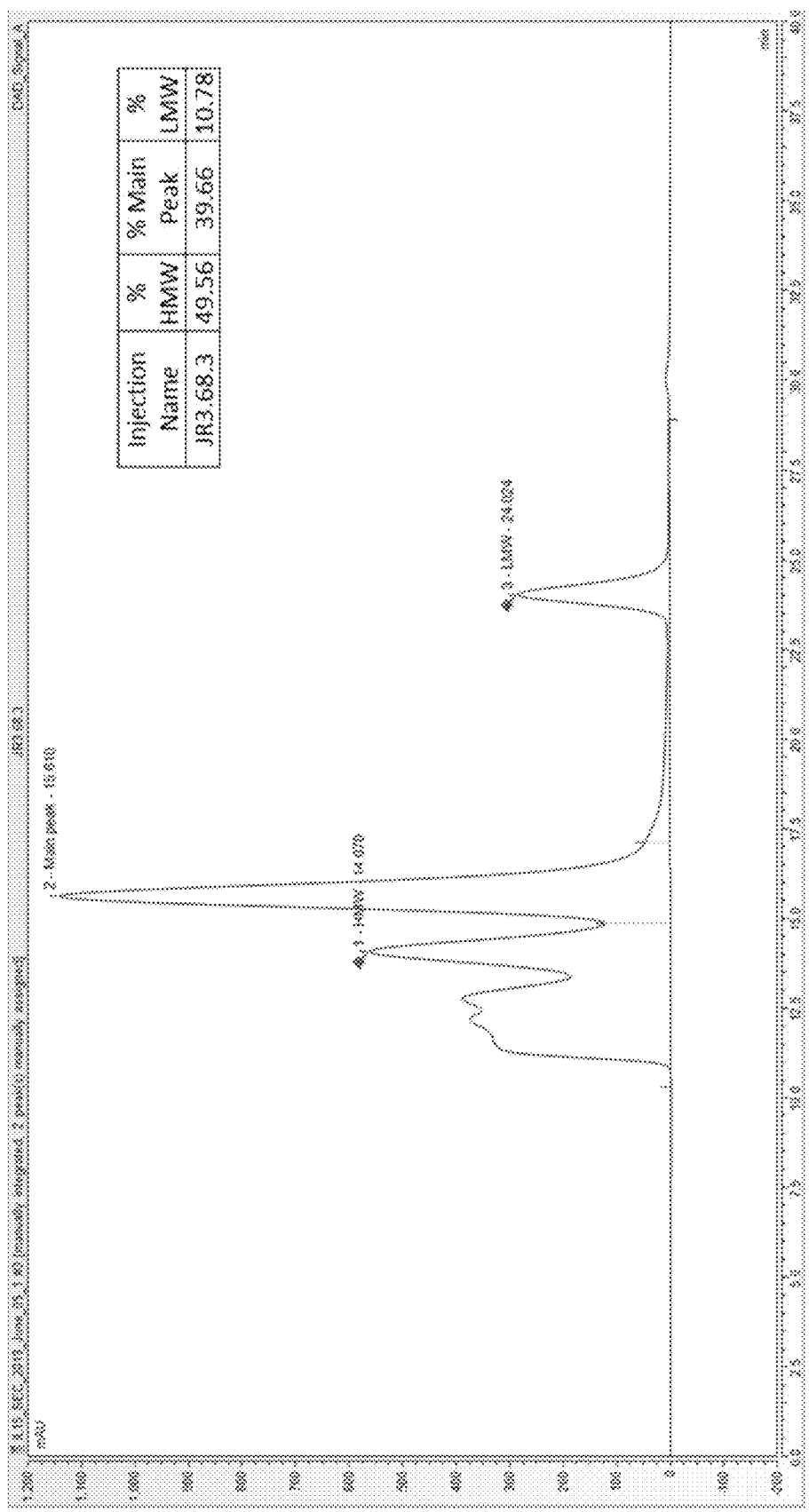
Figure 11B:
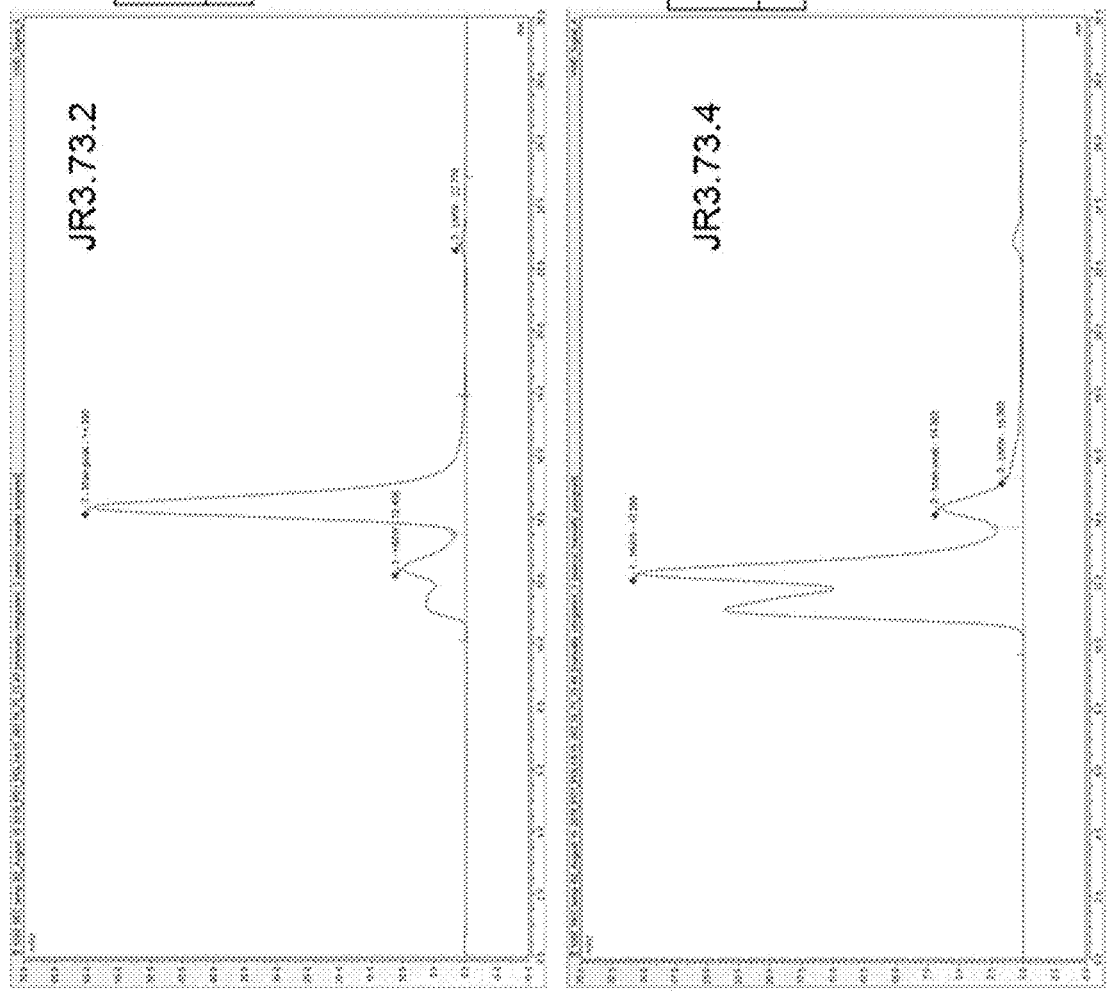

It was surprising that the format, arrangement, relative location or configuration of the several components of the prodrug molecule had significant effects on the levels of drug aggregates, when purified by Protein A affinity column. It was clear that the format of Fc-Sushi-IL-15 (comprising two polypeptide chains SEQ ID NO: 37 and SEQ ID NO: 38) (JR3.68.1) had a significantly higher purity (as evidenced by the higher main peak; FIG. 8A) and lower level of aggregation when compared to the format of Fc-IL-15-Sushi (JR3.68.2, having two polypeptide chains of SEQ ID NO: 37 and SEQ ID NO: 40) (FIG. 8B). Meanwhile, the format where the Sushi domain and the cytokine were on the different heavy chains of the Fc domain had a SEC-HPLC main peak purity better than JR3.68.2 (JR3.68.3, FIG. 8C) but lower than that of JR3.68.1 (FIG. 8A). The trend was essentially the same when the carrier was an antibody (e.g., nivolumab, an antibody against human PD-1; FIG. 11B, JR3.73.2 vs. JR3.73.4).

We also unexpectedly observed that by adding a masking moiety, the purities of the fusion polypeptides were significantly enhanced. We observed that the JR3.73.2 IL-15 prodrug with an antibody as a carrier moiety appeared to have a higher monomer purity by SEC-HPLC than the activated version JR3.74.1) (FIG. 11A and FIG. 11B). We also observed that the monomer peak of JR3.74.1 had a significant shoulder (FIG. 11A), which may indicate potential challenge of further purification.

Example 3: Cell-Based Activities of IL-15 Prodrugs

CTLL2 Assay

Figure 11C:
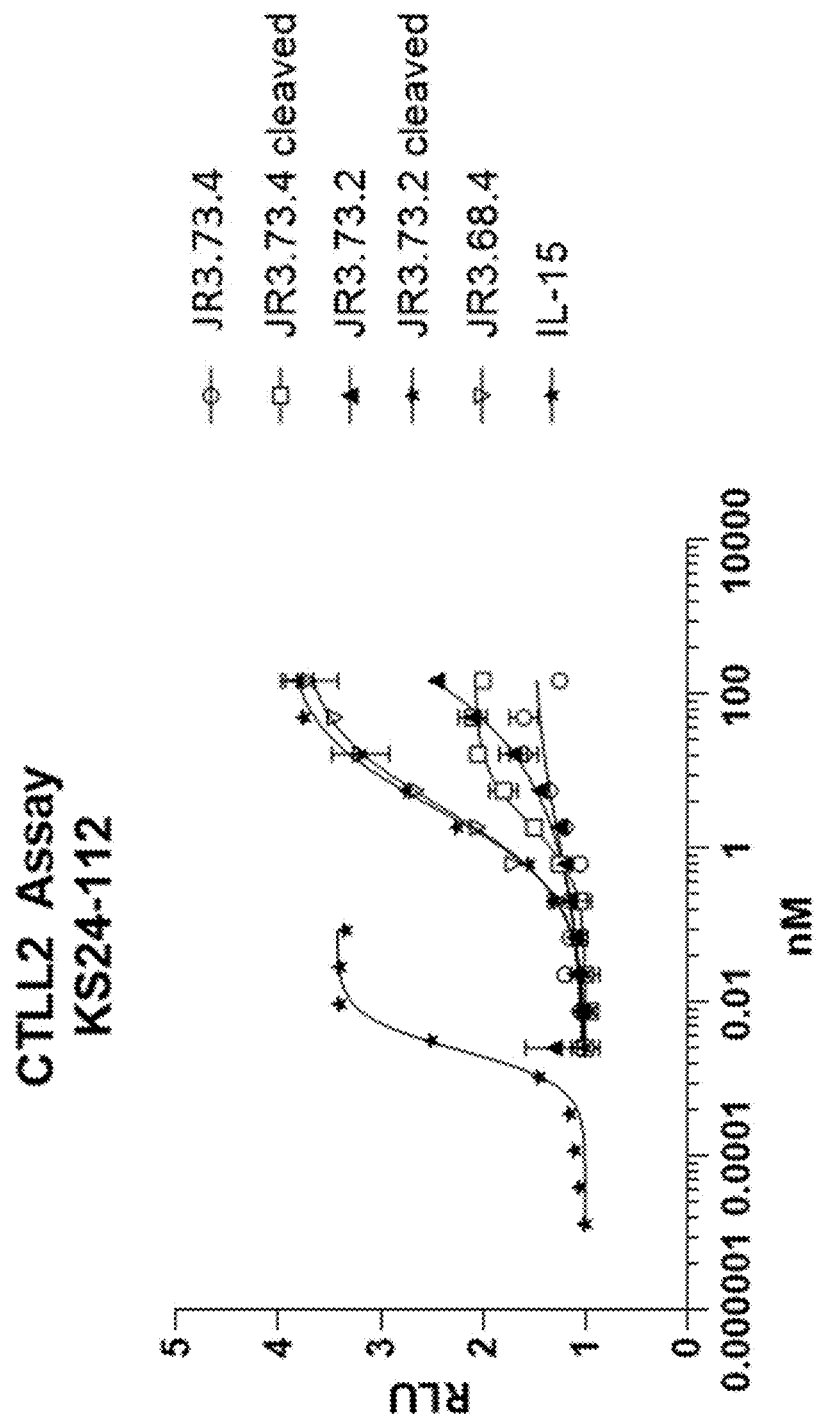
FIG. 11C is a graph showing the results of the CTLL2 proliferation assay on the prodrug samples prior to and after activation with protease treatment.

The CTLL2 cell-based activities of the IL-15 prodrugs JR3.68.1, JR3.68.2, and JR3.68.3 were determined before and after activation, as shown in FIGS. 9A-9C. The results show that JR3.68.1 had significant activation after protease treatment. The cell-based activities of the IL-15 prodrugs with an antibody as a carrier moiety are shown in FIG. 11C. The results show that the IL-15 prodrug JR3.73.2 was activatable.

NK92 Assay

NK92 cell proliferation assays were also carried out for several IL-15 prodrugs masked with scFv molecules (derived from the IL-15 antibody 146B7), IL-2Rβ ECD, or IL-2Rβ ECD and IL-2Rγ ECD. The NK92 proliferation assay results of the IL-15 prodrugs that are masked with scFv1 or scFv2 of IL-15 antibody 146B7 show that both scFv2 and scFv1 significantly masked the activity of the IL-15 WT and IL-15 mutein with N65D mutation (FIG. 12B).

The NK92 cell-based activities of the activatable IL-15 fusion polypeptides prior to and after activation was determined using the pSTAT5 method. FIG. 13A shows that both scFv2 and scFv1 masked the wild type IL-15 to the similar extent, and the fusion polypeptides were activatable upon protease treatment. FIG. 13B shows that scFv2 significantly masked the activity of the IL-15 mutein N65D. The results also demonstrate that scFv1 efficiently masked the IL-15 mutein. It was unexpected that both IL-15 prodrugs were activatable in vitro upon protease treatment but without further purification to remove the cleaved scFv molecules. It was also surprising that scFv2 had significantly stronger masking effect than that of scFv1 for IL-15 mutein N65D.

The NK92 cell-based activities of additional activatable IL-15 fusion polypeptides masked with IL-2Rβ ECD or IL-2Rβ ECD and IL-2Rγ ECD were determined. In these fusion polypeptides, wild type IL-15 was masked with IL-2Rβ ECD and IL-2RγECD. The results show that IL-2Rβ ECD in combination with IL-2RγECD formed an effective mask for the wild type IL-15 and that the IL-15 prodrugs were activatable upon protease treatment (FIG. 14A). The activity of IL-15 mutein Q108E (which was activatable upon protease treatment) was also masked with IL-2Rβ ECD and IL-2RγECD (FIG. 14C).

We also determined the NK92 cell-based assay results of the activatable Fc-IL-15 fusion polypeptide without a Sushi domain (JR2.145.1) and one with a longer linker between the Sushi domain and the IL-15 polypeptide moiety (JR2.145.2). The data showed significant masking of the IL-15 mutein N65D in both cases. The results indicate that the scFv2 mask was effective in masking IL-15 polypeptide in the absence of the Sushi domain. The masking domain also worked well when the linker between the Sushi domain and the IL-15 polypeptide was longer (32 amino acids).

The above non-limiting examples are provided for illustrative purposes only in order to facilitate a more complete understanding of the disclosed subject matter. These examples should not be construed to limit any of the embodiments described in the present specification, including those pertaining to the antibodies, pharmaceutical compositions, or methods and uses for treating cancer, a neurodegenerative or an infectious disease.

SEQUENCES

In the sequences below, boxed residues indicate mutations. Underlines in cleavable linkers indicate protease substrate sequences.

```
SEQ ID NO: 1-Human IL-2
APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT

SEQ ID NO: 2-Human IL-15
NWVNVISDLK KIEDLIQSMH IDATLYTESD VHPSCKVTAM KCFLLELQVI SLESGDASIH

DTVENLIILA NNSLSSNGNV TESGCKECEE LEEKNIKEFL QSFVHIVQMF INT

SEQ ID NO: 3-Human IL-2 Receptor Beta Subunit Extracellular Domain
(uniprot/P14784)
AVNGTSQFTC FYNSRANISC VWSQDGALQD TSCQVHAWPD RRRWNQTCEL LPVSQASWAC

NLILGAPDSQ KLTTVDIVTL RVLCREGVRW RVMAIQDFKP FENLRLMAPI SLQVVHVETH

RCNISWEISQ ASHYFERHLE FEARTLSPGH TWEEAPLLTL KQKQEWICLE TLTPDTQYEF

QVRVKPLQGE FTTWSPWSQP LAFRTKPAAL GKDT

SEQ ID NO: 4-Human IL-2 Receptor Beta Subunit Extracellular Domain
Mutant D68E (uniprot/P14784)
AVNGTSQFTC FYNSRANISC VWSQDGALQD TSCQVHAWPD RRRWNQTCEL LPVSQASWAC

NLILGAPESQ KLTTVDIVTL RVLCREGVRW RVMAIQDFKP FENLRLMAPI SLQVVHVETH

RCNISWEISQ ASHYFERHLE FEARTLSPGH TWEEAPLLTL KQKQEWICLE TLTPDTQYEF

QVRVKPLQGE FTTWSPWSQP LAFRTKPAAL GKDT

SEQ ID NO: 5-Human IL-2 Receptor Beta Subunit Extracellular Domain
Mutant E136Q/H138R (uniprot/P14784)
AVNGTSQFTC FYNSRANISC VWSQDGALQD TSCQVHAWPD RRRWNQTCEL LPVSQASWAC

NLILGAPDSQ KLTTVDIVTL RVLCREGVRW RVMAIQDFKP FENLRLMAPI SLQVVHVETH

RCNISWEISQ ASHYFQRRLE FEARTLSPGH TWEEAPLLTL KQKQEWICLE TLTPDTQYEF

QVRVKPLQGE FTTWSPWSQP LAFRTKPAAL GKDT
```

-continued

SEQ ID NO: 6-Human IL-2 Receptor Gamma Subunit Extracellular Domain
(uniprot/P31785)
LNTTILTPNG NEDTTADFFL TTMPTDSLSV STLPLPEVQC FVFNVEYMNC TWNSSSEPQP

TNLTLHYWYK NSDNDKVQKC SHYLFSEEIT SGCQLQKKEI HLYQTFVVQL QDPREPRRQA

TQMLKLQNLV IPWAPENLTL HKLSESQLEL NWNNRFLNHC LEHLVQYRTD WDHSWTEQSV

DYRHKFSLPS VDGQKRYTFR VRSRFNPLCG SAQHWSEWSH PIHWGSNTSK ENPFLFALEA

SEQ ID NO: 7-IL-15 receptor alpha subunit Sushi domain
ITCPPPMSVE HADIWVKSYS LYSRERYICN SGFKRKAGTS SLTECVLNKA TNVAHWTTPS

LKCIRDPALV HQRPA

SEQ ID NO: 8-Amino acid sequence of IL-15 receptor alpha
MAPRRARGCR TLGLPALLLL LLLRPPATRG ITCPPPMSVE HADIWVKSYS LYSRERYICN

SGFKRKAGTS SLTECVLNKA TNVAHWTTPS LKCIRDPALV HQRPAPPSTV TTAGVTPQPE

SLSPSGKEPA ASSPSSNNTA ATTAAIVPGS QLMPSKSPST GTTEISSHES SHGTPSQTTA

KNWELTASAS HQPPGVYPQG HSDITVAIST STVLLCGLSA VSLLACYLKS RQTPPLASVE

MEAMEALPVT WGTSSRDEDL ENCSHHL

SEQ ID NO: 9-Amino acid sequence of IL-15 receptor alpha Sushi
domain
ITCPPPMSVE HADIWVKSYS LYSRERYICN SGFKRKAGTS SLTECVLNKA TNVAHWTTPS

LKCIR

SEQ ID NO: 10-Human CCL19 amino acid sequence
TNDAEDCC LSVTQKPIPG YIVRNFHYLL IKDGCRVPAV VFTTLRGRQL CAPPDQPWVE

RIIQRLQRTS AKMKRRSS

SEQ ID NOs:11-16 Peptide Linker (noncleavable)
(SEQ ID NO: 11)
GGGGS (SEQ ID NO: 12)
GGGGSGGGGS (SEQ ID NO: 13)
GGGGSGGGGS GGGGS (SEQ ID NO: 14), X = A or N
GGGGSGGGGS XGGGGSGGGG S (SEQ ID NO: 15), X = S, A or N, and Y = A or N
GGGGSGGGGS XGGGGYGGGG S (SEQ ID NO: 16)
GGGGSGGGGS GGGGSAAGGG GSGGGGSGGG GS SEQ ID NOs: 17-23-MMP-2/MMP-9 cleavable peptide linkers
(SEQ ID NO: 17)
GPLGVR (SEQ ID NO: 18)
PLGMWSR (SEQ ID NO: 19)
PLGLWAR (SEQ ID NO: 20)
PQGIAGQR (SEQ ID NO: 21)
PLGLAG (SEQ ID NO: 22)
LALGPR (SEQ ID NO: 23)
GGPLGMLSQS -continued SEQ ID NOs: 24-32-Urokinase plasminogen activator (uPA) cleavable peptide linkers (SEQ ID NO: 24)
GGGGRRGGS (SEQ ID NO: 25)
TGRGPSWV (SEQ ID NO: 26)
SARGPSRW (SEQ ID NO: 27)
TARGPSFK (SEQ ID NO: 28)
TARGPSW (SEQ ID NO: 29)
GGWHTGRN (SEQ ID NO: 30)
HTGRSGAL (SEQ ID NO: 31)
PLTGRSGG (SEQ ID NO: 32)
LTGRSGA SEQ ID NO: 33-matriptase cleavable peptide linker
RQARVVNG SEQ ID NO: 34-matriptase-MMP2/9 dual cleavable peptide linker
VHMPLGFLGP RQARVVNG SEQ ID NO: 35-cleavable peptide linker
GGSLSGRSDN HGGGGS SEQ ID NO: 36-cleavable linker
GGGGSGGGGS GGGGSISSGL LSSGGSGGSL SGRSDNHGGG GS SEQ ID NO: 37-Amino acid sequence of IgG1 Fc fused with IL-2Rβ; Fc with hole mutations and LALA mutations (CX5.51.1)
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSRDELTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSGGGGSGPL

GVRGGGGSGG GGSAVNGTSQ FICEYNSRAN ISCVWSQDGA LQDTSCQVHA WPDRRRWNQT

CELLPVSQAS WACNLILGAP DSQKLTTVDI VTLRVLCREG VRWRVMAIQD FKPFENLRLM

APISLQVVHV ETHRCNISWE ISQASHYFER HLEFEARTLS PGHTWEEAPL LTLKQKQEWI

CLETLTPDTQ YEFQVRVKPL QGEFTTWSPW SQPLAFRTKP AALGKDT

SEQ ID NO: 38-Amino acid sequence of IgG1 Fc fused with IL-15Rα Sushi then IL-15 polypeptide; Fc with knob mutations and LALA mutations (CX5.51.4)
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCRDELTK NQVSLWCLVK GFYPSDIAVE WESNGQPENN YKTTPPVLDS

DGSFFLYSKL TVDKSRWQQG NVFSCSVMHE ALHNHYTQKS LSLSPGAGGG GSGGGSGGGG

-continued

SITCPPPMSV EHADIWVKSY SLYSRERYIC NSGFKRKAGT SSLTECVLNK ATNVAHWTTP

SLKCIRDPAL VHQRPAPPSG GGGSGGGGSG GGGSNWVNVI SDLKKIEDLI QSMHIDATLY

TESDVHPSCK VTAMKCFLLE LQVISLESGD ASIHDTVEX₁LIILANNSLS SNGNVTESGC

KECEELEEKN IKEFLQSFVH IVX₂MFINTS;
wherein X₁ is an amino acid selected from N and D, and X₂ is an amino
acid selected from Q and E.

SEQ ID NO: 39-Amino acid sequence of Fc fused with IL-15Rα Sushi
then IL-15 polypeptide; Fc with knob mutations; with long linker
between A and S
DKTHTCPPCP APE[AA]GGPSV FLFPPKPKDT LMISRTPEVT CVWDVSHED PEVKFNWYVD

GVEVHNAKTK PREEQY[N]STY RVVSVLTVLH QDWLNGKEYK CKVSNKALPA PIEKTISKAK

GQPREPQVYT LPP[C]RDELTK NQVSL[W]CLVK GFYPSDIAVE WESNGQPENN YKTTPPVLDS

DGSFFLYSKL TVDKSRWQQG NVFSCSVMHE ALHNHYTQKS LSLSPG[A]GGG GSGGGSGGG

SITCPPPMSV EHADIWVKSY SLYSRERYIC NSGFKRKAGT SSLTECVLNK ATNVAHWTTP

SLKCIRDPAL VHQRPAPPSG GGGSGGGGSG GGGSAAGGGG SGGGGSGGGG SNWVNVISDL

KKIEDLIQSM HIDATLYTES DVHPSCKVTA MKCFLLELQV ISLESGDASI HDTVEX₁LII

LANNSLSSNG NVTESGCKEC EELEEKNIKE FLQSFVHIVX₂MFINTS; wherein X₁ is an
amino acid selected from N and D, and X₂ is an amino acid selected from
Q and E.

SEQ ID NO: 40 Fc-IL-15-Sushi knob
CX5.51.5
DKTHTCPPCP APE[AA]GGPSV FLFPPKPKDT LMISRTPEVT CVVVDVSHED PEVKFNWYVD

GVEVHNAKTK PREEQY[N]STY RVVSVLTVLH QDWLNGKEYK CKVSNKALPA PIEKTISKAK

GQPREPQVYT LPP[C]RDELTK NQVSL[W]CLVK GFYPSDIAVE WESNGQPENN YKTTPPVLDS

DGSFFLYSKL TVDKSRWQQG NVFSCSVMHE ALHNHYTQKS LSLSPG[A]GGG GSGGGSGGG

SNWVNVISDL KKIEDLIQSM HIDATLYTES DVHPSCKVTA MKCFLLELQV ISLESGDASI

HDTVENLIIL ANNSLSSNGN VTESGCKECE ELEEKNIKEF LQSFVHIVQM FINTSGGSGG

GGSGGGGSGG GGSITCPPPM SVEHADIWVK SYSLYSRERY ICNSGFKRKA GTSSLTECVL

NKATNVAHWT TPSLKCIRDP ALVHQRPAPP S**

SEQ ID NO: 41 Fc-IL-15 knob
CX5.51.6
DKTHTCPPCP APE[AA]GGPSV FLFPPKPKDT LMISRTPEVT CVVVDVSHED PEVKFNWYVD

GVEVHNAKTK PREEQY[N]STY RVVSVLTVLH QDWLNGKEYK CKVSNKALPA PIEKTISKAK

GQPREPQVYT LPP[C]RDELTK NQVSL[W]CLVK GFYPSDIAVE WESNGQPENN YKTTPPVLDS

DGSFFLYSKL TVDKSRWQQG NVFSCSVMHE ALHNHYTQKS LSLSPG[A]GGG GSGGGSGGG

SNWVNVISDL KKIEDLIQSM HIDATLYTES DVHPSCKVTA MKCFLLELQV ISLESGDASI

HDTVENLIIL ANNSLSSNGN VTESGCKECE ELEEKNIKEF LQSFVHIVQM FINTS**

SEQ ID NO: 42 Fc-Sushi-beta hole (CX5.51.7)
DKTHTCPPCP APE[AA]GGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQV[C]T LPPSRDELTK NQVSL[S][C]AVK GFYPSDIAVE WESNGQPENN YKTTPPVLDS

```
DGSFFLVSKL TVDKSRWQQG NVFSCSVMHE ALHNHYTQKS LSLSPGAGGS GGGGSGGGGS

GGGGSITCPP PMSVEHADIW VKSYSLYSRE RYICNSGFKR KAGTSSLTEC VLNKATNVAH

WTTPSLKCIR DPALVHQRPA PPSGGGGSGG GGSGPLGVRG GGGSGGGGSA VNGTSQFTCF

YNSRANISCV WSQDGALQDT SCQVHAWPDR RRWNQTCELL PVSQASWACN LILGAPDSQK

LTTVDIVTLR VLCREGVRWR VMAIQDFKPF ENLRLMAPIS LQVVHVETHR CNISWEISQA

SHYFERHLEF EARTLSPGHT WEEAPLLTLK QKQEWICLET LTPDTQYEFQ VRVKPLQGEF

TTWSPWSQPL AFRTKPAALG KDT**
SEQ ID NO: 43 IgG1 Fc-Hole (CX5.43.8)
DKTHTCPPCP APELLGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSRDELTK NQVSLSCAVK GFYPSDIAVE WESNGQPENN YKTTPPVLDS

DGSFFLVSKL TVDKSRWQQG NVFSCSVMHE ALHNHYTQKS LSLSP

SEQ ID NO: 44 Fc-IL-15 knob, IL-15 mutein E46K/N65D
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCRDELTK NQVSLWCLVK GFYPSDIAVE WESNGQPENN YKTTPPVLDS

DGSFFLYSKL TVDKSRWQQG NVFSCSVMHE ALHNHYTQKS LSLSPGAGGG GSGGGSGGGG

SNWVNVISDL KKIEDLIQSM HIDATLYTES DVHPSCKVTA MKCFLLKLQV ISLESGDASI

HDTVEDLIIL ANNSLSSNGN VTESGCKECE ELEEKNIKEF LQSFVHIVQM FINTS**

SEQ ID NO: 45 PD-L1 antibody 1296 heavy chain fused with Sushi and
then with IL-15 polypeptide, Fc with Knob mutations (CX5.48.1)
EVQLQQSGAE VKKPGATVKI SCTASGFNIK DDYLHWVRQA PGKGLEWIGR IDPANANTKY

APKFQDRVTI TADTSTNTAY LELSSLRSED TAVYYCAARF GYFYGSSFYA VAYWGGILV

TVSSASTKGP SVFPLAPSSK STSGGTAALG CLVKDYFPEP VTVSWNSGAL TSGVHTFPAV

LQSSGLYSLS SVVTVPSSSL GTQTYICNVN HKPSNTKVDK KVEPKSCDKT HTCPPCPAPE

LLGGPSVFLF PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP REPQVYTLPP

CRDELTKNQV SLWCLVKGFY PSDIAVEWES NGQPENNYKT TPPVLDSDGS FFLYSKLTVD

KSRWQQGNVF SCSVMHEALH NHYTQKSLSL SPGAGGGGSG GSGGGGSIT CPPPMSVEHA

DIWVKSYSLY SRERYICNSG FKRKAGTSSL TECVLNKATN VAHWTTPSLK CIRDPALVHQ

RPAPPSGGGG SGGGGSGGGG SAAGGGGSGG GGSGGGGSNW VNVISDLKKI EDLIQSMHID

ATLYTESDVH PSCKVTAMKC FLLELQVISL ESGDASIHDT VEX₁LIILAN NSLSSNGNVT

ESGCKECEEL EEKNIKEFLQ SFVHIVX₂MF INTS; wherein X₁ is an amino acid
selected from N and D, and X₂ is an amino acid selected from Q and E.
```

SEQ ID NO: 46 PD-L1 antibody 1296 heavy chain-IL-15 then with the
Sushi domain, Fc with Knob mutations (CX5.48.2)
EVQLQQSGAE VKKPGATVKI SCTASGFNIK DDYLHWVRQA PGKGLEWIGR IDPANANTKY

APKFQDRVTI TADTSTNTAY LELSSLRSED TAVYYCAARF GYFYGSSFYA VAYWGQGTLV

TVSSASTKGP SVFPLAPSSK STSGGTAALG CLVKDYFPEP VTVSWNSGAL TSGVHTFPAV

LQSSGLYSLS SVVTVPSSSL GTQTYICNVN HKPSNTKVDK KVEPKSCDKT HTCPPCPAPE

LLGGPSVFLF PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP REPQVYTLPP

CRDELTKNQV SLWCLVKGFY PSDIAVEWES NGQPENNYKT TPPVLDSDGS FFLYSKLTVD

KSRWQQGNVF SCSVMHEALH NHYTQKSLSL SPGAGGGGSG GGSGGGGSNW VNVISDLKKI

EDLIQSMHID ATLYTESDVH PSCKVTAMKC FLLELQVISL ESGDASIHDT VENLIILANN

SLSSNGNVTE SGCKECEELE EKNIKEFLQS FVHIVQMFIN TSGGSGGGGS GGGGSAAGGG

GSGGGGSGGG GSITCPPPMS VEHADIWVKS YSLYSRERYI CNSGFKRKAG TSSLTECVLN

KAINVAHWIT PSLKCIRDPA LVHQRPAPPS
SEQ ID NO: 47 PD-L1 antibody 1296 heavy chain fused with IL-2Rβ ECD,
Fc with Hole Mutations
EVQLQQSGAE VKKPGATVKI SCTASGFNIK DDYLHWVRQA PGKGLEWIGR IDPANANTKY

APKFQDRVTI TADTSTNTAY LELSSLRSED TAVYYCAARF GYFYGSSFYA VAYWGQGTLV

TVSSASTKGP SVFPLAPSSK STSGGTAALG CLVKDYFPEP VTVSWNSGAL TSGVHTFPAV

LQSSGLYSLS SVVTVPSSSL GTQTYICNVN HKPSNTKVDK KVEPKSCDKT HTCPPCPAPE

LLGGPSVFLF PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP REPQVCTLPP

SRDELTKNQV SLSCAVKGFY PSDIAVEWES NGQPENNYKT TPPVLDSDGS FFLVSKLTVD

KSRWQQGNVF SCSVMHEALH NHYTQKSLSL SPGAGGGGSG GGSGPLGVR GGGGSGGGGS

AVNGTSQFTC FYNSRANISC VWSQDGALQD TSCQVHAWPD RRRWNQTCEL LPVSQASWAC

NLILGAPDSQ KLTTVDIVTL RVLCREGVRW RVMAIQDFKP FENLRLMAPI SLQVVHVETH

RCNISWEISQ ASHYFERHLE FEARTLSPGH TWEEAPLLTL KQKQEWICLE TLTPDTQYEF

QVRVKPLQGE FTTWSPWSQP LAFRTKPAAL GKDT
SEQ ID NO: 48 PD-L1 antibody 1296 heavy chain fused with scFv1 (VH-VL)
which binds to IL-15, Fc with Hole Mutations
EVQLQQSGAE VKKPGATVKI SCTASGFNIK DDYLHWVRQA PGKGLEWIGR IDPANANTKY

APKFQDRVTI TADTSTNTAY LELSSLRSED TAVYYCAARF GYFYGSSFYA VAYWGQGTLV

TVSSASTKGP SVFPLAPSSK STSGGTAALG CLVKDYFPEP VTVSWNSGAL TSGVHTFPAV

LQSSGLYSLS SVVTVPSSSL GTQTYICNVN HKPSNTKVDK KVEPKSCDKT HTCPPCPAPE

LLGGPSVFLF PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP REPQVCTLPP

SRDELTKNQV SLSCAVKGFY PSDIAVEWES NGQPENNYKT TPPVLDSDGS FFLVSKLTVD

KSRWQQGNVF SCSVMHEALH NHYTQKSLSL SPGAGGGGSG GGSGPLGVR GGGGSGGGGS

EVQLVQSGAE VKKPGESLKI SCKVSGYFFT TYWIGWVRQM PGKGLEYMGI IYPGDSDTRY

```
SPSFQGQVTI SADKSISTAY LQWSSLKASD TAMYYCARGG NWNCFDYWGQ GTLVTVSSGG

GGSGGGGSGG GGSEIVLTQS PGTLSLSPGR EATLSCRASQ SVSSSYLAWY QQKPGQAPRL

LIYGASRRAT GIPDRFSGSG SGTDFTLTIS RLEPEDFAVY YCQRYGSSHT FGQGTKLEIS R
```

SEQ ID NO: 49 PD-L1 antibody 1296 heavy chain fused with scFv2 (VL-VH)
which binds to IL-15, Fc with Hole Mutations
```
EVQLQQSGAE VKKPGATVKI SCTASGFNIK DDYLHWVRQA PGKGLEWIGR IDPANANTKY

APKFQDRVTI TADTSTNTAY LELSSLRSED TAVYYCAARF GYFYGSSFYA VAYWGGILV

TVSSASTKGP SVFPLAPSSK STSGGTAALG CLVKDYFPEP VTVSWNSGAL TSGVHTFPAV

LQSSGLYSLS SVVTVPSSSL GTQTYICNVN HKPSNTKVDK KVEPKSCDKT HTCPPCPAPE

LLGGPSVFLF PPKPKDTLMI SRTPEVTCVV VDVSHEDPEV KFNWYVDGVE VHNAKTKPRE

EQYNSTYRVV SVLTVLHQDW LNGKEYKCKV SNKALPAPIE KTISKAKGQP REPQVCTLPP

SRDELTKNQV SLSCAVKGFY PSDIAVEWES NGQPENNYKT TPPVLDSDGS FFLVSKLTVD

KSRWQQGNVF SCSVMHEALH NHYTQKSLSL SPGAGGGGSG GGGSGPLGVR GGGGSGGGGS

EIVLTQSPGT LSLSPGREAT LSCRASQSVS SSYLAWYQQK PGQAPRLLIY GASRRATGIP

DRFSGSGSGT DFTLTISRLE PEDFAVYYCQ RYGSSHTFGQ GTKLEISRGG GGSGGGGSGG

GGSEVQLVQS GAEVKKPGES LKISCKVSGY FFTTYWIGWV RQMPGKGLEY MGIIYPGDSD

TRYSPSFQGQ VTISADKSIS TAYLQWSSLK ASDTAMYYCA RGGNWNCFDY WGQGTLVTVS S
```

SEQ ID NO: 50 PD-L1 antibody 1296 LC
```
DIQMTQspSS LSASvGDRVT ItCRASQDIS NYLNWYQQKP DGTVKLLIYY TSRLHSGVPS RFSGSGSGTD YtLTISsLqp EDIATYFCQQ GKTLPPTFGG GTKLEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC
```

SEQ ID NO: 51 PD-L1 antibody 1296 LC fused with basal IL-2v
```
DIQMTQspSS LSASvGDRVT ItCRASQDIS NYLNWYQQKP DGTVKLLIYY TSRLHSGVPS RFSGSGSGTD YtLTISsLqp EDIATYFCQQ GKTLPPTFGG GTKLEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGECGGGGSG GGGSGGGGSA PASSSTKKTQ

LQLEHLLLDL QMILNGINNY KNPKLTSMLT AKFAMPKKAT ELKHLQCLEE ALKPLEEVLN

LAQSKNFHLR PRDLISEINV IVLELKGSET TFMCEYADET ATIVEFLNRW ITFSQSIIST LT
```

SEQ ID NO: 52 PD-1 antibody heavy chain fused with Sushi domain and
then with IL-15 polypeptide, Fc with Knob mutations (CX5.48.3)
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPCQEE MTKNQVSLWC

LVKGFYPSDI AVEWESNGQP ENNYKTTPPV LDSDGSFFLY SRLTVDKSRW QEGNVFSCSV

MHEALHNHYT QKSLSLSLGA GGGSGGGGS GGGGSITCPP PMSVEHADIW VKSYSLYSRE
```

```
RYICNSGFKR KAGTSSLTEC VLNKATNVAH WTTPSLKCIR DPALVHQRPA PPSGGSGGGG

SGGGGSGGGG SNWVNVISDL KKIEDLIQSM HIDATLYTES DVHPSCKVTA MKCFLLELQV

ISLESGDASI HDTVENLIIL ANNSLSSNGN VTESGCKECE ELEEKNIKEF LQSFVHIVQM

FINIS

SEQ ID NO: 53 PD-1 antibody heavy chain-IL-15 then with the Sushi
domain, Fc with Knob mutations (CX5.48.4)
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPP[C]QEE MTKNQVSL[W]C

LVKGFYPSDI AVEWESNGQP ENNYKTTPPV LDSDGSFFLY SRLTVDKSRW QEGNVFSCSV

MHEALHNHYT QKSLSLSLG[A] GGGGSGGGGS GGGGSNWVNV ISDLKKIEDL IQSMHIDATL

YTESDVHPSC KVTAMKCFLL ELQVISLESG DASIHDTVEN LIILANNSLS SNGNVTESGC

KECEELEEKN IKEFLQSFVH IVQMFINTSG GSGGGGSGGG GSGGGGSITC PPPMSVEHAD

IWVKSYSLYS RERYICNSGF KRKAGTSSLT ECVLNKATNV AHWTTPSLKC IRDPALVHQR

PAPPS

SEQ ID NO: 54 PD-1 antibody HC-beta hole (CX3.58.3)
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ V[C]TLPPSQEE MTKNQVSL[S]C

[A]VKGFYPSDI AVEWESNGQP ENNYKTTPPV LDSDGSFFL[V] SRLTVDKSRW QEGNVFSCSV

MHEALHNHYT QKSLSLSLG[A] GGGGSGGGGS GPLPVRGGGG SGGGGSAVNG TSQFTCFYNS

RANISCVWSQ DGALQDTSCQ VHAWPDRRRW NQTCELLPVS QASWACNLIL GAPDSQKLTT

VDIVTLRVLC REGVRWRVMA IQDFKPFENL RLMAPISLQV VHVETHRCNI SWEISQASHY

FERHLEFEAR TLSPGHTWEE APLLTLKQKQ EWICLETLTP DTQYEFQVRV KPLQGEFTTW

SPWSQPLAFR TKPAALGKDT

SEQ ID NO: 55 PD-1 antibody LC (CX5.17.1)
EIVLTQSPAT LSLSPGERAT LSCRASQSVS SYLAWYQQKP GQAPRLLIYD ASNRATGIPA

RFSGSGSGTD FTLTISSLEP EDFAVYYCQQ SSNWPRTFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC

SEQ ID NO: 56 PD-1 antibody LC fused with basal IL-2v
EIVLTQSPAT LSLSPGERAT LSCRASQSVS SYLAWYQQKP GQAPRLLIYD ASNRATGIPA

RFSGSGSGTD FTLTISSLEP EDFAVYYCQQ SSNWPRTFGQ GTKVEIKRTV AAPSVFIFPP

SDEQLKSGTA SVVCLLNNFY PREAKVQWKV DNALQSGNSQ ESVTEQDSKD STYSLSSTLT
```

-continued

LSKADYEKHK VYACEVTHQG LSSPVTKSFN RGECGGGGSG GGGSGGGGSA P[A]SSSTKKTQ

LQLEHLLLDL QMILNGINNY KNPKLT[S]MLT [A]KF[A]MPKKAT ELKHLQCLEE ALKPLEEVLN

LAQSKNFHLR PRDLIS[E]INV IVLELKGSET TFMCEYADET ATIVEFLNRW ITF[S]QSIIST LT

SEQ ID NO: 57 PD-1 HC hole (CX3.58.4)
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ V[C]TLPPSQEE MTKNQVSL[S]C

[A]VKGFYPSDI AVEWESNGQP ENNYKTTPPV LDSDGSFFL[V] SRLTVDKSRW QEGNVFSCSV

MHEALHNHYT QKSLSLSLGK

SEQ ID NO: 58 PD-1 antibody heavy chain fused with Sushi domain and
then with IL-15 polypeptide N65D, Fc with Knob mutations
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPP[C]QEE MTKNQVSL[W]C

LVKGFYPSDI AVEWESNGQP ENNYKTTPPV LDSDGSFFLY SRLTVDKSRW QEGNVFSCSV

MHEALHNHYT QKSLSLSLG[A] GGGGSGGGSG GGGSITCPPP MSVEHADIWV KSYSLYSRER

YICNSGFKRK AGTSSLTECV LNKATNVAHW TTPSLKCIRD PALVHQRPAP PSGGGGSGGG

GSGGGGSNWV NVISDLKKIE DLIQSMHIDA TLYTESDVHP SCKVTAMKCF LLELQVISLE

SGDASIHDTV E[D]LIILANNS LSSNGNVTES GCKECEELEE KNIKEFLQSF VHIVQMFINT S

SEQ ID NO: 59 PD-1 antibody heavy chain fused with Sushi domain and
then with IL-15 polypeptide Q108E, Fc with Knob mutations
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPP[C]QEE MTKNQVSL[W]C

LVKGFYPSDI AVEWESNGQP ENNYKTTPPV LDSDGSFFLY SRLTVDKSRW QEGNVFSCSV

MHEALHNHYT QKSLSLSLG[A] GGGGSGGGSG GGGSITCPPP MSVEHADIWV KSYSLYSRER

YICNSGFKRK AGTSSLTECV LNKATNVAHW TTPSLKCIRD PALVHQRPAP PSGGGGSGGG

GSGGGGSNWV NVISDLKKIE DLIQSMHIDA TLYTESDVHP SCKVTAMKCF LLELQVISLE

SGDASIHDTV ENLIILANNS LSSNGNVTES GCKECEELEE KNIKEFLQSF VHIV[E]MFINT S

SEQ ID NO: 60 PD-1 antibody HC-scFV1 (VH-VL) hole
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ V[C]TLPPSQEE MTKNQVSL[S]C

[A]VKGFYPSDI AVEWESNGQP ENNYKTTPPV LDSDGSFFL[V] SRLTVDKSRW QEGNVFSCSV

MHEALHNHYT QKSLSLSLG[A] GGGG<u>SGPLGV R</u>GGGGSGGGG SEVQLVQSGA EVKKPGESLK

ISCKVSGYFF TTYWIGWVRQ MPGKGLEYMG IIYPGDSDTR YSPSFQGQVT ISADKSISTA

YLQWSSLKAS DTAMYYCARG GNWNCFDYWG QGTLVTVSSG GGGSGGGGSG GGGSEIVLTQ

SPGTLSLSPG REATLSCRAS QSVSSSYLAW YQQKPGQAPR LLIYGASRRA TGIPDRFSGS

GSGTDFTLTI SRLEPEDFAV YYCQRYGSSH TFGQGTKLEI SR

SEQ ID NO: 61 PD-1 antibody HC-scfv2 (VL-VH) hole
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ V[C]TLPPSQEE MTKNQVSL[S]C

[A]VKGFYPSDI AVEWESNGQP ENNYKTTPPV LDSDGSFFL[V] SRLTVDKSRW QEGNVFSCSV

MHEALHNHYT QKSLSLSLG[A] GGGG<u>SGPLGV R</u>GGGGSGGGG SEVQLVQSGA EVKKPGESLK

TLSCRASQSV SSSYLAWYQQ KPGQAPRLLI YGASRRATGI PDRFSGSGSG TDFTLTISRL

EPEDFAVYYC QRYGSSHTFG QGTKLEISRG GGGSGGGGSG GGGSEVQLVQ SGAEVKKPGE

SLKISCKVSG YFFTTYWIGW VRQMPGKGLE YMGIIYPGDS DTRYSPSFQG QVTISADKSI

STAYLQWSSL KASDTAMYYC ARGGNWNCFD YWGQGTLVTV SS

SEQ ID NO: 62 PD-1 antibody heavy chain fused with IL-15 polypeptide
E46K, Fc with Knob mutations; no Sushi
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP [P]CPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPP[C]QEE MTKNQVSL[W]C

LVKGFYPSDI AVEWESNGQP ENNYKTTPPV LDSDGSFFLY SRLTVDKSRW QEGNVFSCSV

```
MHEALHNHYT QKSLSLSLGA GGGGSGGGSG GGGSNWVNVI SDLKKIEDLI QSMHIDATLY

TESDVHPSCK VTAMKCFLLK LQVISLESGD ASIHDTVEEL IILANNSLSS NGNVTESGCK

ECEELEEKNI KEFLQSFVHI VQMFINTS
```

SEQ ID NO: 63 PD-1 antibody heavy chain fused with IL-15 polypeptide
E46K/N65D, Fc with Knob mutations; no Sushi
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPCQEE MTKNQVSLWC

LVKGFYPSDI AVEWESNGQP ENNYKTTPPV LDSDGSFFLY SRLTVDKSRW QEGNVFSCSV

MHEALHNHYT QKSLSLSLGA GGGGSGGGSG GGGSNWVNVI SDLKKIEDLI QSMHIDATLY

TESDVHPSCK VTAMKCFLLK LQVISLESGD ASIHDTVEDL IILANNSLSS NGNVTESGCK

ECEELEEKNI KEFLQSFVHI VQMFINTS
```

SEQ ID NO: 64 CX7_71_1 PD1-IL-15vE46K, no Sushi, no KIH
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGS GGGGSNWVNV ISDLKKIEDL IQSMHIDATL

YTESDVHPSC KVTAMKCFLL KLQVISLESG DASIHDTVEN LIILANNSLS SNGNVTESGC

KECEELEEKN IKEFLQSFVH IVQMFINTS
```

SEQ ID NO: 65 PD1-IL-15vE46K/N65D, no Sushi, no KIH
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GGGGSNWVNV ISDLKKIEDL IQSMHIDATL

YTESDVHPSC KVTAMKCFLL kLQVISLESG DASIHDTVED LIILANNSLS SNGNVTESGC

KECEELEEKN IKEFLQSFVH IVQMFINTS
```

SEQ ID NO: 66_CX7_53_2 PD1-ScFv2 no KIH
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GPLGVRGGGG SGGGGSEIVL TQSPGTLSLS

PGERATLSCR ASQSVSSSYL AWYQQKPGQA PRLLIYGASR RATGIPDRFS GSGSGTDFTL

TISRLEPEDF AVYYCQRYGS SHTFGQGTKL EISGGGGSGG GGSGGGGSEV QLVQSGAEVK

KPGESLKISC KVSGYFFTTY WIGWVRQMPG KGLEYMGIIY PGDSDTRYSP SFQGQVTISA

DKSISTAYLQ WSSLKASDTA MYYCARGGNW NCFDYWGQGT LVTVSS**

SEQ ID NO: 67_CX7_53_1 PD1-Sushi-IL-15vN65D no KIH
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GGGGSITCPP PMSVEHADIW VKSYSLYSRE

RYICNSGFKR KAGTSSLTEC VLNKATNVAH WTTPSLKCIR GGSGGGGSGG GSGGGGSNWV

NVISDLKKIE DLIQSMHIDA TLYTESDVHP SCKVTAMKCF LLELQVISLE SGDASIHDTV

EDLIILANNS LSSNGNVTES GCKECEELEE KNIKEFLQSF VHIVQMFINT S

SEQ ID NO: 68_CX7_53_1 PD1-Sushi-IL-15vN65D no KIH, long linker
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GGGSITCPP PMSVEHADIW VKSYSLYSRE

RYICNSGFKR KAGTSSLTEC VLNKATNVAH WTTPSLKCIR GGSGGGGSGG GSGGGGSAAG

GGGSGGGGSG GGGSNWVNVI SDLKKIEDLI QSMHIDATLY TESDVHPSCK VTAMKCFLLE

LQVISLESGD ASIHDTVEDL IILANNSLSS NGNVTESGCK ECEELEEKNI KEFLQSFVHI

VQMFINTS

SEQ ID NO: 69 PD-1 antibody heavy chain fused with Sushi domain and then with IL-15 polypeptide N65D, Fc with Knob mutations, long linker

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLPPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPCQEE MTKNQVSLWC

LVKGFYPSDI AVEWESNGQP ENNYKTTPPV LDSDGSFFLY SRLTVDKSRW QEGNVFSCSV

MHEALHNHYT QKSLSLSLGA GGGGSGGGSG GGGSITCPPP MSVEHADIWV KSYSLYSRER

YICNSGFKRK AGTSSLTECV LNKATNVAHW TTPSLKCIRD PALVHQRPAP SGGGGSGGG

GSGGGGSAAG GGGSGGGGSG GGGSNWVNVI SDLKKIEDLI QSMHIDATLY TESDVHPSCK

VTAMKCFLLE LQVISLESGD ASIHDTVEDL IILANNSLSS NGNVTESGCK ECEELEEKNI

KEFLQSFVHI VQMFINTS

SEQ ID NO: 70 Amino acid sequence of IgG1 Fc fused with scFv1 against IL-15; Fc with hole mutations

DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSRDELTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSVHMPLGFL

GPRQARVVNG GGGGSGGGGS EVQLVQSGAE VKKPGESLKI SCKVSGYFFT TYWIGWVRQM

PGKGLEYMGI IYPGDSDTRY SPSFQGQVTI SADKSISTAY LQWSSLKASD TAMYYCARGG

NWNCFDYWGQ GTLVTVSSGG GGSGGGGSGG GGSEIVLTQS PGTLSLSPGR EATLSCRASQ

SVSSSYLAWY QQKPGQAPRL LIYGASRRAT GIPDRFSGSG SGTDFTLTIS RLEPEDFAVY

YCQRYGSSHT FGQGTKLEIS R

SEQ ID NO: 71 Amino acid sequence of IgG1 Fc fused with scFv against IL-15, ver2; Fc with hole mutations

DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSRDELTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSVHMPLGFL

GPRQARVVNG GGGGSGGGGS EIVLTQSPGT LSLSPGREAT LSCRASQSVS SSYLAWYQQK

PGQAPRLLIY GASRRATGIP DRFSGSGSGT DFTLTISRLE PEDFAVYYCQ RYGSSHTFGQ

GTKLEISRGG GGSGGGGSGG GGSEVQLVQS GAEVKKPGES LKISCKVSGY FFTTYWIGWV

RQMPGKGLEY MGIIYPGDSD TRYSPSFQGQ VTISADKSIS TAYLQWSSLK ASDTAMYYCA

RGGNWNCFDY WGQGTLVTVS S

SEQ ID NO: 72 Amino acid sequence of Fc fused with scFv against IL-15, ver3; Fc with hole mutations
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSREEMTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSVHMPLGFL

GPRQARVVNG GGGGSGGGGS EVQLVQSGAE VKKPGESLKI SCKVSGYFFT TYWIGWVRQM

PGKGLEYMGI IYPGDSDTRY SPSFQGQVTI SADKSISTAY LQWSSLKASD TAMYYCARGG

NWNCFDYWGQ GTLVTVSSGG GGSGGGGSGG GGSEIVLTQS PGTLSLSPGR EATLSCRASQ

SVSSSYLAWY QQKPGQAPRL LIYGASRRAT GIPDRFSGSG SGTDFTLTIS RLEPEDFAVY

YCQRYGSSHT FGQGTKLEIS R

SEQ ID NO: 73 Amino acid sequence of Fc fused with scFv against IL-15, ver4; Fc with hole mutations

DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSREEMTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSVHMPLGFL

GPRQARVVNG GGGGSGGGGS EIVLTQSPGT LSLSPGREAT LSCRASQSVS SSYLAWYQQK

PGQAPRLLIY GASRRATGIP DRFSGSGSGT DFTLTISRLE PEDFAVYYCQ RYGSSHTFGQ

GTKLEISRGG GGSGGGGSGG GGSEVQLVQS GAEVKKPGES LKISCKVSGY FFTTYWIGWV

RQMPGKGLEY MGIIYPGDSD TRYSPSFQGQ VTISADKSIS TAYLQWSSLK ASDTAMYYCA

RGGNWNCFDY WGQGTLVTVS S

SEQ ID NO: 74 IgG1 Fc-knob-Sushi-IL-15 IgG1_allotype EEM, LALA mutation H435RY436F

DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCREEMTK NQVSLWCLVK GFYPSDIAVE WESNGQPENN YKTTPPVLDS

DGSFFLYSKL TVDKSRWQQG NVFSCSVMHE ALHNRFTQKS LSLSPGKGGG GSGGGGSGGG

GSITCPPPMS VEHADIWVKS YSLYSRERYI CNSGFKRKAG TSSLTECVLN KAINVAHWIT

PSLKCIRGGS GGGGSGGGSG GGGSNWVNVI SDLKKIEDLI QSMHIDATLY TESDVHPSCK

VTAMKCFLLE LQVISLESGD ASIHDTVENL IILANNSLSS NGNVTESGCK ECEELEEKNI

KEFLQSFVHI VQMFINTS**

SEQ ID NO: 75 IgG1 Fc-knob-IL-15 (E46K/N65D) IgG1_allotype EEM, LALA mutation

DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCREEMTK NQVSLWCLVK GFYPSDIAVE WESNGQPENN YKTTPPVLDS

DGSFFLYSKL TVDKSRWQQG NVFSCSVMHE ALHNHYTQKS LSLSPGKGGG GSGGGGSGGG

GSITCPPPMS VEHADIWVKS YSLYSRERYI CNSGFKRKAG TSSLTECVLN KAINVAHWIT

PSLKCIRGGS GGGGSGGGSG GGGSNWVNVI SDLKKIEDLI QSMHIDATLY TESDVHPSCK

VTAMKCFLLK LQVISLESGD ASIHDTVEDL IILANNSLSS NGNVTESGCK ECEELEEKNI

KEFLQSFVHI VQMFINTS**

SEQ ID NO: 76 IgG1 Fc-knob-Sushi-IL-15 (N65D) IgG1_allotype EEM, LALA
mutation H435R/Y436F
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCREEMTK NQVSLWCLVK GFYPSDIAVE WESNGQPENN YKTTPPVLDS

DGSFFLYSKL TVDKSRWQQG NVFSCSVMHE ALHNRFTQKS LSLSPGKGGG GSGGGGSGGG

GSITCPPPMS VEHADIWVKS YSLYSRERYI CNSGFKRKAG TSSLTECVLN KAINVAHWIT

PSLKCIRGGS GGGGSGGGSG GGGSNWVNVI SDLKKIEDLI QSMHIDATLY TESDVHPSCK

VTAMKCFLLE LQVISLESGD ASIHDTVEDL IILANNSLSS NGNVTESGCK ECEELEEKNI

KEFLQSFVHI VQMFINTS**

SEQ ID NO: 77 IgG1 Fc-knob-Sushi-IL-15 IgG1_allotype EEM, LALA
mutation H435RY436F
5'XbaI,3'PmeI
ASKGD111_CX5_75_3
DKTHTCPPCP APEAAGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCREEMTK NQVSLWCLVK GFYPSDIAVE WESNGQPENN YKTTPPVLDS

DGSFFLYSKL TVDKSRWQQG NVFSCSVMHE ALHNRFTQKS LSLSPGKGGG GSGGGGSGGG

GSITCPPPMS VEHADIWVKS YSLYSRERYI CNSGFKRKAG TSSLTECVLN KAINVAHWIT

PSLKCIRGGS GGGGSGGGSG GGGSNWVNVI SDLKKIEDLI QSMHIDATLY TESDVHPSCK

VTAMKCFLLE LQVISLESGD ASIHDTVENL IILANNSLSS NGNVTESGCK ECEELEEKNI

KEFLQSFVHI VQMFINTS**

SEQ ID NO: 78 IgG1 Fc-knob-Sushi-IL-15 (D30N,E64Q,N65D) IgG1_allotype
EEM, LALA mutation H435R/Y436F
5'XbaI,3'PmeI
ASKGD111_CX5_74_1
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPPCREEMTKNQV SLWCLVKGFY PSDIAVEWES

NGQPENNYKT TPPVLDSDGS FFLYSKLTVD KSRWQQGNVF SCSVMHEALH NRFTQKSLSL

SPGKGGGGSG GGGSGGGGSI TCPPPMSVEH ADIWVKSYSL YSRERYICNS GFKRKAGISS

LTECVLNKAT NVAHWTTPSL KCIRGGSGGG GSGGGSGGGG SNWVNVISDL KKIEDLIQSM

HIDATLYTES NVHPSCKVTA MKCFLLELQV ISLESGDASI HDTVQDLIIL ANNSLSSNGN

VTESGCKECE ELEEKNIKEF LQSFVHIVQM FINIS**

SEQ ID NO: 79 IgG1 Fc-knob-Sushi-IL-15 (N65D) IgG1_allotype EEM, LALA
mutation H435R/Y436F
5'XbaI,3'PmeI
ASKGD111_CX5_74_2
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

-continued

SNKALPAPIE KTISKAKGQP REPQVYTLPPCREEMTKNQV SLWCLVKGFY PSDIAVEWES

NGQPENNYKT TPPVLDSDGS FFLYSKLTVD KSRWQQGNVF SCSVMHEALH NRFTQKSLSL

SPGKGGGGSG GGGSGGGGSI TCPPPMSVEH ADIWVKSYSL YSRERYICNS GFKRKAGISS

LTECVLNKAT NVAHWTTPSL KCIRGGSGGG GSGGGSGGGG SNWVNVISDL KKIEDLIQSM

HIDATLYTES DVHPSCKVTA MKCFLLELQV ISLESGDASI HDTVEDLIIL ANNSLSSNGN

VTESGCKECE ELEEKNIKEF LQSFVHIVQM FINIS**

SEQ ID NO: 80 IgG4 FC-scFV1 (VH-VL) hole
ESKYGPPCPP CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV CTLPPSQEEM TKNQVSLSCA VKGFYPSDIA VEWESNGQPE NNYKTTPPVL

DSDGSFFLVS RLTVDKSRWQ EGNVFSCSVM HEALHNHYTQ KSLSLSLGAG GGGSVHMPLG

FLGPRQARVV NGGGGGSGGG GSEVQLVQSG AEVKKPGESL KISCKVSGYF FTTYWIGWVR

QMPGKGLEYM GIIYPGDSDT RYSPSFQGQV TISADKSIST AYLQWSSLKA SDTAMYYCAR

GGNWNCFDYW GQGTLVTVSS GGGGSGGGGS GGGGSEIVLT QSPGTLSLSP GREATLSCRA

SQSVSSSYLA WYQQKPGQAP RLLIYGASRR ATGIPDRFSG SGSGTDFTLT ISRLEPEDFA

VYYCQRYGSS HTFGQGTKLE ISR

SEQ ID NO: 81 IgG4 FC-scfv2 (VL-VH) hole
ESKYGPPCPP CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV CTLPPSQEEM TKNQVSLSCA VKGFYPSDIA VEWESNGQPE NNYKTTPPVL

DSDGSFFLVS RLTVDKSRWQ EGNVFSCSVM HEALHNHYTQ KSLSLSLGAG GGGSVHMPLG

FLGPRQARVV NGGGGGSGGG GSEIVLTQSP GTLSLSPGRE ATLSCRASQS VSSSYLAWYQ

QKPGQAPRLL IYGASRRATG IPDRFSGSGS GTDFTLTISR LEPEDFAVYY CQRYGSSHTF

GQGTKLEISR GGGGSGGGGS GGGGSEVQLV QSGAEVKKPG ESLKISCKVS GYFFTTYWIG

WVRQMPGKGL EYMGIIYPGD SDTRYSPSFQ GQVTISADKS ISTAYLQWSS LKASDTAMYY

CARGGNWNCF DYWGQGTLVT VSS

SEQ ID NO: 82 IgG4 Fc-knob-Sushi-IL-15 (N65D)
ESKYGPPCPP CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPPCQEEM TKNQVSLWCL VKGFYPSDIA VEWESNGQPE NNYKTTPPVL

DSDGSFFLYS RLTVDKSRWQ EGNVFSCSVM HEALHNHYTQ KSLSLSLGAG GGGSGGGGSG

GGGSITCPPP MSVEHADIWV KSYSLYSRER YICNSGFKRK AGTSSLTECV LNKATNVAHW

TTPSLKCIRG GSGGGGSGGG SGGGGSNWVN VISDLKKIED LIQSMHIDAT LYTESDVHPS

CKVTAMKCFL LELQVISLES GDASIHDTVE DLIILANNSL SSNGNVTESG CKECEELEEK

NIKEFLQSFV HIVQMFINTS

SEQ ID NO: 83 IgG4 Fc-knob-Sushi-IL-15 (N65D), long linker
ESKYGPPCP[P]CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPP[C]QEEM TKNQVSL[W]CL VKGFYPSDIA VEWESNGQPE NNYKTTPPVL

DSDGSFFLYS RLTVDKSRWQ EGNVFSCSVM HEALHNHYTQ KSLSLSLG[A]G GGGSGGGGSG

GGGSITCPPP MSVEHADIWV KSYSLYSRER YICNSGFKRK AGTSSLTECV LNKATNVAHW

TTPSLKCIRG GSGGGGSGGG SGGGGSAAGG SGGGGSGGGS GGGGSNWVNV ISDLKKIEDL

IQSMHIDATL YTESDVHPSC KVTAMKCFLL ELQVISLESG DASIHDTVE[D]LIILANNSLS

SNGNVTESGC KECEELEEKN IKEFLQSFVH IVQMFINTS

SEQ ID NO: 84 IgG4 Fc-knob-Sushi-IL-15 (Q108E)
ESKYGPPCP[P]CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPP[C]QEEM TKNQVSL[W]CL VKGFYPSDIA VEWESNGQPE NNYKTTPPVL

DSDGSFFLYS RLTVDKSRWQ EGNVFSCSVM HEALHNHYTQ KSLSLSLG[A]G GGGSGGGGSG

GGGSITCPPP MSVEHADIWV KSYSLYSRER YICNSGFKRK AGTSSLTECV LNKATNVAHW

TTPSLKCIRG GSGGGGSGGG SGGGGSNWVN VISDLKKIED LIQSMHIDAT LYTESDVHPS

CKVTAMKCFL LELQVISLES GDASIHDTVE NLIILANNSL SSNGNVTESG CKECEELEEK

NIKEFLQSFV HIV[E]MFINTS

SEQ ID NO: 85 IgG4 Fc-knob-IL-15 E46K, no Sushi
ESKYGPPCP[P]CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPP[C]QEEM TKNQVSL[W]CL VKGFYPSDIA VEWESNGQPE NNYKTTPPVL

DSDGSFFLYS RLTVDKSRWQ EGNVFSCSVM HEALHNHYTQ KSLSLSLG[A]G GGGSGGGGSG

SGGGGSNWVN VISDLKKIED LIQSMHIDAT LYTESDVHPS CKVTAMKCFL L[K]LQVISLES

GDASIHDTVE NLIILANNSL SSNGNVTESG CKECEELEEK NIKEFLQSFV HIVQMFINTS

SEQ ID NO: 86 IgG4 Fc-knob-IL-15 E46K/N65D, no Sushi
ESKYGPPCP[P]CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

AKGQPREPQV YTLPP[C]QEEM TKNQVSL[W]CL VKGFYPSDIA VEWESNGQPE NNYKTTPPVL

DSDGSFFLYS RLTVDKSRWQ EGNVFSCSVM HEALHNHYTQ KSLSLSLG[A]G GGGSGGGGSG

SGGGGSNWVN VISDLKKIED LIQSMHIDAT LYTESDVHPS CKVTAMKCFL L[K]LQVISLES

GDASIHDTVE [D]LIILANNSL SSNGNVTESG CKECEELEEK NIKEFLQSFV HIVQMFINTS

SEQ ID NO: 87 IgG4 FC-IL2R_beta ECD hole
ESKYGPPCP[P]CPAPEFLGGP SVFLFPPKPK DTLMISRTPE VTCVVVDVSQ EDPEVQFNWY

VDGVEVHNAK TKPREEQFNS TYRVVSVLTV LHQDWLNGKE YKCKVSNKGL PSSIEKTISK

```
AKGQPREPQV [C]TLPPSQEEM TKNQVSL[S][C][A] VKGFYPSDIA VEWESNGQPE NNYKTTPPVL

DSDGSFFL[V]S RLTVDKSRWQ EGNVFSCSVM HEALHNHYTQ KSLSLSLG[A]G GGGSVHMPLG

FLGPRQARVV NGGGGGSGGG GSGGGGSAVN GTSQFTCFYN SRANISCVWS QDGALQDTSC

QVHAWPDRRR WNQTCELLPV SQASWACNLI LGAPDSQKLT TVDIVTLRVL CREGVRWRVM

AIQDFKPFEN LRLMAPISLQ VVHVETHRCN ISWEISQASH YFERHLEFEA RTLSPGHTWE

EAPLLTLKQK QEWICLETLT PDTQYEFQVR VKPLQGEFTT WSPWSQPLAF RTKPAALGKD T

SEQ ID NO: 88 cetuximab light chain
DILLTQSPVI LSVSPGERVS FSCRASQSIG TNIHWYQQRT NGSPRLLIKY ASESISGIPS

RFSGSGSGTD FTLSINSVES EDIADYYCQQ NNNWPTTFGA GTKLELKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC

SEQ ID NO: 89 cetuximab heavy chain
QVQLKQSGPG LVQPSQSLSI TCTVSGFSLT NYGVHWVRQS PGKGLEWLGV IWSGGNTDYN

TPFTSRLSIN KDNSKSQVFF KMNSLQSNDT AIYYCARALT YYDYEFAYWG QGTLVTVSAA

STKGPSVFPL APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP CPAPELLGGP

SVFLFPPKPK DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV YTLPPSRDEL

TKNQVSLTCL VKGFYPSDIA VEWESNGQPE NNYKTTPPVL DSDGSFFLYS KLTVDKSRWQ

QGNVFSCSVM HEALHNHYTQ KSLSLSPGK

SEQ ID NO: 90 panitumumab light chain
DIQMTQSPSS LSASVGDRVT ITCQASQDIS NYLNWYQQKP GKAPKLLIYD ASNLETGVPS

RFSGSGSGTD FTFTISSLQP EDIATYFCQH FDHLPLAFGG GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC

SEQ ID NO: 91 panitumumab heavy chain
GHIYYSGNTN YNPSLKSRLT ISIDTSKTQF SLKLSSVTAA DTAIYYCVRD RVTGAFDIWG

QGTMVTVSSA STKGPSVFPL APCSRSTSES TAALGCLVKD YFPEPVTVSW NSGALTSGVH

TFPAVLQSSG LYSLSSVVTV PSSNFGTQTY TCNVDHKPSN TKVDERKCCV ECPAGPSVFL

FPPKPKDTLM ISRTPEVTCV VVDVSHEDPE VQFNWYVDGV EVHNAKTKPR EEQFNSTFRV

VSVLTVVHQD WLNGKEYKCK VSNKGLPAPI EKTISKTKGQ PREPQVYTLP PSREEMTKNQ

VSLTCLVKGF YPSDIAVEWE SNGQPENNYK TTPPMLDSDG SFFLYSKLTV DKSRWQQGNV

FSCSVMHEAL HNHYTQKSLS LSPGK

SEQ ID NO: 92 anti-cMET antibody light chain
DIVMTQAAPS VPVTPGESVS ISCRSSKSLL HSNGNTYLYW FLQRPGQSPQ VLIYRMSNLA

SGVPDRFSGS GSGTAFTLRI RRVEAEDVGV YYCMQNLEYP FTFGGGTKLE IKRTVAAPSV

FIFPPSDEQL KSGTASVVCL LNNFYPREAK VQWKVDNALQ SGNSQESVTE QDSKDSTYSL

SSILTLSKAD YEKHKVYACE VTHQGLSSPV TKSFNRGEC

SEQ ID NO: 93 anti-cMET antibody heavy chain
QVQLQQSGPE LVKSGASVKM SCKASGNTLK DDHVHWVKQR PGQGLEWIGW IYPGGGRTRY

NEKFKGKTTL TADKPSSTVN MLLSSLTSED SAIYFCTNLV FDVWGAGTTV TVSSASTKGP

SVFPLAPSSK STSGGTAALG CLVKDYFPEP VTVSWNSGAL TSGVHTFPAV LQSSGLYSLS

SVVTVPSSSL GTQTYICNVN HKPSNTKVDK KVEPKSCDKT HTCPPCPAPE LLGGPSVFLF
```

```
PPKPKDTLMI SRTPEVTCVV VDVSHEDPEV KFNWYVDGVE VHNAKTKPRE EQYNSTYRVV

SVLTVLHQDW LNGKEYKCKV SNKALPAPIE KTISKAKGQP REPQVYTLPP SREEMTKNQV

SLTCLVKGFY PSDIAVEWES NGQPENNYKT TPPVLDSDGS FFLYSKLTVD KSRWQQGNVF

SCSVMHEALH NHYTQKSLSL SPGK

SEQ ID NO: 94 anti-GPC3 antibody light chain
DVVMTQSPLS LPVTPGEPAS ISCRSSQSLV HSNANTYLHW YLQKPGQSPQ LLIYKVSNRF

SGVPDRFSGS GSGTDFTLKI SRVEAEDVGV YYCSQNTHVP PTFGQGTKLE IKRTVAAPSV

FIFPPSDEQL KSGTASVVCL LNNFYPREAK VQWKVDNALQ SGNSQESVTE QDSKDSTYSL

SSILTLSKAD YEKHKVYACE VTHQGLSSPV TKSFNRGEC

SEQ ID NO: 95 anti-GPC3 antibody heavy chain
QVQLVQSGAE VKKPGASVKV SCKASGYTFT DYEMHWVRQA PGQGLEWMGA LDPKTGDTAY

SQKFKGRVTL TADKSTSTAY MELSSLTSED TAVYYCTRFY SYTYWGQGTL VTVSSASTKG

PSVFPLAPSS KSTSGGTAAL GCLVKDYFPE PVTVSWNSGA LTSGVHTFPA VLQSSGLYSL

SSVVTVPSSS LGTQTYICNV NHKPSNTKVD KKVEPKSCDK THTCPPCPAP ELLGGPSVFL

FPPKPKDTLM ISRTPEVTCV VVDVSHEDPE VKFNWYVDGV EVHNAKTKPR EEQYNSTYRV

VSVLTVLHQD WLNGKEYKCK VSNKALPAPI EKTISKAKGQ PREPQVYTLP PSREEMTKNQ

VSLTCLVKGF YPSDIAVEWE SNGQPENNYK TTPPVLDSDG SFFLYSKLTV DKSRWQQGNV

FSCSVMHEAL HNHYTQKSLS LSPGK

SEQ ID NO: 96 Humanized H8 anti-5T4 version 1 VH (protein sequence)
QVQLVQSGAE VKKPGASVKV SCKASGYSFT GYYMHWVKQS PGQGLEWIGR INPNNGVTLY

NQKFKDRVTM TRDTSISTAY MELSRLRSDD TAVYYCARST MITNYVMDYW GQGTLWTVSS

SEQ ID NO: 97 Humanized H8 anti-5T4 VH version 2 (protein sequence)
QVQLVQSGAE VKKPGASVKV SCKASGYSFT GYYMHWVRQA PGQGLEWMGR INPNNGVTLY

NQKFKDRVTM TRDTSISTAY MELSRLRSDD TAVYYCARST MITNYVMDYW GQGTLVTVSS

SEQ ID NO: 98 Humanized H8 anti-5T4 version 1 VL (protein sequence)
DIVMTQSPDS LAVSLGERAT INCKASQSVS NDVAWYQQKP GQSPKLLISY TSSRYAGVPD

RFSGSGSGTD FTLTISSLQA EDVAVYFCQQ DYNSPPTFGG GTKLEIK

SEQ ID NO: 99 Humanized H8 anti-5T4 VL version 2 (protein sequence)
DIVMTQSPDS LAVSLGERAT INCKASQSVS NDVAWYQQKP GQPPKLLIYY TSSRYAGVPD

RFSGSGSGTD FTLTISSLQA EDVAVYYCQQ DYNSPPTFGG GTKLEIK

SEQ ID NO: 100 Anti-IL-15 antibody 146B7 HC CDR1 (protein sequence)
TYWIG

SEQ ID NO: 101 Anti-IL-15 antibody 146B7 HC CDR2 (protein sequence)
IIYPGDSDTR YSPSFQG SEQ ID NO: 102 Anti-IL-15 antibody 146B7 HC CDR3 (protein sequence)
GNWNCFDY SEQ ID NO: 103 Anti-IL-15 antibody 146B7 LC CDR1 (protein sequence)
RASQSVSSSY LA SEQ ID NO: 104 Anti-IL-15 antibody 146B7 LC CDR2 (protein sequence)
GASRRAT SEQ ID NO: 105 Anti-IL-15 antibody 146B7 LC CDR3 (protein sequence)
QRYGSSHT SEQ ID NO: 106 Anti-IL-15 antibody 146B7 HC CDR3 ver2 (protein
sequence)
GNWNSFDY
```

SEQ ID NO: 107 Anti-IL-15 antibody 146B7 HC variable domain (protein sequence)
EVQLVQSGAE VKKPGESLKI SCKVSGYFFT TYWIGWVRQM PGKGLEYMGI IYPGDSDTRY

SPSFQGQVTI SADKSISTAY LQWSSLKASD TAMYYCARGG NWNCFDYWGQ GTLVTVSS

SEQ ID NO: 108 Anti-IL-15 antibody 146B7 LC variable domain (protein sequence)
EIVLTQSPGT LSLSPGREAT LSCRASQSVS SSYLAWYQQK PGQAPRLLIY GASRRATGIP

DRFSGSGSGT DFTLTISRLE PEDFAVYYCQ RYGSSHTFGQ GTKLEISRTV AAPSVFIFP

SEQ ID NO: 109 anti-IL-15 scFv1
EVQLVQSGAE VKKPGESLKI SCKVSGYFFT TYWIGWVRQM PGKGLEYMGI IYPGDSDTRY

SPSFQGQVTI SADKSISTAY LQWSSLKASD TAMYYCARGG NWNCFDYWGQ GTLVTVSSGG

GGSGGGGSGG GGSEIVLTQS PGTLSLSPGR EATLSCRASQ SVSSSYLAWY QQKPGQAPRL

LIYGASRRAT GIPDRFSGSG SGTDFTLTIS RLEPEDFAVY YCQRYGSSHT FGQGTKLEIS R

SEQ ID NO: 110 anti-IL-15 scFv2
EIVLTQSPGT LSLSPGREAT LSCRASQSVS SSYLAWYQQK PGQAPRLLIY GASRRATGIP

DRFSGSGSGT DFTLTISRLE PEDFAVYYCQ RYGSSHTFGQ GTKLEISRGG GGSGGGGSGG

GGSEVQLVQS GAEVKKPGES LKISCKVSGY FFTTYWIGWV RQMPGKGLEY MGIIYPGDSD

TRYSPSFQGQ VTISADKSIS TAYLQWSSLK ASDTAMYYCA RGGNWNCFDY WGQGTLVTVS S

SEQ ID NO: 111 IgG1 Fc-hole-Hv-Lv
ASKGD111_CX5_101_1
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVCTLPP SREEMTKNQV SLSCAVKGFY PSDIAVEWES

NGQPENNYKT TPPVLDSDGS FFLVSKLTVD KSRWQQGNVF SCSVMHEALH NHYTQKSLSL

SPGAGGGGSG GGGSGPLGVR GGGGSGGGGS EVQLVQSGAE VKKPGESLKI SCKVSGYFFT

TYWIGWVRQM PGKGLEYMGI IYPGDSDTRY SPSFQGQVTI SADKSISTAY LQWSSLKASD

TAMYYCARGG NWNCFDYWGQ GTLVTVSSGG GGSGGGGSGG GGSGIVLTQS PGTLSLSPGE

RATLSCRASQ SVSSSYLAWY QQKPGQAPRL LIYGASRRAT GIPDRFSGSG SGTDFTLTIS

RLEPEDFAVY YCQRYGSSHT FGQGTKLEIS**

SEQ ID NO: 112 IgG1 Fc-hole-Lv-Hv
ASKGD111_CX5_101_2
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVCTLPP SREEMTKNQV SLSCAVKGFY PSDIAVEWES

NGQPENNYKT TPPVLDSDGS FFLVSKLTVD KSRWQQGNVF SCSVMHEALH NHYTQKSLSL

SPGAGGGGSG GGGSGPLGVR GGGGSGGGGS GIVLTQSPGT LSLSPGERAT LSCRASQSVS

SSYLAWYQQK PGQAPRLLIY GASRRATGIP DRFSGSGSGT DFTLTISRLE PEDFAVYYCQ

RYGSSHTFGQ GTKLEISGGG GSGGGGSGGG GSEVQLVQSG AEVKKPGESL KISCKVSGYF

FTTYWIGWVR QMPGKGLEYM GIIYPGDSDT RYSPSFQGQV TISADKSIST AYLQWSSLKA

SDTAMYYCAR GGNWNCFDYW GQGTLVTVSS **

-continued

SEQ ID NO: 113 Fc-hole Fc-hole IgG1, LALA mutation-IL2Rbeta-gamma
ASKGD111_CX5_105_1
MGVKVLFALI CIAVAEADKT HTCPPCPAPE [AA]GGPSVFLF PPKPKDTLMI SRTPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQV[C]TLPP SRDELTKNQV SL[SC]AVKGFY PSDIAVEWES

NGQPENNYKT TPPVLDSDGS FFL[V]SKLTVD KSRWQQGNVF SCSVMHEALH NHYTQKSLSL

SPG[A]GGGGSG PLGVRGGGGS GGGGSAVNGT SQFTCFYNSR ANISCVWSQD GALQDTSCQV

HAWPDRRRWN QTCELLPVSQ ASWACNLILG APDSQKLTTV DIVTLRVLCR EGVRWRVMAI

QDFKPFENLR LMAPISLQVV HVETHRCNIS WEISQASHYF ERHLEFEART LSPGHTWEEA

PLLTLKQKQE WICLETLTPD TQYEFQVRVK PLQGEFTTWS PWSQPLAFRT KPAALGKDTG

GGGSGGGGSG GGGSGGGGSG GGGSGGGGSP LPEVQCFVFN VEYMNCTWNS

SSEPQPTNLT LHYWYKNSDN DKVQKCSHYL FSEEITSGCQ LQKKEIHLYQ TFVVQLDPR

EPRRQATQML KLQNLVIPWA PENLTLHKLS ESQLELNWNN RFLNHCLEHL VQYRTDWDHS

WTEQSVDYRH KFSLPSVDGQ KRYTFRVRSR FNPLCGSAQH WSEWSHPIHW**

SEQ ID NO: 114 Fc-hole IgG1, LALA mutation-IL2R-gamma-beta
ASKGD111_CX5_105_2
MGVKVLFALI CIAVAEADKT HTCPPCPAPE [AA]GGPSVFLF PPKPKDTLMI SRTPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQV[C]TLPP SRDELTKNQV SL[SC]AVKGFY PSDIAVEWES

NGQPENNYKT TPPVLDSDGS FFL[V]SKLTVD KSRWQQGNVF SCSVMHEALH NHYTQKSLSL

SPG[A]GGGGSG PLGVRGGGGS GGGGSPLPEV QCFVFNVTYM NCTWNSSSEP QPTNLTLHYW

YKNSDNDKVQ KCSHYLFSEE ITSGCQLQKK EIHLYQTFVV QLDPREPRR QATQMLKLQN

LVIPWAPENL TLHKLSESQL ELNWNNRFLN HCLEHLVQYR TDWDHSWTEQ SVDYRHKFSL

PSVDGQKRYT FRVRSRFNPL CGSAQHWSEW SHPIHWGGGG SGGGGSGGGG SGGGGSGGGG

SGGGGSGGGG SGGGGSAVNG TSQFTCFYNS RANISCVWSQ DGALQDTSCQ VHAWPDRRRW

NQTCELLPVS QASWACNLIL GAPDSQKLTT VDIVTLRVLC REGVRWRVMA IQDFKPFENL

RLMAPISLQV VHVETHRCNI SWEISQASHY FERHLEFEAR TLSPGHTWEE APLLTLKQKQ

EWICLETLTP DTQYEFQVRV KPLQGEFTTW SPWSQPLAFR TKPAALGKDT**

SEQ ID NO: 115 Fc-hole Fc-hole IgG1, LALA mutation-IL2R-beta-Ctergamma
ASKGD111_CX5_105_3
MGVKVLFALI CIAVAEADKT HTCPPCPAPE [AA]GGPSVFLF PPKPKDTLMI SRTPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQV[C]TLPP SRDELTKNQV SL[SC]AVKGFY PSDIAVEWES

NGQPENNYKT TPPVLDSDGS FFL[V]SKLTVD KSRWQQGNVF SCSVMHEALH NHYTQKSLSL

SPG[A]GGGGSG PLGVRGGGGS GGGGSAVNGT SQFTCFYNSR ANISCVWSQD GALQDTSCQV

HAWPDRRRWN QTCELLPVSQ ASWACNLILG APDSQKLTTV DIVTLRVLCR EGVRWRVMAI

QDFKPFENLR LMAPISLQVV HVETHRCNIS WEISQASHYF ERHLEFEART LSPGHTWEEA

PLLTLKQKQE WICLETLTPD TQYEFQVRVK PLQGEFTTWS PWSQPLAFRT KPAALGKDTG

GGGSGGGGSG GGGSGGGGSG GGGSGGGGSG GGGSGGGGSA PENLTLHKLS ESQLELNWNN

RFLNHCLEHL VQYRTDWDHS WTEQSVDYRH KFSLPSVDGQ KRYTFRVRSR FNPLCGSAQH

WSEWSHPIHW **

SEQ ID NO: 116 Fc-knob-Sushi-IL-15 (Q108E) IgG1_allotype EEM, LALA
mutation H435R/Y436F
5'XbaI,3'PmeI
ASKGD111_CX5_74_3
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPP CREEMTKNQV SLWCLVKGFY PSDIAVEWES

NGQPENNYKT TPPVLDSDGS FFLYSKLTVD KSRWQQGNVF SCSVMHEALH NRFTQKSLSL

SPGKGGGGSG GGGSGGGGSI TCPPPMSVEH ADIWVKSYSL YSRERYICNS GFKRKAGISS

LTECVLNKAT NVAHWTTPSL KCIRGGSGGG GSGGGSGGGG SNWVNVISDL KKIEDLIQSM

HIDATLYTES DVHPSCKVTA MKCFLLELQV ISLESGDASI HDTVENLIIL ANNSLSSNGN

VTESGCKECE ELEEKNIKEF LQSFVHIVEM FINTS**

SEQ ID NO: 117 Fc-hole IgG1, LALA mutation-IL2Rbeta D68E, not
cleavable
ASKGD111_CX5_76_2
MGVKVLFALI CIAVAEADKT HTCPPCPAPE AAGGPSVFLF PPKPKDTLMI SRTPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVCTLPP SRDELTKNQV SLSCAVKGFY PSDIAVEWES

NGQPENNYKT TPPVLDSDGS FFLVSKLTVD KSRWQQGNVF SCSVMHEALH NHYTQKSLSL

SPGAGGGGSG GGGSGGGGSG GGGSAVNGTS QFTCFYNSRA NISCVWSQDG ALQDTSCQVH

AWPDRRRWNQ TCELLPVSQA SWACNLILGA PESQKLTTVD IVTLRVLCRE GVRWRVMAIQ

DFKPFENLRL MAPISLQVVH VETHRCNISW EISQASHYFE RHLEFEARTL SPGHTWEEAP

LLTLKQKQEW ICLETLTPDT QYEFQVRVKP LQGEFTTWSP WSQPLAFRTK PAALGKDT

SEQ ID NO: 118 Fc-Sushi-IL-15vN65D IgG1_allotype EEM, LALA mutation,
YTE.
ASKD215_CX7.40.1
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPP CREEMTKNQV SLWCLVKGFY PSDIAVEWES

NGQPENNYKT TPPVLDSDGS FFLYSKLTVD KSRWQQGNVF SCSVMHEALH NHYTQKSLSL

SPGAGGGGSG GGGSGGGGSI TCPPPMSVEH ADIWVKSYSL YSRERYICNS GFKRKAGTSS

LTECVLNKAT NVAHWTTPSL KCIRGGSGGG GSGGGSGGGG SNWVNVISDL KKIEDLIQSM

HIDATLYTES DVHPSCKVTA MKCFLLELQV ISLESGDASI HDTVEDLIIL ANNSLSSNGN

VTESGCKECE ELEEKNIKEF LQSFVHIVQM FINTS

SEQ ID NO: 119 IgG1 Fc-hole-MMP/matriptase-VL-VH
ASKD215_CX7_40_2
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

-continued

SNKALPAPIE KTISKAKGQP REPQVCTLPP SREEMTKNQV SLSCAVKGFY PSDIAVEWES

NGQPENNYKT TPPVLDSDGS FFLVSKLTVD KSRWQQGNVF SCSVMHEALH NHYTQKSLSL

SPGAGGGGSV HMPLGFLGPR QARVVNGGGG GSGGGGSEIV LTQSPGTLSL SPGERATLSC

RASQSVSSSY LAWYQQKPGQ APRLLIYGAS RRATGIPDRF SGSGSGTDFT LTISRLEPED

FAVYYCQRYG SSHTFGQGTK LEISGGGGSG GGGSGGGGSE VQLVQSGAEV KKPGESLKIS

CKVSGYFFTT YWIGWVRQMP GKGLEYMGII YPGDSDTRYS PSFQGQVTIS ADKSISTAYL

QWSSLKASDT AMYYCARGGN WNCFDYWGQG TLVTVSS

SEQ ID NO: 120 IgG1 Fc-hole-MMP/matriptase-VL-VH with the 2nd cleavage between VL and VH
ASKD215_CX7_40_3
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVCTLPP SREEMTKNQV SLSCAVKGFY PSDIAVEWES

NGQPENNYKT TPPVLDSDGS FFLVSKLTVD KSRWQQGNVF SCSVMHEALH NHYTQKSLSL

SPGAGGGGSG GGGSGPLGVR GGGGSGGGGS EIVLTQSPGT LSLSPGERAT LSCRASQSVS

SSYLAWYQQK PGQAPRLLIY GASRRATGIP DRFSGSGSGT DFTLTISRLE PEDFAVYYCQ

RYGSSHTFGQ GTKLEISGGG GSGGGGSRQA RVVNGGGGGS EVQLVQSGAE VKKPGESLKI

SCKVSGYFFT TYWIGWVRQM PGKGLEYMGI IYPGDSDTRY SPSFQGQVTI SADKSISTAY

LQWSSLKASD TAMYYCARGG NWNCFDYWGQ GTLVTVSS

SEQ ID NO: 121 Fc-IL-15vN65D, Knob chain, without Sushi
ASKD215_CX7.56.2,
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPP CREEMTKNQV SLWCLVKGFY PSDIAVEWES

NGQPENNYKT TPPVLDSDGS FFLYSKLTVD KSRWQQGNVF SCSVMHEALH NHYTQKSLSL

SPGAGGGGSG GGGSGGGGSN WVNVISDLKK IEDLIQSMHI DATLYTESDV HPSCKVTAMK

CFLLELQVIS LESGDASIHD TVEDLIILAN NSLSSNGNVT ESGCKECEEL EEKNIKEFLQ

SFVHIVQMFI NTS

SEQ ID NO: 122 Fc knob chain with longer linker between Sushi and IL-15v
ASKD215_CX7_56_3
MGVKVLFALI CIAVAEADKT HTCPPCPAPE AAGGPSVFLF PPKPKDTLYI TREPEVTCVV

VDVSHEDPEV KFNWYVDGVE VHNAKTKPRE EQYNSTYRVV SVLTVLHQDW LNGKEYKCKV

SNKALPAPIE KTISKAKGQP REPQVYTLPP CREEMTKNQV SLWCLVKGFY PSDIAVEWES

NGQPENNYKT TPPVLDSDGS FFLYSKLTVD KSRWQQGNVF SCSVMHEALH NHYTQKSLSL

SPGAGGGGSG GGGSGGGGSI TCPPPMSVEH ADIWVKSYSL YSRERYICNS GFKRKAGTSS

LTECVLNKAT NVAHWTTPSL KCIRGGGGSG GGSGGGGSAA GGGGSGGGGS GGGGSNWVNV

-continued

ISDLKKIEDL IQSMHIDATL YTESDVHPSC KVTAMKCFLL ELQVISLESG DASIHDTVED

LIILANNSLS SNGNVTESGC KECEELEEKN IKEFLQSFVH IVQMFINTS

SEQ ID NO: 123 Anti-IL-15 antibody 146B7 LC variable domain (protein sequence) ver2
EIVLTQSPGT LSLSPGREAT LSCRASQSVS SSYLAWYQQK PGQAPRLLIY GASRRATGIP

DRFSGSGSGT DFTLTISRLE PEDFAVYYCQ RYGSSHTFGQ GTKLE

SEQ ID NO: 124 anti-IL-15 scFv1 ver2
EVQLVQSGAE VKKPGESLKI SCKVSGYFFT TYWIGWVRQM PGKGLEYMGI IYPGDSDTRY

SPSFQGQVTI SADKSISTAY LQWSSLKASD TAMYYCARGG NWNCFDYWGQ GTLVTVSSGG

GGSGGGGSGG GGSEIVLTQS PGTLSLSPGR EATLSCRASQ SVSSSYLAWY QQKPGQAPRL

LIYGASRRAT GIPDRFSGSG SGTDFTLTIS RLEPEDFAVY YCQRYGSSHT FGQGTKLE

SEQ ID NO: 125 anti-Trop-2 antibody light chain CDR1
KASQDVSIAV A

SEQ ID NO: 126 anti-Trop-2 antibody light chain CDR2
SASYRYT

SEQ ID NO: 127 anti-Trop-2 antibody light chain CDR3
QQHYITPLT

SEQ ID NO: 128 anti-Trop-2 antibody heavy chain CDR1
NYGMN

SEQ ID NO: 129 anti-Trop-2 antibody heavy chain CDR2
WINTYTGEPT YTDDFKG

SEQ ID NO: 130 anti-Trop-2 antibody heavy chain CDR3
GGFGSSYWY FDV

SEQ ID NO: 131 anti-mesothelin antibody light chain CDR1
SASSSVSYM H

SEQ ID NO: 132 anti-mesothelin antibody light chain CDR2
DTSKLAS

SEQ ID NO: 133 anti-mesothelin antibody light chain CDR3
QQWSGY PLT

SEQ ID NO: 134 anti-mesothelin antibody heavy chain CDR1
GYTMN

SEQ ID NO: 135 anti-mesothelin antibody heavy chain CDR2
LITPYNGASS YNQKFRG

SEQ ID NO: 136 anti-mesothelin antibody heavy chain CDR3
GGYDGRGFDY

SEQ ID NO: 137 Homo sapiens interleukin 15 receptor subunit alpha (IL-15Rα), transcript variant 1, mRNA
ctgggcagcg ctcgcccggg gagtccagcg gtgtcctgtg gagctgccgc catggccccg cggcgggcgc gcggctgccg gaccctcggt ctcccggcgc tgctactgct gctgctgctc cggccgccgg cgacgcgggg catcacgtgc cctcccccca tgtccgtgga acacgcagac atctgggtca agagctacag cttgtactcc agggagcggt acatttgtaa ctctggtttc aagcgtaaag ccggcacgtc cagcctgacg gagtgcgtgt tgaacaaggc cacgaatgtc gcccactgga caaccccag tctcaaatgc attagagacc ctgccctggt tcaccaaagg ccagcgccac cctccacagt aacgacggca ggggtgaccc cacagccaga gagcctctcc ccttctggaa aagagcccgc agcttcatct cccagctcaa acaacacagc ggccacaaca gcagctattg tcccgggctc ccagctgatg ccttcaaaat caccttccac aggaaccaca gagataagca gtcatgagtc ctcccacggc acccccctctc agacaacagc caagaactgg gaactcacag catccgcctc ccaccagccg ccaggtgtgt atccacaggg ccacagcgac accactgtgg ctatctccac gtccactgtc ctgctgtgtg ggctgagcgc tgtgtctctc -continued

```
ctggcatgct acctcaagtc aaggcaaact ccccgctgg ccagcgttga aatggaagcc atggaggctc tgccggtgac ttgggggacc agcagcagag atgaagactt ggaaaactgc tctcaccacc tatgaaactc ggggaaacca gcccagctaa gtccggagtg aaggagcctc tctgctttag ctaaagacga ctgagaagag gtgcaaggaa gcgggctcca ggagcaagct caccaggcct tcagaagtc ccagcaggat ctcacggact gccgggtcgg cgcctcctgc gcgagggagc aggttctccg cattcccatg ggcaccacct gcctgcctgt cgtgccttgg acccagggcc cagcttccca ggagagacca aaggcttctg agcaggattt ttatttcatt acagtgtgag ctgcctggaa tacatgtggt aatgaaataa aaaccctgcc ccgaatcttc cgtccctcat cctaactttc agttcacaga gaaaagtgac atacccaaag ctctctgtca attacaaggc ttctcctggc gtgggagacg tctacaggga agacaccagc gtttgggctt ctaaccaccc tgtctccagc tgctctgcac acatggacag ggacctggga aaggtgggag agatgctgag cccagcgaat cctctccatt gaaggattca ggaagaagaa aactcaactc agtgccattt tacgaatata tgcgtttata tttatacttc cttgtctatt atatctatac attatatatt atttgtattt tgacattgta ccttgtataa acaaaataaa acatctattt tcaata
```

SEQ ID NO: 138 noncleavable peptide linker
GSAGSAAGSG EF

SEQ ID NO: 139 noncleavable peptide linker, wherein n1 = 1, 2, or 3, and n2 = 1, 2, or 3.
(GGGGS)n1GSAGSAAGSGEF(GGGGS)n2

SEQ ID NO: 140 noncleavable peptide linker
(GGGGS)n1AA(GGGGS)n2; wherein n1 = 2 or 3, and n2 = 2 or 3.

---

The invention claimed is:

1. A prodrug comprising an IL-15 cytokine moiety (A), a masking moiety (M), a carrier moiety (C), and an IL-15Ra Sushi domain (S), wherein
   the masking moiety comprises an anti-IL-15 antibody fragment comprising a heavy chain CDR (HCDR) 1 comprising SEQ ID NO: 100, an HCDR2 comprising SEQ ID NO: 101, an HCDR3 comprising SEQ ID NO: 102 or 106, a light chain CDR (LCDR) 1 comprising SEQ ID NO: 103, an LCDR2 comprising SEQ ID NO: 104, and an LCDR3 comprising SEQ ID NO: 105,
   the masking moiety and the Sushi domain are each fused to the carrier moiety,
   the carrier moiety comprises an Fc domain derived from human $IgG_1$ or $IgG_4$, and
   the IL-15 cytokine moiety is fused to the Sushi domain, wherein the IL-15 cytokine moiety comprises a mutation at a position that corresponds to residue N65 of SEQ ID NO: 2 and wherein the IL-15 cytokine moiety has reduced affinity for IL-2Rβ compared to wildtype IL-15.

2. The prodrug of claim 1, wherein
   the masking moiety is fused to the carrier moiety through a first peptide linker,
   the Sushi domain is fused to the carrier moiety through a second peptide linker, and
   the IL-15 cytokine moiety is fused to the Sushi domain through a third peptide linker, and
   wherein at least one of the three peptide linkers is cleavable.

3. The prodrug of claim 2, wherein the third peptide linker is at least 15, 20, 25, or 30 amino acids in length, optionally wherein the third peptide linker comprises one or more GGGGS (SEQ ID NO: 11) motifs.

4. The prodrug of claim 2, wherein at least one of the first, second, and third peptide linkers is a noncleavable peptide linker, optionally comprising an amino acid sequence selected from SEQ ID NOs: 11-16.

5. The prodrug of claim 2, wherein at least one of the first, second, and third peptide linkers is a cleavable peptide linker, optionally comprising a substrate sequence of urokinase-type plasminogen activator (uPA); matriptase; matrix metallopeptidase (MMP) 2; MMP9; both uPA and MMP2; both uPA and MMP9; all of uPA, MMP2 and MMP9; or both MMP2 and matriptase.

6. The prodrug of claim 5, wherein the cleavable peptide linker comprises an amino acid sequence selected from SEQ ID NOs: 17-36.

7. The prodrug of claim 5, wherein the cleavable peptide linker is cleavable by one or more proteases located at a tumor site or its surrounding environment, and the cleavage leads to activation of the prodrug at the tumor site or surrounding environment.

8. The prodrug of claim 1, wherein the anti-IL-15 antibody fragment comprises
   a heavy chain variable domain (VH) comprising SEQ ID NO: 107 or an amino acid sequence at least 95% identical thereto, and
   a light chain variable domain (VL) comprising SEQ ID NO: 108 or an amino acid sequence at least 95% identical thereto.

9. The prodrug of claim 8, wherein the antibody fragment is an scFv.

10. The prodrug of claim 9, wherein the VH is C-terminal to the VL in the scFv.

11. The prodrug of claim 1, wherein the masking moiety does not interfere with or has minimum impact on the binding of the IL-15 cytokine moiety to IL-15Rα.

12. The prodrug of claim 1, wherein the IL-15 cytokine moiety comprises SEQ ID NO: 2 with an N65D mutation.

13. The prodrug of claim 1, wherein the Fc domain comprises L234A and L235A ("LALA") mutations (EU numbering).

14. The prodrug of claim 1, wherein the Fc domain comprises knobs-into-holes mutations, and wherein the IL-15 cytokine moiety and the masking moiety are fused to different polypeptide chains of the Fc domain.

15. The prodrug of claim 14, wherein
   the knobs-into-holes mutations comprise a T366Y "knob" mutation on a polypeptide chain of the Fc domain, and a Y407T "hole" mutation in the other polypeptide chain of the Fc domain, or
   the knobs-into-holes mutations comprise Y349C and/or T366W mutations in the CH3 domain of the "knob chain" and E356C, T366S, L368A, and/or Y407V mutations in the CH3 domain of the "hole chain" (EU numbering).

16. The prodrug of claim 1, wherein the Fc domain comprises a first polypeptide comprising an amino acid sequence at least 99% identical SEQ ID NO: 80 or 81, and a second polypeptide chain comprising an amino acid sequence at least 99% identical to one selected from SEQ ID NOs: 82-86.

17. The prodrug of claim 1, wherein the prodrug comprises the following polypeptide pairs (from N-terminus to C-terminus):
 a. C1-S-A and C2-M,
 b. A-S-C1 and M-C2; and
wherein C1 and C2 are the first and second polypeptide chains, respectively, of the Fc domain; and "-" is a direct peptidyl bond or a peptide linker.

18. The prodrug of claim 1, wherein the Sushi domain comprises SEQ ID NO: 7 or 9, or an amino acid sequence at least 90% identical thereto.

19. A pharmaceutical composition comprising the prodrug of claim 1 and a pharmaceutically acceptable excipient.

20. The prodrug of claim 1, wherein the prodrug comprises a first polypeptide comprising SEQ ID NO: 122 without the signal peptide, and a second polypeptide comprising SEQ ID NO: 119 without the signal peptide.

21. The prodrug of claim 1, wherein the prodrug comprises a first polypeptide comprising SEQ ID NO: 79 without the signal peptide, and a second polypeptide comprising SEQ ID NO: 112 without the signal peptide.

\* \* \* \* \*

UNITED STATES PATENT AND TRADEMARK OFFICE
CERTIFICATE OF CORRECTION

| | | |
|---|---|---|
| PATENT NO. | : 11,845,801 B2 | Page 1 of 1 |
| APPLICATION NO. | : 16/900677 | |
| DATED | : December 19, 2023 | |
| INVENTOR(S) | : Lu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 450 days.

Signed and Sealed this
First Day of July, 2025

Coke Morgan Stewart
*Acting Director of the United States Patent and Trademark Office*